(12) United States Patent
Cacatian et al.

(10) Patent No.: US 10,899,758 B2
(45) Date of Patent: Jan. 26, 2021

(54) INHIBITORS OF THE MENIN-MLL INTERACTION

(71) Applicant: Vitae Pharmaceuticals, LLC, Madison, NJ (US)

(72) Inventors: Salvacion Cacatian, Conshohocken, PA (US); David A. Claremon, Maple Glen, PA (US); Chengguo Dong, Staten Island, NY (US); Yi Fan, Doylestown, PA (US); Lanqi Jia, Horsham, PA (US); Stephen D. Lotesta, Burlington, NJ (US); Suresh B. Singh, Kendall Park, NJ (US); Shankar Venkatraman, Lansdale, PA (US); Jing Yuan, Lansdale, PA (US); Yajun Zheng, Hockessin, DE (US); Linghang Zhuang, Chalfont, PA (US)

(73) Assignee: VITAE PHARMACEUTICALS, LLC, Madison, NJ (US)

( * ) Notice: Subject to any disclaimer, the term of this patent is extended or adjusted under 35 U.S.C. 154(b) by 0 days.

(21) Appl. No.: 16/333,852

(22) PCT Filed: Sep. 15, 2017

(86) PCT No.: PCT/US2017/051780
§ 371 (c)(1),
(2) Date: Mar. 15, 2019

(87) PCT Pub. No.: WO2018/053267
PCT Pub. Date: Mar. 22, 2018

(65) Prior Publication Data
US 2019/0202830 A1 Jul. 4, 2019

Related U.S. Application Data

(60) Provisional application No. 62/395,618, filed on Sep. 16, 2016.

(51) Int. Cl.
*C07D 471/04* (2006.01)
*C07D 487/04* (2006.01)
*A61P 35/00* (2006.01)

(52) U.S. Cl.
CPC ............ *C07D 471/04* (2013.01); *A61P 35/00* (2018.01); *C07D 487/04* (2013.01)

(58) Field of Classification Search
CPC ...... A61P 35/00; C07D 471/04; C07D 487/04
See application file for complete search history.

(56) References Cited

U.S. PATENT DOCUMENTS

2010/0144758 A1 6/2010 Dillon et al.

FOREIGN PATENT DOCUMENTS

| WO | WO 2011113798 | * | 9/2011 | ........... C07D 471/04 |
| WO | WO 2015/058084 A1 | | 4/2015 | |

OTHER PUBLICATIONS

Abunada, et al, Synthesis and antimicrobial activity of some new pyrazole, fused pyrazolo[3,4-d]-pyrimidine and pyrazolo[4,3-e][1,2,4]triazolo[1,5-c]pyrimidine derivatives, Molecules, 13(7), 1501-1517 (2008). (Year: 2008).*

* cited by examiner

*Primary Examiner* — Erich A Leeser
(74) *Attorney, Agent, or Firm* — Cooley LLP; Heidi A. Erlacher; Eric A. Owens

(57) ABSTRACT

The present invention is directed to inhibitors of the interaction of menin with MLL and MLL fusion proteins, pharmaceutical compositions containing the same, and their use in the treatment of cancer and other diseases mediated by the menin-MLL interaction.

25 Claims, 1 Drawing Sheet

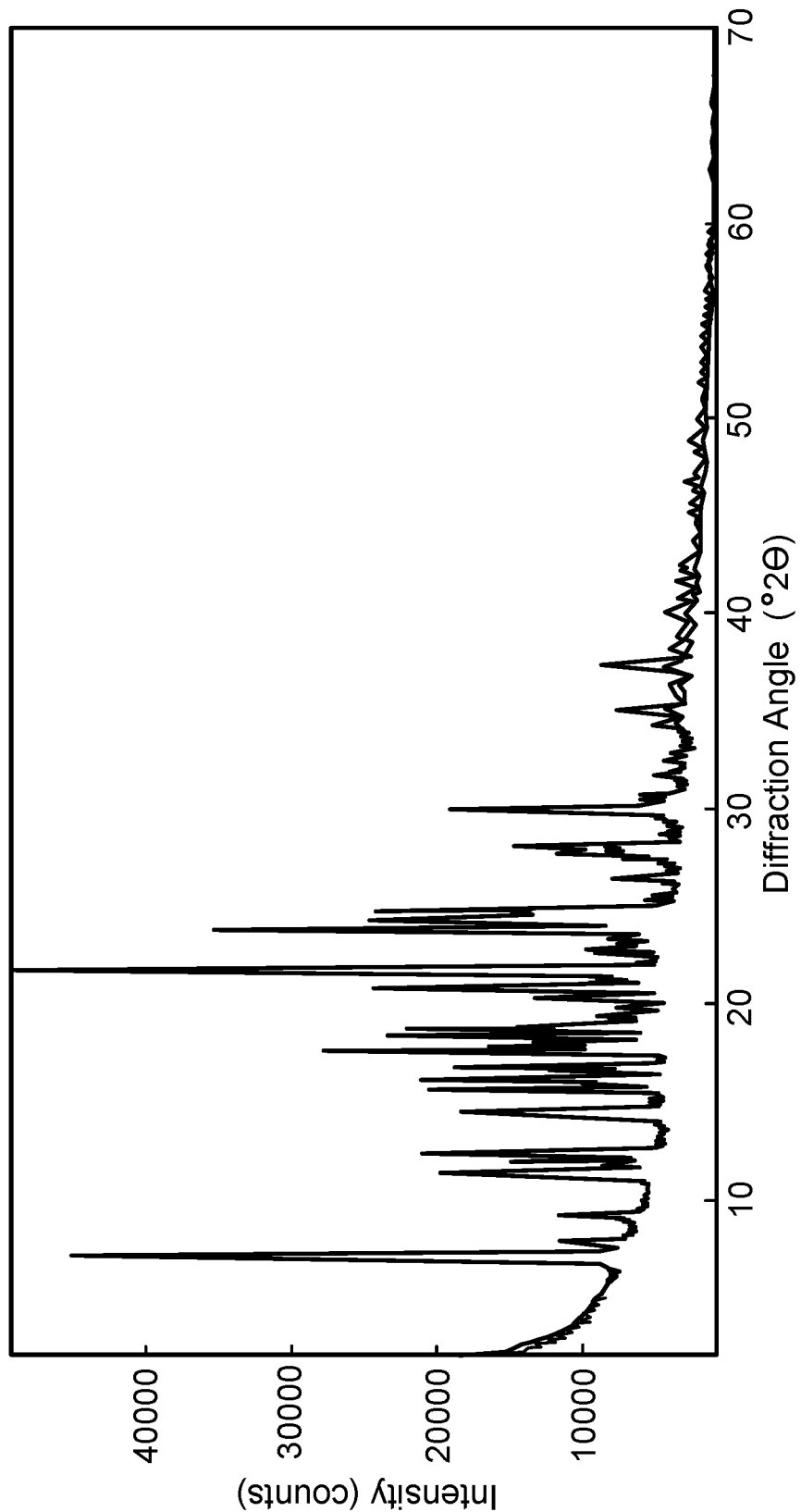

INHIBITORS OF THE MENIN-MLL INTERACTION

CROSS-REFERENCE TO RELATED APPLICATION

This application is a U.S. National Stage Application under 35 U.S.C. § 371 of International Application No. PCT/US2017/051780, filed on Sep. 15, 2017, which claims the benefit of U.S. Provisional Application No. 62/395,618, filed Sep. 16, 2016, which are incorporated by reference in their entireties.

TECHNICAL FIELD

The present invention is directed to inhibitors of the interaction of menin with MLL and MLL fusion proteins, pharmaceutical compositions containing the same, and their use in the treatment of cancer and other diseases mediated by the menin-MLL interaction.

BACKGROUND

The mixed-lineage leukemia (MLL) protein is a histone methyltransferase that is mutated in clinically and biologically distinctive subsets of acute leukemia. Rearranged mixed lineage leukemia (MLL-r) involves recurrent translocations of the 11 q23 chromosome locus which lead to an aggressive form of acute leukemia with limited therapeutic options. These translocations target the MLL gene creating an oncogenic fusion protein comprising the amino-terminus of MLL fused in frame with more than 60 different fusion protein partners. Menin, a ubiquitously expressed, nuclear protein encoded by the multiple endocrine neoplasia type 1 (MEN1) tumor suppressor gene, has a high affinity binding interaction with MLL fusion proteins and is an essential co-factor of oncogenic MLL-r fusion proteins (Yokoyama et al., 2005, Cell, 123:207-18; Cierpicki & Grembecka, 2014, Future Med. Chem., 6:447-462). Disruption of this interaction leads to selective growth inhibition and apoptosis of MLL-r leukemia cells both in vitro (Grembecka et al., 2012, Nat. Chem. Biol., 8:277-284) and in vivo (Yokoyama et al., 2005, op. cit.; Borkin et al., 2015, Cancer Cell, 27:589-602).

The menin-MLL complex plays a role in castration-resistant/advanced prostate cancer, and a menin-MLL inhibitor has been shown to reduce tumor growth in vivo (Malik et al., 2015, Nat. Med., 21:344-352). Additionally, a menin-MLL inhibitor has been shown to enhance human 3 cell proliferation (Chamberlain et al., 2014, J. Clin. Invest., 124:4093-4101), supporting a role for inhibitors of the menin-MLL interaction in the treatment of diabetes (Yang et al., 2010, Proc Natl Acad Sci USA., 107:20358-20363). The interaction between menin and MLL or MLL fusion proteins is an attractive target for therapeutic intervention, and there is a need for novel agents that inhibit the menin-MLL interaction for the treatment of various diseases and conditions, including leukemia, other cancers and diabetes.

BRIEF DESCRIPTION OF THE DRAWINGS

FIG. 1 shows an XRPD pattern characteristic of 5-fluoro-N-isopropyl-N-methyl-2-(3-(1-(((2-oxo-2,3-dihydro-1H-benzo[d]imidazol-5-yl)methyl)piperidin-3-yl)-1H-pyrrolo[2,3-c]pyridin-1-yl)benzamide mono-(2R,3S,4R,5S)-2,3,4,5-tetrahydroxyhexanedioic acid (mucate) salt.

SUMMARY

The present invention provides inhibitors of the menin-MLL interaction, such as a compound of Formula I:

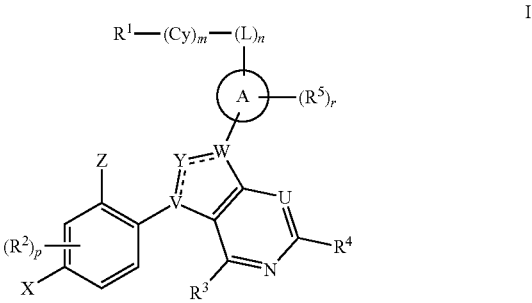

or a pharmaceutically acceptable salt thereof, wherein constituent variables are defined herein.

The present invention further provides a pharmaceutical composition comprising a compound of Formula I, or a pharmaceutically acceptable salt thereof, and at least one pharmaceutically acceptable carrier.

The present invention further provides a method of inhibiting the interaction between menin and MLL comprising contacting the menin and MLL with a compound of any one of Formula I, or a pharmaceutically acceptable salt thereof.

The present invention further provides a method of treating cancer in a patient comprising administering to the patient a therapeutically effective amount of a compound of Formula I, or a pharmaceutically acceptable salt thereof.

The present invention further provides a method of treating insulin resistance, pre-diabetes, diabetes, risk of diabetes, or hyperglycemia in a patient comprising administering to the patient a therapeutically effective amount of a compound of Formula I, or a pharmaceutically acceptable salt thereof.

The present invention further provides the use of a compound of Formula I, or a pharmaceutically acceptable salt thereof, for manufacture of a medicament for inhibiting the interaction between menin and MLL.

The present invention further provides the use of a compound of Formula I, or a pharmaceutically acceptable salt thereof, for manufacture of a medicament for treating cancer in a patient.

The present invention further provides the use of a compound of Formula I, or a pharmaceutically acceptable salt thereof, for manufacture of a medicament for treating insulin resistance, pre-diabetes, diabetes, risk of diabetes, or hyperglycemia in a patient.

The present application further provides a compound of Formula I, or a pharmaceutically acceptable salt thereof, for use in inhibiting the interaction between menin and MLL.

The present application further provides a compound of Formula I, or a pharmaceutically acceptable salt thereof, for use in treatment of cancer in a patient.

The present application further provides a compound of Formula I, or a pharmaceutically acceptable salt thereof, for use in treatment of insulin resistance, pre-diabetes, diabetes, risk of diabetes, or hyperglycemia in a patient.

DETAILED DESCRIPTION

The present invention provides inhibitors of the menin-MLL interaction, such as a compound of Formula I:

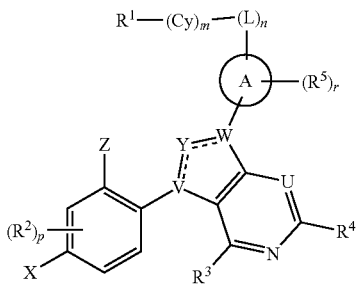

or a pharmaceutically acceptable salt thereof, wherein:

Ring A is a $C_{6-10}$ aryl group, 5-14 membered heteroaryl group, $C_{3-14}$ cycloalkyl group, or 4-14 membered heterocycloalkyl group;

U is N or $CR^U$, wherein $R^U$ is H, halo, CN, OH, $C_{1-4}$ alkyl, $C_{1-4}$ alkoxy, amino, $C_{1-4}$ alkyl amino, or $C_{2-8}$ dialkylamino; the moiety

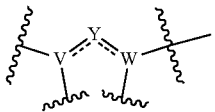

is selected from:

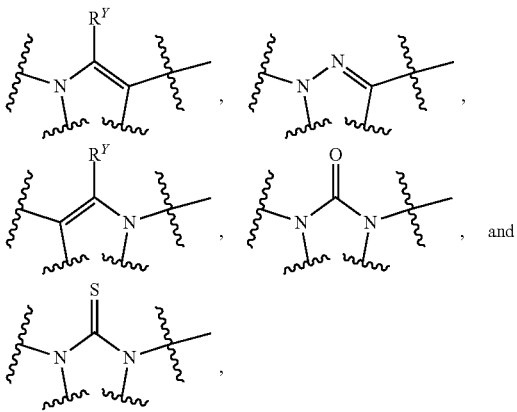

wherein $R^Y$ is H, halo, CN, OH, $C_{1-4}$ alkyl, $C_{1-4}$ alkoxy, amino, $C_{1-4}$ alkyl amino, or $C_{2-8}$ dialkylamino;

X is F or Cl;

L is selected from $-C_{1-6}$ alkylene- and $-(C_{1-4}$ alkylene$)_a$-Q-$(C_{1-4}$ alkylene$)_b$-, wherein the $C_{1-6}$ alkylene group and any $C_{1-4}$ alkylene group of the $-(C_{1-4}$ alkylene$)_a$-Q-$(C_{1-4}$ alkylene$)_b$- group is optionally substituted with 1, 2, or 3 substituents independently selected from halo, CN, OH, $C_{1-3}$ alkyl, $C_{1-3}$ alkoxy, $C_{1-3}$ hydroxyalkyl, $C_{1-3}$ haloalkyl, $C_{1-3}$ haloalkoxy, amino, $C_{1-3}$ alkylamino, and di($C_{1-3}$ alkyl)amino;

Q is $-O-$, $-S-$, $-S(=O)-$, $-S(=O)_2-$, $-C(=O)-$, $-C(=O)NR^{q1}-$, $-C(=O)O-$, $-OC$ $(=O)NR^{q1}-$, $-NR^{q1}-$, $-NR^{q1}C(=O)O-$, $-NR^{q1}C$ $(=O)NR^{q1}-$, $-S(=O)_2NR^{q1}-$, $-C(=NR^{q2})-$, or $-C(=NR^{q2})-NR^{q1}-$, wherein each $R^{q1}$ is independently selected from H, $C_{1-6}$ alkyl, and $C_{1-3}$ hydroxyalkyl and wherein each $R^{q2}$ is independently selected from H, $C_{1-6}$ alkyl, and CN;

Cy is a linking $C_{6-14}$ aryl, linking $C_{3-18}$ cycloalkyl, linking 5-16 membered heteroaryl, or linking 4-18 membered heterocycloalkyl group, each of which is optionally substituted with 1, 2, 3, or 4 substituents independently selected from $R^{Cy}$;

each $R^{Cy}$ is independently selected from halo, $C_{1-6}$ alkyl, $C_{1-4}$ haloalkyl, $C_{1-4}$ cyanoalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl are each optionally substituted by 1, 2, 3, or 4 substituents independently selected from CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

$R^1$ is H, $Cy^1$, halo, $C_{1-6}$ alkyl, $C_{1-4}$ haloalkyl, $C_{1-4}$ cyanoalkyl, $C_{2-6}$ alkenyl, $C_{2-6}$ alkynyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$ and $S(O)_2NR^{c2}R^{d2}$, wherein said $C_{1-6}$ alkyl, $C_{2-6}$ alkenyl, and $C_{2-6}$ alkynyl are each optionally substituted by 1, 2, 3, or 4 substituents independently selected from halo, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$;

Z is $Cy^2$, halo, $C_{1-6}$ alkyl, $C_{1-4}$ haloalkyl, $C_{1-4}$ cyanoalkyl, $C_{2-6}$ alkenyl, $C_{2-6}$ alkynyl, CN, $NO_2$, $OR^{a3}$, $SR^{a3}$, $C(O)R^{b3}$, $C(O)NR^{c3}R^{d3}$, $C(S)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, $S(O)_2NR^{c3}R^{d3}$, and $P(O)R^{c3}R^{d3}$, wherein said $C_{1-6}$ alkyl, $C_{2-6}$ alkenyl, and $C_{2-6}$ alkynyl are each optionally substituted by 1, 2, 3, or 4 substituents independently selected from $Cy^2$, halo, CN, $NO_2$, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{b3}R^{d3}$;

each $R^2$, $R^3$, $R^4$, and $R^5$ is independently selected from H, halo, $C_{1-6}$ alkyl, $C_{1-4}$ haloalkyl, $C_{1-4}$ cyanoalkyl, $C_{2-6}$ alkenyl, $C_{2-6}$ alkynyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $C(=NR^{e4})NR^{c4}R^{d4}$, $NR^{c4}C(=NR^{e4})NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$, wherein said $C_{1-6}$ alkyl, $C_{2-6}$ alkenyl, and $C_{2-6}$ alkynyl are each optionally substituted by 1, 2, 3, or 4 substituents independently selected from halo, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $C(=NR^{e4})NR^{c4}R^{d4}$, $NR^{c4}C(=NR^{e4})NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$;

each $Cy^1$ is independently selected from $C_{6-14}$ aryl, $C_{3-18}$ cycloalkyl, 5-16 membered heteroaryl, and 4-18 membered heterocycloalkyl, each of which is optionally substituted with 1, 2, 3, or 4 substituents independently selected from $R^{Cy1}$;

each $Cy^2$ is independently selected from $C_{6-14}$ aryl, $C_{3-18}$ cycloalkyl, 5-16 membered heteroaryl, and 4-18 membered heterocycloalkyl, each of which is optionally substituted with 1, 2, 3, or 4 substituents independently selected from $R^{Cy2}$;

each $R^{Cy1}$ and $R^{Cy2}$ is independently selected from halo, $C_{1-6}$ alkyl, $C_{1-4}$ haloalkyl, $C_{1-4}$ cyanoalkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $C(=NR^{e5})NR^{c5}R^{d5}$. $NR^{c5}C(=NR^{e5})NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$, wherein said $C_{1-6}$ alkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl are each optionally substituted by 1, 2, 3, or 4 substituents independently selected from CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $C(=NR^{e5})NR^{c5}R^{d5}$, $NR^{c5}C(=NR^{e5})NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$;

each $R^{a1}$, $R^{b1}$, $R^{c1}$, $R^{d1}$, $R^{a2}$, $R^{b2}$, $R^{c2}$, $R^{d2}$, $R^{a3}$, $R^{b3}$, $R^{c3}$, $R^{d3}$, $R^{a4}$, $R^{b4}$, $R^{c4}$, $R^{d4}$, $R^{a5}$, $R^{b5}$, $R^{c5}$, and $R^{d5}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl, $C_{3-10}$ cycloalkyl-$C_{1-6}$ alkyl, (5-10 membered heteroaryl)-$C_{1-6}$ alkyl, and (4-10 membered heterocycloalkyl)-$C_{1-6}$ alkyl, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl, $C_{3-10}$ cycloalkyl-$C_{1-6}$ alkyl, (5-10 membered heteroaryl)-$C_{1-6}$ alkyl, and (4-10 membered heterocycloalkyl)-$C_{1-6}$ alkyl are each optionally substituted with 1, 2, 3, 4, or 5 substituents independently selected from $R^g$;

each $R^{e1}$, $R^{e2}$, $R^{e3}$, $R^{e4}$, and $R^{e5}$ is independently selected from H, $C_{1-4}$ alkyl, and CN;

each $R^g$ is independently selected from the group consisting of OH, $NO_2$, CN, halo, $C_{1-20}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thiol, $C_{1-6}$ alkylthio, $C_{1-6}$ alkylsulfinyl, $C_{1-6}$ alkylsulfonyl, carboxy, $C_{1-6}$ alkylcarbonyl, and $C_{1-6}$ alkoxycarbonyl;

n is 0 or 1;
m is 0 or 1;
p is 0, 1, 2, or 3;
r is 0, 1, or 2;
a is 0 or 1; and
b is 0 or 1, wherein any cycloalkyl or heterocycloalkyl group is optionally further substituted by 1 or 2 oxo groups, and wherein the compound is not:

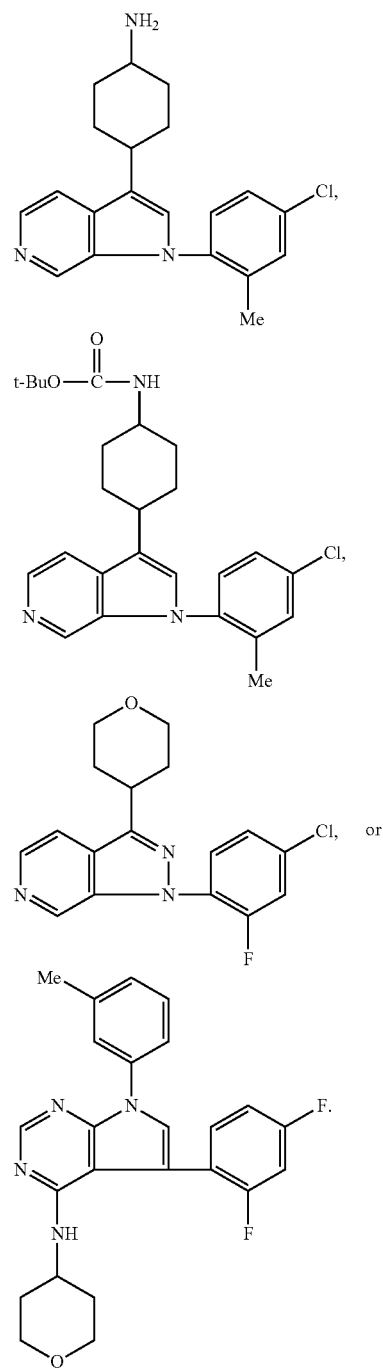

In some embodiments:

Ring A is a $C_{6-10}$ aryl group, 5-14 membered heteroaryl group, $C_{3-14}$ cycloalkyl group, or 4-14 membered heterocycloalkyl group;

U is N or CR$^U$, wherein R$^U$ is H, halo, CN, OH, C$_{1-4}$ alkyl, C$_{1-4}$ alkoxy, amino, C$_{1-4}$ alkyl amino, or C$_{2-8}$ dialkylamino; the moiety

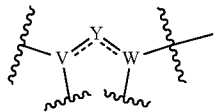

is selected from:

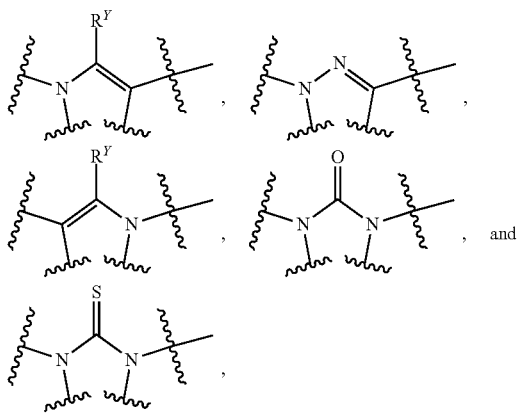

, and wherein R$^Y$ is H, halo, CN, OH, C$_{1-4}$ alkyl, C$_{1-4}$ alkoxy, amino, C$_{1-4}$ alkyl amino, or C$_{2-8}$ dialkylamino;

X is F or Cl;

L is selected from —C$_{1-6}$ alkylene- and —(C$_{1-4}$ alkylene)$_a$-Q-(C$_{1-4}$ alkylene)$_b$-, wherein the C$_{1-6}$ alkylene group and any C$_{1-4}$ alkylene group of the —(C$_{1-4}$ alkylene)$_a$-Q-(C$_{1-4}$ alkylene)$_b$- group is optionally substituted with 1, 2, or 3 substituents independently selected from halo, CN, OH, C$_{1-3}$ alkyl, C$_{1-3}$ alkoxy, C$_{1-3}$ haloalkyl, C$_{1-3}$ haloalkoxy, amino, C$_{1-3}$ alkylamino, and di(C$_{1-3}$ alkyl)amino;

Q is —O—, —S—, —S(=O)—, —S(=O)$_2$—, —C(=O)—, —C(=O)NR$^{q1}$—, —C(=O)O—, —OC(=O)NR$^{q1}$—, —NR$^{q1}$—, —NR$^{q1}$C(=O)O—, —NR$^{q1}$C(=O)NR$^{q1}$—, —S(=O)$_2$NR$^{q1}$—, —C(=NR$^{q2}$)—, or —C(=NR$^{q2}$)—NR$^{q1}$—, wherein each R$^{q1}$ is independently selected from H and C$_{1-6}$ alkyl, and wherein each R$^{q2}$ is independently selected from H, C$_{1-6}$ alkyl, and CN;

Cy is a linking C$_{6-14}$ aryl, linking C$_{3-18}$ cycloalkyl, linking 5-16 membered heteroaryl, or linking 4-18 membered heterocycloalkyl group, each of which is optionally substituted with 1, 2, 3, or 4 substituents independently selected from R$^{Cy}$;

each R$^{Cy}$ is independently selected from halo, C$_{1-6}$ alkyl, C$_{1-4}$ haloalkyl, C$_{1-4}$ cyanoalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, C(=NR$^{e1}$)NR$^{c1}$R$^{d1}$, NR$^{c1}$C(=NR$^{e1}$)NR$^{c1}$R$^{d1}$, NR$^{c1}$R$^{d1}$, NR$^{c1}$C(O)R$^{b1}$, NR$^{c1}$C(O)OR$^{a1}$, NR$^{c1}$C(O)NR$^{c1}$R$^{d1}$, NR$^{c1}$S(O)R$^{b1}$, NR$^{c1}$S(O)$_2$R$^{b1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, and S(O)$_2$NR$^{c1}$R$^{d1}$, wherein said C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, and 4-10 membered heterocycloalkyl are each optionally substituted by 1, 2, 3, or 4 substituents independently selected from CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, C(=NR$^{e1}$)NR$^{c1}$R$^{d1}$, NR$^{c1}$C(=NR$^{e1}$)NR$^{c1}$R$^{d1}$, NR$^{c1}$R$^{d1}$, NR$^{c1}$C(O)R$^{b1}$, NR$^{c1}$C(O)OR$^{a1}$, NR$^{c1}$C(O)NR$^{c1}$R$^{d1}$, NR$^{c1}$S(O)R$^{b1}$, NR$^{c1}$S(O)$_2$R$^{b1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, and S(O)$_2$NR$^{c1}$R$^{d1}$;

R$^1$ is H, Cy$^1$, halo, C$_{1-6}$ alkyl, C$_{1-4}$ haloalkyl, C$_{1-4}$ cyanoalkyl, C$_{2-6}$ alkenyl, C$_{2-6}$ alkynyl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, C(=NR$^{e2}$)NR$^{c2}$R$^{d2}$, NR$^{c2}$C(=NR$^{e2}$)NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, NR$^{c2}$S(O)R$^{b2}$, NR$^{c2}$S(O)$_2$R$^{b2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$ and S(O)$_2$NR$^{c2}$R$^{d2}$, wherein said C$_{1-6}$ alkyl, C$_{2-6}$ alkenyl, and C$_{2-6}$ alkynyl are each optionally substituted by 1, 2, 3, or 4 substituents independently selected from halo, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, C(=NR$^{e2}$)NR$^{c2}$R$^{d2}$, NR$^{c2}$C(=NR$^{e2}$)NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, NR$^{c2}$S(O)R$^{b2}$, NR$^{c2}$S(O)$_2$R$^{b2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, and S(O)$_2$NR$^{c2}$R$^{d2}$;

Z is Cy$^2$, C$_{2-6}$ alkyl, C$_{1-4}$ haloalkyl, C$_{1-4}$ cyanoalkyl, C$_{2-6}$ alkenyl, C$_{2-6}$ alkynyl, CN, NO$_2$, OR$^{a3}$, SR$^{a3}$, C(O)R$^{b3}$, C(O)NR$^{c3}$R$^{d3}$, C(S)NR$^{c3}$R$^{d3}$, C(O)OR$^{a3}$, OC(O)R$^{b3}$, OC(O)NR$^{c3}$R$^{d3}$, C(=NR$^{e3}$)NR$^{c3}$R$^{d3}$, NR$^{c3}$C(=NR$^{e3}$)NR$^{c3}$R$^{d3}$, NR$^{c3}$R$^{d3}$, NR$^{c3}$C(O)R$^{b3}$, NR$^{c3}$C(O)OR$^{a3}$, NR$^{c3}$C(O)NR$^{c3}$R$^{d3}$, NR$^{c3}$S(O)R$^{b3}$, NR$^{c3}$S(O)$_2$R$^{b3}$, NR$^{c3}$S(O)$_2$NR$^{c3}$R$^{d3}$, S(O)R$^{b3}$, S(O)NR$^{c3}$R$^{d3}$, S(O)$_2$R$^{b3}$, S(O)$_2$NR$^{c3}$R$^{d3}$, and P(O)R$^{c3}$R$^{d3}$ wherein said C$_{1-6}$ alkyl, C$_{2-6}$ alkenyl, and C$_{2-6}$ alkynyl are each optionally substituted by 1, 2, 3, or 4 substituents independently selected from Cy$^2$, halo, CN, NO$_2$, CN, NO$_2$, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, C(=NR$^{e3}$)NR$^{c3}$R$^{d3}$, NR$^{c3}$C(=NR$^{e3}$)NR$^{c3}$R$^{d3}$, NR$^{c3}$R$^{d3}$, NR$^{c3}$C(O)R$^{b3}$, NR$^{c3}$C(O)OR$^{a3}$, NR$^{c3}$C(O)NR$^{c3}$R$^{d3}$, NR$^{c3}$S(O)R$^{b3}$, NR$^{c3}$S(O)$_2$R$^{b3}$, NR$^{c3}$S(O)$_2$NR$^{c3}$R$^{d3}$, S(O)R$^{b3}$, S(O)NR$^{c3}$R$^{d3}$, S(O)$_2$R$^{b3}$, and S(O)$_2$NR$^{c3}$R$^{d3}$;

each R$^2$, R$^3$, R$^4$, and R$^5$ is independently selected from H, halo, C$_{1-6}$ alkyl, C$_{1-4}$ haloalkyl, C$_{1-4}$ cyanoalkyl, C$_{2-6}$ alkenyl, C$_{2-6}$ alkynyl, CN, NO$_2$, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, C(=NR$^{e4}$)NR$^{c4}$R$^{d4}$, NR$^{c4}$C(=NR$^{e4}$)NR$^{c4}$R$^{d4}$, NR$^{c4}$R$^{d4}$, NR$^{c4}$C(O)R$^{b4}$, NR$^{c4}$C(O)OR$^{a4}$, NR$^{c4}$C(O)NR$^{c4}$R$^{d4}$, NR$^{c4}$S(O)R$^{b4}$, NR$^{c4}$S(O)$_2$R$^{b4}$, NR$^{c4}$S(O)$_2$NR$^{c4}$R$^{d4}$, S(O)R$^{b4}$, S(O)NR$^{c4}$R$^{d4}$, S(O)$_2$R$^{b4}$, and S(O)$_2$NR$^{c4}$R$^{d4}$, wherein said C$_{1-6}$ alkyl, C$_{2-6}$ alkenyl, and C$_{2-6}$ alkynyl are each optionally substituted by 1, 2, 3, or 4 substituents independently selected from halo, CN, NO$_2$, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, C(=NR$^{e4}$)NR$^{c4}$R$^{d4}$, NR$^{c4}$C(=NR$^{e4}$)NR$^{c4}$R$^{d4}$, NR$^{c4}$R$^{d4}$, NR$^{c4}$C(O)R$^{b4}$, NR$^{c4}$C(O)OR$^{a4}$, NR$^{c4}$C(O)NR$^{c4}$R$^{d4}$, NR$^{c4}$S(O)R$^{b4}$, NR$^{c4}$S(O)$_2$R$^{b4}$, NR$^{c4}$S(O)$_2$NR$^{c4}$R$^{d4}$, S(O)R$^{b4}$, S(O)NR$^{c4}$R$^{d4}$, S(O)$_2$R$^{b4}$, and S(O)$_2$NR$^{c4}$R$^{d4}$;

each Cy$^1$ is independently selected from C$_{6-14}$ aryl, C$_{3-18}$ cycloalkyl, 5-16 membered heteroaryl, and 4-18 membered heterocycloalkyl, each of which is optionally substituted with 1, 2, 3, or 4 substituents independently selected from R$^{Cy1}$;

each Cy$^2$ is independently selected from C$_{6-14}$ aryl, C$_{3-18}$ cycloalkyl, 5-16 membered heteroaryl, and 4-18 membered heterocycloalkyl, each of which is optionally substituted with 1, 2, 3, or 4 substituents independently selected from R$^{Cy2}$;

each R$^{Cy1}$ and R$^{Cy2}$ is independently selected from halo, C$_{1-6}$ alkyl, C$_{1-4}$ haloalkyl, C$_{1-4}$ cyanoalkyl, C$_{2-6}$ alkenyl, C$_{2-6}$ alkynyl, phenyl, C$_{3-7}$ cycloalkyl, 5-6 membered heteroaryl, and 4-7 membered heterocycloalkyl, CN, NO$_2$, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, C(=NR$^{e5}$)NR$^{c5}$R$^{d5}$, NR$^{c5}$C(=NR$^{e5}$)NR$^{c5}$R$^{d5}$, NR$^{c5}$R$^{d5}$, NR$^{c5}$C(O)R$^{b5}$, NR$^{c5}$C(O)OR$^{a5}$, NR$^{c5}$C(O)NR$^{c5}$R$^{d5}$, NR$^{c5}$S(O)R$^{b5}$, NR$^{c5}$S(O)$_2$R$^{b5}$, NR$^{c5}$S(O)$_2$NR$^{c5}$R$^{d5}$, S(O)R$^{b5}$, S(O)NR$^{c5}$R$^{d5}$, S(O)$_2$R$^{b5}$, and S(O)$_2$NR$^{c5}$R$^{d5}$, wherein said C$_{1-6}$ alkyl, C$_{2-6}$ alkenyl, C$_{2-6}$ alkynyl, phenyl, C$_{3-7}$ cycloalkyl, 5-6 membered heteroaryl, and 4-7 membered heterocycloalkyl are each optionally substituted by 1, 2, 3, or 4 substituents independently selected from CN, NO$_2$, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, C(=NR$^{e5}$)NR$^{c5}$R$^{d5}$, NR$^{c5}$C(=NR$^{e5}$)NR$^{c5}$R$^{d5}$, NR$^{c5}$R$^{d5}$, NR$^{c5}$C(O)R$^{b5}$, NR$^{c5}$C(O)OR$^{a5}$, NR$^{c5}$C(O)NR$^{c5}$R$^{d5}$, NR$^{c5}$S(O)R$^{b5}$, NR$^{c5}$S(O)$_2$R$^{b5}$, NR$^{c5}$S(O)$_2$NR$^{c5}$R$^{d5}$, S(O)R$^{b5}$, S(O)NR$^{c5}$R$^{d5}$, S(O)$_2$R$^{b5}$, and S(O)$_2$NR$^{c5}$R$^{d5}$;

each R$^{a1}$, R$^{b1}$, R$^{c1}$, R$^{d1}$, R$^{a2}$, R$^{b2}$, R$^{c2}$, R$^{d2}$, R$^{a3}$, R$^{b3}$, R$^{c3}$, R$^{d3}$, R$^{a4}$, R$^{b4}$, R$^{c4}$, R$^{d4}$, R$^{a5}$, R$^{b5}$, R$^{c5}$, and R$^{d5}$ is independently selected from H, C$_{1-6}$ alkyl, C$_{1-4}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl, C$_{3-10}$ cycloalkyl-C$_{1-6}$ alkyl, (5-10 membered heteroaryl)-C$_{1-6}$ alkyl, and (4-10 membered heterocycloalkyl)-C$_{1-6}$ alkyl, wherein said C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl, C$_{3-10}$ cycloalkyl-C$_{1-6}$ alkyl, (5-10 membered heteroaryl)-C$_{1-6}$ alkyl, and (4-10 membered heterocycloalkyl)-C$_{1-6}$ alkyl are each optionally substituted with 1, 2, 3, 4, or 5 substituents independently selected from R$^g$;

each R$^{e1}$, R$^{e2}$, R$^{e3}$, R$^{e4}$, and R$^{e5}$ is independently selected from H, C$_{1-4}$ alkyl, and CN;

each R$^g$ is independently selected from the group consisting of OH, NO$_2$, CN, halo, C$_{1-6}$ alkyl, C$_{2-6}$ alkenyl, C$_{2-6}$ alkynyl, C$_{1-4}$ haloalkyl, C$_{1-6}$ alkoxy, C$_{1-6}$ haloalkoxy, cyano-C$_{1-3}$ alkyl, HO—C$_{1-3}$ alkyl, amino, C$_{1-6}$ alkylamino, di(C$_{1-6}$ alkyl)amino, thiol, C$_{1-6}$ alkylthio, C$_{1-6}$ alkylsulfinyl, C$_{1-6}$ alkylsulfonyl, carboxy, C$_{1-6}$ alkylcarbonyl, and C$_{1-6}$ alkoxycarbonyl, wherein the C$_{1-6}$ alkyl is further substituted by a C$_{1-6}$ alkyl group;

n is 0 or 1;

m is 0 or 1;

p is 0, 1, 2, or 3;

r is 0, 1, or 2;

a is 0 or 1; and b is 0 or 1, wherein any cycloalkyl or heterocycloalkyl group is optionally further substituted by 1 or 2 oxo groups.

In some embodiments, U is N.

In some embodiments, U is CR$^U$.

In some embodiments, X is F.

In some embodiments, X is Cl.

In some embodiments, the moiety

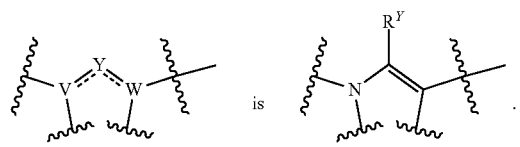

In some embodiments, the moiety

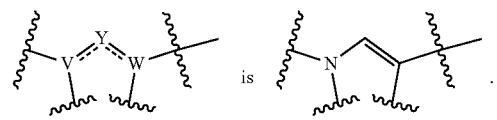

In some embodiments, the moiety

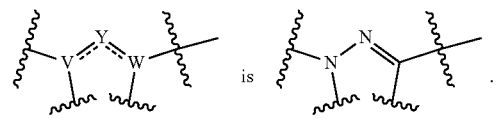

In some embodiments, the moiety

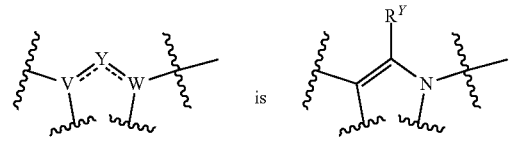

In some embodiments, the moiety

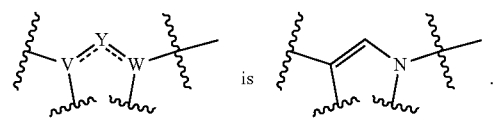

In some embodiments, the moiety

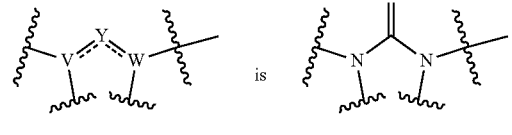

In some embodiments, the moiety

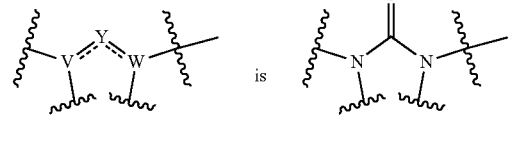

In some embodiments, Ring A is a 5-10 membered heteroaryl group, C$_{3-10}$ cycloalkyl group, or a 4-10 membered heterocycloalkyl group. In some embodiments, Ring A is a C$_{3-6}$ cycloalkyl group or 4-10 membered heterocycloalkyl group. In some embodiments, Ring A is a monocyclic ring group. In some embodiments, Ring A is a polycyclic ring group (e.g., a bicyclic, fused, or spiro ring group).

In some embodiments, Ring A is a group having the formula:

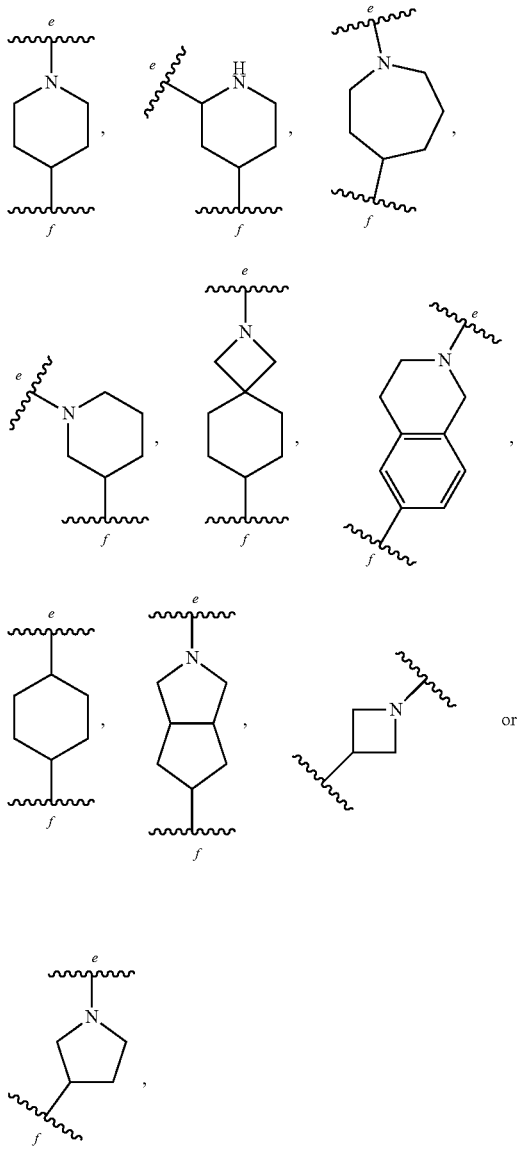

wherein e and f indicate points of attachment to the remainder of the molecule.

In some embodiments, Ring A is a group having the formula:

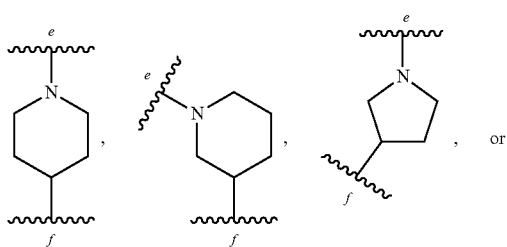

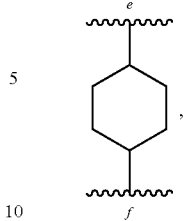

wherein e and f indicate points of attachment to the remainder of the molecule.

In some embodiments, L is selected from —$C_{1-6}$ alkylene- and —($C_{1-4}$ alkylene)$_a$-Q-($C_{1-4}$ alkylene)$_b$-, wherein the $C_{1-6}$ alkylene group and any $C_{1-4}$ alkylene group of the —($C_{1-4}$ alkylene)$_a$-Q-($C_{1-4}$ alkylene)$_b$- group is optionally substituted with 1, 2, or 3 substituents independently selected from halo, CN, OH, $C_{1-3}$ alkyl, $C_{1-3}$ alkoxy, $C_{1-3}$ hydroxyalkyl, $C_{1-3}$ haloalkyl, $C_{1-3}$ haloalkoxy, amino, $C_{1-3}$ alkylamino, and di($C_{1-3}$ alkyl)amino;

In some embodiments, L is —$C_{1-6}$ alkylene- optionally substituted with 1, 2, or 3 substituents independently selected from halo, CN, OH, $C_{1-3}$ alkyl, $C_{1-3}$ alkoxy, $C_{1-3}$ haloalkyl, $C_{1-3}$ haloalkoxy, amino, $C_{1-3}$ alkylamino, and di($C_{1-3}$ alkyl)amino.

In some embodiments, L is —$C_{1-6}$ alkylene-.

In some embodiments, L is selected from methylene, ethylene, and butylene.

In some embodiments, L is —($C_{1-4}$ alkylene)$_a$-Q-($C_{1-4}$ alkylene)$_b$-, wherein any $C_{1-4}$ alkylene group of the —($C_{1-4}$ alkylene)$_a$-Q-($C_{1-4}$ alkylene)$_b$- group is optionally substituted with 1, 2, or 3 substituents independently selected from halo, CN, OH, $C_{1-3}$ alkyl, $C_{1-3}$ alkoxy, $C_{1-3}$ haloalkyl, $C_{1-3}$ haloalkoxy, amino, $C_{1-3}$ alkylamino, and di($C_{1-3}$ alkyl)amino.

In some embodiments, Q is —O—, —S—, —S(=O)—, —S(=O)$_2$—, —C(=O)—, —C(=O)NR$^{q1}$—, —C(=O)O—, —OC(=O)NR$^{q1}$—, —NR$^{q1}$—, —NR$^{q1}$C(=O)O—, —NR$^{q1}$C(=O)NR$^{q1}$—, —S(=O)$_2$NR$^{q1}$—, —C(=NR$^{q2}$)—, or —C(=NR$^{q2}$)—NR$^{q1}$—, wherein each R$^{q1}$ is independently selected from H, and $C_{1-6}$ alkyl, and wherein each R$^{q2}$ is independently selected from H, $C_{1-6}$ alkyl, and CN;

In some embodiments, Q is —O—, —C(=O)—, —C(=O)NR$^{q1}$—, —C(=O)O—, —OC(=O)NR$^{q1}$—, —NR$^{q1}$—, —NR$^{q1}$C(=O)O—, —NR$^{q1}$C(=O)NR$^{q1}$—, or —C(=NR$^{q2}$)—NR$^{q1}$—.

In some embodiments, Q is —O—, —C(=O)—, —NR$^{q1}$, or —NR$^{q1}$C(=O)O—.

In some embodiments, L is selected from —NH$_2$CH$_2$—, —N(CH$_3$)CH$_2$—, —NHC(O)—, —O—, —C(O)—, and —C(O)CH$_2$—.

In some embodiments, Cy is a linking $C_{6-10}$ aryl, linking $C_{3-10}$ cycloalkyl, linking 5-10 membered heteroaryl, or linking 4-10 membered heterocycloalkyl group, each of which is optionally substituted with 1, 2, 3, or 4 substituents independently selected from R$^{Cy}$.

In some embodiments, Cy is a linking $C_{6-10}$ aryl, linking $C_{6-10}$ cycloalkyl, linking 5-10 membered heteroaryl, or linking 4-10 membered heterocycloalkyl group, each of which is optionally substituted with 1 or 2 substituents independently selected from R$^{Cy}$.

In some embodiments, Cy is a linking phenyl, linking $C_{3-10}$ cycloalkyl, linking 5-membered heteroaryl, or linking 4-10 membered heterocycloalkyl group, each of which is optionally substituted with 1, 2, 3, or 4 substituents independently selected from $R^{Cy}$.

In some embodiments, Cy is a linking phenyl, linking $C_{3-10}$ cycloalkyl, linking 5-membered heteroaryl, or linking 4-10 membered heterocycloalkyl group, each of which is optionally substituted with 1 or 2 substituents independently selected from $R^{Cy}$.

In some embodiments, Cy is a linking group having the formula:

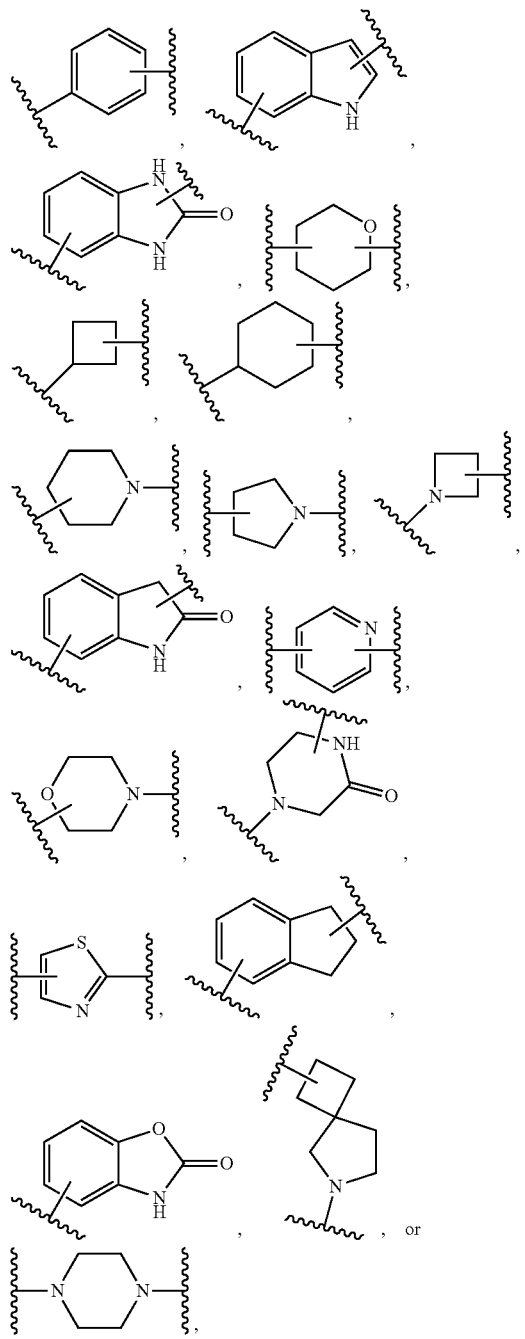

each of which is optionally substituted with 1, 2, 3, or 4 substituents independently selected from $R^{Cy}$.

In some embodiments, Cy is a linking group having the formula:

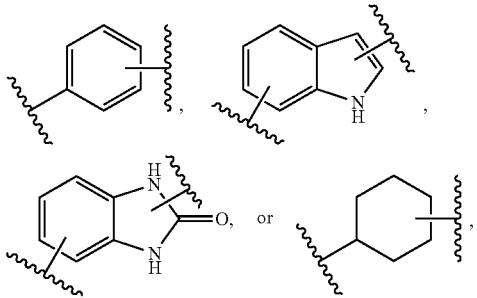

each of which is optionally substituted with 1, 2, 3, or 4 substituents independently selected from $R^{Cy}$.

In some embodiments, each $R^{Cy}$ is independently selected from halo, $C_{1-6}$ alkyl, $C_{1-4}$ haloalkyl, $C_{1-4}$ cyanoalkyl, CN, $OR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$, wherein said $C_{1-6}$ alkyl is optionally substituted by 1, 2, 3, or 4 substituents independently selected from CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$.

In some embodiments, each $R^{Cy}$ is independently selected from halo, $C_{1-6}$ alkyl, $C_{1-4}$ haloalkyl, $C_{1-4}$ cyanoalkyl, CN, $OR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$, wherein said $C_{1-6}$ alkyl is optionally substituted by 1 or 2 substituents independently selected from $OR^{a1}$ and $OC(O)R^{b1}$.

In some embodiments, each $R^{Cy}$ is independently selected from halo, $C_{1-6}$ alkyl, $C_{1-4}$ haloalkyl, $C_{1-4}$ cyanoalkyl, CN, $OR^{a1}$, $C(O)OR^{a1}$, $C(O)NR^{c1}R^{d1}$, $NR^{c1}C(O)R^{b1}$, $NR^{c1}C(O)OR^{a1}$, $NR^{c1}S(O)_2R^{b1}$, and $S(O)_2R^{b1}$, wherein said $C_{1-6}$ alkyl is optionally substituted by 1 or 2 substituents independently selected from $OR^{a1}$ and $OC(O)R^{b1}$.

In some embodiments, Z is $Cy^2$, $C_{1-6}$ alkyl, $OR^{a3}$, $C(O)R^{b3}$, $C(O)NR^{c3}R^{d3}$, or $C(O)OR^{a3}$, wherein $Cy^2$ is optionally substituted with 1 or 2 substituents independently selected from $R^{Cy2}$.

In some embodiments, Z is $Cy^2$, $C_{1-6}$ alkyl, $OR^{a3}$, or $C(O)NR^{c3}R^{d3}$, wherein $Cy^2$ is optionally substituted with 1 or 2 substituents independently selected from $R^{Cy2}$.

In some embodiments, Z is $Cy^2$, $OR^{a3}$, or $C(O)NR^{c3}R^{d3}$, wherein $Cy^2$ is optionally substituted with 1 or 2 substituents independently selected from $R^{Cy2}$.

In some embodiments, Z is $C(O)NR^{c3}R^{d3}$.

In some embodiments, Z is $C(O)NR^{c3}R^{d3}$, and $R^{c3}$ and $R^{d3}$ are independently selected from H and $C_{1-6}$ alkyl, wherein said $C_{1-6}$ alkyl is optionally substituted with 1 or 2 substituents independently selected from $R^g$.

In some embodiments, Z is $C(O)NR^{c3}R^{d3}$, and $R^{c3}$ and $R^{d3}$ are independently selected from H and $C_{1-6}$ alkyl.

In some embodiments, Z is $C(O)NR^{c3}R^{d3}$, and $R^{c3}$ and $R^{d3}$ are both $C_{1-6}$ alkyl.

In some embodiments, Z is C(O)NR$^{c3}$R$^{d3}$, and R$^{c3}$ and R$^{d3}$ are independently selected from methyl and isopropyl.

In some embodiments, R$^3$ is H.

In some embodiments, R$^4$ is H.

In some embodiments, R$^5$ is H.

In some embodiments, n is 0.

In some embodiments, n is 1.

In some embodiments, m is 0.

In some embodiments, m is 1.

In some embodiments, p is 0.

In some embodiments, p is 1.

In some embodiments, r is 0.

In some embodiments, r is 1.

In some embodiments, a is 0.

In some embodiments, a is 1.

In some embodiments, b is 0.

In some embodiments, b is 1.

In some embodiments, the compound of Formula I, or a pharmaceutically acceptable salt thereof, is a compound having Formula IIa, IIb, IIc, IId, IIe, IIIa, IIIb, IIIc, or IIId:

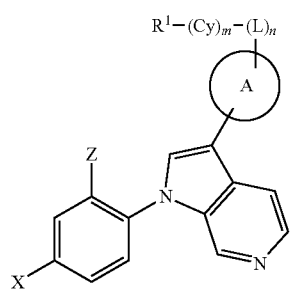

IIa

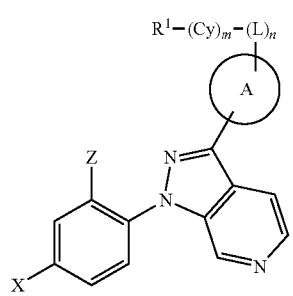

IIb

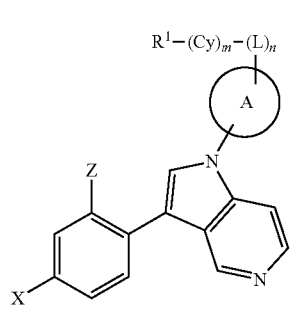

IIc

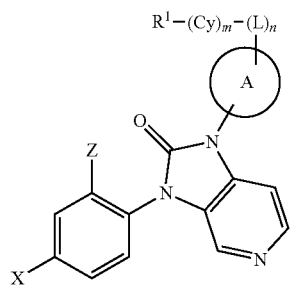

IId

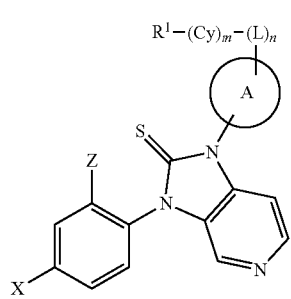

IIe

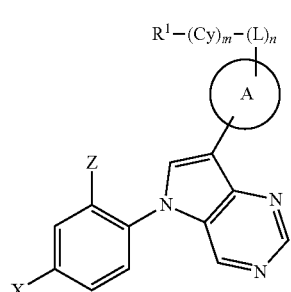

IIIa

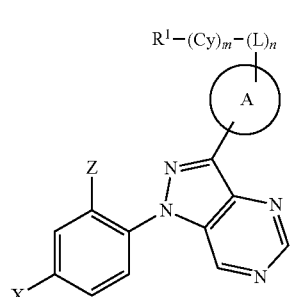

IIIb

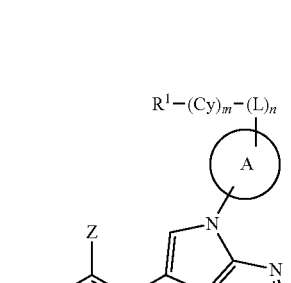

IIIc

IIId 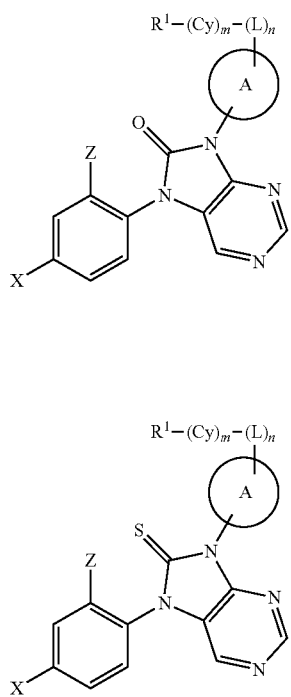
IIIe 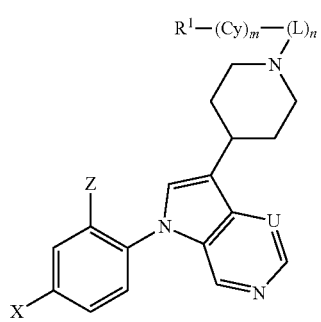
or a pharmaceutically acceptable salt thereof.
In some embodiments, the compound of Formula I, or a pharmaceutically acceptable salt thereof, is a compound having Formula IVa, IVb, IVc, IVd, Va, Vb, or Vc:
IVa 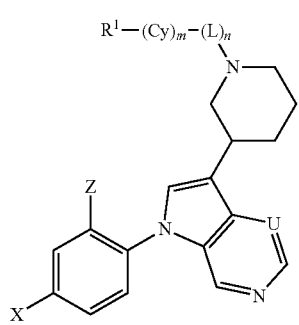
IVb
IVc 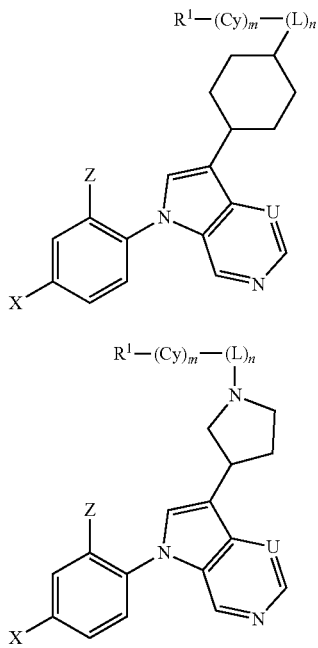
IVd 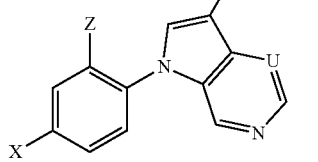
Va 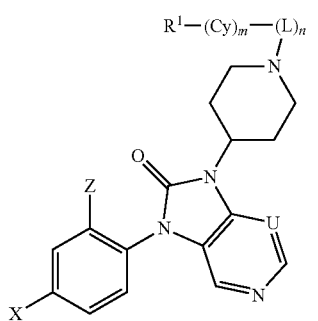
Vb 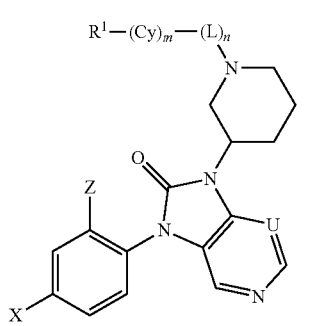
Vc 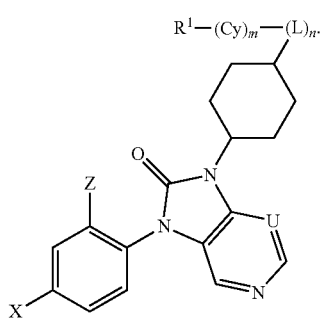
or a pharmaceutically acceptable salt thereof.

In some embodiments, the compound or pharmaceutically acceptable salt of the compound of Formula I provided herein is crystalline. As used herein, "crystalline" or "crystalline form" is meant to refer to a certain lattice configuration of a crystalline substance. Different crystalline forms of the same substance typically have different crystalline lattices (e.g., unit cells) which are attributed to different physical properties that are characteristic of each of the crystalline forms. In some instances, different lattice configurations have different water or solvent content.

Different crystalline forms of the same compound or salt can have different bulk properties relating to, for example, hygroscopicity, solubility, stability, and the like. Forms with high melting points often have good thermodynamic stability which is advantageous in prolonging shelf-life drug formulations containing the solid form. Forms with lower melting points often are less thermodynamically stable, but are advantageous in that they have increased water solubility, translating to increased drug bioavailability. Forms that are weakly hygroscopic are desirable for their stability to heat and humidity and are resistant to degradation during long storage.

The different crystalline forms can be identified by solid state characterization methods such as by X-ray powder diffraction (XRPD). Other characterization methods such as differential scanning calorimetry (DSC), thermogravimetric analysis (TGA), dynamic vapor sorption (DVS), and the like further help identify the form as well as help determine stability and solvent/water content.

An XRPD pattern of reflections (peaks) is typically considered a fingerprint of a particular crystalline form. It is well known that the relative intensities of the XRPD peaks can widely vary depending on, inter alia, the sample preparation technique, crystal size distribution, various filters used, the sample mounting procedure, and the particular instrument employed. In some instances, new peaks may be observed or existing peaks may disappear, depending on the type of the instrument or the settings. As used herein, the term "peak" refers to a reflection having a relative height/intensity of at least about 5% of the maximum peak height/intensity. Moreover, instrument variation and other factors can affect the 2-theta values. Thus, peak assignments, such as those reported herein, can vary by plus or minus about 0.2° (2-theta), and the term "substantially" and "about" as used in the context of XRPD herein is meant to encompass the above-mentioned variations.

The present invention provides crystalline forms of certain compounds of Formula I, or salts thereof. In some embodiments, the present invention is directed to a pharmaceutically acceptable salt of 5-fluoro-N-isopropyl-N-methyl-2-(3-(1-((2-oxo-2,3-dihydro-1H-benzo[d]imidazol-5-yl)methyl)piperidin-3-yl)-1H-pyrrolo[2,3-c]pyridin-1-yl)benzamide.

In some embodiments, the pharmaceutically acceptable salt is 5-fluoro-N-isopropyl-N-methyl-2-(3-(1-((2-oxo-2,3-dihydro-1H-benzo[d]imidazol-5-yl)methyl)piperidin-3-yl)-1H-pyrrolo[2,3-c]pyridin-1-yl)benzamide mono-(2R,3S,4R,5S)-2,3,4,5-tetrahydroxyhexanedioic acid (mucate) salt. In further embodiments, the mucate salt is crystalline.

In some embodiments, the crystalline form of 5-fluoro-N-isopropyl-N-methyl-2-(3-(1-((2-oxo-2,3-dihydro-1H-benzo[d]imidazol-5-yl)methyl)piperidin-3-yl)-1H-pyrrolo[2,3-c]pyridin-1-yl)benzamide mono-(2R,3S,4R,5S)-2,3,4,5-tetrahydroxyhexanedioic acid (mucate) salt is characterized by an XRPD pattern having at least one, at least two, at least three, or at least four peaks, in terms of 2-theta, selected from about 7.2°, about 11.4°, about 12.4°, about 14.5°, about 15.7°, about 16.2°, about 17.6°, about 18.4°, about 18.8°, about 20.9°, about 21.6°, about 21.8°, about 23.9°, about 24.6°, about 24.8°, about 29.9°, about 28.0°, about 35.0°, and about 37.3°.

In some embodiments, the crystalline form of 5-fluoro-N-isopropyl-N-methyl-2-(3-(1-((2-oxo-2,3-dihydro-1H-benzo[d]imidazol-5-yl)methyl)piperidin-3-yl)-1H-pyrrolo[2,3-c]pyridin-1-yl)benzamide mono-(2R,3S,4R,5S)-2,3,4,5-tetrahydroxyhexanedioic acid (mucate) salt is characterized by an XRPD pattern having at least one, at least two, at least three, or at least four peaks, in terms of 2-theta, selected from about 7.2°, about 12.4°, about 17.6°, about 18.4°, about 20.9°, about 21.6°, about 21.8°, about 23.9°, about 24.6°, about 24.8°, and about 29.9°.

In some embodiments, the 5-fluoro-N-isopropyl-N-methyl-2-(3-(1-((2-oxo-2,3-dihydro-1H-benzo[d]imidazol-5-yl)methyl)piperidin-3-yl)-1H-pyrrolo[2,3-c]pyridin-1-yl)benzamide mono-(2R,3S,4R,5S)-2,3,4,5-tetrahydroxyhexanedioic acid (mucate) salt is crystalline and is characterized by an XRPD profile substantially as shown in FIG. 1.

It is appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

As used herein, the phrase "optionally substituted" means unsubstituted or substituted. As used herein, the term "substituted" means that a hydrogen atom is removed and replaced by a substituent. The term "substituted" may also mean that two hydrogen atoms are removed and replaced by a divalent substituent such as an oxo or sulfide group. It is to be understood that substitution at a given atom is limited by valency.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

The term "z-membered" (where z is an integer) typically describes the number of ring-forming atoms in a moiety where the number of ring-forming atoms is z. For example, piperidinyl is an example of a 6-membered heterocycloalkyl ring, pyrazolyl is an example of a 5-membered heteroaryl ring, pyridyl is an example of a 6-membered heteroaryl ring, and 1, 2, 3, 4-tetrahydro-naphthalene is an example of a 10-membered cycloalkyl group.

At various places in the present specification, linking substituents are described. It is specifically intended that each linking substituent include both the forward and backward forms of the linking substituent. For example, —NR(CR'R")$_n$— includes both —NR(CR'R")$_n$— and —(CR'R")$_n$NR—. Where the structure clearly requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

At various places in the present specification various aryl, heteroaryl, cycloalkyl, and heterocycloalkyl rings are described. Unless otherwise specified, these rings can be attached to the rest of the molecule at any ring member as permitted by valency. For example, the term "a pyridine ring" or "pyridinyl" may refer to a pyridin-2-yl, pyridin-3-yl, or pyridin-4-yl ring.

For compounds of the invention in which a variable appears more than once, each variable can be a different moiety independently selected from the group defining the variable. For example, where a structure is described having two R groups that are simultaneously present on the same compound, the two R groups can represent different moieties independently selected from the group defined for R.

As used herein, the term "$C_{i-j}$ alkyl," employed alone or in combination with other terms, refers to a saturated hydrocarbon group that may be straight-chain or branched, having i to j carbons. In some embodiments, the alkyl group contains from 1 to 6 carbon atoms, or from 1 to 4 carbon atoms, or from 1 to 3 carbon atoms. Examples of alkyl moieties include, but are not limited to, chemical groups such as methyl, ethyl, n-propyl, isopropyl, n-butyl, s-butyl, and t-butyl. In some embodiments, where an alkyl group is a linking group, it may be referred to as "$C_{i-j}$ alkylene."

As used herein, the term "$C_{i-j}$ alkoxy," employed alone or in combination with other terms, refers to a group of formula —O-alkyl, wherein the alkyl group has i to j carbons. Example alkoxy groups include methoxy, ethoxy, and propoxy (e.g., n-propoxy and isopropoxy). In some embodiments, the alkyl group has 1 to 3 carbon atoms.

As used herein, "$C_{i-j}$ alkenyl," employed alone or in combination with other terms, refers to an unsaturated hydrocarbon group having one or more double carbon-carbon bonds and having i to j carbons. In some embodiments, the alkenyl moiety contains 2 to 6 or 2 to 4 carbon atoms. Example alkenyl groups include, but are not limited to, ethenyl, n-propenyl, isopropenyl, n-butenyl, sec-butenyl, and the like.

As used herein, "$C_{i-j}$ alkynyl," employed alone or in combination with other terms, refers to an unsaturated hydrocarbon group having one or more triple carbon-carbon bonds and having i to j carbons. Example alkynyl groups include, but are not limited to, ethynyl, propyn-1-yl, propyn-2-yl, and the like. In some embodiments, the alkynyl moiety contains 2 to 6 or 2 to 4 carbon atoms.

As used herein, the term "$C_{i-j}$ alkylamino," employed alone or in combination with other terms, refers to a group of formula —NH(alkyl), wherein the alkyl group has i to j carbon atoms. In some embodiments, the alkyl group has 1 to 6 or 1 to 4 carbon atoms.

As used herein, the term "di-$C_{i-j}$-alkylamino," employed alone or in combination with other terms, refers to a group of formula —N(alkyl)$_2$, wherein each of the two alkyl groups has, independently, i to j carbon atoms. In some embodiments, each alkyl group independently has 1 to 6 or 1 to 4 carbon atoms. In some embodiments, the dialkylamino group is —N($C_{1-4}$ alkyl)$_2$ such as, for example, dimethylamino or diethylamino.

As used herein, the term "$C_{i-j}$ alkylthio," employed alone or in combination with other terms, refers to a group of formula —S-alkyl, wherein the alkyl group has i to j carbon atoms. In some embodiments, the alkyl group has 1 to 6 or 1 to 4 carbon atoms. In some embodiments, the alkylthio group is $C_{1-4}$ alkylthio such as, for example, methylthio or ethylthio.

As used herein, the term "thiol," employed alone or in combination with other terms, refers to —SH.

As used herein, the term "amino," employed alone or in combination with other terms, refers to a group of formula —NH$_2$.

As used herein, "$C_{i-j}$ haloalkoxy," employed alone or in combination with other terms, refers to a group of formula —O-haloalkyl having i to j carbon atoms. An example haloalkoxy group is OCF$_3$. An additional example haloalkoxy group is OCHF$_2$. In some embodiments, the haloalkoxy group is fluorinated only. In some embodiments, the alkyl group has 1 to 6 or 1 to 4 carbon atoms. In some embodiments, the haloalkoxy group is $C_{1-4}$ haloalkoxy.

As used herein, the term "halo," employed alone or in combination with other terms, refers to a halogen atom selected from F, Cl, I or Br. In some embodiments, "halo" refers to a halogen atom selected from F, Cl, or Br. In some embodiments, the halo substituent is F.

As used herein, the term "$C_{i-j}$ haloalkyl," employed alone or in combination with other terms, refers to an alkyl group having from one halogen atom to 2s+1 halogen atoms which may be the same or different, where "s" is the number of carbon atoms in the alkyl group, wherein the alkyl group has i to j carbon atoms. In some embodiments, the haloalkyl group is fluorinated only. In some embodiments, the haloalkyl group is fluoromethyl, difluoromethyl, or trifluoromethyl. In some embodiments, the haloalkyl group is trifluoromethyl. In some embodiments, the haloalkyl group is 2,2,2-trifluoroethyl. In some embodiments, the haloalkyl group is 2,2-difluoroethyl. In some embodiments, the haloalkyl group has 1 to 6 or 1 to 4 carbon atoms.

As used herein, "$C_{i-j}$ cyanoalkyl," employed alone or in combination with other terms, refers to a group of formula CN—($C_{i-j}$ alkyl)-.

As used herein, the term "$C_{i-j}$ hydroxyalkyl," employed alone or in combination with other terms, refers to an alkyl group having from one hydroxy group (i.e., OH group) to 2s+1 hydroxy groups which may be the same or different, where "s" is the number of carbon atoms in the alkyl group, wherein the alkyl group has i to j carbon atoms. In some embodiments, the $C_{i-j}$ hydroxyalkyl group comprises one, two, or three hydroxy groups. In some embodiments, the $C_{i-j}$ hydroxyalkyl group comprises one hydroxy group. In some embodiments, the hydroxyalkyl group has 1 to 6 or 1 to 3 carbon atoms. As used herein, the term "aryl," employed alone or in combination with other terms, refers to a monocyclic or polycyclic (e.g., having 2, 3 or 4 fused rings) aromatic hydrocarbon, such as, but not limited to, phenyl, 1-naphthyl, 2-naphthyl, anthracenyl, phenanthrenyl, and the like. In some embodiments, aryl is $C_{6-10}$ aryl. In some embodiments, aryl is $C_{6-14}$ aryl. In some embodiments, the aryl group is a naphthalene ring or phenyl ring. In some embodiments, the aryl group is phenyl.

As used herein, the term "$C_{i-j}$ cycloalkyl," employed alone or in combination with other terms, refers to a non-aromatic cyclic hydrocarbon moiety having i to j ring-forming carbon atoms, which may optionally contain one or more alkenylene groups as part of the ring structure. Cycloalkyl groups can include mono- or polycyclic ring systems. Polycyclic ring systems can include fused ring systems and spirocycles. Also included in the definition of cycloalkyl are moieties that have one or more aromatic rings fused (i.e., having a bond in common with) to the cycloalkyl ring, for example, benzo or pyrido derivatives of cyclopentane, cyclopentene, cyclohexane, and the like. A heterocycloalkyl group that includes a fused aromatic (e.g., aryl or heteroaryl) moiety can be attached to the molecule through an atom from either the aromatic or non-aromatic portion. One or more ring-forming carbon atoms of a cycloalkyl group can be oxidized to form carbonyl linkages. In some embodiments, cycloalkyl is $C_{3-10}$ cycloalkyl, $C_{3-7}$ cycloalkyl, or $C_{5-6}$ cycloalkyl. Exemplary cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, and the like. Further exemplary cycloalkyl groups include cyclopropyl, cyclobutyl, cyclopentyl, and cyclohexyl. Additional example cycloalkyl groups, where the cycloalkyl group has a fused aryl or heteroaryl moiety, include tetrahydronaphthalen-2-yl, 2,3-dihydro-1H-inden-2-yl; 2,3,4,9-tetrahydro-1H-carbazol-7-yl; 2,6,7,8-tetrahydrobenzo[cd]indazol-4-yl; and 5,6,7,8,9,10-hexahydrocyclohepta[b]indol-3-yl.

As used herein, the term "heteroaryl," employed alone or in combination with other terms, refers to a monocyclic or polycyclic (e.g., having 2, 3 or 4 fused rings) aromatic heterocylic moiety, having one or more heteroatom ring members selected from nitrogen, sulfur and oxygen. In some embodiments, the heteroaryl group has 1, 2, 3, or 4 heteroatom ring members. In some embodiments, the heteroaryl group has 1, 2, or 3 heteroatom ring members. In some embodiments, the heteroaryl group has 1 or 2 heteroatom ring members. In some embodiments, the heteroaryl group has 1 heteroatom ring member. In some embodiments, the heteroaryl group is 5- to 10-membered or 5- to 6-membered. In some embodiments, the heteroaryl group is 5-membered. In some embodiments, the heteroaryl group is 6-membered. In some embodiments, the heteroaryl group is 9- or 10-membered bicyclic. In some embodiments, the heteroaryl is 9-member bicyclic. When the heteroaryl group contains more than one heteroatom ring member, the heteroatoms may be the same or different. The nitrogen atoms in the ring(s) of the heteroaryl group can be oxidized to form N-oxides. Example heteroaryl groups include, but are not limited to, pyridinyl, pyrimidinyl, pyrazinyl, pyridazinyl, pyrrolyl, pyrazolyl, azolyl, oxazolyl, isoxazolyl, thiazolyl, isothiazolyl, imidazolyl, furanyl, thiophenyl, triazolyl, tetrazolyl, thiadiazolyl, quinolinyl, isoquinolinyl, indolyl, benzothiophenyl, benzofuranyl, benzisoxazolyl, benzoimidazolyl, imidazo[1, 2-b]thiazolyl, purinyl, triazinyl, and the like. In some embodiments, the heteroaryl group is 9H-carbazol-2-yl; 1H-benzo[d]imidazol-6-yl; 1H-indol-6-yl; 1H-indazol-6-yl; 2H-indazol-4-yl; 1H-benzo[d][1,2,3]triazol-6-yl; benzo[d]oxazol-2-yl; quinolin-6-yl; or benzo[d]thiazol-2-yl.

As used herein, the term "heterocycloalkyl," employed alone or in combination with other terms, refers to a non-aromatic heterocyclic ring system, which may optionally contain one or more unsaturations as part of the ring structure, and which has at least one heteroatom ring member independently selected from nitrogen, sulfur and oxygen. In some embodiments, the heterocycloalkyl group has 1, 2, 3, or 4 heteroatom ring members. In some embodiments, the heterocycloalkyl group has 1, 2, or 3 heteroatom ring members. In some embodiments, the heterocycloalkyl group has 1 or 2 heteroatom ring members. In some embodiments, the heterocycloalkyl group has 1 heteroatom ring member. When the heterocycloalkyl group contains more than one heteroatom in the ring, the heteroatoms may be the same or different. Example ring-forming members include CH, $CH_2$, C(O), N, NH, O, S, S(O), and $S(O)_2$. Heterocycloalkyl groups can include mono- or polycyclic (e.g., having 2, 3 or 4 fused rings) ring systems. Polycyclic rings can include both fused systems and spirocycles. Also included in the definition of heterocycloalkyl are moieties that have one or more aromatic rings fused (i.e., having a bond in common with) to the non-aromatic ring, for example, 1, 2, 3, 4-tetrahydro-quinoline, dihydrobenzofuran and the like. A heterocycloalkyl group that includes a fused aromatic moiety can be attached to the molecule through an atom from either the aromatic or non-aromatic portion. The carbon atoms or heteroatoms in the ring(s) of the heterocycloalkyl group can be oxidized to form a carbonyl, sulfinyl, or sulfonyl group (or other oxidized linkage) or a nitrogen atom can be quaternized. In some embodiments, heterocycloalkyl is 5- to 10-membered, 4- to 10-membered, 4- to 7-membered, 5-membered, or 6-membered. Examples of heterocycloalkyl groups include 1, 2, 3, 4-tetrahydro-quinolinyl, dihydrobenzofuranyl, azetidinyl, azepanyl, pyrrolidinyl, piperidinyl, piperazinyl, morpholinyl, thiomorpholinyl, and pyranyl. Examples of heterocycloalkyl groups that include one or more fused aromatic groups (e.g., aryl or heteroaryl) include N-(2'-oxospiro[cyclohexane-1,3'-indolin]-6'-yl; 1,2,3,4-tetrahydroisoquinolin-6-yl; 2,3-dihydro-1H-benzo[d]imidazol-5-yl; 1,3-dihydrospiro[indene-2,3'-indolin]-6'-yl; 2,3-dihydrobenzo[d]oxazol-5-yl; 1,2-dihydroquinolin-7-yl; indolin-6-yl; spiro[cyclopentane-1,3'-indolin]-6'-yl; spiro[cyclohexane-1,3'-indolin]-6'-yl; chroman-6-yl; 3,4-dihydro-2H-benzo[b][1,4]oxazin-6-yl; and benzo[d][1,3]dioxol-5-yl.

As used herein, the term "arylalkyl," employed alone or in combination with other terms, refers to an alkyl group substituted by an aryl group.

As used herein, the term "cycloalkylalkyl," employed alone or in combination with other terms, refers to an alkyl group substituted by a cycloalkyl group.

As used herein, the term "heteroarylalkyl," employed alone or in combination with other terms, refers to an alkyl group substituted by a heteroaryl group.

As used herein, the term "hetercycloalkylalkyl," employed alone or in combination with other terms, refers to an alkyl group substituted by a heterocycloalkyl group.

As used herein, the term "$C_{i-j}$ alkylsulfinyl," employed alone or in combination with other terms, refers to a group of formulate —S(=O)—($C_{i-j}$ alkyl).

As used herein, the term "$C_{i-j}$ alkylsulfinyl," employed alone or in combination with other terms, refers to a group of formulate —S(=O)$_2$—($C_{i-j}$ alkyl).

As used herein, the term "carboxy," employed alone or in combination with other terms, refers to a —C(=O)OH group.

As used herein, the term "$C_{i-j}$ alkylcarbonyl," employed alone or in combination with other terms, refers to a group of formula —C(=O)—($C_{i-j}$ alkyl).

As used herein, the term "$C_{i-j}$ alkoxycarbonyl," employed alone or in combination with other terms, refers to a group of formula —C(=O)O—($C_{i-j}$ alkyl).

As used herein, the term "aminocarbonyl," employed alone or in combination with other terms, refers to a group of formula —C(=O)NH$_2$.

The compounds described herein can be asymmetric (e.g., having one or more stereocenters). All stereoisomers, such as enantiomers and diastereoisomers, are intended unless otherwise indicated. Where a compound name or structure is silent with respect to the stereochemistry of a stereocenter, all possible configurations at the stereocenter are intended. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

When the compounds of the invention contain a chiral center, the compounds can be any of the possible stereoisomers. In compounds with a single chiral center, the stereochemistry of the chiral center can be (R) or (S). In compounds with two chiral centers, the stereochemistry of the chiral centers can each be independently (R) or (S) so the configuration of the chiral centers can be (R) and (R), (R) and (S); (S) and (R), or (S) and (S). In compounds with three chiral centers, the stereochemistry each of the three chiral centers can each be independently (R) or (S) so the configuration of the chiral centers can be (R), (R) and (R); (R), (R) and (S); (R), (S) and (R); (R), (S) and (S); (S), (R) and (R); (S), (R) and (S); (S), (S) and (R); or (S), (S) and (S).

Resolution of racemic mixtures of compounds can be carried out by any of numerous methods known in the art. An examplary method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of ca-methylbenzylamine (e.g., S and R forms, or diastereoisomerically pure forms), 2-phenylglycinol, norephedrine, ephedrine, N-methylephedrine, cyclohexylethylamine, 1, 2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

When a disclosed compound is named or depicted without indicating the stereochemistry of one or more stereocenters, each of the stereoisomers resulting from the possible stereochemistries at the undefined stereocenter(s) are intended to be encompassed. For example, if a stereocenter is not designated as R or S, then either or both are intended.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone—enol pairs, amide—imidic acid pairs, lactam—lactim pairs, amide—imidic acid pairs, enamine—imine pairs, and annular forms where a proton can occupy two or more positions of a heterocyclic system, for example, 1H- and 3H-imidazole, 1H-, 2H- and 4H-1, 2, 4-triazole, 1H- and 2H-isoindole, and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers. Isotopes of constituent atoms of the compounds of the invention can be present in natural or non-natural abundance. Examples of isotopes of hydrogen include deuterium and tritium. In some embodiments, the compounds of the invention are deuterated, meaning at least one deuterium atom is present in the place of a hydrogen atom. In some embodiments, 1, 2, 3, 4, 5, 6, 7, or 8 hydrogens in a compound of the invention are replaced by deuterium. Methods for replacing hydrogen with deuterium in a molecule are known in the art.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified (e.g., in the case of purine rings, unless otherwise indicated, when the compound name or structure has the 9H tautomer, it is understood that the 7H tautomer is also encompassed).

All compounds, and pharmaceutically acceptable salts thereof, can be found together with other substances such as water and solvents (e.g., hydrates and solvates) or can be isolated.

In some embodiments, the compounds of the invention, or salts thereof, are substantially isolated. By "substantially isolated" is meant that the compound is at least partially or substantially separated from the environment in which it was formed or detected. Partial separation can include, for example, a composition enriched in a compound of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g., a reaction temperature, that is about the temperature of the room in which the reaction is carried out, for example, a temperature from about 20° C. to about 30° C.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (MeCN) are preferred. Lists of suitable salts are found in *Remington's Pharmaceutical Sciences*, 17th Ed., (Mack Publishing Company, Easton, 1985), p. 1418, Berge et al., *J. Pharm. Sci.*, 1977, 66(1), 1-19, and in Stahl et al., *Handbook of Pharmaceutical Salts: Properties, Selection, and Use*, (Wiley, 2002).

As used herein the terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject or patient is a human in need of treatment.

Synthesis

Compounds of the invention, including salts thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups ("Pg"), can be readily determined by one skilled in the art. The chemistry of protecting groups ("Pg") can be found, for example, in P. G. M. Wuts and T. W. Greene, *Protective Groups in Organic Synthesis*, 4$^{th}$ Ed., Wiley & Sons, Inc., New York (2006), which is incorporated herein by reference in its entirety.

Compounds of the invention can be prepared employing conventional methods that utilize readily available reagents and starting materials. The reagents used in the preparation of the intermediates of this invention can be either commercially obtained or can be prepared by standard procedures described in the literature. Various technologies such as solid phase chemistry, microwave chemistry or flow chemistry etc., can also be utilized to synthesize intermediates or final compounds. Furthermore, other methods of preparing compounds of the invention will be readily apparent to person of ordinary skill in the art in light of the following reaction and schemes and examples. Unless otherwise indicated all the variables are defined below. Suitable method of synthesis are described in the following references: March, *Advanced Organic Chemistry*, 3$^{rd}$ edition, John Wiley & Sons, 1985; Greene and Wuts, *Protective Groups in Organic Chemistry*, 2$^{nd}$ edition, John Wiley & Sons 1991; and Larock, *Comprehensive Organic Transformations*, 4$^{th}$ edition, VCH publishers Inc., 1989. Furthermore, in any one synthesis, one or more of the reagents, intermediates or chemicals may be used in excess amount to ensure the completion of reaction. Suitable reaction temperatures generally range from about 0° C. to about the boiling point of the solvent. More typically, temperatures are sufficiently high to allow refluxing, for example, about 68° C. for tetrahydrofuran. In some cases, such as microwave conditions, the temperature of the reaction may exceed the boiling point of the solvent.

The compounds of the invention can be synthesized by the methods described in Schemes 1-3 below. Many of the synthetic steps are well described in as in F. A. Carey, R. J. Sundberg, *Advanced Organic Chemistry*, 2$^{nd}$ ed., Plenum publication in 1983. The synthesis of various hydroxyl-substituted heterocycles is well documented in the literature and can be synthesized by known literature methods. The general synthesis of useful heterocyclic rings are referenced in *The Handbook of Heterocyclic Chemistry*, Alan R. Katritzky, Pergamon Press, NY, USA, 1$^{st}$ ed., 1986. The depicted intermediates may also be available as commercial reagents from numerous vendors.

The compounds of the invention can be synthesized by numerous methods, based on retro synthetic analysis of final targets. Exemplary methods are shown in Schemes 1-3.

Scheme 1. Synthesis of Intermediate A

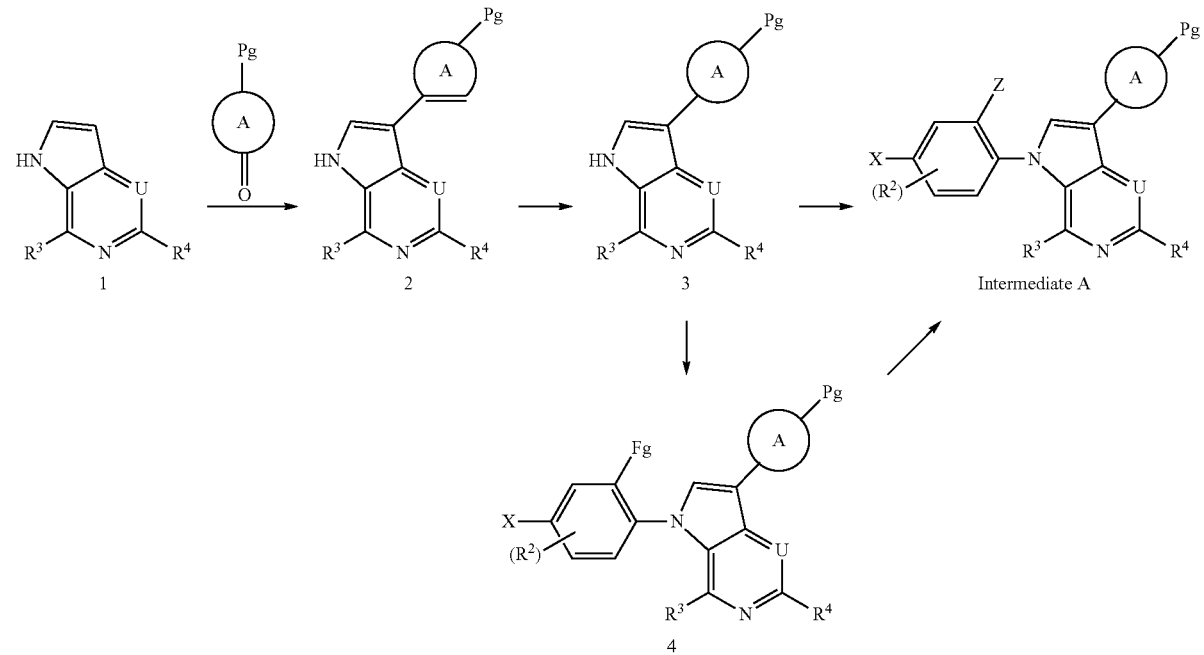

Pg = Protecting group
Fg = Cl, Br, I, NO$_2$, ester group

Commercially available starting heterocycles can be reacted with various ketones containing an α-acidic proton either under basic conditions or under acidic condition to yield Intermediate 2 of Scheme 1. The basic condition can include various organic and inorganic bases and can be carried out in wide variety of protic or aprotic solvents at varying temperatures to refluxing temperatures of the solvent. Similarly, various organic or inorganic acids may be used in protic or aprotic solvents at varying temperatures to refluxing temperatures of the solvent. One method of synthesis involves use of one or more inorganic bases and and one or more protic solvents. An exemplary reaction may be performed using NaOH as base an alcoholic solvent and refluxing conditions as described in Agarwal, Atul et al in JMC, 36(25), 4006-14; 1993. The intermediate described above can be hydrogenated in the presence of a variety of metal catalysts and hydrogen in various solvents. For example, the hydrogenation reaction may performed using hydrogen gas or hydrogen transfer conditions. An exemplary method involves use of palladium catalyst in an alcoholic solvent under a hydrogen atmosphere.

Intermediate 3 of Scheme 1 can be arylated under a variety of conditions. For example, the arylation reaction can be selected from from an SNAr reaction or a metal mediated aromatic coupling. Various methods of N-arylation of nitrogen heterocycles are described in "Copper-Mediated Cross-Coupling Reactions", Gwilherm Evano (ed.), John Wiley & Sons, 1$^{st}$ ed., 2013. An exemplary method involves reaction of suitably substituted halo-aryl compounds with Intermediate 3 of Scheme 1 in the presence of a metal catalyst, in one or more aprotic solvents, and one or more organic or inorganic bases. Exemplary metal catalysyts include, but are not limited to, palladium or copper with appropriate ligands. Exemplary aprotic polar solvents include, but are not limited to, dioxane, dimethyl formamide, and dimethyl acetamide. A further example involves the reaction of appropriately substituted chloro-, bromo- or iodo-aryl compounds with cupreous iodide, in the presence of 1,2-diamine in dimethylformamide along with potassium phosphate or cesium carbonate in 1,4-dioxane. Alternatively, the bromoaryl halide can contain one or more appropriate functional groups that can be modified further after the cross coupling reaction. The functional groups are chosen such that they are compatible for a cross coupling reaction and can be further modified to introduce a desired group. For example, an acid may be chosen as a functional group and then further modified to yield various desired substituents. In some embodiments, an acid is converted to the corresponding amide by standard amide coupling procedure.

Scheme 1A. Synthesis of Intermediate A

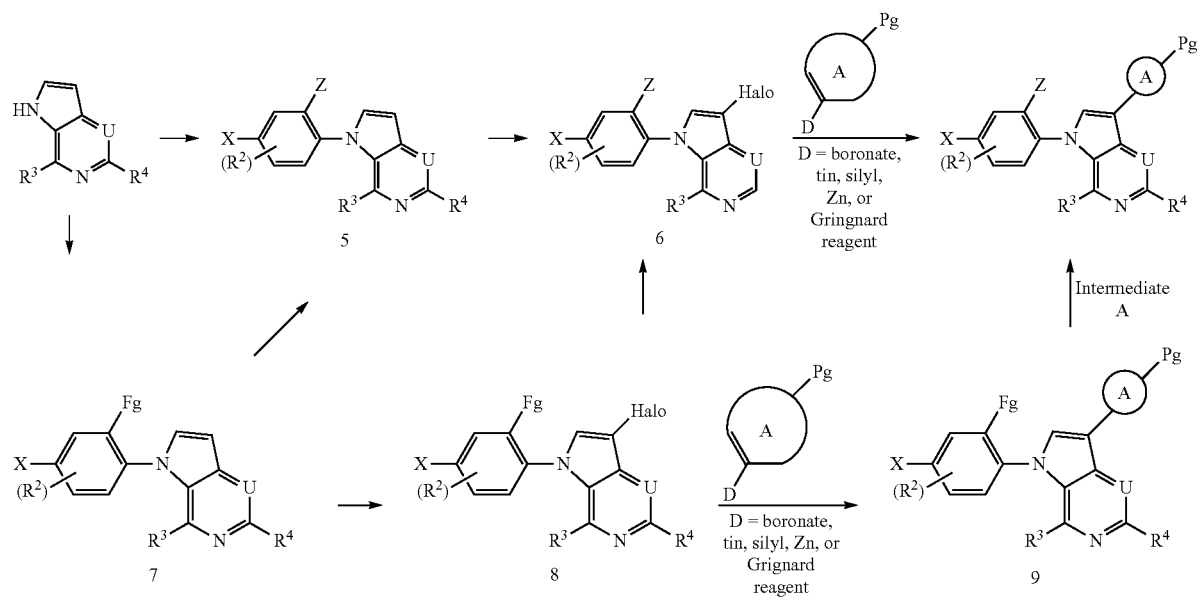

Pg = Protecting group
U = C or N
Fg = Cl, Br, I, NO$_2$, ester group

The first step of Scheme 1A involves N-arylation of a heterocycle. The procedure and methods employed are similar to those described in Scheme 1. The second step involves reaction of Intermediate 5 or 7 of Scheme 2 with an electrophilic halogenating agent to introduce a halo group into the molecule. This can be achieved by various methods as described in "*Heterocyclic Chemistry*", John A. Joule & Keith Mills (eds.). John Wiley & Sons, 1$^{st}$ ed., 2013. An exemplary method involves use of an electrophilic halogenating reagent such as N-halo succinimide in an aprotic solvent (e.g., a halogenated solvent or formamide), or the use of a halogen as an electrophile in the presence of a base and an aprotic solvent. An additional example involves the use of N-bromosuccinimide in an aprotic solvent (e.g., dimethyl formamide) at RT. The cross coupling reactions of aryl halides (i.e., Intermediate 6 or 8 of Scheme 1A) with various reagents such as boranates (Suzuki), tin reagents (Stille), zinc reagents (Negishi), or magnesium reagents (Grignard) are well known in literature. Alternatively, the halide can be converted into a metallated reagent for coupling with various electrophiles, as is well known in the art. These transformations are described in, for example, "Cross- Coupling Reactions: A Practical Guide" by Norio Miyaura, 1st ed., 2003, Springer. An exemplary method involves reaction of an aryl boronate or vinyl boronate with Intermediate 6 or 8 of Scheme 2 under palladium catalyzed reaction conditions in the presence of an inorganic base and a solvent (e.g., protic or aprotic) at elevated temperatures.

In some embodiments, the Intermediate A of Schemes 1-1A is a compound of Formula I provided herein, or a pharmaceutically acceptable salt thereof.

Various synthetic methods for the synthesis of Intermediate A2 are reported in literature (see, for example, Pryde et al., 2013, Bioorg Med. Chem. Lett., 23(3):827-833). This involves nucleophilic displacement with amine starting with appropriately substituted 4-halo-3-nitropyridine or 4-halo-5-nitropyrimidine (where X is halo). The reduction of nitro groups by hydrogenation or other methods are well known in literature and to those of ordinary skill in the art. The Scheme 2A. Synthesis of Intermediate A1

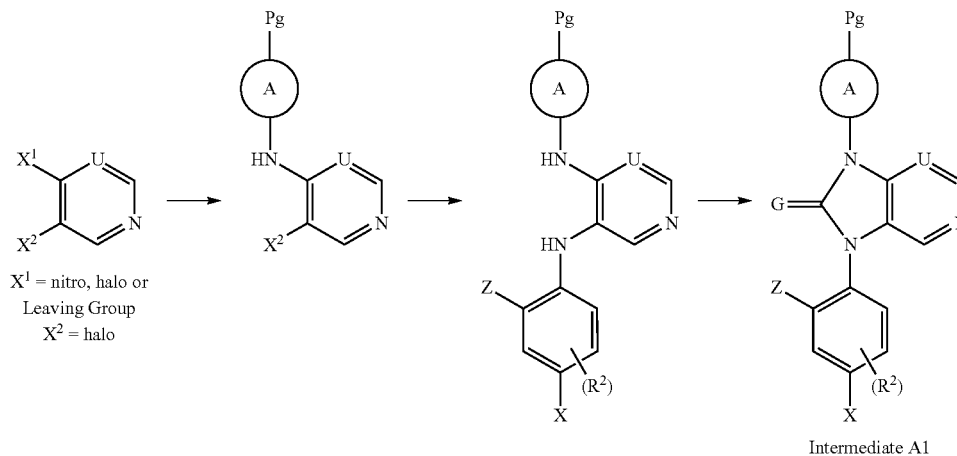

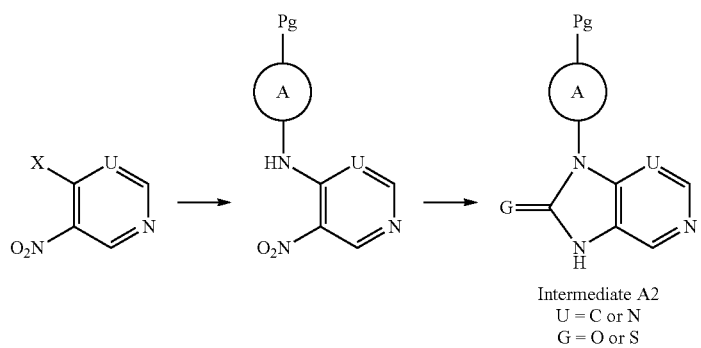

Intermediate A1 containing 1,3-dihydro-2H-imidazo or 7,9-dihydro-8H-purin-8-one can be synthesized from appropriate di-halo pyridine or pyrimidine or any other suitable starting material, as described in Burgey et al., 2006, Bioorg Med. Chem. Lett., 16(19):5052-5056. The halo can be sequentially aminated by appropriate choice of amines at the 3- and 4-position. The displacement of halo at the 4-position can be achieved by nucleophilic displacements. The displacement of halo at 3-position of pyridine or 5-position of pyrimidine can be achieved through cross coupling reactions using, for example, various palladium or copper catalyzed reactions as described in "Synthesis and Modification of Heterocycles by Metal-Catalyzed Cross-coupling Reactions", Patonay & Kónya (eds.), 1st ed., 2016, Springer.

diamine can be further condensed in the presence of triphosgene or carbonyl diimidazole etc at elevated temperature in aprotic solvents.

An exemplary method involves use of 4-chloropyridine or 4-chloropyrimidine with displacement by amines in the presence of inorganic base, (e.g. cesium carbonate) in DMF. The reduction of nitro may be achieved through metal/acid mediated reduction. For example, one exemplary method uses zinc and HCl at elevated temperatures. An exemplary method for cyclization is performed by condensation of a diamine with 1,1-carbonyldiimidazole at elevated temperature in the presence of one or more aprotic solvent (e.g. acetonitrile). Thio analogs may be condensed, for example, with 1,1-thiocarbonyldiimidazole to yield Intermediate A2.

Scheme 2B. Synthesis of Intermediate A3

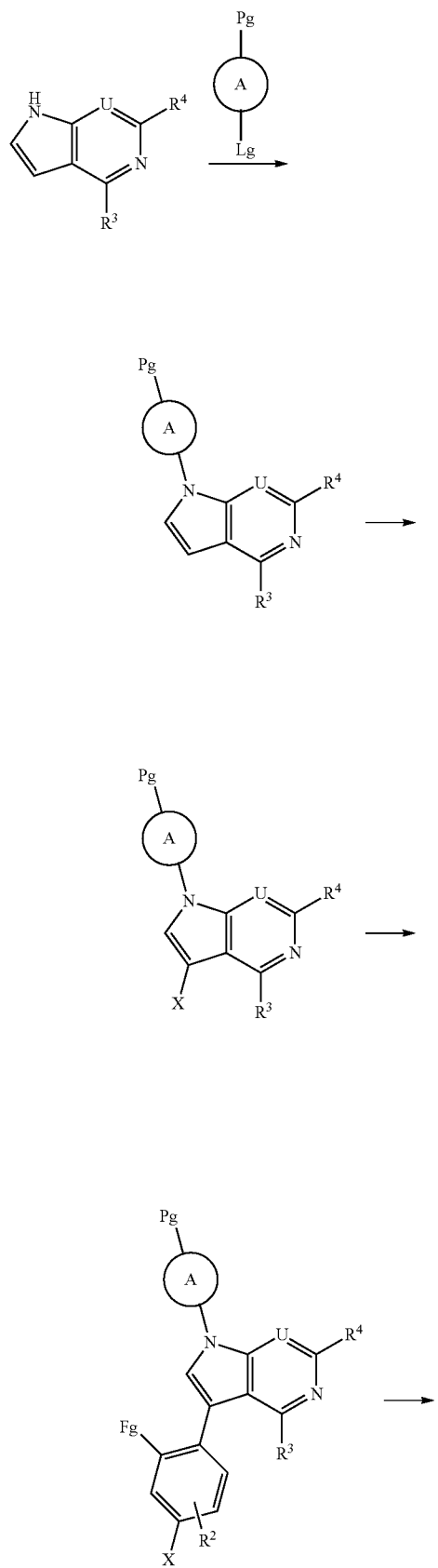

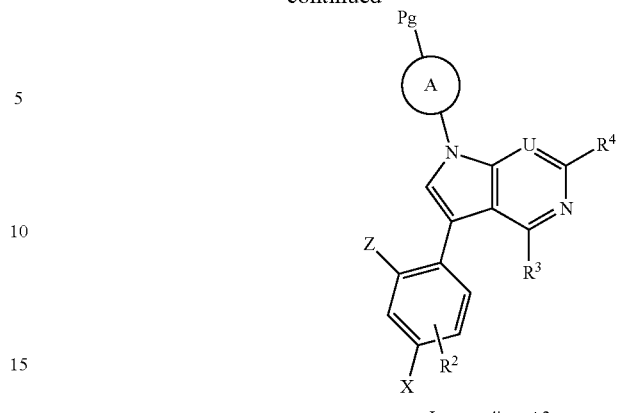

Intermediate A3

Lg = leaving group
Pg = protecting group
Fg = Cl, Br, I, NO$_2$, ester group

Appropriately substituted pyridine/pyrimidine can be condensed with various aliphatic alcohols, for example, via Mitsunobu reaction or by converting alcohols into suitable nucleophilic displacement, each of which are well known in literature and to those of ordinary skill in the art. An exemplary method involves reaction of a heterocycle with an aliphatic alcohol using Mitsunobu conditions in an aprotic solvent. In some embodiments, the aliphatic alcohol is converted into a suitable leaving group (e.g. triflate), and then reacted with a heterocycle in the presence of an inorganic base (e.g. cesium carbonate), in one or more aprotic solvents (e.g., DMF or acetonitrile) at elevated temperature. A further exemplary method involves reaction of an aliphatic alcohol with a heterocycle in the presence of triphenylphosphine and diethyl azo dicarboxylate in one or more aprotic solvents (e.g., THF) at RT or elevated temperature. The product so obtained can be halogenated using various methods, for example, as shown in Step 2 of Scheme 2B. A further exemplary method involves use of N-bromo succinimide in an aprotic solvent, which can be performed at various temperatures. The bromo product so obtained can be reacted with an appropriate aryl boronate under standard metal catalyzed reaction conditions (e.g., Suzuki reaction). One embodiment involves use of an aryl boronate with a palladium catalyst (e.g., Pd(dppf)$_2$Cl$_2$), in the presence of a base (e.g., cesium carbonate), and a combination of aprotic solvent and water at elevated temperature. The product so obtained can serve as Intermediate A or can be further elaborated by modification of functional groups as described herein. For example, such functional group modification can include conversion of acid to amide or replacement of bromo by various alkyl and amide groups, and the like. In some embodiments, the functional group is an acid or ester that is subsequently converted into an amide.

Scheme 2C. Synthesis of Intermediate A4

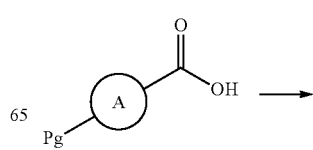

-continued

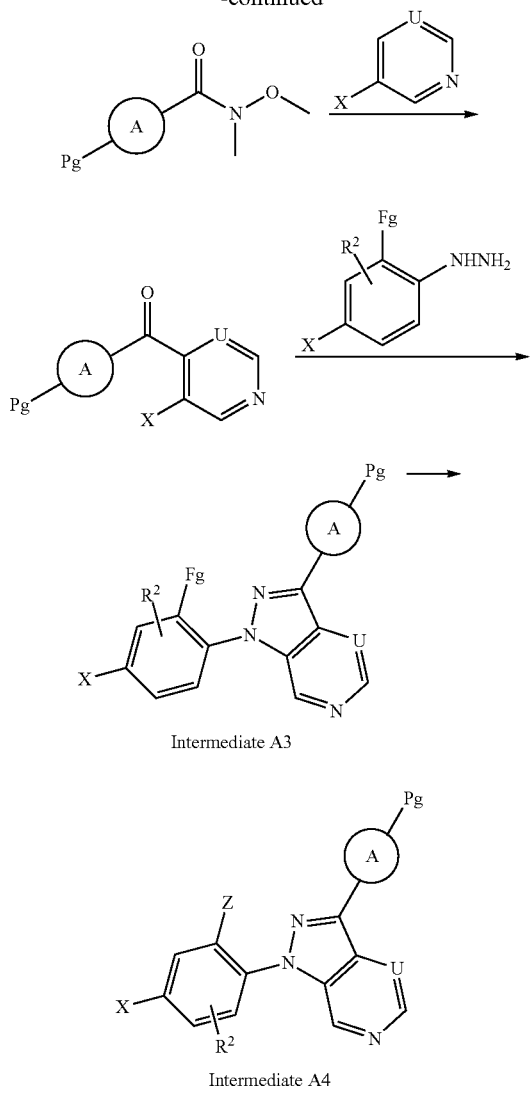

Intermediate A3

Intermediate A4

Pg = Protecting Group
Fg = Cl, Br, I, NO₂, ester group
X = halo
U = C or N

Intermediates A3-A4 containing a pyrazole moiety can be synthesized, for example, by numerous methods well known to the art. An exemplary synthesis involves the use of an aliphatic acid. For example, the aliphatic acid is converted into an aldehyde or Weinreb amide, by procedures well known to the art, and which are then reacted with appropriately substituted 3-halo pyridine or 5-halo pyrimidines (where X is halo, Scheme 2C) by ortho lithiation (see e.g., *Tetrahedron*, vol. 39, 1983, 2009-2021). The aryl ketone so obtained is then condensed with appropriately substituted phenylhydrazine to yield the desired Intermediate A3. Further modification by functional group elaboration of the phenyl hydrazine can yield Intermediate A4.

A further exemplary method involves conversion of an aliphatic acid into a Wienreb amide by reaction of an appropriately substituted acid with N-methyl-O-methyl hydroxylamine under coupling conditions (e.g., reaction with HATU) in presence of an organic base in one or more aprotic solvent. The chloro pyrimidine or pyridine can then be lithiated (e.g., with lithium diisopropylamide at low temperature) in an aprotic solvent (e.g., THF or diethyl ether) and then reacted with the Weinreb amide to yield the desired aryl ketone. The aryl ketone is then condensed with an appropriately substituted phenylhydrazine to yield indazole Intermediate A3. This reaction may be performed, for example, at elevated temperature in the presence of inorganic base (e.g., potassium carbonate) in one or more aprotic solvents (e.g. DMF) or a protic solvent (e.g., an alcoholic solvent such as ethanol and the like). In some embodiments, the phenyl hydrazine is appropriately substituted 2-hydrazinylbenzoic acid, which can be further modified to incorporate various functional groups as described herein. A further embodiment involves conversion of acid into amide.

Scheme 3. Synthesis of Compounds of Formula I

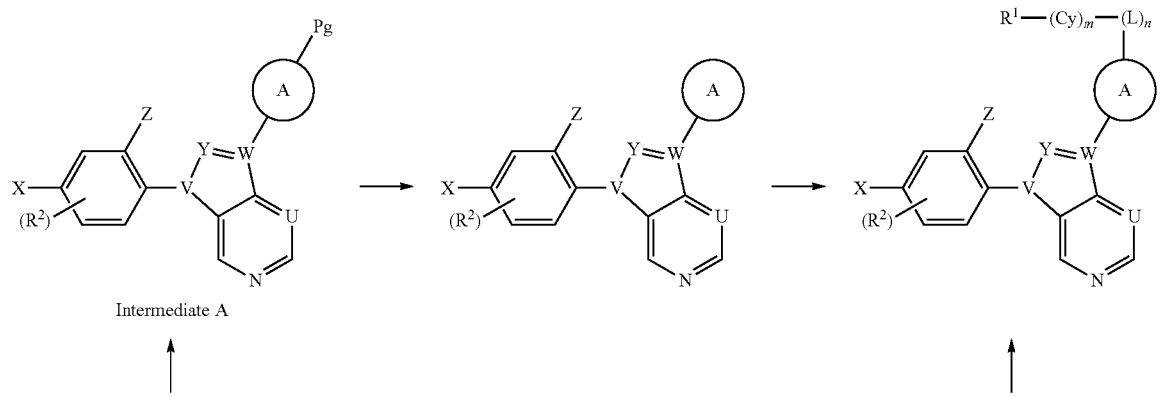

Intermediate A

-continued

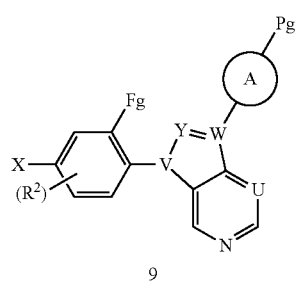
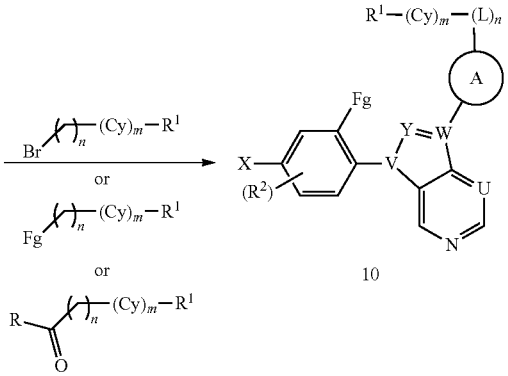

Pg = Protecting Group
Fg = Cl, Br, I, $NO_2$, ester group
X = halo
U = C or N

The final compound (e.g., a compound of Formula I, or a pharmaceutically acceptable salt thereof) can be synthesized from Intermediate A by further modifying Ring A as shown in Scheme 3, wherein the protecting group (Pg) is connected to a nitrogen atom of Ring A or a nitrogen atom of a functional group attached to Ring A, which may be prepared as described herein. The removal of protecting groups (Pg) is well known in the literature and protecting groups for amines, alcohols, ketones, etc are well documented in Greene and Wuts, *Protective Groups in Organic Chemistry*, $2^{nd}$ edition, John Wiley & Sons 1991. The functional group may be, for example, an acid, alcohol, amine, ketone, and the like. Exemplary functional groups include, but are not limited to, amines, alcohols, and ketones that were appropriately protected during the synthesis of Intermediate A. An exemplary protecting group for an amine is tert-butoxycarbonyl. An exemplary protecting group for a ketone is a ketal. For amines, once the protecting group is removed, the free amine (i.e., the unprotected amine group) may be reacted with an acylation agent (e.g., acyl chloride, sulfonyl chloride, isocyanates, and the like) or can be arylated using, for example, an aryl halide, boronate, or diazonium salt using procedures well known in the art. The free amine can also be reacted with aldehydes and ketones under reductive amination conditions. An exemplary method involves the reaction of an aldehyde and amine in a protic or aprotic solvent under reductive amination conditions (e.g., reaction with sodium cyanoborohydride, at either RT or elevated temperature). r Scheme 3A. Synthesis of Compounds of Formula I

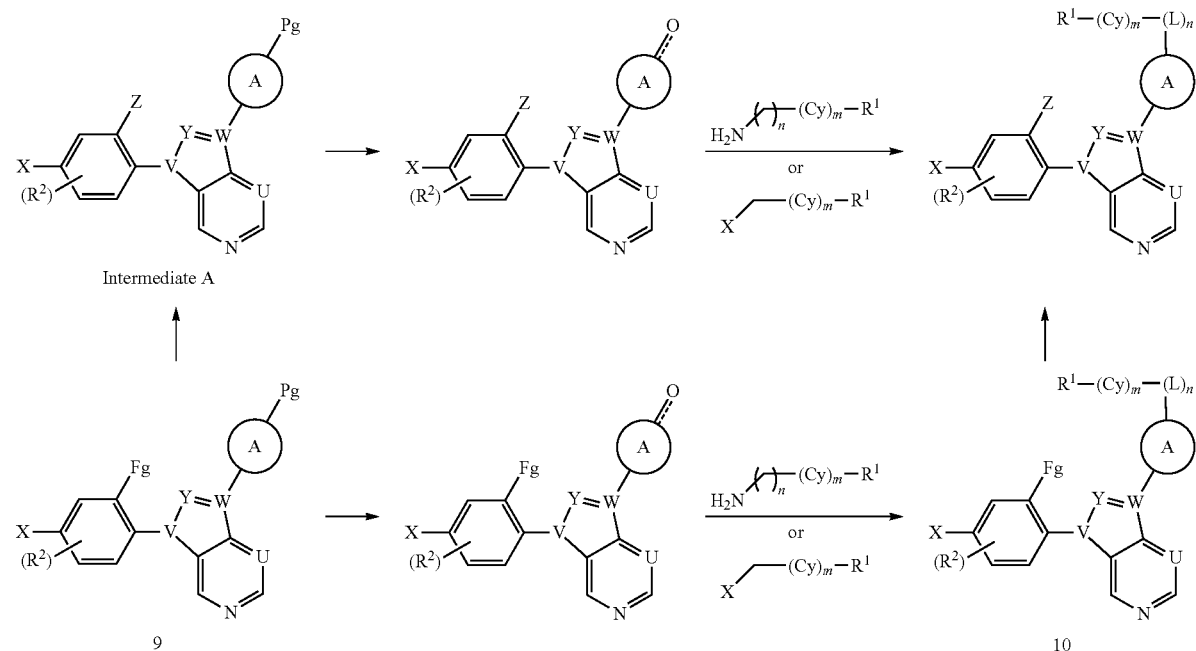

Pg = Protecting Group
Fg = Cl, Br, I, $NO_2$, ester group
X = halo
U = C or N

In some embodiments, the protecting group is a carbon protecting group (Scheme 3A). For example, in some embodiments Pg is a ketone protecting group, (e.g., a ketal, an alcohol, or an acid, and the like). As described herein, these functional groups can be further transformed to various other functional groups and additional modifications of the scaffold can be carried out by various synthetic transformations. These reactions are described herein and well known in the literature and are extensively described, for example, in March, *Advanced Organic Chemistry*, 3$^{rd}$ edition, John Wiley & Sons.

An exemplary reaction where Pg is a ketone protecting group involves reductive amination with an amine in the presence of a reducing agent in a solvent (e.g., protic or aprotic) and can be performed in a variety of conditions ranging from low temperatures to refluxing of the solvent. An additional examplary method involves reaction of an amine with a ketone in the presence of an alcoholic solvent and a reducing agent (e.g., sodium cyanoborohydride). The product so obtained from this reductive amination can be further elaborated to yield the final compound of Formula I, or a pharmaceutically acceptable salt thereof, as described herein.

In some embodiments, one or more of the intermediates shown in Scheme 3 may be the final desired product (e.g., a compound of Formula I, or a pharmaceutically acceptable salt thereof) and may not require any additional modifications.

Methods of Use

The compounds of the invention are inhibitors of the interaction of menin with MLL and MLL fusion proteins. In some embodiments, the present invention is directed to a method of inhibiting the interaction between menin and MLL or an MLL fusion protein by contacting menin and MLL or the MLL fusion protein with a compound of the invention. The contacting can be carried out in vitro or in vivo. In some embodiments, the compounds of the invention can bind to menin, thereby interfering with the binding of MLL to menin. In some embodiments, the present invention provides a method of inhibiting the activity of menin by contacting menin with a compound of the invention in the presence of MLL or an MLL fusion protein. In further embodiments, the present invention provides a method of inhibiting the binding of MLL or an MLL fusion protein to menin, comprising contacting menin with a compound of the invention in the presence of the MLL or MLL fusion protein.

The compounds of the invention are also useful in treating diseases associated with the menin-MLL interaction or menin-MLL fusion protein interaction. For example, diseases and conditions treatable according to the methods of the invention include cancer, such as leukemia, and other diseases or disorders mediated by the menin-MLL interaction or menin-MLL fusion protein interaction such as diabetes.

Accordingly, the compounds of the invention are believed to be effective against a broad range of cancers, including, but not limited to, hematological cancer (e.g., leukemia and lymphoma), bladder cancer, brain cancer (e.g., glioma, diffuse intrinsic pontine glioma (DIPG)), breast cancer (e.g., triple-negative breast cancer, estrogen-receptor-positive breast cancer (i.e., ER+ breast cancer)), colorectal cancer, cervical cancer, gastrointestinal cancer (e.g., colorectal carcinoma, gastric cancer), genitourinary cancer, head and neck cancer, liver cancer, lung cancer, melanoma, ovarian cancer, pancreatic cancer, prostate cancer (e.g., castration resistant prostate cancer), renal cancer (e.g., renal cell carcinoma), skin cancer, thyroid cancer (e.g., papillary thyroid carcinoma), testicular cancer, sarcoma (e.g., Ewing's sarcoma), and AIDS-related cancers. In some embodiments, the cancer is associated with a rearranged MLL gene. In some embodiments, the pathophysiology of the cancer is dependent on the MLL gene. In some embodiments, the cancer is associated with mutant p53 gain-of-function.

In some embodiments, the specific cancers that may be treated by the compounds, compositions and methods described herein include cardiac cancers, such as for example, sarcoma (e.g., angiosarcoma, fibrosarcoma, rhabdomyosarcoma, and liposarcoma), myxoma, rhabdomyoma, fibroma, lipoma and teratoma; lung cancers, including, for example, bronchogenic carcinoma (e.g., squamous cell, undifferentiated small cell, undifferentiated large cell, and adenocarcinoma), alveolar and bronchiolar carcinoma, bronchial adenoma, sarcoma, lymphoma, chondromatous hamartoma, mesothelioma, non-small cell lung cancer, small cell lung cancer, bronchial adenomas/carcinoids, and pleuropulmonary blastoma; gastrointestinal cancer, including, for example, cancers of the esophagus (e.g., squamous cell carcinoma, adenocarcinoma, leiomyosarcoma, and lymphoma), cancers of the stomach (e.g., carcinoma, lymphoma, and leiomyosarcoma), cancers of the pancreas (e.g., ductal adenocarcinoma, insulinoma, glucagonoma, gastrinoma, carcinoid tumors, and vipoma), cancers of the small bowel (e.g., adenocarcinoma, lymphoma, carcinoid tumors, Kaposi's sarcoma, leiomyoma, hemangioma, lipoma, neurofibroma, and fibroma), cancers of the large bowel or colon, (e.g., adenocarcinoma, tubular adenoma, villous adenoma, hamartoma, and leiomyoma), and other cancers of the digestive tract (e.g., anal cancer, anorectal cancer, appendix cancer, cancer of the anal canal, cancer of the tongue, gallbladder cancer, gastrointestinal stromal tumor (GIST), colon cancer, colorectal cancer, extrahepatic bile duct cancer, intrahepatic bile duct cancer, rectal cancer, and small intestine cancer); genitourinary tract cancers, including, for example, cancers of the kidney (e.g., adenocarcinoma, Wilm's tumor (nephroblastoma), lymphoma, and leukemia), cancers of the bladder and urethra (e.g., squamous cell carcinoma, transitional cell carcinoma, and adenocarcinoma), cancers of the prostate (e.g., adenocarcinoma and sarcoma), cancers of the testis, (e.g., seminoma, teratoma, embryonal carcinoma, teratocarcinoma, choriocarcinoma, sarcoma, interstitial cell carcinoma, fibroma, fibroadenoma, adenomatoid tumors, and lipoma), as well as transitional cell cancer, transitional cell cancer of the renal pelvis and ureter and other urinary organs, urethral cancer, and urinary bladder cancer; liver cancers, including, for example, hepatoma (e.g., hepatocellular carcinoma), cholangiocarcinoma, hepatoblastoma, angiosarcoma, hepatocellular adenoma, and hemangioma; bone cancers, including, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors; nervous system cancers, including, for example, cancers of the skull (e.g., osteoma, hemangioma, granuloma, xanthoma, and osteitis deformans); cancers of the meninges (e.g., meningioma, meningiosarcoma, and gliomatosis); cancers of the brain (e.g., astrocytoma, medulloblastoma, glioma, ependymoma, germinoma (pinealoma), glioblastoma multiforme, oligodendroglioma, schwannoma, retinoblastoma, and congenital tumors); cancers of the spinal cord (e.g., neurofibroma, meningioma, glioma, and sarcoma), and other nervous system cancers (e.g., brain stem glioma, diffuse intrinsic pontine glioma (DIPG), brain tumor, central nervous system cancer, cerebellar astrocytoma, cerebral astrocytoma/malignant glioma, childhood cerebellar astrocytoma, childhood cerebral astrocytoma, primary central nervous system lymphoma, visual pathway and hypothalamic glioma, nervous system lymphoma, supratentorial primitive neuroectodeimal tumors, pineoblastoma and supratentorial primitive neuroectodermal tumors); gynecological cancers, including, for example, cancers of the uterus (e.g., endometrial carcinoma), cancers of the cervix (e.g., cervical carcinoma, and pre tumor cervical dysplasia), cancers of the ovaries (e.g., ovarian carcinoma, including serous cystadenocarcinoma, mucinous cystadenocarcinoma, unclassified carcinoma, granulosa thecal cell tumors, Sertoli Leydig cell tumors, dysgerminoma, and malignant teratoma), cancers of the vulva (e.g., squamous cell carcinoma, intraepithelial carcinoma, adenocarcinoma, fibrosarcoma, and melanoma), cancers of the vagina (e.g., clear cell carcinoma, squamous cell carcinoma, botryoid sarcoma, and embryonal rhabdomyosarcoma), and cancers of the fallopian tubes (e.g., carcinoma); other reproductive tract cancers, including, for example, endometrial cancer, endometrial uterine cancer, germ cell tumor, gestational trophoblastic tumor, gestational trophoblastic tumor glioma, ovarian epithelial cancer, ovarian germ cell tumor, ovarian low malignant potential tumor, penile cancer, vaginal cancer, vulvar cancer, extracranial germ cell tumor, extragonadal germ cell tumor, uterine cancer, uterine corpus cancer, uterine sarcoma; lymphatic and hematologic cancers, including, for example, cancers of the blood (e.g., acute myeloid leukemia (AML), chronic myeloid leukemia (CML), acute lymphoblastic leukemia (ALL), chronic lymphoblastic leukemia, chronic lymphocytic leukemia, myeloproliferative diseases, multiple myeloma, and myelodysplastic syndrome, Hodgkin's lymphoma, non Hodgkin's lymphoma (malignant lymphoma) and Waldenstrom's macroglobulinemia), and other lymphatic or hematologic cancers including, for example, childhood leukemia, myeloproliferative disorders (e.g., primary myelofibrosis), plasma cell neoplasm/multiple myeloma, myelodysplasia, myelodysplastic syndrome, cutaneous T-cell lymphoma, lymphoid neoplasm, AIDS-related lymphoma, thymoma, thymoma and thymic carcinoma, mycosis fungoides, and Sézary Syndrome; skin cancers, including, for example, malignant melanoma, basal cell carcinoma, squamous cell carcinoma, Kaposi's sarcoma, moles dysplastic nevi, lipoma, angioma, dermatofibroma, keloids, psoriasis, merkel cell carcinoma, merkel cell skin carcinoma, melanoma, and carcinoid tumor; adrenal gland cancers, including, for example, neuroblastoma; other cancers associated with the endocrine system including, for example, adrenocortical carcinoma, multiple endocrine neoplasia (e.g., multiple endocrine neoplasia type I), multiple endocrine neoplasia syndrome, parathyroid cancer, pituitary tumor, pheochromocytoma, islet cell pancreatic cancer, and islet cell tumors); connective tissue cancer (e.g., bone cancer, bone and joint cancer, osteosarcoma and malignant fibrous histiocytoma); cancer associated with the head, neck, and mouth (e.g., head and neck cancer, paranasal sinus and nasal cavity cancer, metastatic squamous neck cancer, mouth cancer, throat cancer, esophageal cancer, laryngeal cancer, pharyngeal cancer, hypopharyngeal cancer, lip and oral cavity cancer, nasopharyngeal cancer, oral cancer, oropharyngeal cancer, and salivary gland cancer); and cancer associated with the eye (e.g., ocular cancer, intraocular melanoma). In some embodiments, the cancer is Ewing's sarcoma.

In some embodiments, the cancer is a hematological cancer such as leukemia or lymphoma. Example leukemia and lymphomas treatable by the compounds of the invention include mixed lineage leukemia (MLL), MLL-related leukemia, MLL-associated leukemia, MLL-positive leukemia, MLL-induced leukemia, rearranged mixed lineage leukemia (MLL-r), leukemia associated with a MLL rearrangement or a rearrangement of the MLL gene, acute leukemia, chronic leukemia, indolent leukemia, lymphoblastic leukemia, lymphocytic leukemia, myeloid leukemia, myelogenous leukemia, childhood leukemia, acute lymphocytic leukemia (ALL) (also referred to as acute lymphoblastic leukemia or acute lymphoid leukemia), acute myeloid leukemia (AML) (also referred to as acute myelogenous leukemia or acute myeloblastic leukemia), acute granulocytic leukemia, acute nonlymphocytic leukemia, chronic lymphocytic leukemia (CLL) (also referred to as chronic lymphoblastic leukemia), chronic myelogenous leukemia (CML) (also referred to as chronic myeloid leukemia), therapy related leukemia, myelodysplastic syndrome (MDS), myeloproliferative disease (MPD) (such as primary myelofibrosis (PMF)), myeloproliferative neoplasia (MPN), plasma cell neoplasm, multiple myeloma, myelodysplasia, cutaneous T-cell lymphoma, lymphoid neoplasm, AIDS-related lymphoma, thymoma, thymic carcinoma, mycosis fungoides, Alibert-Bazin syndrome, granuloma fungoides, Sézary Syndrome, hairy cell leukemia, T-cell prolymphocytic leukemia (T-PLL), large granular lymphocytic leukemia, meningeal leukemia, leukemic leptomeningitis, leukemic meningitis, multiple myeloma, Hodgkin's lymphoma, non Hodgkin's lymphoma (malignant lymphoma), and Waldenstrom's macroglobulinemia. In some embodiments, the acute myeloid leukemia (AML) is abstract nucleophosmin (NPM1)-mutated acute myeloid leukemia (i.e., NPM1$^{mut}$ acute myloid leukemia).

In particular embodiments, compounds of the invention are used to treat leukemia associated with a MLL rearrangement, acute lymphocytic leukemia associated with a MLL rearrangement, acute lymphoblastic leukemia associated with a MLL rearrangement, acute lymphoid leukemia associated with a MLL rearrangement, acute myeloid leukemia associated with a MLL rearrangement, acute myelogenous leukemia associated with a MLL rearrangement, or acute myeloblastic leukemia associated with a MLL rearrangement. As used herein, "MLL rearrangement" means a rearrangement of the MLL gene.

In some embodiments, diseases and conditions treatable with compounds of the invention include insulin resistance, pre-diabetes, diabetes (e.g., Type 2 diabetes or Type 1 diabetes), and risk of diabetes. In some embodiments, diseases and conditions treatable with compounds of the invention include hyperglycemia. In some embodiments, the hyperglycemia is associated with diabetes, such as Type 2 diabetes. In some embodiments, compounds of the invention are used to treat loss of response to other anti-diabetic agents and/or reduced beta cell function in a patient or subject. In some embodiments, compounds of the invention are used to restore response to other anti-diabetic agents and/or to restore beta cell function and/or to reduce the need for insulin in a patient or subject. In some embodiments, compounds of the invention are used to reduce insulin resistance, reduce the risk of diabetes, or reduce increases in blood glucose caused by a statin in a subject taking a statin. In some embodiments, compounds of the invention are used to treat diabetes in a subject taking a statin or to prevent diabetes in a subject taking a statin. Methods of the invention include decreasing, reducing, inhibiting, suppressing, limiting or controlling in the patient elevated blood glucose levels. In further aspects, methods of the invention include increasing, stimulating, enhancing, promoting, inducing or activating in the subject insulin sensitivity. Statins include, but are not limited to atorvastatin, cerivastatin, fluvastatin, lovastatin, mevastatin, pitavastatin, pravastatin, rousuvastatin and simvastatin.

In some embodiments, a patient is treated with (e.g., administered) a compound of the present invention in an amount sufficient to treat or ameliorate one or more of the diseases and conditions recited above (e.g., a therapauetically effective amount). The compounds of the invention may also be useful in the prevention of one or more of the diseases recited therein.

Combination Therapy

The invention further relates to a combination therapy for treating a disease or a disorder described herein. In some embodiments, the combination therapy comprises administering at least one compound of the present invention in combination with one or more other pharmaceutically active agents for treating cancer or other disorders mediated by menin/MLL. In some embodiments, the combination therapy comprises administering at least one compound of the present invention in combination with one or more other pharmaceutically active agents, such as for the treatment of cancer. The pharmaceutically active agents can be combined with a compound of the invention in a single dosage form, or the therapeutics can be administered simultaneously or sequentially as separate dosage forms.

The compounds according to the invention may also be used in combination with immunotherapies, including but not limited to cell-based therapies, antibody therapies and cytokine therapies, for the treatment of a disease or disorder disclosed herein.

In certain embodiments, compounds according to the invention are used in combination with one or more passive immunotherapies, including but not limited to naked monoclonal antibody drugs and conjugated monoclonal antibody drugs. Examples of naked monoclonal antibody drugs that can be used include, but are not limited to rituximab (Rituxan®), an antibody against the CD20 antigen; trastuzumab (Herceptin®), an antibody against the HER2 protein; alemtuzumab (Lemtrada, Campath®), an antibody against the CD52 antigen; cetuximab (Erbitux®), an antibody against the EGFR protein; and bevacizumab (Avastin®) which is an anti-angiogenesis inhibitor of VEGF protein.

Examples of conjugated monoclonal antibodies that can be used include, but are not limited to, radiolabeled antibody ibritumomab tiuxetan (Zevalin®); radiolabeled antibody tositumomab (Bexxar®); and immunotoxin gemtuzumab ozogamicin (Mylotarg®) which contains calicheamicin; BL22, an anti-CD22 monoclonal antibody-immunotoxin conjugate; radiolabeled antibodies such as OncoScint® and ProstaScint®; brentuximab vedotin (Adcetris®); ado-trastuzumab emtansine (Kadcyla®, also called TDM-1).

Further examples of therapeutic antibodies that can be used include, but are not limited to, REOPRO® (abciximab), an antibody against the glycoprotein IIb/IIIa receptor on platelets; ZENAPAX® (daclizumab) an immunosuppressive, humanized anti-CD25 monoclonal antibody; PANOREX™, a murine anti-17-IA cell surface antigen IgG2a antibody; BEC2, a murine anti-idiotype (GD3 epitope) IgG antibody; IMC-C225, a chimeric anti-EGFR IgG antibody; VITAXIN™ a humanized anti-αVβ3 integrin antibody; Campath 1H/LDP-03, a humanized anti CD52 IgG1 antibody; Smart M195, a humanized anti-CD33 IgG antibody; LYMPHOCIDE™, a humanized anti-CD22 IgG antibody; LYMPHOCIDE™ Y-90; Lymphoscan; Nuvion® (against CD3; CM3, a humanized anti-ICAM3 antibody; IDEC-114 a primatized anti-CD80 antibody; IDEC-131 a humanized anti-CD40L antibody; IDEC-151 a primatized anti-CD4 antibody; IDEC-152 a primatized anti-CD23 antibody; SMART anti-CD3, a humanized anti-CD3 IgG; 5G1.1, a humanized anti-complement factor 5 (C5) antibody; D2E7, a humanized anti-TNF-α antibody; CDP870, a humanized anti-TNF-α Fab fragment; IDEC-151, a primatized anti-CD4 IgG1 antibody; MDX-CD4, a human anti-CD4 IgG antibody; CD20-streptdavidin (+biotin-yttrium 90); CDP571, a humanized anti-TNF-α IgG4 antibody; LDP-02, a humanized anti-α4β7 antibody; OrthoClone OKT4A, a humanized anti-CD4 IgG antibody; ANTOVA™, a humanized anti-CD40L IgG antibody; ANTEGREN™, a humanized anti-VLA-4 IgG antibody; and CAT-152, a human anti-TGF-β₂ antibody.

In certain embodiments, compounds according to the invention are used in combination with one or more targeted immunotherapies containing toxins but not an antibody, including but not limited to denileukin diftitox (Ontak®), IL-2 linked to diphtheria toxin.

The compounds according to the invention may also be used in combination with adjuvant immunotherapies for the treatment of a disease or disorder disclosed herein. Such adjuvant immunotherapies include, but are not limited to, cytokines, such as granulocyte-macrophage colony-stimulating factor (GM-CSF), granulocyte-colony stimulating factor (G-CSF), macrophage inflammatory protein (MIP)-1-alpha, interleukins (including IL-1, IL-2, IL-4, IL-6, IL-7, IL-12, IL-15, IL-18, IL-21, and IL-27), tumor necrosis factors (including TNF-alpha), and interferons (including IFN-alpha, IFN-beta, and IFN-gamma); aluminum hydroxide (alum); Bacille Calmette-Guérin (BCG); Keyhole limpet hemocyanin (KLH); Incomplete Freund's adjuvant (IFA); QS-21; DETOX; Levamisole; and Dinitrophenyl (DNP), and combinations thereof, such as, for example, combinations of interleukins, for example IL-2, with other cytokines, such as IFN-alpha.

In certain embodiments, compounds according to the invention are used in combination with vaccine therapy, including but not limited to autologous and allogeneic tumor cell vaccines, antigen vaccines (including polyvalent antigen vaccines), dendritic cell vaccines, and viral vaccines.

In another embodiment, the present disclosure comprises administering to a subject with cancer an effective amount of a compound of the invention and one or more additional anti-cancer therapies selected from: surgery, anti-cancer agents/drugs, biological therapy, radiation therapy, anti-angiogenesis therapy, immunotherapy, adoptive transfer of effector cells, gene therapy or hormonal therapy. Examples of anti-cancer agents/drugs are described below.

In some embodiments, the anti-cancer agents/drug is, for example, adriamycin, aactinomycin, bleomycin, vinblastine, cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin;

cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride; palbociclib; Yervoy® (ipilimumab); Mekinist™ (trametinib); peginterferon alfa-2b, recombinant interferon alfa-2b; Sylatron™ (peginterferon alfa-2b); Tafinlar® (dabrafenib); Zelboraf® (vemurafenib); or nivolumab.

The compounds according to the present invention can be administered in combination with existing methods of treating cancers, for example by chemotherapy, irradiation, or surgery. Thus, there is further provided a method of treating cancer comprising administering an effective amount of a compound of the invention, or a pharmaceutically acceptable salt form thereof, to a subject in need of such treatment, wherein an effective amount of at least one additional cancer chemotherapeutic agent is administered to the subject. Examples of suitable cancer chemotherapeutic agents include any of: abarelix, ado-trastuzumab emtansine, aldesleukin, alemtuzumab, alitretinoin, allopurinol, altretamine, anastrozole, arsenic trioxide, asparaginase, azacitidine, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, emtansine, epirubicin, eribulin, erlotinib, estramustine, etoposide phosphate, etoposide, everolimus, exemestane, fentanyl citrate, filgrastim, floxuridine, fludarabine, fluorouracil, fruquintinib, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, ixabepilone, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, paclitaxel albumin-stabilized nanoparticle formulation, pamidronate, panitumumab, pegaspargase, pegfilgrastim, pemetrexed disodium, pentostatin, pertuzuma, pipobroman, plicamycin, procarbazine, quinacrine, rasburicase, rituximab, sorafenib, streptozocin, sulfatinib, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, volitinib, vorinostat, and zoledronate.

In particular embodiments, compounds according to the invention are used in combination with one or more anti-cancer agent selected from methotrexate, paclitaxel albumin-stabilized nanoparticle formulation, ado-trastuzumab emtansine, eribulin, doxorubicin, fluorouracil, everolimus, anastrozole, pamidronate disodium, exemestane, capecitabine, cyclophosphamide, docetaxel, epirubicin, toremifene, fulvestrant, letrozole, gemcitabine, gemcitabine hydrochloride, goserelin acetate, trastuzumab, ixabepilone, lapatinib ditosylate, megestrol acetate, tamoxifen citrate, pamidronate disodium, palbociclib, and pertuzumab for the treatment of breast cancer.

Other anti-cancer agents/drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; andrographolide; angiogenesis inhibitors; antagonist D; antagonist G; antarelix; anti-dorsalizing morphogenetic protein-1; antiandrogen; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors; castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclin-dependent kinase inhibitors; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitors; microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; zanoterone; zilascorb; zinostatin stimalamer; 5-fluorouracil; and leucovorin.

In some embodiments, the anti-cancer agent/drug is an agent that stabilizes microtubules. As used herein, a "microtubulin stabilizer" means an anti-cancer agent/drug which acts by arresting cells in the G2-M phases due to stabilization of microtubules. Examples of microtubulin stabilizers include ACLITAXEL® and Taxol® analogues. Additional examples of microtubulin stabilizers include without limitation the following marketed drugs and drugs in development: Discodermolide (also known as NVP-XX-A-296); Epothilones (such as Epothilone A, Epothilone B, Epothilone C (also known as desoxyepothilone A or dEpoA); Epothilone D (also referred to as KOS-862, dEpoB, and desoxyepothilone B); Epothilone E; Epothilone F; Epothilone B N-oxide; Epothilone A N-oxide; 16-aza-epothilone B; 21-aminoepothilone B (also known as BMS-310705); 21-hydroxyepothilone D (also known as Desoxyepothilone F and dEpoF), 26-fluoroepothilone); FR-182877 (Fujisawa, also known as WS-9885B), BSF-223651 (BASF, also known as ILX-651 and LU-223651); AC-7739 (Ajinomoto, also known as AVE-8063A and CS-39.HCl); AC-7700 (Ajinomoto, also known as AVE-8062, AVE-8062A, CS-39-L-Ser.HCl, and RPR-258062A); Fijianolide B; Laulimalide; Caribaeoside; Caribaeolin; Taccalonolide; Eleutherobin; Sarcodictyin; Laulimalide; Dictyostatin-1; Jatrophane esters; and analogs and derivatives thereof.

In another embodiment, the anti-cancer agent/drug is an agent that inhibits microtubules. As used herein, a "microtubulin inhibitor" means an anti-cancer agent which acts by inhibiting tubulin polymerization or microtubule assembly. Examples of microtubulin inhibitors include without limitation the following marketed drugs and drugs in development: Erbulozole (also known as R-55104); Dolastatin 10 (also known as DLS-10 and NSC-376128); Mivobulin isethionate (also known as CI-980); Vincristine; NSC-639829; ABT-751 (Abbott, also known as E-7010); Altorhyrtins (such as Altorhyrtin A and Altorhyrtin C); Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9); Cemadotin hydrochloride (also known as LU-103793 and NSC-D-669356); Auristatin PE (also known as NSC-654663); Soblidotin (also known as TZT-1027), LS-4559-P (Pharmacia, also known as LS-4577); LS-4578 (Pharmacia, also known as LS-477-P); LS-4477 (Pharmacia), LS-4559 (Pharmacia); RPR-112378 (Aventis); Vincristine sulfate; DZ-3358 (Daiichi); GS-164 (Takeda); GS-198 (Takeda); KAR-2 (Hungarian Academy of Sciences); SAH-49960 (Lilly/Novartis); SDZ-268970 (Lilly/Novartis); AM-97 (Armad/Kyowa Hakko); AM-132 (Armad); AM-138 (Armad/Kyowa Hakko); IDN-5005 (Indena); Cryptophycin 52 (also known as LY-355703); Vitilevuamide; Tubulysin A; Canadensol; Centaureidin (also known as NSC-106969); T-138067 (Tularik, also known as T-67, TL-138067 and TI-138067); COBRA-1 (Parker Hughes Institute, also known as DDE-261 and WHI-261); H10 (Kansas State University); H16 (Kansas State University); Oncocidin A1 (also known as BTO-956 and DIME); DDE-313 (Parker Hughes Institute); SPA-2 (Parker Hughes Institute); SPA-1 (Parker Hughes Institute, also known as SPIKET-P); 3-IAABU (Cytoskeleton/Mt. Sinai School of Medicine, also known as MF-569); Narcosine (also known as NSC-5366); Nascapine, D-24851 (Asta Medica), A-105972 (Abbott); Hemiasterlin; 3-BAABU (Cytoskeleton/Mt. Sinai School of Medicine, also known as MF-191); TMPN (Arizona State University); Vanadocene acetylacetonate; T-138026 (Tularik); Monsatrol; Inanocine (also known as NSC-698666); 3-IAABE (Cytoskeleton/Mt. Sinai School of Medicine); A-204197 (Abbott); T-607 (Tularik, also known as T-900607); RPR-115781 (Aventis); Eleutherobins (such as Desmethyleleutherobin, Desaetyleleutherobin, Isoeleutherobin A, and Z-Eleutherobin); Halichondrin B; D-64131 (Asta Medica); D-68144 (Asta Medica); Diazonamide A; A-293620 (Abbott); NPI-2350 (Nereus); TUB-245 (Aventis); A-259754 (Abbott); Diozostatin; (-)-Phenylahistin (also known as NSCL-96F037); D-68838 (Asta Medica); D-68836 (Asta Medica); Myoseverin B; D-43411 (Zentaris, also known as D-81862); A-289099 (Abbott); A-318315 (Abbott); HTI-286 (also known as SPA-110, trifluoroacetate salt) (Wyeth); D-82317 (Zentaris); D-82318 (Zentaris); SC-12983 (NCI); Resverastatin phosphate sodium; BPR-0Y-007 (National Health Research Institutes); SSR-250411 (Sanofi); Combretastatin A4; eribulin (Halaven®); and analogs and derivatives thereof.

In further embodiments, compounds according to the invention are used in combination with one or more alkylating agents, antimetabolites, natural products, or hormones.

Examples of alkylating agents useful in the methods of the invention include but are not limited to, nitrogen mustards (e.g., mechloroethamine, cyclophosphamide, chlorambucil, melphalan, etc.), ethylenimine and methylmelamines (e.g., hexamethylmelamine, thiotepa, alkyl sulfonates (e.g., busulfan), nitrosoureas (e.g., carmustine, lomusitne, semustine, streptozocin, etc.), or triazenes (decarbazine, etc.).

Examples of antimetabolites useful in the methods of the invention include but are not limited to folic acid analog (e.g., methotrexate), or pyrimidine analogs (e.g., fluorouracil, floxouridine, cytarabine), and purine analogs (e.g., mercaptopurine, thioguanine, pentostatin). Examples of natural products useful in the methods of the invention include but are not limited to vinca alkaloids (e.g., vinblastin, vincristine), epipodophyllotoxins (e.g., etoposide, teniposide), antibiotics (e.g., actinomycin D, daunorubicin, doxorubicin, bleomycin, plicamycin, mitomycin) or enzymes (e.g., L-asparaginase).

Examples of hormones and antagonists useful for the treatment of cancer include but are not limited to adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), and gonadotropin releasing hormone analog (e.g., leuprolide).

Other agents that can be used in combination with the compounds of the invention for the treatment of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), and adrenocortical suppressant (e.g., mitotane, aminoglutethimide). Other anti-cancer agents/drugs that can be used in combination with the compounds of the invention include, but are not limited to, liver X receptor (LXR) modulators, including LXR agonists and LXR beta-selective agonists; aryl hydrocarbon receptor (AhR) inhibitors; inhibitors of the enzyme poly ADP ribose polymerase (PARP), including olaparib, iniparib, rucaparib, veliparib; inhibitors of vascular endothelial growth factor (VEGF) receptor tyrosine kinases, including cediranib; programmed cell death protein 1 (PD-1) inhibitors, including nivolumab (Bristol-Myers Squibb Co.) and pembrolizumab (Merck & Co., Inc.; MK-3475); MEK inhibitors, including cobimetinib; B-Raf enzyme inhibitors, including vemurafenib; cytotoxic T lymphocyte antigen (CTLA-4) inhibitors, including tremelimumab; programmed death-ligand 1 (PD-L1) inhibitors, including MEDI4736 (AstraZeneca); inhibitors of the Wnt pathway; inhibitors of epidermal growth factor receptor (EGFR) including AZD9291 (AstraZeneca), erlotinib, gefitinib, panitumumab, and cetuximab; adenosine A2A receptor inhibitors; adenosine A2B receptor inhibitors; colony-stimulating factor-1 receptor (CSF1R) inhibitors, including PLX3397 (Plexxikon), and inhibitors of CD73.

The compounds of the invention can be used in combination with one or more therapeutic strategies including immune checkpoint inhibitors, including inhibitors of PD-1, PD-L1, and CTLA-4.

The compounds of the invention can be used in combination with one or more anti-cancer agents selected from MCL-1 inhibitors, e.g., homoharringtonin (HHT) and omacetaxine; BCL-2 inhibitors, e.g., venetoclax (ABT-199), navitoclax (ABT-263), ABT-737, gossypol (AT-101), apogossypolone (ApoG2) and obatoclax; selective inhibitors of nuclear export (SINEs), e.g., selinexor (KPT-330).

In particular embodiments, the compounds of the invention are used in combination with one or more anti-cancer agents selected from methotrexate (Abitrexate®; Folex®; Folex PFS®; Mexate®; Mexate-AQ®); nelarabine (Arranon®); blinatumomab (Blincyto®); rubidomycin hydrochloride or daunorubicin hydrochloride (Cerubidine®); cyclophosphamide (Clafen®; Cytoxan®; Neosar®); clofarabine (Clofarex®; Clolar®); cytarabine (Cytosar-U®; Tarabine PFS®); dasatinib (Sprycel®); doxorubicin hydrochloride; asparaginase *Erwinia chrysanthemi* (Erwinaze); imatinib mesylate (Gleevec®); ponatinib hydrochloride (Iclusig®); mercaptopurine (Purinethol; Purixan); pegaspargase (Oncaspar®); prednisone; vincristine sulfate (Oncovin®, Vincasar PFS®, Vincrex®); vincristine sulfate liposome (Marqibo®); hyper-CVAD (fractionated cyclophosphamide, vincristine, adriamycin, and dexamethasone); arsenic trioxide (Trisenox®); idarubicin hydrochloride (Idamycin®); mitoxantrone hydrochloride; thioguanine (Tabloid®); ADE (cytarabine, daunorubicin, and etoposide); alemtuzumab (Lemtrada®, Campath®); chlorambucil (Ambochlorin®, Amboclorin®, Leukeran®, Linfolizin®); ofatumumab (Arzerra®); bendamustine hydrochloride (Treanda®); fludarabine phosphate (Fludara®); obinutuzumab (Gazyva®); ibrutinib (Imbruvica®); idelalisib (Zydelig®); mechlorethamine hydrochloride (Mustargen®); rituximab (Rituxan®); chlorambucil-prednisone; CVP (cyclophosphamide, vincristine, and prednisone); bosutinib (Bosulif®); busulfan (Busulfex®; Myleran®); omacetaxine mepesuccinate (Synribo®); nilotinib (Tasigna®); Intron® A (recombinant interferon Alfa-2b); DOT1L inhibitors, including EPZ-5676 (Epizyme, Inc.); and inhibitors of bromodomain and extra-terminal motif (BET) proteins (BET inhibitors), including MS417, JQ1, I-BET 762, and I-BET 151 for the treatment of leukemia.

Compounds of the invention can be used in combination with one or more other agents or therapies for the treatment of insulin resistance, pre-diabetes, diabetes (e.g., Type 2 diabetes or Type 1 diabetes), and risk of diabetes, including but not limited to insulins and insulin analogues, such as Humulin® (Eli Lilly), Lantus® (Sanofi Aventis), Novolin® (Novo Nordisk), and Exubera® (Pfizer); Avandamet® (metformin HCl and rosiglitazone maleate, GSK); Avandaryl® (glimepiride and rosiglitazone maleate, GSK); Metaglip® (glipizide and metformin HCl, Bristol Myers Squibb); Glucovance® (glyburide and metformin HCl, Bristol Myers Squibb); PPAR gamma agonists, such as Avandia® (rosiglitizone maleate, GSK) and Actos® (pioglitazone hydrochloride, Takeda/Eli Lilly); sulfonylureas, such as Amaryl® (glimepiride, Sanofi Aventis), Diabeta® (glyburide, Sanofi Aventis), Micronase®/Glynase® (glyburide, Pfizer), and Glucotrol®/Glucotrol XL® (glipizide, Pfizer); meglitinides, such as Prandin®/NovoNorm® (repaglinide, Novo Nordisk), Starlix® (nateglinide, Novartis), and Glufast® (mitiglinide, Takeda); biguanides, such as Glucophase®/Glucophase XR® (metformin HCl, Bristol Myers Squibb) and Glumetza® (metformin HCl, Depomed); thiazolidinediones; amylin analogs; GLP-1 analogs; DPP-IV inhibitors such as Januvia® (sitagliptin, Merck) and Galvus® (vildagliptin, Novartis); PTB-1 B inhibitors; protein kinase inhibitors (including AMP-activated protein kinase inhibitors); glucagon antagonists, glycogen synthase kinase-3 beta inhibitors; glucose-6-phoshatase inhibitors; glycogen phosphorylase inhibitors; sodium glucose co-transporter inhibitors; and alpha-glucosidase inhibitors, such as Glycet® (miglitol, Pfizer); statins, fibrates, and Zetia® (ezetimibe); alpha-blockers; beta-blockers; calcium channel blockers; diuretics; angiotensin converting enzyme (ACE) inhibitors; dual ACE and neutral endopeptidase (NEP) inhibitors; angiotensin-receptor blockers (ARBs); aldosterone synthase inhibitors; aldosterone-receptor antagonists; endothelin receptor antagonists; orlistat; phentermine; sibutramine; Acomplia® (rimonabant); thiazolidinediones (e.g., rosiglitazone, pioglitazone); SGLT 2 inhibitors (e.g., dapagliflozin, remogliflozin etabonate, sergliflozin, canagliflozin, and 1-chloro-4-(β-D-glucopyranos-1-yl)-2-[4-(('S)-tetrahydrofuran-3-yloxy)-benzyl]-benzene); PPAR-gamma-agonists (e.g., Gl 262570) and antagonists; PPAR-gamma/alpha modulators (e.g., KRP 297); alpha-glucosidase inhibitors (e.g., acarbose, voglibose); DPPIV inhibitors (e.g., Januvia® (sitagliptin), Galvus®/Zomelis® (vildagliptin), Onglyza®(saxagliptin), Nesina®/Vipidia® (alogliptin), and Tradjenta®/Trajenta® (linagliptin)); alpha2-antagonists; glucagon-like protein-1 (GLP-1) receptor agonists and analogues (e.g., exendin-4); amylin; inhibitors of protein tyrosinephosphatase 1; substances that affect deregulated glucose production in the liver, e.g., inhibitors of glucose-6-phosphatase, or fructose-1,6-bisphosphatase, glycogen phosphorylase; glucagon receptor antagonists; inhibitors of phosphoenol pyruvate carboxykinase; glycogen synthase kinase and glucokinase activators; lipid lowering agents such as HMG-CoA-reductase inhibitors (e.g., simvastatin, atorvastatin); fibrates (e.g., bezafibrate, fenofibrate), nicotinic acid and the derivatives thereof, PPAR-alpha agonists, PPAR-delta agonists; ACAT inhibitors (e.g., avasimibe); cholesterol absorption inhibitors such as ezetimibe; bile acid-binding substances such as cholestyramine; inhibitors of ileac bile acid transport; HDL-raising compounds such as CETP inhibitors and ABC1 regulators; active substances for treating obesity such as sibutramine and tetrahydrolipostatin; SDRIs; axokine; leptin; leptin mimetics; antagonists of the cannabinoid 1 receptor; and MCH-1 receptor antagonists; MC4 receptor agonists; NPY5 and NPY2 antagonists; beta3 adrenergic agonists such as SB-418790 and AD-9677; agonists of the 5HT2c receptor; GABA-receptor antagonists; Na-channel blockers; topiramate; protein-kinase C inhibitors; advanced glycation end product inhibitors; and aldose reductase inhibitors.

Pharmaceutical Formulations, Administration, and Dosage Forms

When employed as pharmaceuticals, the compounds of the invention can be administered in the form of a pharmaceutical composition which refers to a combination of a compound of the invention, or its pharmaceutically acceptable salt, and at least one pharmaceutically acceptable carrier. These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal, or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, one or more of the compounds of the invention above in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

Compounds or compositions described herein may be administered to a patient using any amount and any route of administration effective for treating or lessening the severity of one or more of the diseases and conditions described herein. The exact amount required will vary from subject to subject, depending on the species, age, and general condition of the subject, the severity of the infection, disease or disorder, the particular agent, its mode of administration, and the like. Provided compounds are preferably formulated in a particular unit dosage form for ease of administration and uniformity of dosage. The expression "unit dosage form" as used herein refers to a physically discrete unit of agent appropriate for the patient to be treated.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

EXAMPLES

As depicted in the Examples below, compounds were prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Microwave reactions were performed in a CEM reactor using discovery SP system. Where NMR data are presented, spectra were obtained in a Varian-400 (400 MHz). Spectra are reported as ppm downfield from tetramethylsilane with the number of proton, multiplicities and, in certain instances, coupling constants indicated parenthetically along with reference to deuterated solvent. Compounds were also purified by ISCO flash chromatography system utilizing standard methods described in the manual.

Compounds were purified by acidic, basic, or neutral preparative HPLC method as described below.

Preparative RP-HPLC Method A

RP-HPLC (C-18, Boston Green ODS 150*30 mm*5 µm; eluent-gradient: water+0.1% TFA/acetonitrile=81:19 to 51:49)

Mobile phase A: water+0.1% TFA; Mobile phase B: $CH_3CN$; Flow rate: 30 mL/min; Detection: UV 220 nm/254 nm; Column: Boston Green ODS 150*30 mm*5 µm; Column temperature: 30° C.

| Time in min | % A | % B |
| --- | --- | --- |
| 0.00 | 81 | 19 |
| 8.00 | 51 | 49 |
| 8.20 | 0 | 100 |
| 10.00 | 0 | 100 |

Preparative RP-HPLC Method B

RP-HPLC (C-18, Phenomenex Synergi C18 250*21.2 mm*4 µm; eluent-gradient: water+0.1% TFA/acetonitrile=75:25 to 45:55).

Mobile phase A: water+0.1% TFA; Mobile phase B: $CH_3CN$; Flow rate: 25 mL/min; Detection: UV 220 nm/254 nm; Column: Phenomenex Synergi C18 250*21.2 mm*4 µm; Column temperature: 30° C.

| Time in min | % A | % B |
| --- | --- | --- |
| 0.00 | 75 | 25 |
| 10.00 | 45 | 55 |
| 10.20 | 0 | 100 |
| 12.00 | 0 | 100 |

Preparative RP-HPLC Method C

RP-HPLC (C-18, Phenomenex Synergi C18 250*21.2 mm*4 µm; eluent-gradient: water+0.05% HCl/acetonitrile=82:18 to 52:48).

Mobile phase A: water with 0.05% HCl; Mobile phase B: $CH_3CN$; Flow rate: 30 mL/min; Detection: UV 220 nm/254 nm; Column: Phenomenex Gemini 150*30 mm*4 µm; Column temperature: 30° C.

| Time in min | % A | % B |
| --- | --- | --- |
| 0.00 | 82 | 18 |
| 8.00 | 52 | 48 |
| 8.20 | 0 | 100 |
| 10.00 | 0 | 100 |

Preparative RP-HPLC Method D

RP-HPLC (C-18, Phenomenex Gemini 150*25 mm*10 µm; eluent-gradient: water+0.05% ammonia hydroxide/acetonitrile=30:70 to 0:100).

Mobile phase A: water with 0.05% ammonia hydroxide; Mobile phase B: $CH_3CN$; Flow rate: 25 mL/min; Detection: UV 220 nm/254 nm; Column: Phenomenex Gemini 150*25 mm*10 µm; Column temperature: 30° C.

| Time in min | % A | % B |
| --- | --- | --- |
| 0.00 | 30 | 70 |
| 8.00 | 0 | 100 |
| 8.20 | 0 | 100 |
| 10.00 | 0 | 100 |

Preparative RP-HPLC Method E

Mobile phase A: water with 0.1% TFA; Mobile phase B: acetonitrile with 0.1% TFA; Flow rate: 25 mL/min; Detection: UV 220 nm/254 nm; Column: C-18 Synergi Max-RP 150*30 mm*4 µm; Column temperature: 30° C.

| Time in min | % A | % B |
| --- | --- | --- |
| 0.00 | 90 | 10 |
| 12.00 | 60 | 40 |
| 12.20 | 10 | 90 |
| 13.5 | 90 | 10 |

Neutral Preparative HPLC Method F
  Mobile phase A: water
  Mobile phase B: $CH_3CN$
  Flow rate: 120 mL/min.
  Detection: UV 220 nm/254 nm
  Column: Phenomenex Synergi Max-RP 250*50 mm*10 um
  Column temperature: 30° C.

| Time in min | % A | % B |
| --- | --- | --- |
| 0.00 | 80 | 20 |
| 23.00 | 35 | 65 |
| 23.20 | 0 | 100 |
| 26.00 | 0 | 100 |

Preparative HPLC Method G
  Mobile phase A: water (10 mM $NH_4HCO_3$)
  Mobile phase B: $CH_3CN$
  Flow rate: 25 mL/min.
  Detection: UV 220 nm/254 nm
  Column: Xtimate C18 150*25 mm*5 um
  Column temperature: 30° C.

| Time in min | % A | % B |
| --- | --- | --- |
| 0.00 | 72 | 28 |
| 10.00 | 52 | 48 |
| 10.20 | 0 | 100 |
| 13.00 | 0 | 100 |

LCMS data were obtained by utilizing the following chromatographic conditions:
LCMS Method A
  HPLC System: Waters ACQUITY; Column: Waters ACQUITY CSH™ C18 1.7 µM. Guard column: Waters Assy. Frit, 0.2 µM, 2.1 mm; Column temperature: 40° C.
  Mobile Phase: A: TFA:Water (1:1000, v:v); Mobile phase B: TFA:ACN (1:1000, v:v); Flow Rate: 0.65 mL/min; Injection Volume: 2 µL; Acquisition time: approximately 1.5 min.

| Time (min) | B % |
| --- | --- |
| 0 | 10 |
| 1.0 | 90 |
| 1.2 | 10 |

Mass Spectrometer: Waters SQD; Ionization: Positive Electrospray Ionization (ESI); Mode Scan (100-1400 m/z in every 0.2 second); ES Capillary Voltage: 3.5 kV; ES Cone Voltage: 25 V. Source Temperature: 120° C.; Desolvation Temperature: 500° C.; Desolvation Gas Flow: Nitrogen Setting 650 (L/h); Cone Gas Flow: Nitrogen Setting 50 (L/h).
LCMS Method B
  HPLC System: Waters ACQUITY; Column: Waters ACQUITY CSH™ C18 1.7 µM. Guard column: Waters Assy. Frit, 0.2 µM, 2.1 mm; Column tem: 40° C.
  Mobile Phase: A: TFA:Water (1:1000, v:v); Mobile phase B: TFA:ACN (1:1000, v:v); Flow Rate: 0.65 mL/min; Injection Volume: 2 µL; Acquisition time: approximately 1.5 min.

| Time (min) | B % |
| --- | --- |
| 0.00 | 10 |
| 2 | 90 |
| 2.20 | 90 |

Mass Spectrometer: Waters SQD; Ionization: Positive Electrospray Ionization (ESI); Mode Scan (100-1400 m/z in every 0.2 second); ES Capillary Voltage: 3.5 kV; ES Cone Voltage: 25 v. Source Temperature: 120° C.; Desolvation Temperature: 500° C.; Desolvation Gas Flow: Nitrogen Setting 650 (L/h); Cone Gas Flow: Nitrogen Setting 50 (L/h).
LCMS Method C

| Column | MERCK, RP-18e 25-2 mm |
| --- | --- |
| | A: water (4 L) + TFA (1.5 mL) |
| | B: acetonitrile (4 L) + TFA (0.75 mL) |

| TIME (min) | B % |
| --- | --- |
| 0 | 5 |
| 0.7 | 95 |
| 1.1 | 95 |
| 1.11 | 5 |
| 1.5 | 5 |

| Flow Rate | 1.5 mL/min |
| --- | --- |
| wavelength | UV 220, 224 nm |
| Oven Temp | 50° C. |
| MS ionization | ESI |

LCMS Method D

| Column | Xbrige Shield RP-18.5 µm, 2.1 * 50 mm |
| --- | --- |
| | A: water (1 L) + $NH_3H_2O$ (0.5 mL) |
| | B: acetonitrile |

| TIME (min) | B % |
| --- | --- |
| 0 | 10 |
| 2 | 80 |
| 2.48 | 80 |
| 2.49 | 10 |
| 3 | 10 |

| Flow Rate | 1.0 mL/min |
| --- | --- |
| wavelength | UV 220 nm |
| Oven Temp | 30° C. |
| MS ionization | ESI |

LCMS Method E

| Column | Xtimate C18 2.1 * 30 mm, 3 µm |
| --- | --- |
| | A: water (4 L) + TFA (1.5 mL) |
| | B: acetonitrile (4 L) + TFA (0.75 mL) |

| TIME (min) | B % |
| --- | --- |
| 0 | 10 |
| 0.9 | 80 |
| 1.5 | 80 |
| 1.51 | 10 |
| 2 | 10 |

| Flow Rate | 1.2 mL/min |
| --- | --- |
| wavelength | UV 220 nm |

| Oven Temp | 50° C. |
| MS ionization | ESI |

LCMS Method F

| Column | Xtimate C18 2.1 * 30 mm, 3 μm |
| | A: water (4 L) + TFA (1.5 mL) |
| | B: acetonitrile (4 L) + TFA (0.75 mL) |

| TIME (min) | B % |
| --- | --- |
| 0 | 0 |
| 0.9 | 60 |
| 1.5 | 60 |
| 1.51 | 0 |
| 2 | 0 |

| Flow Rate | 1.2 mL/min |
| wavelength | UV 220 nm |
| Oven Temp | 50° C. |
| MS ionization | ESI |

LCMS Method G

HPLC System: Waters ACQUITY; Column: Waters ACQUITY CSH™ C18 1.7 μM. Guard column: Waters Assy. Frit, 0.2 μM, 2.1 mm; Column tem: 40° C.

Mobile Phase: A: TFA: Water (1:1000, v:v); Mobile phase B: TFA:ACN (1:1000, v:v); Flow Rate: 1 mL/min; Injection Volume: 2 μL; Acquisition time: approximately 115 min.

| Time in min | B % |
| --- | --- |
| 0.1 | 10 |
| 2.0 | 10 |
| 14 | 90 |
| 15 | 90 |
| 16 | 10 |

Mass Spectrometer: Waters SQD; Ionization: Positive Electrospray Ionization (ESI); Mode Scan (100-1400 m/z in every 0.2 second); ES Capillary Voltage: 3.5 kV; ES Cone Voltage: 25 v.

Source Temperature: 120° C.; Desolvation Temperature: 500° C.; Desolvation Gas Flow: Nitrogen Setting 650 (L/h); Cone Gas Flow: Nitrogen Setting 50 (L/h).

The following are Supercritical Fluid Chromatography (SFC) separation methods for racemic compounds:
Method A
Instrument: Thar SFC 80; Column: AD 250 mm*30 mm, 5 μm; Mobile phase: A: Supercritical $CO_2$, B: IPA (0.05% DEA), A:B=80:20 at 60 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm.
Method B
Instrument: SFC MG2; Column: OJ 250 mm*30 mm, 5 μm; Mobile phase: A: Supercritical $CO_2$, B: MeOH (0.05% DEA), A:B=90:10 at 70 mL/min; Column Temp: 38° C.; Nozzle Pressure: 100 Bar Nozzle Temp: 60° C.; Evaporator Temp: 20° C.; Trimmer Temp: 25° C.; Wavelength: 220 nm.
X-Ray Powder Diffraction (XRPD) Method A

| Parameter | Value |
| --- | --- |
| Instrument | Rigaku SmartLab System |
| Geometry | Reflection BB |
| X-ray Tube | copper |
| Monochromatization | beta filter |
| Detector | D'teX PSD |
| Voltage (kV) | 40.00 |
| Current (mA) | 44.00 |
| Start Angle (2θ) | 2.00 |
| End Angle (2θ) | 70.00 |
| Step Size (2θ) | 0.04 |
| Scan Speed (2θ) | 3.00 |
| Slits (S0deg, S1deg, S3mm) | 1/3, 4, 13 |
| Measurement Type | symmetric θ:2θ |
| Sample Holder | Si low-background |
| Sample Rotation (RPM) | 75 |

The invention is illustrated by the following examples, in which the following abbreviations may be employed:

| Abbreviation | Meaning |
| --- | --- |
| ACN | acetonitrile |
| BOP | (Benzotriazol-1-yloxy)tris(dimethylamino)phosphonium hexafluorophosphate |
| BTC | Bis(trichloromethyl) carbonate |
| DCE | 1,2-dichloroethane |
| DCM | methylene chloride |
| DIEA | diisopropylethyl amine |
| DMA | dimethyl acetamide |
| DMF | dimethyl formamide |
| dppf | 1,1-bis(diphenylphosphino)ferrocene |
| EtN | triethylamine |
| EtOAc | ethyl acetate |
| EtOH | ethanol |
| h | hour(s) |
| HATU | 1-[bis(dimethylamino)methylene]-1H-1,2,3-triazolo[4,5-b]pyridinium 3-oxid hexafluorophosphate. |
| HBTU | 2-(1H-benzotriazole-1-yl)-1,1,3,3-tetramethyluronium hexafluorophosphate |
| HCl | hydrochloric acid |
| HPLC | high performance liquid chromatography |
| Im | imidazaole |
| KI | potassium iodide |
| K3PO4 | Potassium phosphate |
| LCMS | liquid chromatography-mass spectorphotmetry |
| LDA | Lithium Diisoprpyl amide |
| min | minute(s) |
| Me | methyl |
| mL | milliliters |
| mmol | millimoles |
| mg | milligram |
| $NaBH_3CN$ | sodium cyanoborohydride |
| RP | reverse phase |
| RT | room temperature |
| SFC | super critical fluid chromatography |
| SPhos Gen 2 | Chloro(2-dicyclohexylphosphino-2',6'-dimethoxy-1,1'-biphenyl)[2-(2'-amino-1,1'-biphenyl)]palladium(II), |
| $t_R$; $t_r$, $R_t$ | retention time |
| TBAF | tetra butyl ammonium fluoride |
| TBDMS | tert butyl dimethyl silyl |
| TEA | triethylamine |
| TFA | trifluoroacetic acid |
| THF | tetrahydrofuran |
| TLC | thin layer chromatography |
| XPhos | dicyclohexyphosphino-2',4',6' triiso-propyl-1,1'-biphenyl |

Intermediate 1. tert-butyl 4-(1-(4-fluoro-2-(isopropyl(methyl)carbamoyl)phenyl)-1H-pyrrolo[2,3-c]pyridin-3-yl)piperidine-1-carboxylate

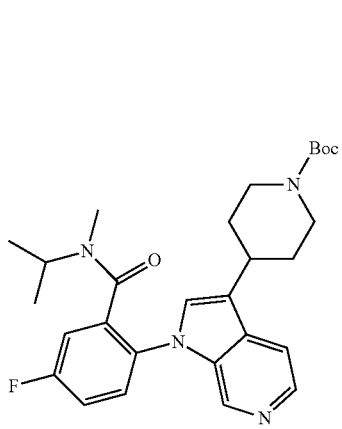 [SMILES: CC(C)N(C)C(=O)c1cc(F)ccc1-n1cc(C2CCN(C(=O)OC(C)(C)C)CC2)c2ccncc21]

Step 1: tert-butyl 4-(1H-pyrrolo[2,3-c]pyridin-3-yl)-5,6-dihydropyridine-1(2H)-carboxylate

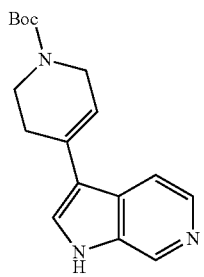 [SMILES: CC(C)(C)OC(=O)N1CC=C(c2c[nH]c3cnccc23)CC1]

To solution of 1H-pyrrolo[2,3-c]pyridine (25 g, 21.2 mmmol) in ethanediol (250 mL) was added tert-butyl 4-oxopiperidine-1-carboxylate (5 g, 25.4 mmol) and KOH (24 g, 42.4 mmol). The mixture was stirred at 100° C. for 2 days. The mixture was diluted with water and extracted with EtOAc (500 mL×3). The combined organic layers were washed with brine (2 L×3), dried over Na₂SO₄, and filtered. The filtrate was concentrated, and the residue was purified by ISCO column (from 100% DCM to 6% MeOH in DCM) to give tert-butyl 4-(1H-pyrrolo[2,3-c]pyridin-3-yl)-5,6-dihydropyridine-1(2H)-carboxylate as yellow oil. Yield: 40 g (47%); LCMS method D: R$_t$=1.819 min; (M+H)⁺=300.2. ¹H NMR (DMSO-d6,): δ ppm 11.66 (s, 1H), 8.74 (s, 1H), 8.12 (d, J=7.2 Hz, 1H), 7.77 (d, J=6.4 Hz, 1H), 7.67 (s, 1H), 6.17 (s, 1H), 4.04-4.05 (m, 2H), 3.56 (t, J=5.6 Hz, 2H), 3.17 (s, 1H), 2.50-2.55 (m, 1H), 1.43 (s, 9H).

Step 2: tert-butyl 4-(1H-pyrrolo[2,3-c]pyridin-3-yl)piperidine-1-carboxylate

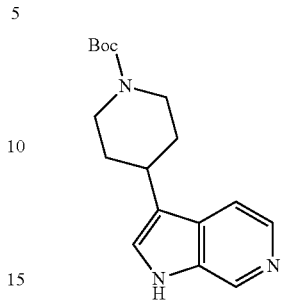

To solution of tert-butyl 4-(1H-pyrrolo[2,3-c]pyridin-3-yl)-5,6-dihydropyridine-1(2H)-carboxylate (40 g, 134 mmol) in anhydrous MeOH:THF (500 mL, 1:1) was added Pd(OH)₂/C (4 g, 10%). The mixture was purged and disgassed with H₂ (40 psi) three times followed by stirring at 45° C. for 24 h under H₂ (40 psi). The mixture was filtered and the filtrate was concentrated to give tert-butyl 4-(1H-pyrrolo[2,3-c]pyridin-3-yl)piperidine-1-carboxylate (30 g, 74% yield). LCMS method D: R$_t$=1.825 min; (M+H)⁺= 302.2. ¹H NMR (DMSO-d6): δ ppm 11.34 (s, 1H), 8.69 (s, 1H), 8.05 (d, J=5.6 Hz, 1H), 7.53 (d, J=5.2 Hz, 1H), 7.38 (s, 1H), 4.06 (d, J=11.6 Hz, 2H), 2.91-2.98 (m, 3H), 1.92 (d, J=12.0 Hz, 2H), 1.48-1.57 (m, 2H), 1.41 (s, 9H).

Step 3: 2-(3-(1-(tert-butoxycarbonyl)piperidin-4-yl)-1H-pyrrolo[2,3-c]pyridin-1-yl)-5-fluorobenzoic acid

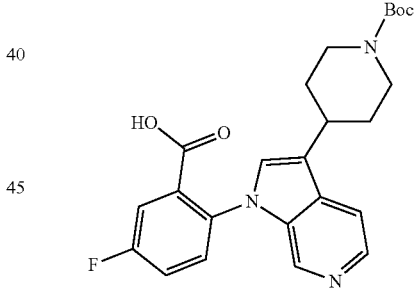

To a mixture of tert-butyl 4-(1H-pyrrolo[2,3-c]pyridin-3-yl)piperidine-1-carboxylate (10 g, 0.03 mol) in DMF (200 mL) was added 5-fluoro-2-iodobenzoic acid (8.3 g, 0.03 mol), Cu (384 mg, 0.01 mol) and K₂CO₃ (12 g, 0.09 mol). The mixture was degassed and purged with N₂ 3 times followed by heating under N₂ at 130° C. for 17 h. The reaction mixture was filtered and the filtrate was concentrated under reduced pressure. The residue was added to water (500 mL) and 3 M HCl (aq.) to a pH=3-4, extracted with EtOAc/i-PrOH (v/v, 10/3, 3×400 mL), and the combined organic layers were dried over anhydrous Na₂SO₄ and filtered. The filtrate was concentrated under reduced pressure to give 2-(3-(1-(tert-butoxycarbonyl)piperidin-4-yl)-1H-pyrrolo[2,3-c]pyridin-1-yl)-5-fluorobenzoic acid as brown solid. Yield: 14 g (100% crude); LCMS method C: R$_t$=0.645 min; (M+H)⁺=440.3.

Step 4: tert-butyl 4-(1-(4-fluoro-2-(isopropyl(methyl)carbamoyl)phenyl)-1H-pyrrolo[2,3-c]pyridin-3-yl)piperidine-1-carboxylate To a mixture of 2-(3-(1-(tert-butoxycarbonyl)piperidin-4-yl)-1H-pyrrolo[2,3-c]pyridin-1-yl)-5-fluorobenzoic acid (5 g, 0.01 mol) in DMF (100 mL) was added N-methylpropan-2-amine (1.2 g, 0.02 mol), HATU (7.6 g, 0.02 mol), and DIEA (6.5 g, 0.05 mol). The mixture was degassed and purged with $N_2$ 3 times followed by heating under $N_2$ at 20-28° C. for 2 h. The reaction was concentrated under reduced pressure. The residue was added to water (50 mL), extracted with EtOAc (3×80 mL), and the combined organic layers were washed with water (3×60 mL). The combined organic layers were dried over anhydrous $Na_2SO_4$, filtered, and the filtrate was concentrated under reduced pressure. The residue was purified by column chromatograph on silica gel (eluting with petroleum ether/EtOAc=1/1) to give tert-butyl 4-(1-(4-fluoro-2-(isopropyl(methyl)carbamoyl)phenyl)-1H-pyrrolo[2,3-c]pyridin-3-yl)piperidine-1-carboxylate as yellow oil. Yield: 5.2 g (92%); LCMS method D: $R_t$=2.574 min; $(M+H)^+$=495.2. $^1$H NMR (CD3OD): δ ppm 8.50-8.65 (m, 1H), 8.15-8.25 (m, 1H), 7.70-7.80 (m, 1H), 7.60-7.70 (m, 1H), 7.40-7.50 (m, 2H), 7.35-7.40 (m, 1H), 4.40-4.55 (m, 0.5H), 4.15-4.30 (m, 2H), 3.55-3.65 (m, 0.5H), 3.05-3.15 (m, 1H), 2.90-3.05 (m, 2H), 2.65-2.70 (m, 1.5H), 2.45-2.50 (m, 1.5H), 2.00-2.10 (m, 2H), 1.60-1.75 (m, 2H), 1.45-1.55 (m, 9H), 0.95-1.15 (m, 3H), 0.15-0.60 (m, 3H). $^{19}$F NMR (CD3OD): δ ppm −113.22~−113.44.

Intermediates 2-17

The following intermediates were synthesized by method described above for Intermediate 1. Characterization data for Intermediates 2-17 is shown in Table 2.

TABLE 1

| Int. # | Structure | Name | Starting Ketone | Overall Yield % |
|---|---|---|---|---|
| 2 | 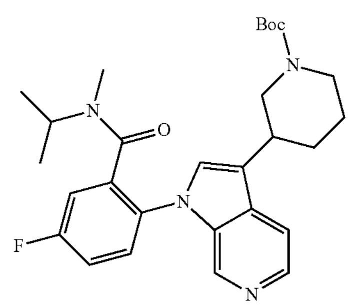 [SMILES: CC(C)N(C)C(=O)c1cc(F)ccc1-n1cc(C2CCCN(C(=O)OC(C)(C)C)C2)c2ccncc21] | tert-butyl 3-(1-(4-fluoro-2-(isopropyl(methyl)carbamoyl)phenyl)-1H-pyrrolo[2,3-c]pyridin-3-yl)piperidine-1-carboxylate | 1-Boc-3-Piperidone | 32 |
| 3 | 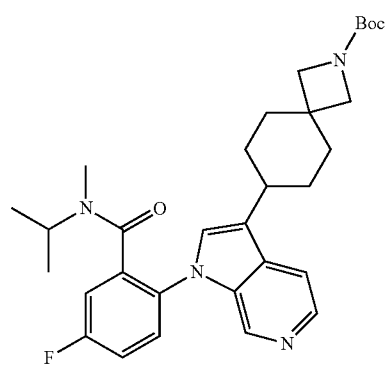 [SMILES: CC(C)N(C)C(=O)c1cc(F)ccc1-n1cc(C2CCC3(CC2)CN(C(=O)OC(C)(C)C)C3)c2ccncc21] | tert-butyl 7-(1-(4-fluoro-2-(isopropyl(methyl)carbamoyl)phenyl)-1H-pyrrolo[2,3-c]pyridin-3-yl)-2-azaspiro[3.5]nonane-2-carboxylate | tert-butyl 7-oxo-2-azaspiro[3.5]nonane-2-carboxylate | 20 |
| 4 | 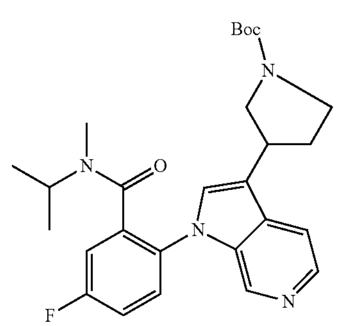 [SMILES: CC(C)N(C)C(=O)c1cc(F)ccc1-n1cc(C2CCN(C(=O)OC(C)(C)C)C2)c2ccncc21] | tert-butyl 3-(1-(4-fluoro-2-(isopropyl(methyl)carbamoyl)phenyl)-1H-pyrrolo[2,3-c]pyridin-3-yl)pyrrolidine-1-carboxylate | Boc-3-pyrrolodinone | 26 |

TABLE 1-continued

| Int. # | Structure | Name | Starting Ketone | Overall Yield % |
|---|---|---|---|---|
| 5 | 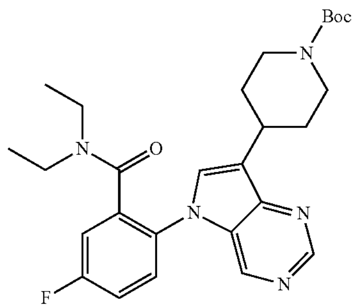 [SMILES: CCN(CC)C(=O)c1cc(F)ccc1-n1cc(C2CCN(C(=O)OC(C)(C)C)CC2)c2ncncc21] | tert-butyl 4-(5-(2-(diethylcarbamoyl)-4-fluorophenyl)-5H-pyrrolo[3,2-d]pyrimidin-7-yl)piperidine-1-carboxylate | Boc-4-Piperidone | 28 |
| 6 | 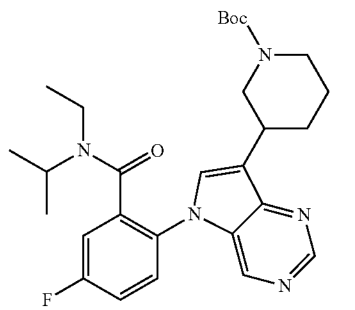 [SMILES: CCN(C(=O)c1cc(F)ccc1-n1cc(C2CCCN(C(=O)OC(C)(C)C)C2)c2ncncc21)C(C)C] | tert-butyl 3-(5-(4-fluoro-2-(isopropyl(ethyl)carbamoyl)phenyl)-5H-pyrrolo[3,2-d]pyrimidin-7-yl)piperidine-1-carboxylate | Boc-3-Piperidone | 31 |
| 7 | 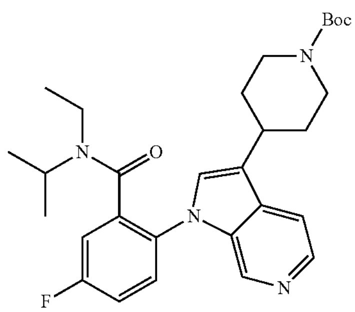 [SMILES: CCN(C(=O)c1cc(F)ccc1-n1cc(C2CCN(C(=O)OC(C)(C)C)CC2)c2ccncc21)C(C)C] | tert-butyl 4-(5-(4-fluoro-2-(isopropyl(ethyl)carbamoyl)phenyl)-5H-pyrrolo[3,2-d]pyrimidin-7-yl)piperidine-1-carboxylate | Boc-4-Piperidone | 21 |
| 8 | 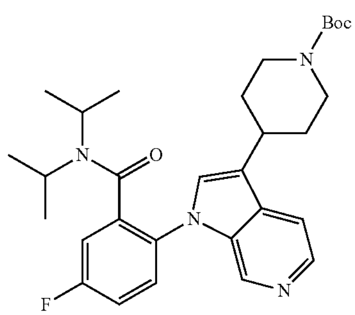 [SMILES: CC(C)N(C(=O)c1cc(F)ccc1-n1cc(C2CCN(C(=O)OC(C)(C)C)CC2)c2ccncc21)C(C)C] | tert-butyl 4-(1-(2-(diisopropylcarbamoyl)-4-fluorophenyl)-1H-pyrrolo[2,3-c]pyridin-3-yl)piperidine-1-carboxylate | Boc-4-Piperidone | 8 |
| 9 | 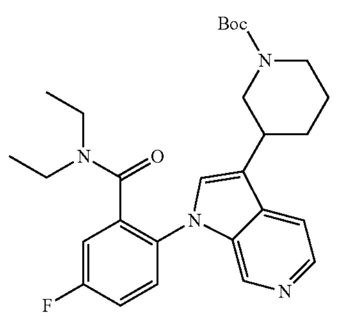 [SMILES: CCN(CC)C(=O)c1cc(F)ccc1-n1cc(C2CCCN(C(=O)OC(C)(C)C)C2)c2ccncc21] | tert-butyl 3-(1-(2-(diethylcarbamoyl)-4-fluorophenyl)-1H-pyrrolo[2,3-c]pyridin-3-yl)piperidine-1-carboxylate | Boc-4-Piperidone | 29 |

TABLE 1-continued

| Int. # | Structure | Name | Starting Ketone | Overall Yield % |
|---|---|---|---|---|
| 10 | 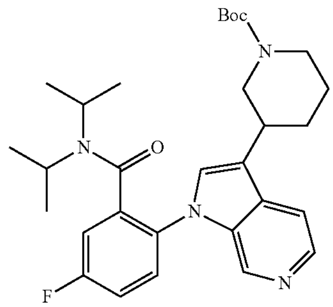 [SMILES: CC(C)N(C(=O)c1cc(F)ccc1-n1cc(C2CCCN(C(=O)OC(C)(C)C)C2)c2ccncc21)C(C)C] | tert-butyl 3-(1-(2-(diisopropylcarbamoyl)-4-fluorophenyl)-1H-pyrrolo[2,3-c]pyridin-3-yl)piperidine-1-carboxylate | Boc-4-Piperidone | 8 |
| 11 | 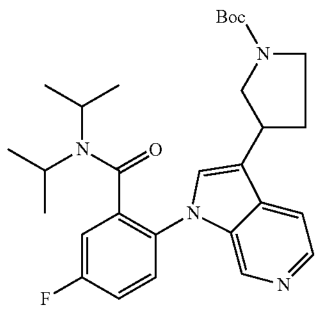 [SMILES: CC(C)N(C(=O)c1cc(F)ccc1-n1cc(C2CCN(C(=O)OC(C)(C)C)C2)c2ccncc21)C(C)C] | tert-butyl 3-(1-(2-(diisopropylcarbamoyl)-4-fluorophenyl)-1H-pyrrolo[2,3-c]pyridin-3-yl)pyrrolidine-1-carboxylate | 1-Boc-3-Pyrrolidinone | 20 |
| 12 | 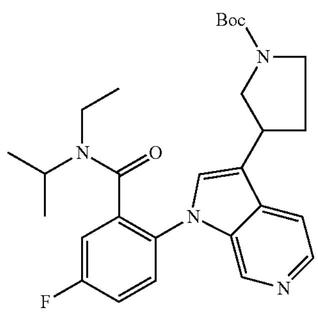 [SMILES: CCN(C(=O)c1cc(F)ccc1-n1cc(C2CCN(C(=O)OC(C)(C)C)C2)c2ccncc21)C(C)C] | tert-butyl 3-(1-(2-(ethyl(isopropyl)carbamoyl)-4-fluorophenyl)-1H-pyrrolo[2,3-c]pyridin-3-yl)pyrrolidine-1-carboxylate | 1-Boc-3-Pyrrolidinone | 25 |
| 13 | 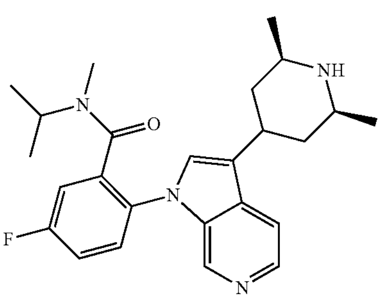 [SMILES: CC(C)N(C)C(=O)c1cc(F)ccc1-n1cc(C2C[C@@H](C)N[C@@H](C)C2)c2ccncc21] | 2-(3-((2S,6R)-2,6-dimethylpiperidin-4-yl)-1H-pyrrolo[2,3-c]pyridin-1-yl)-5-fluoro-N-isopropyl-N-methylbenzamide | (2S,6R)-1-benzyl-2,6,dimethyl-piperidin-4-one | 35 |
| 14 | 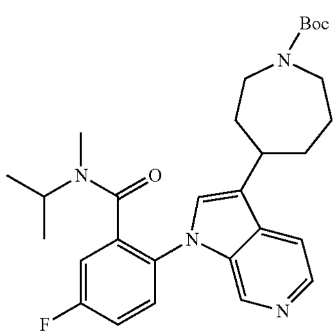 [SMILES: CC(C)N(C)C(=O)c1cc(F)ccc1-n1cc(C2CCCN(C(=O)OC(C)(C)C)CC2)c2ccncc21] | tert-butyl 4-(1-(4-fluoro-2-(isopropyl(methyl)carbamoyl)phenyl)-1H-pyrrolo[2,3-c]pyridin-3-yl)azepane-1-carboxylate | tert-butyl 4-oxoazepane-1-carboxylate | 31 |

TABLE 1-continued

| Int. # | Structure | Name | Starting Ketone | Overall Yield % |
|---|---|---|---|---|
| 15 | 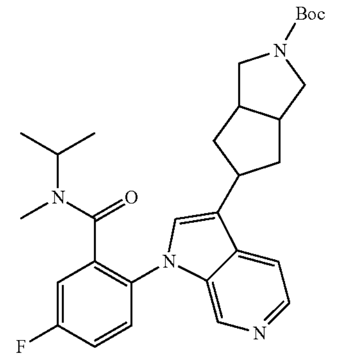 [SMILES: CC(C)N(C)C(=O)c1cc(F)ccc1-n1cc(C2CC3CN(C(=O)OC(C)(C)C)CC3C2)c2ccncc21] | tert-butyl (3aR,6aS)-5-(1-(4-fluoro-2-(isopropyl(methyl)carbamoyl)phenyl)-1H-pyrrolo[2,3-c]pyridin-3-yl)hexahydrocyclopenta[c]pyrrole-2(1H)-carboxylate | tert-butyl (3aR,6aS)-5-oxohexahydrocyclopenta[c]pyrrole-2(1H)-carboxylate | 15 |
| 16 | 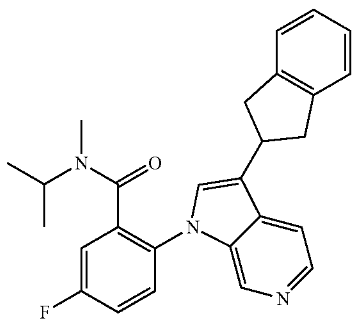 [SMILES: CC(C)N(C)C(=O)c1cc(F)ccc1-n1cc(C2Cc3ccccc3C2)c2ccncc21] | 2-(3-(2,3-dihydro-1H-inden-2-yl)-2,3-dihydro-1H-pyrrolo[2,3-c]pyridin-1-yl)-5-fluoro-N-isopropyl-N-methylbenzamide | 2-Indanone | 45 |
| 17 | 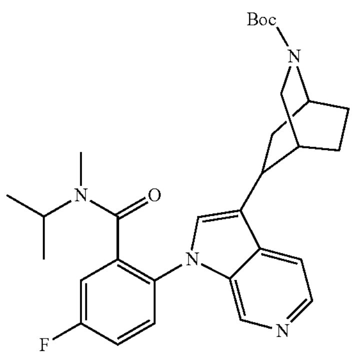 [SMILES: CC(C)N(C)C(=O)c1cc(F)ccc1-n1cc(C2CC3CCC2CN3C(=O)OC(C)(C)C)c2ccncc21] | tert-butyl (1S,4R)-5-(1-(4-fluoro-2-(isopropyl(methyl)carbamoyl)phenyl)-1H-pyrrolo[2,3-c]pyridin-3-yl)-2-azabicyclo[2.2.2]octane-2-carboxylate | tert-butyl 5-oxo-2-azabicyclo[2.2.2]octane-2-carboxylate | 15 |

TABLE 2

| Int. # | Structure | Spectra details |
|---|---|---|
| 2 | 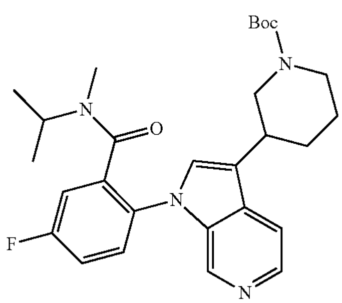 [SMILES: CC(C)N(C)C(=O)c1cc(F)ccc1-n1cc(C2CCCN(C(=O)OC(C)(C)C)C2)c2ccncc21] | LCMS method E = 0.905 min, [M + H]$^+$ = 495.3; $^1$H NMR (CDCl3): δ ppm 8.72-8.79 (m, 1H), 8.28 (s, 1H), 7.78 (s, 1H), 7.45-7.60 (m, 2H), 7.25-7.35 (m, 1H), 7.10-7.25 (m, 1H), 4.55-4.65 (m, 0.5 H), 4.05-4.50 (m, 2H), 3.65-3.90 (m, 2H), 3.40-3.50 (m, 0.5H), 2.95-3.05 (m, 1H), 2.80-2.90 (m, 1H), 2.70-2.80 (m, 1H), 2.30-2.70 (m, 3H), 2.10-2.20 (m, 1H), 1.60-1.80 (m, 3H), 1.45 (s, 9H), 0.05-1.00 (m, 6H). $^{19}$F NMR (CDCl3): δ ppm −110.49~−110.02. |

TABLE 2-continued

| Int. # | Structure | Spectra details |
|---|---|---|
| 3 | 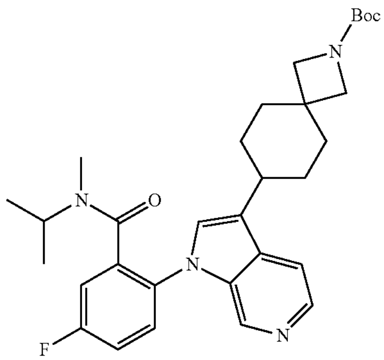 [SMILES: CC(C)N(C)C(=O)c1cc(F)ccc1-n1cc(C2CCC3(CC2)CN(C(=O)OC(C)(C)C)C3)c2ccncc21] | LCMS method E = 1.675 min, [M + H]⁺ = 535.3; ¹H NMR (CD3OD): δ ppm 8.51-8.66 (m, 1H), 8.19 (dd, J = 7.6, 5.6 Hz, 1H), 7.61-7.75 (m, 2H), 7.40-7.50 (m, 1H), 7.33-7.39 (m, 2H), 4.35-4.51 (m, 0.5H), 3.61-3.77 (m, 4H), 3.53-3.60 (m, 0.5H), 2.80-2.95 (m, 1H), 2.41-2.71 (m, 3H), 2.00-2.10 (m, 4H), 1.65-1.80 (m, 2H), 1.50-1.65 (m, 2H), 1.47 (s, 9H), 0.95-1.16 (m, 3H), 0.15-0.65 (m, 3H). ¹⁹F NMR (CD3OD): δ ppm −113.32~−113.54. |
| 4 | 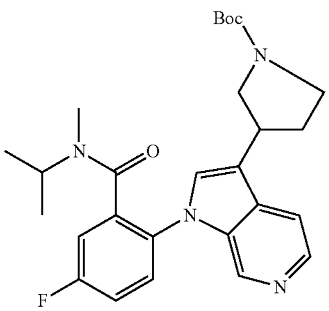 [SMILES: CC(C)N(C)C(=O)c1cc(F)ccc1-n1cc(C2CCN(C(=O)OC(C)(C)C)C2)c2ccncc21] | LCMS method E = 1.012 min, [M + H]⁺ = 481.3; |
| 5 | 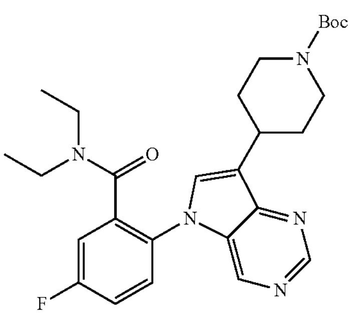 [SMILES: CCN(CC)C(=O)c1cc(F)ccc1-n1cc(C2CCN(C(=O)OC(C)(C)C)CC2)c2ncncc21] | LCMS method E = 1.175 min, [M + H]⁺ = 496.3; |
| 6 | 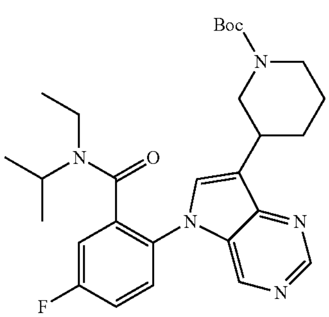 [SMILES: CCN(C(=O)c1cc(F)ccc1-n1cc(C2CCCN(C(=O)OC(C)(C)C)C2)c2ncncc21)C(C)C] | LCMS method E = 1.325 min, [M + H]⁺ = 510.3; |
| 7 | 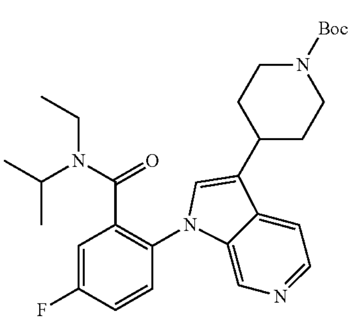 [SMILES: CCN(C(=O)c1cc(F)ccc1-n1cc(C2CCN(C(=O)OC(C)(C)C)CC2)c2ccncc21)C(C)C] | LCMS method E = 1.355 min, [M + H]⁺ = 510.3; |

TABLE 2-continued

| Int. # | Structure | Spectra details |
| --- | --- | --- |
| 8 | 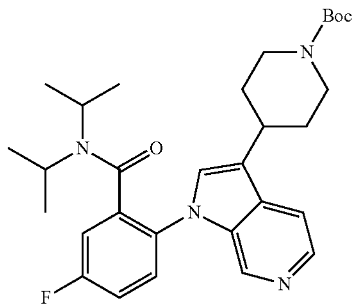 [SMILES: CC(C)N(C(=O)c1cc(F)ccc1-n1cc(C2CCN(C(=O)OC(C)(C)C)CC2)c2ccncc21)C(C)C] | LCMS method B = 0.725 min, [M + H]⁺ = 523.3; |
| 9 | 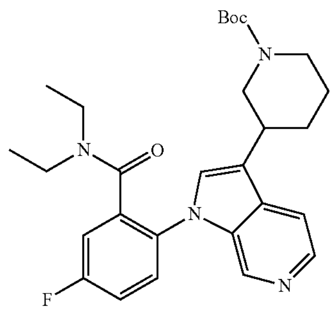 [SMILES: CCN(CC)C(=O)c1cc(F)ccc1-n1cc(C2CCCN(C(=O)OC(C)(C)C)C2)c2ccncc21] | LCMS method F = 1.215 min, [M + H]⁺ = 496.3; |
| 10 | 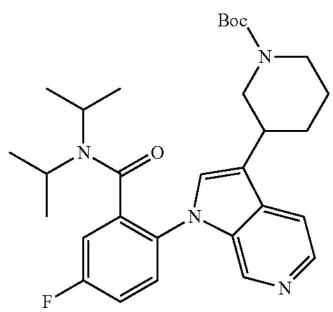 [SMILES: CC(C)N(C(=O)c1cc(F)ccc1-n1cc(C2CCCN(C(=O)OC(C)(C)C)C2)c2ccncc21)C(C)C] | LCMS method B = 0.775 min, [M + H]⁺ = 523.3; |
| 11 | 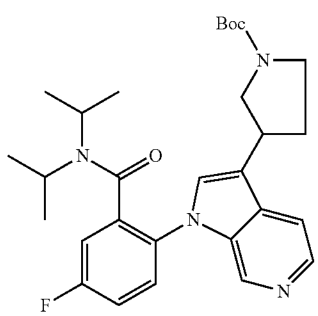 [SMILES: CC(C)N(C(=O)c1cc(F)ccc1-n1cc(C2CCN(C(=O)OC(C)(C)C)C2)c2ccncc21)C(C)C] | LCMS method C = 0.912 min, [M + H]⁺ = 509.3; $^1$H NMR (CD$_3$OD): δ ppm 8.62 (s, 1H), 8.22 (s, 1H), 7.76 (d, J = 4.4 Hz, 1H), 7.64-7.67 (m, 1H), 7.54 (m, 1H), 7.40-7.45 (m, 1H), 7.30-7.33 (m, 1H), 3.87-3.94 (m, 1H), 3.71-3.72 (m, 1H), 3.35-3.67 (m, 5H), 2.40-2.41 (m, 1H), 2.12-2.18 (m, 1H), 1.45-1.50 (m, 12H), 1.04 (d, J = 6.0 Hz, 6H), 0.20-0.32 (m, 3H). $^{19}$F NMR (CD$_3$OD,): δ ppm −113.11. |
| 12 | 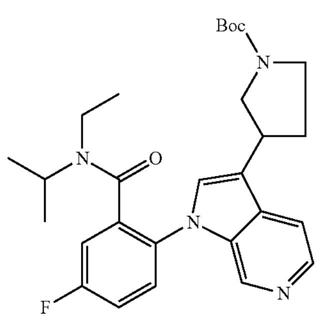 [SMILES: CCN(C(=O)c1cc(F)ccc1-n1cc(C2CCN(C(=O)OC(C)(C)C)C2)c2ccncc21)C(C)C] | LCMS method C = 0.882 min, [M + H]⁺ = 495.3; |

TABLE 2-continued

| Int. # | Structure | Spectra details |
| --- | --- | --- |
| 13 | 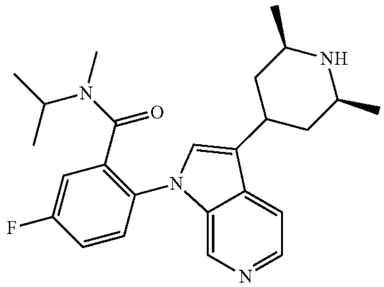 [SMILES: CC(C)N(C)C(=O)c1cc(F)ccc1-n1cc(C2C[C@@H](C)N[C@@H](C)C2)c2ccncc21] | LCMS method D = 0.671 min, [M + H]⁺ = 423.3; ¹H NMR (CD₃OD): δ ppm 8.85-9.00 (m, 1H), 8.30-8.40 (m, 2H), 8.10-8.20 (m, 1H), 7.70-7.80 (m, 1H), 7.45-7.55 (m, 2H), 4.35-4.45 (m, 0.5H), 3.90-4.00 (m, 1H), 3.70-3.80 (m, 2.5H), 2.60-2.70 (m, 3H), 2.25-2.40 (m, 1H), 2.00-2.25 (m, 2H), 1.60-2.20 (m, 4H), 1.41 (d, J = 6.4 Hz, 3H), 0.45-1.20 (m, 6H). ¹⁹F NMR (CD₃OD): δ ppm −110.60, −76.89. |
| 14 | 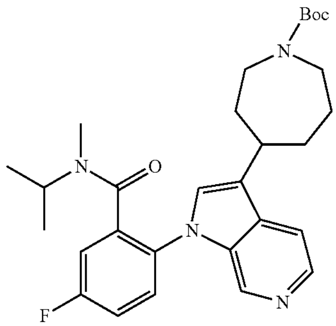 [SMILES: CC(C)N(C)C(=O)c1cc(F)ccc1-n1cc(C2CCCN(C(=O)OC(C)(C)C)CC2)c2ccncc21] | LCMS method F = 1.342 min, [M + H]⁺ = 509.3 ¹H NMR (CD₃OD): δ ppm 8.75-8.90 (m, 1H), 8.30-8.35 (m, 1H), 8.20-8.25 (m, 1H), 8.05-8.15 (m, 1H), 7.65-7.75 (m, 1H), 7.35-7.55 (m, 2H), 4.30-4.45 (m, 0.5H), 3.70-3.80 (m, 1.5H), 3.35-3.60 (m, 3H), 3.15-3.25 (m, 1H), 2.63 (s, 1H), 1.75-2.25 (m, 6H), 1.35-1.55 (m, 9H), 0.25-1.25 (m, 6H). ¹⁹F NMR (CD₃OD): δ ppm −77.09, −110.84. |
| 15 | 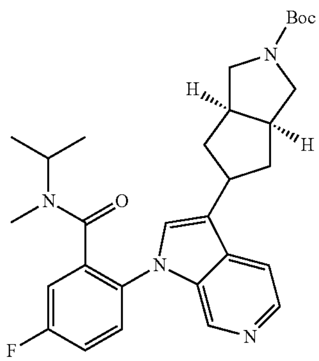 [SMILES: CC(C)N(C)C(=O)c1cc(F)ccc1-n1cc(C2C[C@@H]3CN(C(=O)OC(C)(C)C)C[C@@H]3C2)c2ccncc21] | LCMS method F = 1.441 min, [M + H]⁺ = 521.3. ¹H NMR (CD₃OD): δ ppm 6.25-6.30 (m, 1H), 3.40-3.60 (m, 4H), 2.85-2.95 (m, 2H), 2.55-2.65 (m, 1H), 2.25-2.35 (m, 1H), 1.44 (s, 9H), 1.26 (s, 12H). |
| 16 | 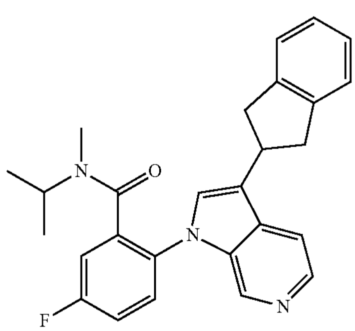 [SMILES: CC(C)N(C)C(=O)c1cc(F)ccc1-n1cc(C2Cc3ccccc3C2)c2ccncc21] | LCMS method F = 1.721 min, [M + H]⁺ = 430.2. ¹H NMR (CD₃OD): δ ppm 8.51-8.60 (m, 1H), 8.10-8.20 (m, 1H), 7.55-7.70 (m, 1H), 7.35-7.45 (m, 3H), 7.25-7.30 (m, 1H), 7.20-7.25 (m, 2H), 7.10-7.15 (m, 2H), 4.35-4.45 (m, 0.5H), 3.90-3.95 (m, 1H), 3.40-3.60 (m, 2.5H), 3.05-3.20 (m, 2H), 2.30-2.50 (m, 3H), 0.90-1.05 (m, 3H), 0.10-0.55 (m, 3H). ¹⁹F NMR (CD₃OD): δ ppm −113.41. |

TABLE 2-continued

| Int. # | Structure | Spectra details |
|---|---|---|
| 17 | 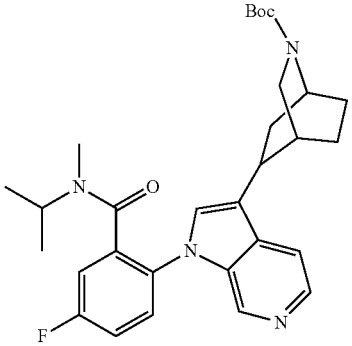 [SMILES: CC(C)N(C)C(=O)c1cc(F)ccc1-n1cc(C2CC3CCC2CN3C(=O)OC(C)(C)C)c2ccncc21] | LCMS method E = 1.661 min, [M + H]⁺ = 521.3 |

Intermediates 17A-17B. 2-(3-(1,4-dioxaspiro[4.5]dec-8-yl)-1H-pyrrolo[2,3-c]pyridin-1-yl)-5-fluoro-N-isopropyl-N-methylbenzamide (Intermediate 17A) and 5-fluoro-N-isopropyl-N-methyl-2-(3-(4-oxocyclohexyl)-1H-pyrrolo[2,3-c]pyridin-1-yl)benzamide (Intermediate 17B)

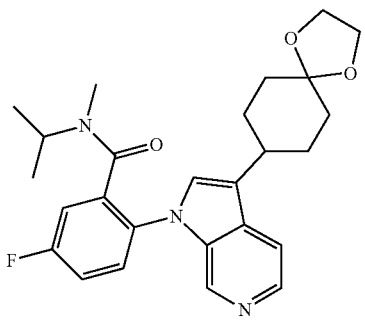

and

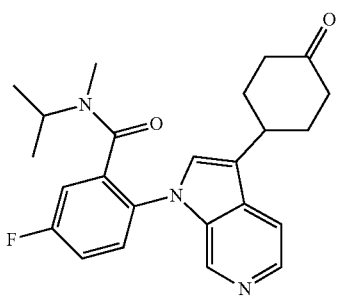

Step 1: 3-(1,4-dioxaspiro[4.5]dec-7-en-8-yl)-1H-pyrrolo[2,3-c]pyridine

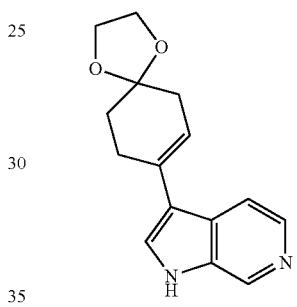

To a solution of 1H-pyrrolo[2,3-c]pyridine (20.0 g, 169.29 mmol) in 600 mL of ethane-1,2-diol was added KOH (28.5 g, 507.87 mmol), after all of KOH was dissolved completely, then 1,4-dioxaspiro[4.5]decan-8-one (53.0 g, 338.58) was added. The mixture was degassed and purged with N₂. The resulting mixture was stirred at 100~110° C. (oil temperature) under N₂ for 24 h. The reaction was cooled to 30~40° C., then diluted with EtOAc (600 mL) and washed with H₂O (3×800 mL). The organic layer was dried over anhydrous Na₂SO₄, filtered, and the filtrate was concentrated under reduced pressure. The resulting residue was washed with EtOAc (50 mL) and filtered. The filtered cake was collected and dried under reduced pressure to afford 3-(1,4-dioxaspiro[4.5]dec-7-en-8-yl)-1H-pyrrolo[2,3-c]pyridine as white solid. Yield: 29.0 g (67%); LCMS method C: $R_t$=0.547 min; (M+H)⁺=257.0. ¹H NMR (CD3OD): δ ppm 8.64 (d, J=1.2 Hz, 1H), 8.07 (d, J=6.0 Hz, 1H), 7.77-7.80 (m, 1H), 7.74-7.78 (m, 1H), 7.52 (s, 1H), 6.08 (t, J=4.0 Hz, 1H), 3.99 (s, 4H), 2.60-2.70 (m, 2H), 2.40-2.50 (m, 2H), 1.89-1.95 (t, J=6.8 Hz, 2H).

Step 2: 3-(1,4-dioxaspiro[4.5]decan-8-yl)-1H-pyrrolo[2,3-c]pyridine

To a solution of 3-(1,4-dioxaspiro[4.5]dec-7-en-8-yl)-1H-pyrrolo[2,3-c]pyridine (29.0 g, 113.15 mmol) in 400 mL of MeOH and 200 mL of THF was added Pd(OH)₂/C (6.0 g, 10%, dry). The mixture was degassed and purged with H₂ 3 times. The resulting mixture was hydrogenated under H₂ (40 Psi) at 40-50° C. for 24 h. The reaction mixture was then filtered through a pad of celite. The filtrate was concentrated under reduced pressure to give 3-(1,4-dioxaspiro[4.5]decan-8-yl)-1H-pyrrolo[2,3-c]pyridine as white solid, which was used for the next step directly without further purification. Yield: 28.0 g (96%); LCMS method C: $R_f$=0.560 min; (M+H)$^+$=259.0. $^1$H NMR (CD3OD): δ ppm 8.63 (d, J=0.8 Hz, 1H), 8.04 (d, J=5.2 Hz, 1H), 7.77-7.80 (dd, J=0.8, 5.2 Hz, 1H), 7.34 (s, 1H), 3.95-4.05 (m, 4H), 2.85-2.95 (m, 1H), 2.00-2.10 (m, 2H), 1.80-1.95 (m, 4H), 1.70-1.80 (m, 2H).

Step 3: 2-(3-(1,4-dioxaspiro[4.5]decan-8-yl)-1H-pyrrolo[2,3-c]pyridin-1-yl)-5-fluorobenzoic acid

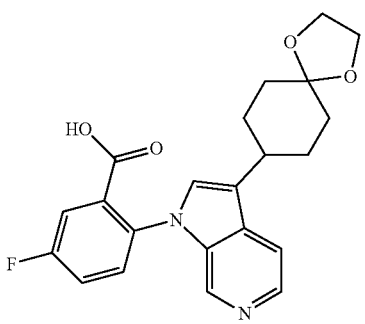 [SMILES: O=C(O)c1cc(F)ccc1-n1cc(C2CCC3(CC2)OCCO3)c2ccncc21]

To a solution of 3-(1,4-dioxaspiro[4.5]decan-8-yl)-1H-pyrrolo[2,3-c]pyridine (9.0 g, 34.84 mmol) in 200 mL of anhydrous DMF was added 5-fluoro-2-iodobenzoic acid (9.3 g, 34.84 mmol), Cu (442 mg, 6.97 mmol) and K$_2$CO$_3$ (14.4 g, 104.52 mmol). The resulting mixture was degassed and purged with N$_2$ 3 times, then stirred at 130° C. for 24 h under N$_2$. The reaction mixture was then filtered through celite. The filtered cake was washed with EtOAc (150 mL) and the filtrate was concentrated under reduced pressure to remove most of the EtOAc and DMF. The resulting residue was poured into water (300 mL). The aqueous layer was adjusted by 6 N HCl to pH=6-7, extracted with EtOAc (3×300 mL), and some white precipitate was formed. The suspension was then filtered. The filtered cake was collected and dried under reduced pressure to give a first batch of 2-(3-(1,4-dioxaspiro[4.5]decan-8-yl)-1H-pyrrolo[2,3-c]pyridin-1-yl)-5-fluorobenzoic acid (7.5 g) as white solid. The organic layers was washed with brine (3×300 mL), then dried over anhydrous Na$_2$SO$_4$, filtered and filtrate was concentrated under reduced pressure to give a second batch of 2-(3-(1,4-dioxaspiro[4.5]decan-8-yl)-1H-pyrrolo[2,3-c]pyridin-1-yl)-5-fluorobenzoic acid (4.5 g) as brown solid. Yield: 12.0 g (87%); LCMS method E: $R_f$=0.649 min; (M+H)$^+$=397.0. $^1$H NMR (DMSO-d6): δ ppm 8.45 (s, 1H), 8.20-8.22 (d, J=5.6, 1H), 7.60-7.80 (m, 4H), 7.53 (s, 1H), 3.95 (4, 1H), 2.90-3.00 (m, 1H), 2.03-2.10 (m, 2H), 1.65-1.85 (m, 6H). $^{19}$F NMR (DMSO-d6): δ ppm −112.83.

Step 4: 2-(3-(1,4-dioxaspiro[4.5]decan-8-yl)-1H-pyrrolo[2,3-c]pyridin-1-yl)-5-fluoro-N-isopropyl-N-methylbenzamide (Intermediate 17A)

To a solution of 2-(3-(1,4-dioxaspiro[4.5]decan-8-yl)-1H-pyrrolo[2,3-c]pyridin-1-yl)-5-fluorobenzoic acid (6.0 g, 15.14 mmol) in 120 mL of anhydrous CH$_2$Cl$_2$ was added N-methylpropan-2-amine (1.7 g, 22.71 mmol), HATU (6.3 g, 16.65 mmol) and DIEA (5.9 g, 45.42 mmol). The resulting mixture was stirred at RT for 18 h. The reaction mixture was then concentrated under reduced pressure. The residue was dissolved in H$_2$O (50 mL) and extracted with CH$_2$Cl$_2$ (2×100 mL), then the organic layers were concentrated under reduced pressure to give crude 2-(3-(1,4-dioxaspiro[4.5]decan-8-yl)-1H-pyrrolo[2,3-c]pyridin-1-yl)-5-fluoro-N-isopropyl-N-methylbenzamide (7 g, 98% crude) as yellow oil, then got 2.2 g of crude was purified by basic preparative RP-HPLC method G to give 2-(3-(1,4-dioxaspiro[4.5]decan-8-yl)-1H-pyrrolo[2,3-c]pyridin-1-yl)-5-fluoro-N-isopropyl-N-methylbenzamide (Intermediate 17A) (1.2 g) as white solid. LCMS method E: $R_f$=0.668 min; (M+H)$^+$=452.1. $^1$H NMR (CD3OD): δ ppm 8.52-8.61 (m, 1H), 8.15-8.18 (m, 1H), 7.61-7.73 (m, 2H), 7.33-7.43 (m, 3H), 4.45-4.48 (m, 0.5H), 3.97 (s, 4H), 3.54-3.59 (m, 0.5H), 2.90-3.00 (m, 1H), 2.43-2.66 (m, 3H), 1.70-2.10 (m, 8H), 0.95-1.04 (m, 3H), 0.15-0.60 (m, 3H). $^{19}$F NMR (CD3OD): δ ppm −109.72~−106.43.

Step 5: 5-fluoro-N-isopropyl-N-methyl-2-(3-(4-oxocyclohexyl)-1H-pyrrolo[2,3-c]pyridin-1-yl)benzamide (Intermediate 17B)

To a solution of 2-(7-(1,4-dioxaspiro[4.5]decan-8-yl)-5H-pyrrolo[3,2-d]pyrimidin-5-yl)-5-fluoro-N-isopropyl-N-methylbenzamide (3.9 g, 8.64 mmol) in THF (30 mL) was added aq. HCl (30 mL, 3 N in H$_2$O). The resulting mixture was stirred at 40° C. (oil temperature) for 20 h The reaction mixture was adjusted by NH$_3$—H$_2$O to pH=10 and extracted with EtOAc (3×50 mL). The organic layers were washed with brine (2×100 mL), dried over anhydrous Na$_2$SO$_4$, filtered, and the filtrate was concentrated under reduced pressure to give 5-fluoro-N-isopropyl-N-methyl-2-(7-(4-oxocyclohexyl)-5H-pyrrolo[3,2-d]pyrimidin-5-yl)benzamide as yellow solid. Yield: 2.8 g (80%); LCMS method C: $R_f$=0.616 min; (M+H)$^+$=408.1. $^1$H NMR (CD3OD): δ ppm 8.55-8.65 (m, 1H), 8.20-8.25 (m, 1H), 7.80-7.84 (m, 1H), 7.67-7.75 (m, 1H), 7.36-7.50 (m, 3H), 4.43-4.49 (m, 0.5H), 3.40-3.60 (m, 1.5H), 2.44-2.80 (m, 9H), 1.90-2.05 (m, 2H), 0.95-1.13 (m, 3H), 0.18-0.60 (m, 2H). $^{19}$F NMR (CD3OD): δ ppm −113.62~−113.11.

Intermediate 17C. 5-fluoro-N-isopropyl-N-methyl-2-(3-(1,2,3,4-tetrahydroisoquinolin-6-yl)-1H-pyrrolo[2,3-c]pyridin-1-yl)benzamide

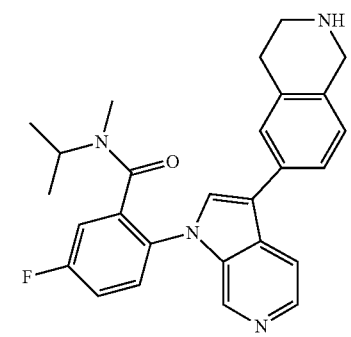 [SMILES: CC(C)N(C)C(=O)c1cc(F)ccc1-n1cc(-c2ccc3c(c2)CCNC3)c2ccncc21]

Step 1: 2-(3-bromo-1H-pyrrolo[2,3-c]pyridin-1-yl)-5-fluorobenzoic acid

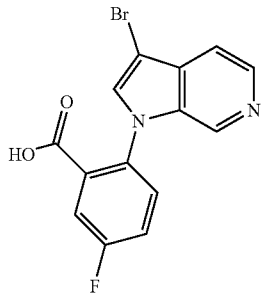 [SMILES: O=C(O)c1cc(F)ccc1-n1cc(Br)c2ccncc21]

A mixture of 3-bromo-1H-pyrrolo[2,3-c]pyridine (5 g, 25.38 mmol), 5-fluoro-2-iodobenzoic acid (6.8 g, 25.38 mmol), Cu (322 mg, 5.08 mmol) and $K_2CO_3$ (10.5 g, 76.13 mmol) in anhydrous DMF (50 mL) was stirred at 130° C. for 18 h. The mixture was concentrated under high vacuum and the residue was diluted with $H_2O$ (50 mL) and acidified to pH=3-4 with 3N aq. HCl solution. The resulting yellow solid was collected by filtration, washed with $H_2O$ (3×20 mL) and dried under high vacuum to give 2-(3-bromo-1H-pyrrolo[2,3-c]pyridin-1-yl)-5-fluorobenzoic acid as yellow solid, which was used for the next step directly without further purification. Yield: 5.8 g (68%); LCMS method C: $R_t$=0.551 min; $(M+H)^+$=334.8, 336.8 (bromo isotopes).

Step 2: 2-(3-bromo-1H-pyrrolo[2,3-c]pyridin-1-yl)-5-fluoro-N-isopropyl-N-methylbenzamide

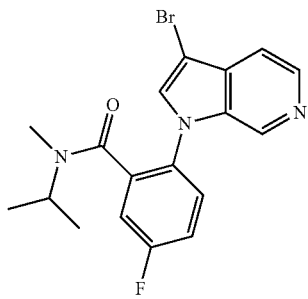 [SMILES: CC(C)N(C)C(=O)c1cc(F)ccc1-n1cc(Br)c2ccncc21]

To a solution of 2-(3-bromo-1H-pyrrolo[2,3-c]pyridin-1-yl)-5-fluorobenzoic acid (4.8 g, 14.32 mmol) in anhydrous DCM (150 mL) was added $(COCl)_2$ (18.2 g, 12 mL, 143.23 mmol) and DMF (2 mL) in turn. The mixture was stirred at 19-25° C. for 2 h under $N_2$. Additional $(COCl)_2$ (2 mL) was added and stirred at 19-25° C. for 2 h. The mixture was concentrated under reduced pressure. The residue was diluted with DCM (150 mL). DIEA (7.4 g, 57.28 mmol) and N-methylpropan-2-amine (2.1 g, 28.64 mmol) were added and the mixture was stirred at 19-25° C. for 18 h. The reaction was concentrated under reduced pressure and the residue was purified by column chromatography on silica gel (eluting with petroleum ether/EtOAc=10/1 to 2/3) to give 2-(3-bromo-1H-pyrrolo[2,3-c]pyridin-1-yl)-5-fluoro-N-isopropyl-N-methylbenzamide as brown oil. Yield: 3.8 g (68%); LCMS method C: $R_t$=0.634 min; $(M+H)^+$=389.9, 391.9 (bromo isotopes).

Step 3: tert-butyl 6-(1-(4-fluoro-2-(isopropyl(methyl)carbamoyl)phenyl)-1H-pyrrolo[2,3-c]pyridin-3-yl)-3,4-dihydroisoquinoline-2(1H)-carboxylate

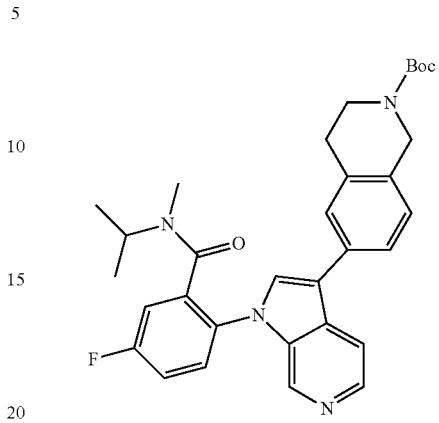

A mixture of 2-(3-bromo-1H-pyrrolo[2,3-c]pyridin-1-yl)-5-fluoro-N-isopropyl-N-methylbenzamide (100 mg, 0.26 mmol), tert-butyl 6-(4,4,5,5-tetramethyl-1,3,2-dioxaborolan-2-yl)-3,4-dihydroisoquinoline-2(1H)-carboxylate (138 mg, 0.38 mmol), $Pd(dppf)Cl_2$ (19 mg, 0.026 mmol) and $Na_2CO_3$ (68 mg, 0.64 mmol) in dioxane/$H_2O$ (3 mL/1 mL, v/v) was bubbled with $N_2$ for 5 min. The mixture was stirred at 80° C. under $N_2$ for 18 h. The mixture was diluted with $H_2O$ (20 mL), extracted with EtOAc (3×20 mL) and the combined organic layers were dried over anhydrous sodium sulfate, filtered, and concentrated under reduced pressure and purified by column chromatography on silica gel (eluting with petroleum ether/ethyl acetate=10/1 to 2/3) to give tert-butyl 6-(1-(4-fluoro-2-(isopropyl(methyl)carbamoyl)phenyl)-1H-pyrrolo[2,3-c]pyridin-3-yl)-3,4-dihydroisoquinoline-2(1H)-carboxylate) (200 mg, 96% yield) as yellow oil. LCMS method E: $R_t$=2.246 min; $(M+H)^+$ 543.2; $^1H$ NMR ($CD_3OD$): δ ppm 8.61-8.67 (m, 1H), 8.25 (d, J=1.2 Hz, 1H), 7.95 (d, J=6.0 Hz, 1H), 7.81 (s, 1H), 7.70-7.75 (m, 1H), 7.45-7.50 (m, 3H), 7.39 (d, J=2.8 Hz, 1H), 7.25 (d, J=8.0 Hz, 1H), 4.63 (s, 2H), 4.40-4.50 (m, 0.5H), 3.60-3.70 (m, 2.5H), 2.90-2.95 (m, 2H), 2.47-2.64 (m, 3H), 1.50 (s, 9H), 0.95-1.05 (m, 3H), 0.30-0.55 (m, 3H). $^{19}F$ NMR ($CD_3OD$): δ ppm −111.70.

Step 4: 5-fluoro-N-isopropyl-N-methyl-2-(3-(1,2,3,4-tetrahydroisoquinolin-6-yl)-1H-pyrrolo[2,3-c]pyridin-1-yl)benzamide To a mixture of tert-butyl 6-(1-(4-fluoro-2-(isopropyl(methyl)carbamoyl)phenyl)-1H-pyrrolo[2,3-c]pyridin-3-yl)-3,4-dihydroisoquinoline-2(1H)-carboxylate (170 mg, 0.31 mmol) in anhydrous DCM (20 mL) was added HCl-dioxane (5 mL, 4 N) at 0° C. The mixture was stirred at 16-24° C. for 2 h until LC-MS showed the reaction was complete. The mixture was concentrated under reduced pressure to give crude 5-fluoro-N-isopropyl-N-methyl-2-(3-(1,2,3,4-tetrahydroisoquinolin-6-yl)-1H-pyrrolo[2,3-c]pyridin-1-yl)benzamide (138 mg, 100% crude yield) as yellow oil, which was used for the next step directly without further purification. LCMS method E: $R_t$=1.935 min; $(M+H)^+$= 443.2; $^1H$ NMR ($CD_3OD$): δ ppm 8.59-8.65 (m, 1H), 8.25 (d, J=1.2 Hz, 1H), 7.93 (d, J=6.0 Hz, 1H), 7.77 (s, 1H), 7.70-7.75 (m, 1H), 7.35-7.50 (m, 4H), 7.16 (d, J=8.0 Hz, 1H), 4.45-4.50 (m, 0.5H), 4.00 (s, 2H), 3.60-3.65 (m, 0.5H), 3.13 (t, J=5.6 Hz, 2H), 2.92 (t, J=5.6 Hz, 2H), 2.45-2.63 (m, 3H), 1.00-1.05 (m, 3H), 0.30-0.55 (m, 3H). $^{19}$F NMR (CD$_3$OD): δ ppm −112.80.

Intermediate 18. tert-butyl 4-(5H-pyrrolo[3,2-d]pyrimidin-7-yl)piperidine-1-carboxylate

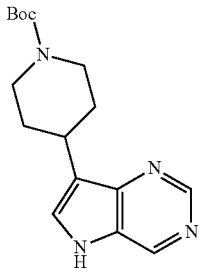 [SMILES: CC(C)(C)OC(=O)N1CCC(c2c[nH]c3cncnc23)CC1]

Step 1: tert-butyl 4-(5H-pyrrolo[3,2-d]pyrimidin-7-yl)-5,6-dihydropyridine-1(2H)-carboxylate

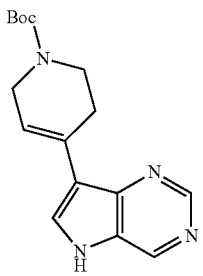 [SMILES: CC(C)(C)OC(=O)N1CC=C(c2c[nH]c3cncnc23)CC1]

To solution of 5H-pyrrolo[3,2-d]pyrimidine (2 g, 16.8 mmmol) in 1,2-ethanediol (40 mL) was added tert-butyl 4-oxopiperidine-1-carboxylate (6.7 g, 33.5 mmol) and KOH (3.8 g, 6.72 mmol). The mixture was stirred at 95° C. for 18 h. The mixture was then diluted with ethyl acetate (30 mL) and washed with brine (50 mL×3), dried over Na$_2$SO$_4$, and filtered. The filtrate was concentrated and the residue was purified by ISCO column on silica gel (from 100% DCM to DCM/MeOH=10/1) to give tert-butyl 4-(5H-pyrrolo[3,2-d]pyrimidin-7-yl)-5,6-dihydropyridine-1 (2H)-carboxylate as yellow oil. Yield: 3 g (60%); LCMS method D: R$_t$=1.679 min; (M+H)$^+$=301.2.

Step 2. tert-butyl 4-(5H-pyrrolo[3,2-d]pyrimidin-7-yl)piperidine-1-carboxylate

To a solution of tert-butyl 4-(5H-pyrrolo[3,2-d]pyrimidin-7-yl)-5,6-dihydropyridine-1(2H)-carboxylate (3 g, 10 mmol) in anhydrous MeOH-THF (20 mL) was added Pd(OH)$_2$ (0.3 g, 10%). The mixture was purged and disgassed with H$_2$ three times followed by stirring at 45° C. for 5 days under H$_2$ (50 psi). The mixture was filtered and filtrate was concentrated to give crude tert-butyl 4-(5H-pyrrolo[3,2-d]pyrimidin-7-yl)piperidine-1-carboxylate as black solid. Yield: 3 g (99% crude); LCMS method D: R$_t$=1.585 min; (M+H)$^+$=303.2.

Intermediate 19. 6-formyl-1H-indole-2-carbonitrile

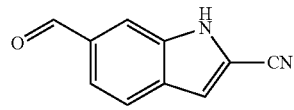 [SMILES: N#Cc1cc2ccc(C=O)cc2[nH]1]

Step 1: 6-bromo-1H-indole-2-carboxylic acid

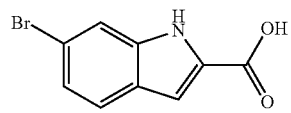 [SMILES: O=C(O)c1cc2ccc(Br)cc2[nH]1]

To a solution of ethyl 6-bromo-1H-indole-2-carboxylate (1.0 g, 3.73 mmol) in THF (15 mL) and H$_2$O (2 mL) was added LiOH*H$_2$O (313 mg, 7.46 mmol). The resulting mixture was stirred at 7-20° C. for about 20 h. The reaction mixture was then adjusted by 3N HCl to pH=7.0. The mixture was concentrated under reduced pressure to give crude 6-bromo-1H-indole-2-carboxylic acid as yellow solid, which was used for next step directly. Yield: 1.2 g; $^1$H NMR (DMSO-d6): δ ppm 7.66 (s, 1H), 7.53 (d, J=8.8 Hz, 1H), 7.11 (dd, J=8.8, 2.0 Hz, 1H), 6.94 (s, 1H).

Step 2: 6-bromo-1H-indole-2-carboxamide

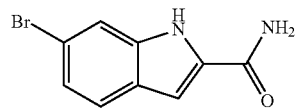 [SMILES: NC(=O)c1cc2ccc(Br)cc2[nH]1]

To a solution of 6-bromo-1H-indole-2-carboxylic acid (1.2 g, 5.0 mmol, crude) in CH$_2$Cl$_2$ (50 mL, anhydrous) was added (COCl)$_2$ (1.9 g, 15.0 mmol) and DMF (2 drops, cat., anhydrous). The resulting mixture was stirred at 50° C. for about 2 h. Then NH$_3$—H$_2$O (15 mL) was added dropwise over 5 min. The resulting mixture was stirred at 5-15° C. for about 20 h. The reaction mixture was then filtered and the filter cake was collected and dried under reduced pressure to give crude 6-bromo-1H-indole-2-carboxamide as light-yellow powder. Yield: 1.0 g (84% crude); $^1$H NMR (DMSO-d$_6$): δ ppm 11.75 (s, 1H), 7.96-8.03 (m, 2H), 7.81 (s, 1H), 7.67 (s, 1H), 7.41 (s, 1H), 7.34-7.37 (m, 1H), 7.25-7.28 (m, 1H), 7.08 (s, 1H).

Step 3: 6-bromo-1H-indole-2-carbonitrile

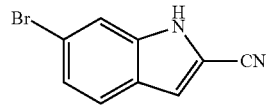

To a solution of 6-bromo-1H-indole-2-carboxamide (1.0 g, 4.2 mmol, crude) in CHCl$_3$ (15 mL) was added POCl$_3$ (2.2 g, 1.4 mL, 14.7 mmol). The resulting mixture was stirred at 70° C. under N₂ for about 20 h. The reaction mixture was diluted with water (30 mL) and adjusted by NH₃—H₂O to pH=7.0. The aqueous layer was extracted with EtOAc (2×30 mL). The organic layers were concentrated under reduced pressure. The residue was purified by column chromatography on silica gel (petroleum ether/EtOAc=20/1 to 4/1) to give 6-bromo-1H-indole-2-carbonitrile as brown powder. Yield: 850 mg (92%); ¹H NMR (CDCl₃): δ ppm 8.65 (s, 1H), 7.83 (s, 1H), 7.48 (d, J=8.8, 1H), 7.31 (d, J=8.8, 1H), 7.14 (s, 1H).

Step 4: 6-formyl-1H-indole-2-carbonitrile

To a solution of 6-bromo-1H-indole-2-carbonitrile (500 mg, 2.26 mmol) in THF (20 mL, anhydrous) was added NaH (362 mg, 9.04 mmol, 60% in mineral oil) in one portion at 10-15° C. The mixture was stirred at 10-15° C. for 15 min. The mixture was then cooled to −70° C., and t-BuLi (4.35 mL, 5.65 mmol, 1.3 M in pentane) was added dropwise via syringe and the mixture was stirred at −70° C. for 20 min. Anhydrous DMF (991 mg, 1 mL, 13.56 mmol) was added dropwise at −70° C. via syringe and the mixture was stirred at −70° C. for under N₂ for 2 h. The mixture was then quenched with saturated NH₄Cl solution (30 mL) and extracted with EtOAc (3×30 mL). The combined organic layers were washed with brine (2×40 mL), dried over anhydrous Na₂SO₄, filtered and the filtrate was concentrated under reduced pressure. The residue was diluted with EtOAc (15 mL) and the suspension was stirred for 10 min. The solid was collected by filtration and dried by concentrated under reduced pressure to give 6-formyl-1H-indole-2-carbonitrile as brown solid. Yield: 290 mg (75%); ¹H NMR (CDCl₃): δ ppm 10.00 (s, 1H), 8.16 (s, 1H), 7.89 (d, J=8.4, 1H), 7.47 (d, J=8.4, 1H), 7.30 (s, 1H).

Intermediate 20.
6-formyl-3-methyl-2-oxoindoline-3-carbonitrile

Step 1: methyl 4-(2-cyano-1-ethoxy-1-oxopropan-2-yl)-3-nitrobenzoate

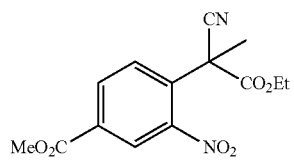 [SMILES: CCOC(=O)C(C)(C#N)c1ccc(C(=O)OC)cc1[N+](=O)[O-]]

To a 60% suspension of sodium hydride (2.0 g, 50 mmol) in dry DMF (50 mL) at 0° C. was added ethyl 2-cyanoacetate (5.33 mL, 50 mmol) dropwise. The mixture was stirred for another 30 minutes at 0° C. To the resulting gray suspension was added methyl 4-fluoro-3-nitrobenzoate (7.97 g, 40 mmol) at 0° C. The resulting deep red mixture was stirred at 0° C. for 30 minutes and warmed to RT over 2 h. The reaction mixture was cooled to 0° C., and MeI (7.8 mL) was added, followed by KOtBu (8.4 g, 75 mmol). After the addition, the mixture was stirred for 2 days at RT before being quenched with aqueous NH₄Cl solution. The mixture was extracted with EtOAc twice and the organic layers were combined and washed with H₂O and brine successively dried over anhydrous sodium sulfate, filtered and concentrated. The residue was purified by flash-chromatography to afford methyl 4-(2-cyano-1-ethoxy-1-oxopropan-2-yl)-3-nitrobenzoate. Yield 6.04 g. LCMS method B: R_t=1.42 min.

Step 2: methyl 3-cyano-3-methyl-2-oxoindoline-6-carboxylate

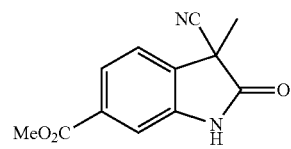 [SMILES: COC(=O)c1ccc2c(c1)NC(=O)C2(C)C#N]

To a solution of methyl 4-(2-cyano-1-ethoxy-1-oxopropan-2-yl)-3-nitrobenzoate (6.039 g, 19.72 mmol) in EtOH (60 mL) was added saturated aqueous NH₄Cl solution (15 mL) and iron powder (5.803 g, 98.61 mmol). The mixture was heated to reflux overnight. The mixture was then cooled to RT and filtered through a short pad of Celite, washed with EtOAc. The filtrate was washed with H₂O, brine, dried over anhydrous sodium sulfate, filtered, and concentrated. The residue was purified by flash-chromatography to afford methyl 3-cyano-3-methyl-2-oxoindoline-6-carboxylate. Yield 4.404 g. LCMS method B: R_t=1.07 min; (M+H)⁺=231.1.

Step 3: 6-(hydroxymethyl)-3-methyl-2-oxoindoline-3-carbonitrile

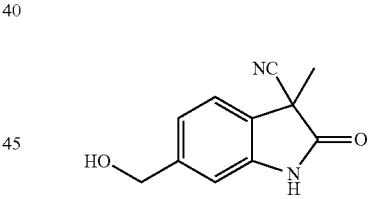

To a solution of methyl 3-cyano-3-methyl-2-oxoindoline-6-carboxylate (2.101 g, 9.12 mmol) in dry THF (40 mL) under N₂ atmosphere was added a solution of LiBH₄ (9.1 mL, 18.2 mmol), followed by MeOH (0.2 mL). The mixture was heated to reflux for 2 h before being quenched with aqueous NH₄Cl solution. The mixture was extracted with EtOAc twice and the organic layers were combined and washed with H₂O and brine successively, dried over anhydrous sodium sulfate, filtered, and concentrated. The residue was purified by flash-chromatography to afford 6-(hydroxymethyl)-3-methyl-2-oxoindoline-3-carbonitrile. Yield 1.42 g. LCMS method B: R_t=0.79 min; (M+H)⁺=203.1.

Step 4: 6-formyl-3-methyl-2-oxoindoline-3-carbonitrile

To a solution of 6-(hydroxymethyl)-3-methyl-2-oxoindoline-3-carbonitrile (0.597 g, 2.95 mmol) in DCM was added active MnO₂ (2.57 g, 29.56 mmol). The mixture was stirred at RT for overnight before being filtered through a short pad of Celite. The filtrate was concentrated to remove solvent and the resulting residue was purified by flash-chromatography to afford 6-formyl-3-methyl-2-oxoindoline-3-carbonitrile. Yield 0.347 g. LCMS method B: $R_t$=1.25 min.

Intermediate 21.
N-(trans-4-formylcyclohexyl)methanesulfonamide

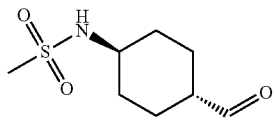

Step 1: trans-methyl 4-(methylsulfonamido)cyclohexanecarboxylate

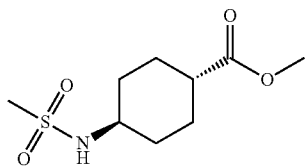

To a solution of trans-methyl 4-aminocyclohexanecarboxylate hydrochloride (7.0 g, 36.14 mmol) in 200 mL of anhydrous $CH_2Cl_2$ was added $(MeSO_2)_2O$ (7.5 g, 43.37 mmol) and $Et_3N$ (11.0 g, 108.42 mmol). The resulting mixture was stirred at 8-18° C. for 18 h. The reaction mixture was adjusted to pH=6-7 by 1N aq. HCl. The mixture was concentrated under reduced pressure and extracted with EtOAc (3×150 mL). The combined organic layers was washed with brine (2×100 mL), dried over anhydrous $Na_2SO_4$ and concentrated under reduced pressure to give trans-methyl 4-(methylsulfonamido)cyclohexanecarboxylate as white solid. Yield: 9.0 g (100% crude); $^1$H NMR ($CD_3OD$): δ ppm 3.65 (s, 3H), 3.15-3.25 (m, 1H), 2.95 (s, 3H), 2.20-2.35 (m, 1H), 1.95-2.10 (m, 4H), 1.40-1.60 (m, 2H), 1.25-1.40 (m, 2H).

Step 2: N-(trans-4-formylcyclohexyl)methanesulfonamide

A solution of trans-methyl 4-(methylsulfonamido)cyclohexanecarboxylate (4.0 g, 17.00 mmol) in anhydrous toluene (100 mL) was degassed and purged with $N_2$ 3 times followed by cooling to −75° C. A solution of DIBAL-H (11.9 mL, 11.90 mol, 1M in toluene) was added dropwise under $N_2$ (keeping the internal temperature below −70° C.). After addition, the mixture was stirred vigorously at −75° C. for 3 h. MeOH (5 mL) was added dropwise below −70° C. followed by addition of a solution of saturated Rochell salt (aq., 200 mL) dropwise at −70° C. and EtOAc (200 mL). The mixture was warmed to RT and stirred at RT for 18 h. The aqueous layer was separated and extracted with EtOAc (2×200 mL). The combined organic layer was dried over anhydrous $Na_2SO_4$, filtered, and concentrated under reduced pressure. The crude product was then purified by column chromatography on silica gel (petroleum ether/EtOAc=1/1) to give N-(trans-4-formylcyclohexyl)methanesulfonamide as white solid. Yield: 2.0 g (57%); $^1$H NMR (MeOD): δ9.59 (s, 1H), 3.10-3.25 (m, 1H), 2.90-3.00 (m, 3H), 2.10-2.30 (m, 1H), 1.85-2.10 (m, 4H), 1.30-1.45 (m, 2H), 1.10-1.30 (m, 2H).

Intermediate 22. tert-butyl (trans-3-formylcyclobutyl)carbamate

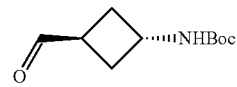 [SMILES: CC(C)(C)OC(=O)N[C@H]1C[C@H](C=O)C1]

A mixture of tert-butyl (trans-3-(hydroxymethyl)cyclobutyl)carbamate (250 mg, 1.24 mmol) and PCC (535 mg, 2.48 mmol) in anhydrous DCM (12 mL) was stirred at 19-28° C. for 18 h until TLC (petroleum ether: ethyl acetate=3:1) showed the reaction was complete. The mixture was filtered and the filtrate was concentrated under reduced pressure below 35° C. The residue was purified by column chromatography on silica gel (eluting with petroleum ether/ EtOAc=4/1 to 2/1) to give tert-butyl (trans-3-formylcyclobutyl)carbamate as colourless oil. Yield: 240 mg (96%); $^1$H NMR ($CDCl_3$): δ ppm 9.76 (d, J=2.0 Hz, 1H), 4.65-4.70 (m, 1H), 2.95-3.00 (m, 1H), 2.55-2.65 (m, 2H), 2.05-2.10 (m, 2H), 1.37 (s, 9H).

Intermediate 23. tert-butyl (trans-4-(2-oxoethyl)cyclohexyl)carbamate

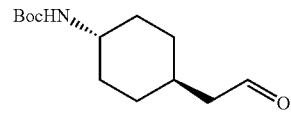 [SMILES: CC(C)(C)OC(=O)N[C@H]1CC[C@H](CC=O)CC1]

A mixture of tert-butyl (trans-4-(2-hydroxyethyl)cyclohexyl)carbamate (250 mg, 1.03 mmol) and PCC (444 mg, 2.06 mmol) in anhydrous DCM (10 mL) was stirred at 5-17° C. for 2 h. The mixture was filtered and the filtrate was concentrated under reduced pressure. The residue was purified by column chromatograph on silica gel (eluting with petroleum ether/ethyl acetate=3/1) to give tert-butyl (trans-4-(2-oxoethyl)cyclohexyl)carbamate as white solid. Yield: 190 mg (76%); $^1$H NMR ($CDCl_3$): δ ppm 9.69 (s, 1H), 4.30-4.34 (m, 1H), 3.32-3.35 (m, 1H), 2.26 (d, J=6.4 Hz, 2H), 1.93-1.98 (m, 2H), 1.70-1.77 (m, 3H), 1.37 (s, 9H), 1.01-1.09 (m, 4H).

Intermediates 24-24A. 2-(5-formyl-2-oxo-2,3-dihydro-1H-benzo[d]imidazol-1-yl)ethyl formate (Intermediate 24) and 1-(2-hydroxyethyl)-2-oxo-2,3-dihydro-1H-benzo[d]imidazole-5-carbaldehyde (Intermediate 24A)

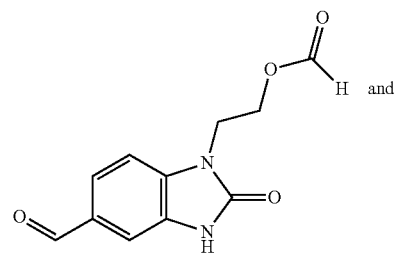

-continued

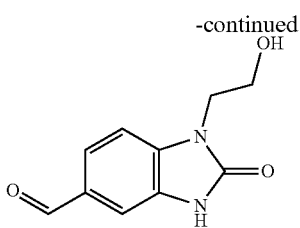

Step 1.
4-((2-hydroxyethyl)amino)-3-nitrobenzonitrile

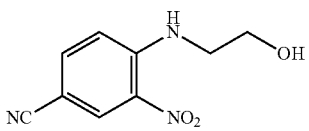 [SMILES: N#Cc1ccc(NCCO)c([N+](=O)[O-])c1]

To a solution of 4-fluoro-3-nitrobenzonitrile (15 g, 90.4 mmol) and 2-aminoethanol (11.0 g, 180.7 mmol) in anhydrous DMF (600 mL) was added $K_2CO_3$ (37.4 g, 271.2 mmol) under $N_2$, then the reaction mixture was stirred at 25° C. for 2 h. The reaction mixture was filtered and the filtrate was concentrated under reduced pressure. The residue was washed with $H_2O$ (100 mL) and the mixture was extracted with EtOAc (3×500 mL). The organic layers were washed with brine (20 mL), dried over anhydrous $Na_2SO_4$, filtered, and concentrated to afford 4-((2-hydroxyethyl)amino)-3-nitrobenzonitrile. The residue was used for the next step without further purification as a yellow solid. Yield: 17.3 g. LCMS method E: $R_t$=1.016 min; $(M+H)^+$=207.9.

Step 2.
3-amino-4-((2-hydroxyethyl)amino)benzonitrile

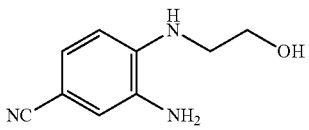

To a solution of 4-((2-hydroxyethyl)amino)-3-nitrobenzonitrile (17.3 g, 83.6 mmol) in EtOH (800 mL) and $H_2O$ (400 mL) were added Fe (23.4 g, 418.0 mmol) and $NH_4Cl$ (44.8 g, 836.0 mmol) under $N_2$ and the reaction mixture was stirred at 80° C. for 2 h. The reaction mixture was filtered and the filtrate was concentrated under reduced pressure. The resulting residue was dissolved in EtOAc (500 mL), washed with $H_2O$ (2×100 mL), brine (20 mL), dried over anhydrous $Na_2SO_4$, filtered, and concentrated to afford 3-amino-4-((2-hydroxyethyl)amino)benzonitrile. The residue was used for the next step without further purification as a brown red solid. Yield: 11.6 g. LCMS Method D: $R_t$=0.941 min; $(M+H)^+$=178.2.

Step 3. 3-amino-4-((2-((tert-butyldimethylsilyl)oxy)ethyl)amino)benzonitrile

To a solution of 3-amino-4-((2-hydroxyethyl)amino)benzonitrile (11.6 g, 65.46 mmol) and tert-butylchlorodimethylsilane (11.84 g, 78.55 mmol) in anhydrous DMF (300 mL) was added imidazole (11.14 g, 163.65 mmol), then the reaction was stirred at 35° C. for 16 h. The reaction mixture was filtered and the filtrate was concentrated under reduced pressure. The reaction mixture was added to water (1000 mL) and extracted with EtOAc (3×500 mL). The organic layer was washed with brine (100 mL), dried over anhydrous $Na_2SO_4$, filtered, and concentrated under reduced pressure to afford 3-amino-4-((2-((tert-butyldimethylsilyl)oxy)ethyl)amino)benzonitrile as a black oil, which was used for the next step without further purification. Yield: 25 g. LCMS method C: $R_t$=0.878 min; $(M+H)^+$=292.1

Step 4. 1-(2-((tert-butyldimethylsilyl)oxy)ethyl)-2-oxo-2,3-dihydro-1H-benzo[d]imidazole-5-carbonitrile

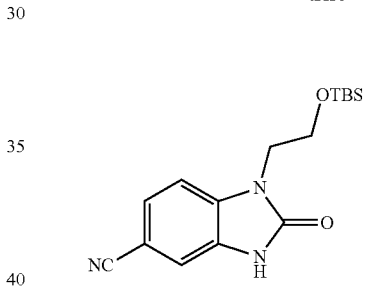

To a solution of 3-amino-4-((2-((tert-butyldimethylsilyl)oxy)ethyl)amino)benzonitrile (14 g, 48.1 mmol) in anhydrous THF (400 mL) was added a solution of bis(trichloromethyl)carbonate (BTC, 28.5 g, 96.2 mmol) at at 0° C. Then $Et_3N$ (33 mL) was added dropwise to the mixture under at 0° C. After addition, the reaction was stirred at 25° C. for 2 h. The reaction was poured into sat. aq. $NaHCO_3$ (500 mL), extracted with EtOAc (3×300 mL). The organic layer was washed with brine, dried over anhydrous $Na_2SO_4$, filtered, and concentrated. The residue was purified by column chromatograph on silica gel (eluting with petroleum ether:EtOAc=5:1 to 1:1) to afford 1-(2-((tert-butyldimethylsilyl)oxy)ethyl)-2-oxo-2,3-dihydro-1H-benzo[d]imidazole-5-carbonitrile. Yield: 4.8 g (31%). LCMS method F: $R_t$=1.378 min. $(M+H)^+$=318.3 $^1H$ NMR ($CDCl_3$): δ 10.06 (brs, 1H), 7.31 (d, J=8.4 Hz, 1H), 7.16 (s, 1H), 7.11 (d, J=8.0 Hz, 1H), 3.94-3.96 (m, 2H), 3.83-3.85 (m, 2H), 0.67 (s, 9H), −0.198 (s, 6H).

Step 5. 1-(2-hydroxyethyl)-2-oxo-2,3-dihydro-1H-benzo[d]imidazole-5-carbaldehyde (Intermediate 24A) and 2-(5-formyl-2-oxo-2,3-dihydro-1H-benzo[d]imidazol-1-yl)ethyl Formate (Intermediate 24)

To a solution of 1-(2-((tert-butyldimethylsilyl)oxy)ethyl)-2-oxo-2,3-dihydro-1H-benzo[d]imidazole-5-carbonitrile (6.1 g, 19.2 mmol) in HCOOH (120 mL) and H₂O (40 mL) was added Ni—Al (8.27 g, 96.2 mmol) under N₂, then the reaction mixture was stirred at 90° C. for 16 h. The reaction mixture was then filtered and the filtrate was concentrated under reduced pressure. The residue was purified by column chromatograph on silica gel (eluting with DCM:MeOH=10:1) to afford 1-(2-hydroxyethyl)-2-oxo-2,3-dihydro-1H-benzo[d]imidazole-5-carbaldehyde (Intermediate 24A) as a white solid and 2-(5-formyl-2-oxo-2,3-dihydro-1H-benzo[d]imidazol-1-yl)ethyl formate (Intermediate 24) as a yellow solid.

Intermediate 24. 2-(5-formyl-2-oxo-2,3-dihydro-1H-benzo[d]imidazol-1-yl)ethyl formate: Yield: 1.7 g (27%). LCMS method F: $R_t$=0.858 min; (M+H)⁺=235.2 ¹H NMR (DMSO-d₆): δ 11.27 (brs, 1H), 9.87 (s, 1H), 8.12 (s, 1H), 7.63 (dd, J=8.0, 1.2 Hz, 1H), 7.42 (s, 1H), 7.37 (d, J=8.0 Hz, 1H), 4.35-4.38 (m, 2H), 4.12-4.14 (m, 2H).

Intermediate 24A. 1-(2-hydroxyethyl)-2-oxo-2,3-dihydro-1H-benzo[d]imidazole-5-carbaldehyde: Yield: 1.5 g (27%). LCMS method F: $R_t$=0.788 min; (M+H)⁺=207.2 ¹H NMR (DMSO-d₆): δ 11.20 (brs, 1H), 9.86 (s, 1H), 7.60 (d, J=8.0 Hz, 1H), 7.40 (s, 1H), 7.31 (d, J=8.0 Hz, 1H), 4.86 (s, 1H), 3.85-3.86 (m, 2H), 3.63-3.65 (m, 2H).

Example 1. 5-((7-(5-(4-fluoro-2-(trifluoromethyl) phenoxy)pyrimidin-4-yl)-2,7-diazaspiro[4.4]nonan-2-yl)methyl)-1H-benzo[d]imidazol-2(3H)-one

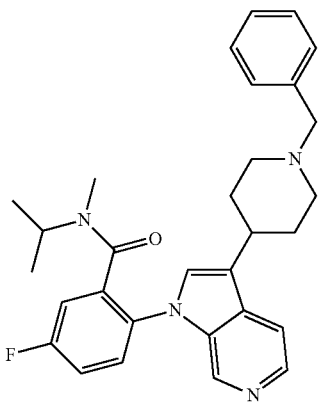 [SMILES: CC(C)N(C)C(=O)c1cc(F)ccc1-n1cc(C2CCN(Cc3ccccc3)CC2)c2ccncc21]

Step 1: 5-fluoro-N-isopropyl-N-methyl-2-(3-(piperidin-4-yl)-1H-pyrrolo[2,3-c]pyridin-1-yl)benzamide

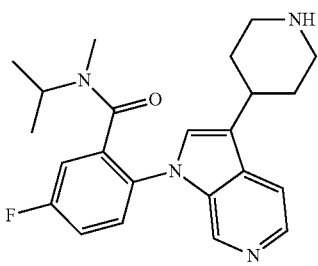 [SMILES: CC(C)N(C)C(=O)c1cc(F)ccc1-n1cc(C2CCNCC2)c2ccncc21]

To a mixture of tert-butyl 4-(1-(4-fluoro-2-(isopropyl (methyl)carbamoyl)phenyl)-1H-pyrrolo[2,3-c]pyridin-3-yl) piperidine-1-carboxylate (Intermediate 1, 840 mg, 1.69 mmol) in CH₂Cl₂ (20 mL) was added HCl-dioxane (3 mL) under ice-cold water. The mixture was stirred at RT for 2 h. The mixture was then concentrated under reduced pressure and the residue was basified to pH=10-12 with 10% NaOH solution, and extracted with DCM/isopropanol=10/1 (3×40 mL). The combined organic layers were dried over anhydrous sodium sulfate, filtered, and the filtrate was concentrated under reduced pressure to give 5-fluoro-N-isopropyl-N-methyl-2-(3-(piperidin-4-yl)-1H-pyrrolo[2,3-c]pyridin-1-yl)benzamide as yellow oil, which was used for the next step directly without further purification. Yield: 640 mg (96% crude); LCMS method B: $R_t$=0.758 min; (M+H)⁺=395.4. ¹H NMR (CD3OD): δ ppm 8.53-8.61 (m, 1H), 8.15-8.19 (m, 1H), 7.74-7.76 (d, J=5.2 Hz, 1H), 7.62-7.68 (m, 1H), 7.33-7.45 (m, 3H), 4.43-4.47 (m, 0.5H), 3.55-3.58 (m, 0.5H), 3.15-3.25 (m, 2H), 3.00-3.10 (m, 1H), 2.85-2.95 (m, 2H), 2.43-2.65 (m, 3H), 2.09 (d, J=12.8 Hz, 2H), 1.70-1.85 (m, 2H), 0.95-1.05 (m, 3H), 0.20-0.55 (m, 3H). ¹⁹F NMR (CD3OD): δ ppm −113.21~−113.49.

Step 2: 2-(3-(1-benzylpiperidin-4-yl)-1H-pyrrolo[2,3-c]pyridin-1-yl)-5-fluoro-N-isopropyl-N-methyl-benzamide A mixture of 5-fluoro-N-isopropyl-N-methyl-2-(3-(piperidin-4-yl)-1H-pyrrolo[2,3-c]pyridin-1-yl)benzamide (25 mg, 0.06 mmol), benzaldehyde (13 mg, 0.13 mmol), NaBH₃CN (15 mg, 0.24 mmol) in MeOH (4 mL) was stirred at 70° C. for 17 h. The mixture was then concentrated under reduced pressure. The residue was purified by basic preparative RP-HPLC method D to give 2-(3-(1-benzylpiperidin-4-yl)-1H-pyrrolo[2,3-c]pyridin-1-yl)-5-fluoro-N-isopropyl-N-methylbenzamide as white solid. Yield: 7.6 mg (25%); LCMS method E: $R_t$=0.907 min; (M+H)⁺=485.4. ¹H NMR (CD3OD): δ ppm 8.50-8.60 (m, 1H), 8.13-8.17 (m, 1H), 7.73-7.74 (d, J=5.2 Hz, 1H), 7.55-7.65 (m, 1H), 7.20-7.45 (m, 8H), 4.43-4.46 (m, 1H), 3.61 (s, 2H) 3.00-3.07 (m, 2H) 2.85-2.94 (m, 1H), 2.42-2.63 (m, 3H), 2.20-2.30 (m, 2H), 1.84-2.04 (m, 4H), 0.98-1.03 (m, 3H), 0.20-0.51 (m, 3H). ¹⁹F NMR (CD3OD): δ ppm −113.33~−113.62.

Examples 2-17

The following Examples were synthesized by method described above for Example 1.

TABLE 3

| Ex No. | Structural formula | Name | LCMS method; Rt in min; [M + H]+ |
|---|---|---|---|
| | | 2-(3-(1-((2-cyano-4-methyl-1H-indol-5-yl)methyl)piperidin-4-yl)-1H-pyrrolo[2,3-c]pyridin-1-yl)-5-fluoro-N-isopropyl-N-methylbenzamide | D; 0.766 min; 563.4 |

$^1$H NMR (CD3OD): δ 8.87-8.96 (m, 1H), 8.28-8.34 (m, 2H), 8.07-8.10 (d, J = 12.8 Hz, 1H), 7.70 (s, 1H), 7.41-7.49 (m, 4H), 4.56 (s, 2H), 4.30-4.35 (m, 1H) 3.68-3.71 (d, J = 11.6 Hz, 2H) 3.36-3.47 (m, 3H), 2.50-2.75 (m, 4H), 2.31-2.34 (d, J = 13.6 Hz, 2H), 1.95-2.10 (m, 2H), 1.09 (s, 3H), 0.05-0.55 (m, 6H). $^{19}$F NMR (CD3OD): δ −110.49~−110.69.

| Ex No. | Structural formula | Name | LCMS method; Rt in min; [M + H]+ |
|---|---|---|---|
| | | 5-((7-(5-(2,4-dichlorophenoxy)pyrimidin-4-yl)-2,7-diazaspiro[4.4]nonan-2-yl)methyl)-1H-benzo[d]imidazol-2(3H)-one | E; 0.938; 499.4 |

$^1$H NMR (CD3OD): δ ppm 8.31-8.40 (m, 1H), 7.94-7.97 (m, 1H), 7.54-7.55 (d, J = 5.2 Hz, 1H), 7.35-7.45 (m, 1H), 7.15-7.25 (m, 2H), 6.90-7.15 (m, 6H), 4.21-4.28 (m, 1H) 3.34-3.37 (m, 1H) 2.96-2.98 (m, 2H), 2.60-2.75 (m, 3H), 2.20-2.50 (m, 4H), 2.05-2.14 (m, 2H), 1.80-1.90 (m, 2H), 1.60-1.75 (m, 2H), 0.77-0.82 (m, 3H), 0.00-0.31 (m, 3H). $^{19}$F NMR (CD3OD): δ ppm −113.29~−113.57.

| Ex No. | Structural formula | Name | LCMS method; Rt in min; [M + H]+ |
|---|---|---|---|
|  | 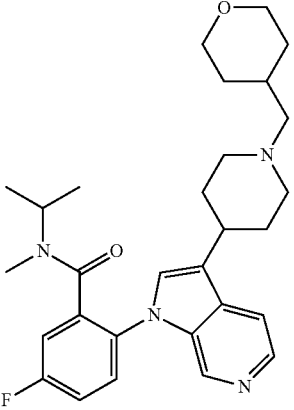 [SMILES: CC(C)N(C)C(=O)c1cc(F)ccc1-n1cc(C2CCN(CC3CCOCC3)CC2)c2ccncc21] | 5-fluoro-N-isopropyl-N-methyl-2-(3-(1-((tetrahydro-2H-pyran-4-yl)methyl)piperidin-4-yl)-1H-pyrrolo[2,3-c]pyridin-1-yl)benzamide | E: 0.850; 493.4 |

$^{1}$H NMR (CD3OD): δ ppm 8.32-8.41 (m, 1H), 7.90-7.98 (m, 1H), 7.54 (d, J = 5.6 Hz, 1H), 7.40-7.50 (m, 1H), 7.10-7.25 (m, 3H), 4.22-4.29 (m, 1H), 3.70-3.80 (m, 2H), 3.15-3.40 (m, 3H), 2.65-2.90 (m, 3H), 2.23-2.46 (m, 3H), 2.10 (d, J = 7.2 Hz, 2H), 1.90-2.00 (m, 2H), 1.75-1.85 (m, 2H), 1.60-1.70 (m, 3H), 1.45-1.55 (m, 2H), 1.00-1.15 (m, 2H), 0.75-0.90 (m, 2H), 0.00-0.33 (m, 3H). $^{19}$F NMR (CD3OD): δ ppm −113.30~−113.61.

| | | | |
|---|---|---|---|
| 5 | 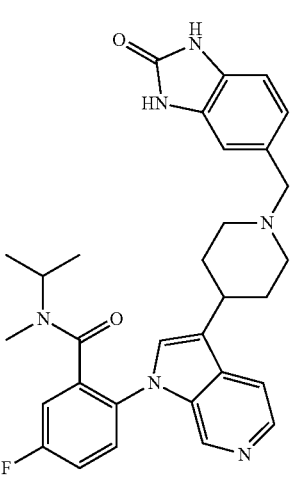 [SMILES: CC(C)N(C)C(=O)c1cc(F)ccc1-n1cc(C2CCN(Cc3ccc4[nH]c(=O)[nH]c4c3)CC2)c2ccncc21] | 5-fluoro-N-isopropyl-N-methyl-2-(3-(1-((2-oxo-2,3-dihydro-1H-benzo[d]imidazol-5-yl)methyl)piperidin-4-yl)-1H-pyrrolo[2,3-c]pyridin-1-yl)benzamide | D; 0.834; 541.5 |

$^{1}$H NMR (CD3OD): δ ppm 8.32-8.41 (m, 1H), 7.95-7.98 (m, 1H), 7.54 (d, J = 5.2 Hz, 1H), 7.35-7.50 (m, 1H), 7.10-7.30 (m, 3H), 6.81-6.91 (m, 3H), 4.24-4.27 (m, 1H), 3.44 (s, 2H), 2.86-2.89 (d, J = 10.8 Hz, 2H), 2.65-2.75 (m, 3H), 2.23-2.46 (m, 3H), 2.05-2.11 (m, 2H), 1.83-1.86 (m, 2H), 1.65-1.74 (m, 2H), 0.79-0.84 (m, 3H), 0.01-0.31 (m, 3H). $^{19}$F NMR (CD3OD): δ ppm −113.59~−113.30.

TABLE 3-continued

| Ex No. | Structural formula | Name | LCMS method; Rt in min; [M + H]+ |
|---|---|---|---|
| | 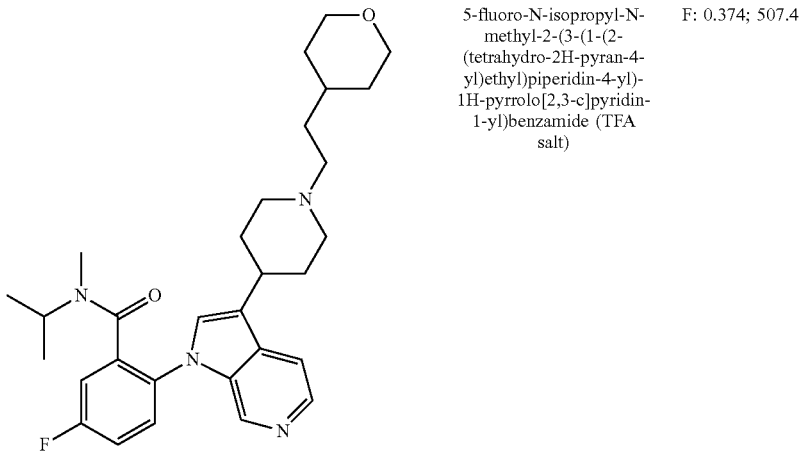 | 5-fluoro-N-isopropyl-N-methyl-2-(3-(1-(2-(tetrahydro-2H-pyran-4-yl)ethyl)piperidin-4-yl)-1H-pyrrolo[2,3-c]pyridin-1-yl)benzamide (TFA salt) | F: 0.374; 507.4 |

$^1$H NMR (CD3OD): δ ppm 8.88-8.99 (m, 1H), 8.36 (s, 2H), 8.10-8.18 (m, 1H), 7.74 (dd, J = 8.4 4.8 Hz, 1H), 7.40-7.55 (m, 2H), 3.90-4.00 (m, 2H), 3.70-3.80 (m, 2H), 3.85-4.00 (m, 4H), 3.15-3.30 (m, 4H), 2.63 (s, 3H), 2.25-2.40 (m, 2H), 2.05-2.25 (m, 2H), 1.60-1.78 (m, 5H), 1.25-1.40 (m, 2H), 0.50-1.20 (m, 6H).
$^{19}$F NMR (CD3OD): δ ppm −77.24, −110.46~−110.66.

| | 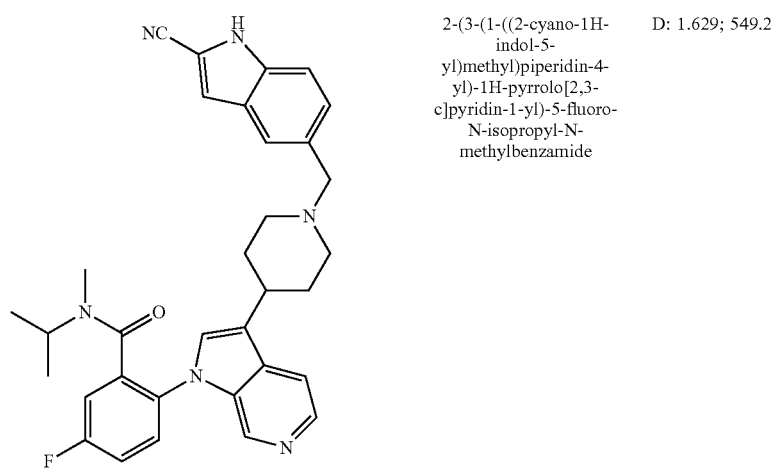 | 2-(3-(1-((2-cyano-1H-indol-5-yl)methyl)piperidin-4-yl)-1H-pyrrolo[2,3-c]pyridin-1-yl)-5-fluoro-N-isopropyl-N-methylbenzamide | D: 1.629; 549.2 |

$^1$H NMR (CD3OD): δ ppm 8.86-9.04 (m, 1H), 8.26-8.43 (m, 2H), 8.10-8.16 (m, 1H), 7.92 (s, 1H), 7.70-7.76 (m, 1H), 7.58-7.65 (m, 1H), 7.44-7.56 (m, 3H), 7.32 (s, 1H), 4.35-4.55 (m, 2.5H), 3.65-3.75 (m, 2.5H), 3.38-3.46 (m, 1H), 3.24-3.31 (m, 2H), 2.63 (s, 3H), 2.30-2.39 (m, 2H), 1.98-2.18 (m, 2H), 0.52-1.17 (m, 6H). $^{19}$F NMR (CD3OD): δ ppm −110.57~−110.40, −77.17.

TABLE 3-continued

| Ex No. | Structural formula | Name | LCMS method; Rt in min; [M + H]+ |
|---|---|---|---|
| 8 | 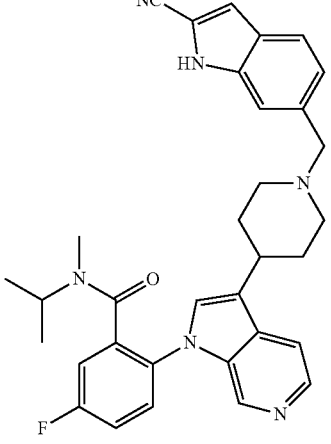 | 2-(3-(1-((2-cyano-1H-indol-6-yl)methyl)piperidin-4-yl)-1H-pyrrolo[2,3-c]pyridin-1-yl)-5-fluoro-N-isopropyl-N-methylbenzamide | D; 1.665; 549.3 |

1H NMR (CD3OD): δ ppm 8.49-8.65 (m, 1H), 8.15-8.20 (m, 1H), 7.75-7.78 (m, 1H), 7.58-7.70 (m, 2H), 7.30-7.50 (m, 5H), 7.21 (s, 1H), 4.44-4.50 (m, 0.5H), 3.72 (s, 2H), 3.50-3.65 (m, 1H), 3.05-3.15 (m, 2H), 2.80-2.99 (m, 1H), 2.42-2.69 (m, 3H), 2.25-2.35 (m, 2H), 2.00-2.12 (m, 2H), 1.79-1.96 (m, 2H), 0.87-1.17 (m, 3H), 0.20-0.55 (m, 3H). 19F NMR (CD3OD): δ ppm −113.56~−113.29.

| | 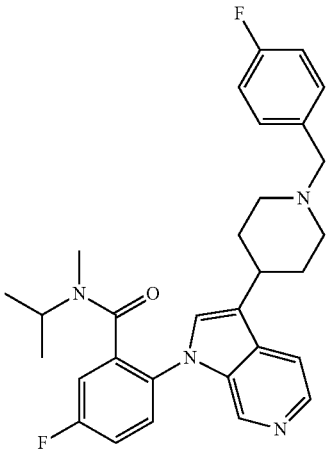 [SMILES: CC(C)N(C)C(=O)c1cc(F)ccc1-n1cc(C2CCN(Cc3ccc(F)cc3)CC2)c2ccncc21] | 5-fluoro-2-(3-(1-(4-fluorobenzyl)piperidin-4-yl)-1H-pyrrolo[2,3-c]pyridin-1-yl)-N-isopropyl-N-methylbenzamide | E; 0.919; 503.3 |

1H NMR (CD3OD): δ ppm 8.30-8.40 (m, 1H), 7.90-7.98 (m, 1H), 7.53 (d, J = 5.6 Hz, 1H), 7.35-7.45 (m, 1H), 7.10-7.25 (m, 5H), 6.80-6.90 (m, 2H), 4.21-4.28 (m, 0.5H) 3.34-3.39 (m, 2.5H) 2.60-2.85 (m, 3H), 2.23-2.45 (m, 3H), 2.00-2.10 (m, 2H), 1.75-1.85 (m, 2H), 1.55-1.75 (m, 2H), 0.75-0.85 (m, 3H), 0.00-0.35 (m, 3H).
19F NMR (CD3OD): δ ppm −117.59, −113.57~−113.30, −76.95.

TABLE 3-continued

| Ex No. | Structural formula | Name | LCMS method; Rt in min; [M + H]+ |
|---|---|---|---|
| | 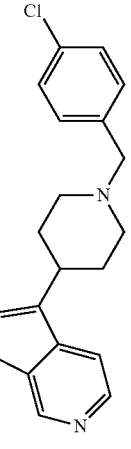 | 2-(3-(1-(4-chorobenzyl)piperidin-4-yl)-1H-pyrrolo[2,3-c]pyridin-1-yl)-5-fluoro-N-isopropyl-N-methylbenzamide | D; 0.964; 519.3 |

$^1$H NMR (CD$_3$OD): δ pm 8.30-8.40 (m, 1H), 7.94-7.98 (m, 1H), 7.53-7.54 (d, J = 6.0 Hz, 1H), 7.40-7.47 (m, 1H), 7.10-7.25 (m, 7H), 4.22-4.28 (0.5H) 3.34-3.38 (m, 2.5H) 2.68-2.83 (m, 3H), 2.22-2.45 (m, 3H), 2.02-2.08 (m, 2H), 1.75-1.85 (m, 2H), 1.55-1.70 (m, 2H), 0.75-0.85 (m, 3H), 0.00-0.35 (m, 3H). $^{19}$F NMR (CD3OD): δ ppm −113.58~113.29, −76.95.

| | 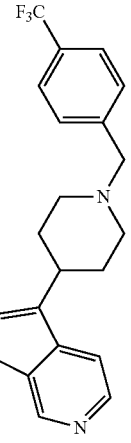 | 5-fluoro-N-isopropyl-N-methyl-2-(3-(1-(4-(trifluoromethyl)benzyl)piperidin-4-yl)-1H-pyrrolo[2,3-c]pyridin-1-yl)benzamide | D; 0.804; 553.3 |

$^1$H NMR (CD3OD): δ ppm 8.85-9.10 (m, 1H), 8.25-8.40 (m, 1H), 8.10-8.20 (m, 1H), 7.70-7.95 (m, 5H), 7.40-7.60 (m, 2H), 4.51 (s, 2H), 3.60-3.80 (m, 3H), 3.30-3.55 (m, 3H), 2.64 (s, 3H), 2.25-2.45 (m, 2H), 2.00-2.25 (m, 2H), 0.50-1.40 (m, 6H). $^{19}$F NMR (CD3OD): δ ppm −110.51~−110.36, −77.34, −64.46.

TABLE 3-continued

| Ex No. | Structural formula | Name | LCMS method; Rt in min; [M + H]+ |
|---|---|---|---|
| | 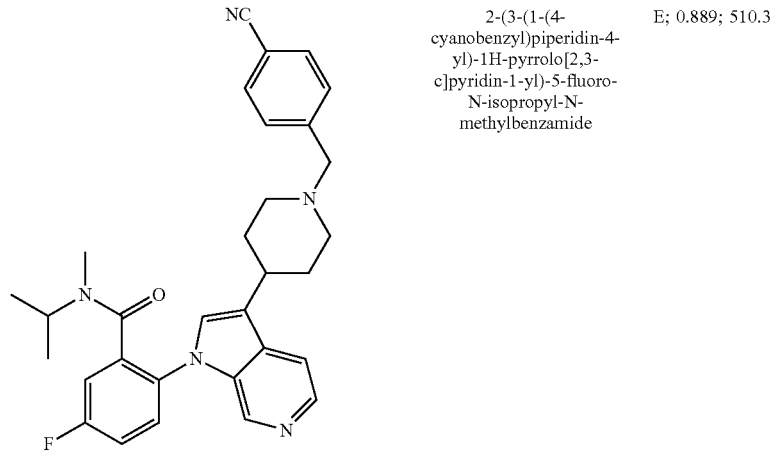 | 2-(3-(1-(4-cyanobenzyl)piperidin-4-yl)-1H-pyrrolo[2,3-c]pyridin-1-yl)-5-fluoro-N-isopropyl-N-methylbenzamide | E; 0.889; 510.3 |
| | 1H NMR (CD3OD): δ ppm 8.33-8.41 (m, 1H), 7.95-7.98 (m, 1H), 7.50-7.55 (m, 3H), 7.40-7.50 (m, 1H), 7.38 (d, J = 8.4 Hz, 2H), 7.13-7.26 (m, 3H), 4.24-4.28 (m, 0.5H), 3.47 (s, 2H), 3.35-3.38 (m, 0.5H), 2.65-2.85 (m, 3H), 2.46 (S, 1.5H), 2.23 (s, 1.5H), 2.05-2.77 (m, 2H), 1.80-1.86 (m, 2H), 1.60-1.75 (m, 2H), 0.79-0.85 (m, 3H), 0.00-0.35 (m, 3H). 19F NMR (CD3OD): δ ppm −113.57~−113.29. | | |
| | 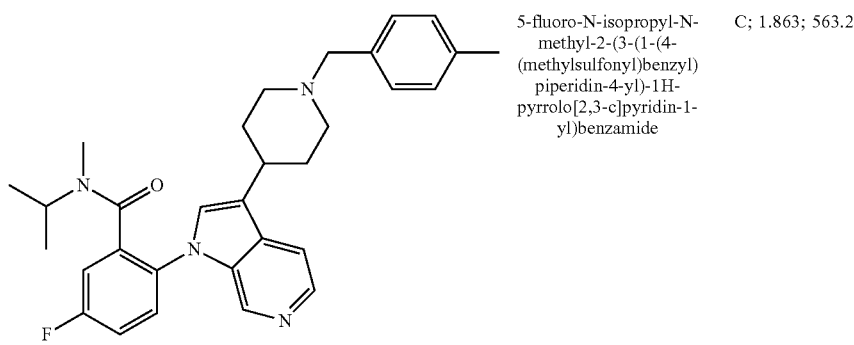 | 5-fluoro-N-isopropyl-N-methyl-2-(3-(1-(4-(methylsulfonyl)benzyl)piperidin-4-yl)-1H-pyrrolo[2,3-c]pyridin-1-yl)benzamide | C; 1.863; 563.2 |
| | 1H NMR (CD3OD): δ ppm 8.53-8.63 (s, 1H), 8.10-8.20 (m, 1H), 7.96 (d, J = 8.0 Hz, 2H), 7.75 (d, J = 5.6 Hz, 1H), 7.60-7.69 (m, 3H), 7.35-7.50 (m, 2H), 7.30-7.35 (m, 1H), 4.40-4.50 (m, 0.5 H), 3.72 (s, 3H), 3.50-3.60 (m, 1H), 3.13 (s, 3H), 3.00-3.05 (m, 2H), 2.85-2.97 (m, 1H), 2.40-2.70 (m, 3H), 2.25-2.35 (m, 2H), 2.00-2.10 (m, 2H), 1.75-1.95 (m, 2H), 0.95-1.10 (m, 3H), 0.21-0.52 (m, 3H). 19F NMR (CD3OD): δ ppm −113.26~113.52. | | |

TABLE 3-continued

| Ex No. | Structural formula | Name | LCMS method; Rt in min; [M + H]+ |
|---|---|---|---|
| | 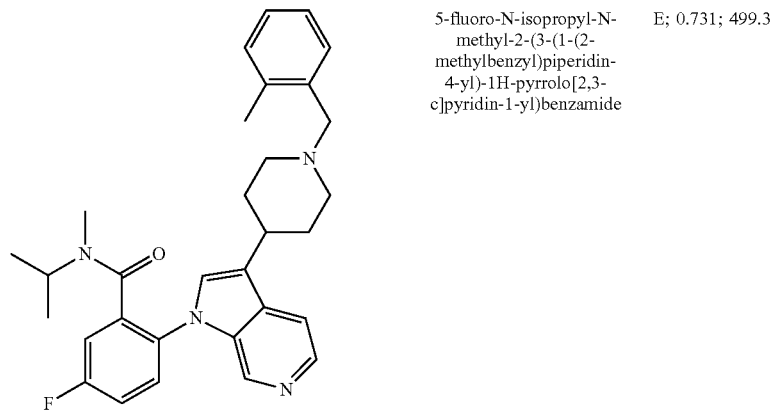 | 5-fluoro-N-isopropyl-N-methyl-2-(3-(1-(2-methylbenzyl)piperidin-4-yl)-1H-pyrrolo[2,3-c]pyridin-1-yl)benzamide | E; 0.731; 499.3 |

$^1$H NMR (CD$_3$OD): δ 8.85-9.00 (m, 1 H), 8.45-8.50 (m, 1 H), 8.35-8.40 (m, 1 H), 8.15-8.25 (m, 1 H), 7.70-7.80 (m, 1 H), 7.60-7.70 (m, 1 H), 7.30-7.55 (m, 5 H), 4.50 (s, 2 H), 4.30-4.45 (m, 0.5 H), 3.65-3.75 (m, 2.5 H), 3.40-3.60 (m, 3 H), 2.60 (s, 3 H), 2.55 (s, 3 H), 2.15-2.40 (m, 4 H), 0.55-1.20 (m, 6 H). $^{19}$F NMR (CD$_3$OD): δ ppm −110.64~−110.43.

| | 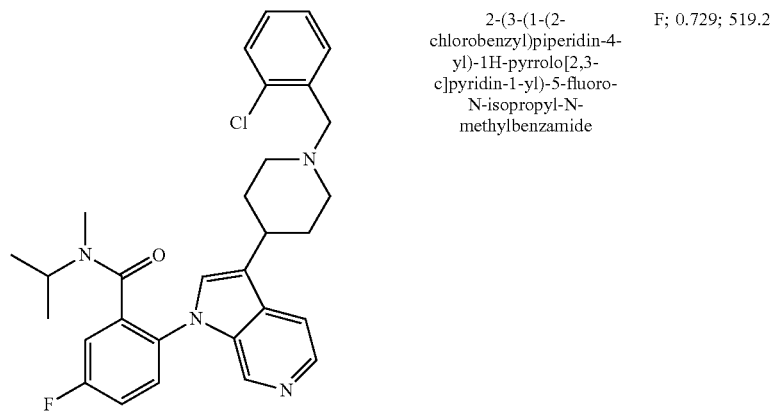 | 2-(3-(1-(2-chlorobenzyl)piperidin-4-yl)-1H-pyrrolo[2,3-c]pyridin-1-yl)-5-fluoro-N-isopropyl-N-methylbenzamide | F; 0.729; 519.2 |

$^1$H NMR (CD$_3$OD): δ 8.85-9.0 (m, 1 H), 8.45-8.55 (m, 1 H), 8.35-8.40 (m, 1 H), 8.15-8.25 (m, 1 H), 7.85-7.95 (m, 1 H), 7.70-7.80 (m, 1 H), 7.60-7.75 (m, 1 H), 7.45-7.60 (m, 3 H), 7.40-7.50 (m, 1 H), 4.65 (s, 2 H), 4.30-4.45 (m, 0.5 H), 3.65-3.80 (m, 2.5 H), 3.40-3.60 (m, 3 H), 2.65 (s, 3 H), 2.20-2.45 (m, 4 H), 0.55-1.15 (m, 6 H). $^{19}$F NMR (CD$_3$OD): δ ppm −110.72~−110.53.

TABLE 3-continued

| Ex No. | Structural formula | Name | LCMS method; Rt in min; [M + H]+ |
|---|---|---|---|
| | 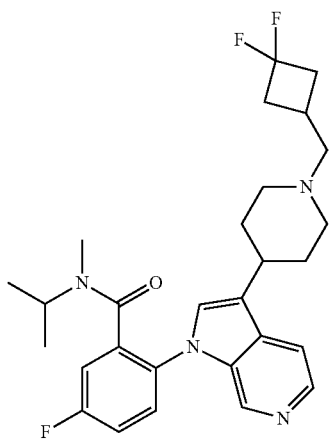 [SMILES: CC(C)N(C)C(=O)c1cc(F)ccc1-n1cc(C2CCN(CC3CC(F)(F)C3)CC2)c2ccncc21] | 2-(3-(1-(((3,3-difluorocyclobutyl)methyl)piperidin-4-yl)-1H-pyrrolo[2,3-c]pyridin-1-l)-5-fluoro-N-isopropyl-N-methylbenzamide | C; 1.513; 499.3 |

$^1$H NMR (CD3OD): δ 8.53-8.62 (m, 1H), 8.15-8.20 (m, 1H), 7.74-7.76 (m, 1H), 7.55-7.70 (m, 1H), 7.35-7.36 (m, 2H), 7.30-7.35 (m, 1H), 4.43-4.50 (m, 0.5 H), 3.50-3.60 (m, 0.5 H), 3.04-3.07 (m, 2H), 2.85-2.95 (m, 1H), 2.65-2.75 (m, 2H), 2.40-2.66 (m, 5H), 2.24-2.30 (m, 3H), 1.97-2.04 (m, 2H), 1.59-1.87 (m, 2H), 1.25-1.50 (m, 2H), 0.98-1.04 (m, 3H), 0.15-0.52 (m, 3H). $^1$F NMR (CD3OD): δ ppm −83.84~−83.32, −97.78~−97.27, −113.52~−113.25.

| | 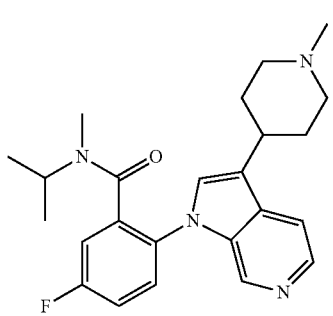 [SMILES: CC(C)N(C)C(=O)c1cc(F)ccc1-n1cc(C2CCN(C)CC2)c2ccncc21] | 5-fluoro-N-isopropyl-N-methyl-2-(3-(1-methylpiperidin-4-yl)-1H-pyrrolo[2,3-c]pyridin-1-yl)benzamide | C; 0.776; 409.3 |

$^1$H NMR (CD3OD): δ ppm 8.30-8.39 (m, 1H), 7.93-7.96 (m, 1H), 7.52 (d, J = 5.6 Hz, 1H), 7.39-7.46 (m, 1H), 7.05-7.25 (m, 3H), 4.20-4.25 (m, 0.5H), 3.31-3.37 (m, 0.5H), 2.65-2.85 (m, 3H), 2.22-2.44 (m, 3H), 2.14 (s, 3H), 2.02-2.08 (m, 2H), 1.80-1.90 (m, 2H) 1.55-1.75 (m, 2H), 0.75-0.85 (m, 3H), 0.02-0.30 (m, 3H). $^{19}$F NMR (CD3OD): δ ppm −113.55~−113.28.

Examples 18-18A. tert-butyl (trans-4-(2-(4-(1-(4-fluoro-2-(isopropyl(methyl)carbamoyl)phenyl)-1H-pyrrolo[2,3-c]pyridin-3-yl)piperidin-1-yl)ethyl)cyclohexyl)carbamate (Example 18A) and 2-(3-(1-(2-(trans-4-acetamidocyclohexyl)ethyl)piperidin-4-yl)-1H-pyrrolo[2,3-c]pyridin-1-yl)-5-fluoro-N-isopropyl-N-methylbenzamide (Example 18)

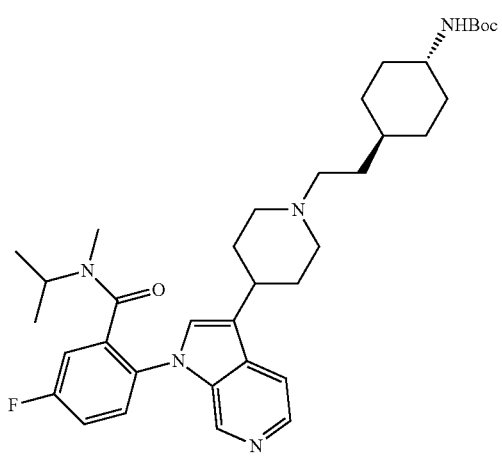 [SMILES: CC(C)N(C)C(=O)c1cc(F)ccc1-n1cc(C2CCN(CC[C@H]3CC[C@H](NC(=O)OC(C)(C)C)CC3)CC2)c2ccncc21]

and

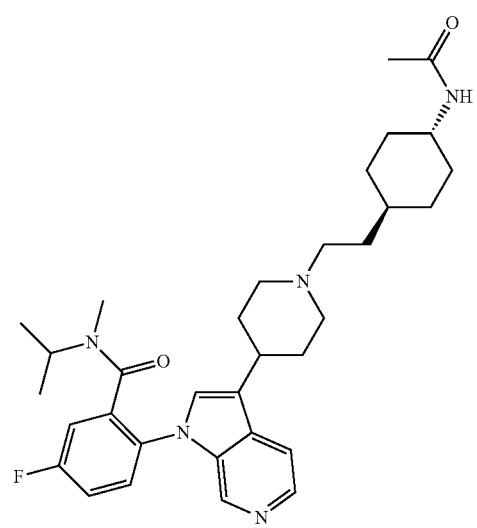

Step 1: tert-butyl (trans-4-(2-(4-(1-(4-fluoro-2-(isopropyl(methyl)carbamoyl)phenyl)-1H-pyrrolo[2,3-c]pyridin-3-yl)piperidin-1-yl)ethyl)cyclohexyl)carbamate (Example 18A)

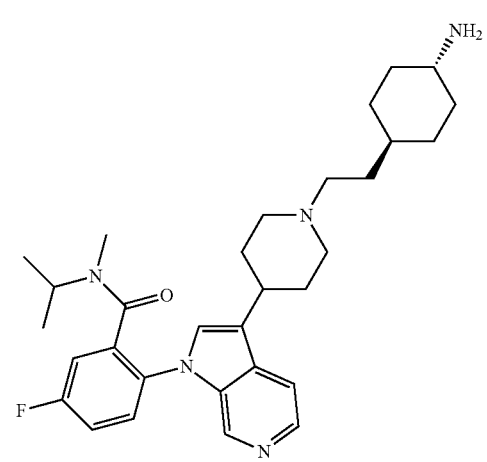 [SMILES: CC(C)N(C)C(=O)c1cc(F)ccc1-n1cc(C2CCN(CC[C@H]3CC[C@H](N)CC3)CC2)c2ccncc21]

A mixture of 5-fluoro-N-isopropyl-N-methyl-2-(3-(piperidin-4-yl)-1H-pyrrolo[2,3-c]pyridin-1-yl)benzamide (Example 1, Step 1, 120 mg, 0.24 mmol, HCl salt), Intermediate 23 (87 mg, 0.36 mmol), Et$_3$N (121 mg, 0.17 mL, 1.2 mmol) and NaBH$_3$CN (75 mg, 1.2 mmol) in anhydrous MeOH (6 mL) was stirred at 70° C. for 18 h. The mixture was then concentrated under reduced pressure. The residue was added to H$_2$O (20 mL) and extracted with EtOAc (3×40 mL). The combined organic layers were dried over anhydrous sodium sulfate, filtered, and the filtrate was concentrated under reduced pressure. The residue was purified by column chromatograph on silica gel (eluting with CH$_2$Cl$_2$/MeOH=9/1) to give tert-butyl (trans-4-(2-(4-(1-(4-fluoro-2-(isopropyl(methyl)carbamoyl)phenyl)-1H-pyrrolo[2,3-c]pyridin-3-yl)piperidin-1-yl)ethyl)cyclohexyl)carbamate (100 mg, 68% yield) as white solid. LCMS method E: R$_f$=0.836 min; (M+H)$^+$=620.5. $^1$H NMR (CD3OD): δ ppm 8.52-8.61 (m, 1H), 8.14-8.18 (m, 1H), 7.74-7.75 (m, 1H), 7.60-7.7 (m, 1H), 7.30-7.45 (m, 3H), 4.40-4.49 (m, 1H), 3.50-3.60 (m, 1H), 2.85-3.25 (m, 5H), 2.40-2.66 (m, 5H), 2.15-2.25 (m, 2H), 2.00-2.10 (m, 2H), 1.75-1.95 (m, 6H), 1.40-1.60 (m, 10H), 0.95-1.35 (m, 7H), 0.20-0.55 (m, 3H). $^{19}$F NMR (CD3OD δ ppm −117.52~−113.25.

Step 2: 2-(3-(1-(2-(trans-4-aminocyclohexyl)ethyl)piperidin-4-yl)-1H-pyrrolo[2,3-c]pyridin-1-yl)-5-fluoro-N-isopropyl-N-methylbenzamide To a mixture of tert-butyl (trans-4-(2-(4-(1-(4-fluoro-2-(isopropyl(methyl)carbamoyl)phenyl)-1H-pyrrolo[2,3-c]pyridin-3-yl)piperidin-1-yl)ethyl)cyclohexyl)carbamate (60 mg, 0.1 mmol) in anhydrous DCM (5 mL) was added HCl-dioxane (1 mL, 4 N). The mixture was stirred at 5-18° C. for 1 h. White solid was formed. The mixture was concentrated under reduced pressure to give 2-(3-(1-(2-(trans-4-aminocyclohexyl)ethyl)piperidin-4-yl)-1H-pyrrolo[2,3-c]pyridin-1-yl)-5-fluoro-N-isopropyl-N-methylbenzamide as white solid as HCl salt, which was used for the next step directly without further purification. Yield: 60 mg (100% crude); LCMS method B: $R_t$=0.474 min; $(M+H)^+$=520.2

Step 3: 2-(3-(1-(2-(trans-4-acetamidocyclohexyl)ethyl)piperidin-4-yl)-1H-pyrrolo[2,3-c]pyridin-1-yl)-5-fluoro-N-isopropyl-N-methylbenzamide (Example 18)

To a mixture of 2-(3-(1-(2-(trans-4-aminocyclohexyl)ethyl)piperidin-4-yl)-1H-pyrrolo[2,3-c]pyridin-1-yl)-5-fluoro-N-isopropyl-N-methylbenzamide (60 mg, 0.1 mmol, HCl salt) and Et$_3$N (61 mg, 0.08 mL, 0.6 mmol) in anhydrous CH$_2$Cl$_2$ (5 mL) was added Ac$_2$O (20 mg, 0.2 mmol). The mixture was stirred at 5-18° C. for 18 h. The mixture was concentrated under reduced pressure. The residue was purified preparative RP-HPLC Method A to give 2-(3-(1-(2-(trans-4-acetamidocyclohexyl)ethyl)piperidin-4-yl)-1H-pyrrolo[2,3-c]pyridin-1-yl)-5-fluoro-N-isopropyl-N-methylbenzamide) (TFA salt) as white solid. Yield: 13 mg (23%); LCMS method E: $R_t$=0.440 min; $(M+H)^+$=562.5. $^1$H NMR (CD3OD): δ ppm 8.90-9.00 (m, 1H), 8.30-8.40 (m, 2H), 8.10-8.20 (m, 1H), 7.70-7.80 (m, 1H), 7.45-7.55 (m, 2H), 4.35-4.45 (m, 0.6H), 3.70-3.80 (m, 2.6H), 3.50-3.65 (m, 1H), 3.40-3.50 (m, 1H), 3.15-3.25 (m, 4H), 2.65 (s, 3H), 2.05-2.40 (m, 4H), 1.70-2.00 (m, 10H), 0.50-1.50 (m, 10H). $^{19}$F NMR (CD3OD): δ ppm −110.66~−110.48, −77.44~−76.67.

Example 19. 5-fluoro-N-isopropyl-N-methyl-2-(3-(1-(2-(trans-4-(methylsulfonamido)cyclohexyl)ethyl)piperidin-4-yl)-1H-pyrrolo[2,3-c]pyridin-1-yl)benzamide To a solution of 2-(3-(1-(2-(trans-4-aminocyclohexyl)ethyl)piperidin-4-yl)-1H-pyrrolo[2,3-c]pyridin-1-yl)-5-fluoro-N-isopropyl-N-methylbenzamide (Example 18, Step 2, 34 mg, 0.065 mmol, HCl salt), (MeSO$_2$)$_2$O (34 mg, 0.20 mmol) and Et$_3$N (33 mg, 0.33 mmol) in anhydrous DCM (20 mL) was stirred at 3-16° C. for 0.5 h. The mixture was concentrated under reduced pressure. The residue purified by basic preparative RP-HPLC Method D to afford 5-fluoro-N-isopropyl-N-methyl-2-(3-(1-(2-(trans-4-(methylsulfonamido)cyclohexyl)ethyl) piperidin-4-yl)-1H-pyrrolo[2,3-c]pyridin-1-yl)benzamide) as white solid. Yield: 12.3 mg (31%); LCMS method E: $R_t$=2.011 min; $(M+H)^+$=598.3 $^1$H NMR (CD3OD): δ ppm 8.54-8.63 (m, 1H), 8.15-8.25 (m, 1H), 7.76 (d, J=5.6 Hz, 1H), 7.60-7.70 (m, 1H), 7.40-7.50 (m, 2H), 7.35-7.37 (m, 1H), 4.37-4.51 (m, 0.5H), 3.55-3.65 (m, 0.5H), 3.11-3.20 (m, 3H), 2.60-3.00 (m, 6H), 2.40-2.51 (m, 3H), 1.75-2.30 (m, 10H), 0.90-1.52 (m, 10H), 0.20-0.60 (m, 3H). $^{19}$F NMR (CD3OD): δ ppm −113.24~113.58.

Examples 20-20A. tert-butyl (trans-4-((4-(1-(4-fluoro-2-(isopropyl(methyl)carbamoyl)phenyl)-1H-pyrrolo[2,3-c]pyridin-3-yl)piperidin-1-yl)methyl)cyclohexyl)carbamate (Example 20A) and 2-(3-(1-(1-(trans-4-acetamidocyclohexyl)methyl)piperidin-4-yl)-1H-pyrrolo[2,3-c]pyridin-1-yl)-5-fluoro-N-isopropyl-N-methylbenzamide (Example 20)

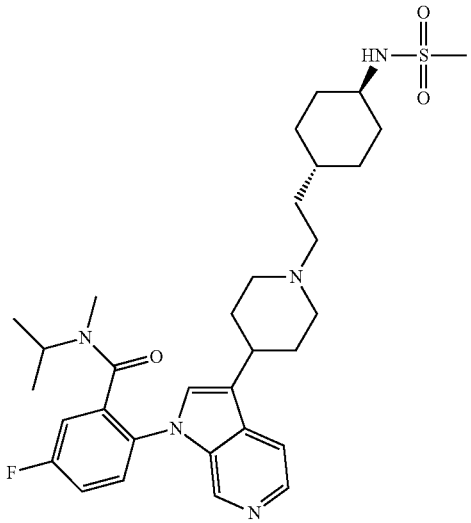 [SMILES: CC(C)N(C)C(=O)c1cc(F)ccc1-n1cc(C2CCN(CC[C@H]3CC[C@H](NS(C)(=O)=O)CC3)CC2)c2ccncc21]

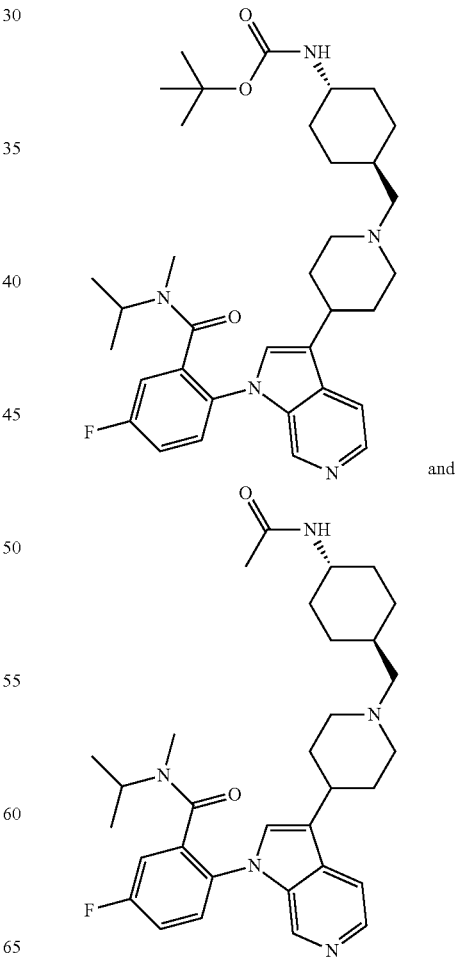

Step 1: tert-butyl ((1r,4r)-4-((4-(1-(4-fluoro-2-(iso-propyl(methyl)carbamoyl)phenyl)-1H-pyrrolo[2,3-c]pyridin-3-yl)piperidin-1-yl)methyl)cyclohexyl)carbamate (Example 20A)

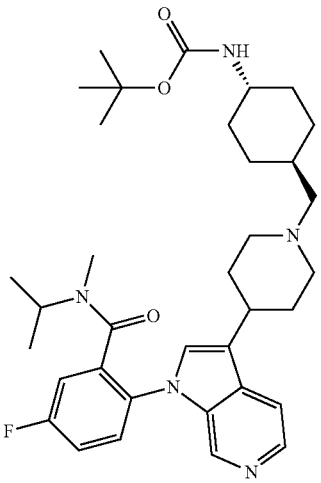 [SMILES: CC(C)N(C)C(=O)c1cc(F)ccc1-n1cc(C2CCN(C[C@H]3CC[C@H](NC(=O)OC(C)(C)C)CC3)CC2)c2ccncc21]

To a solution of 5-fluoro-N-isopropyl-N-methyl-2-(3-(piperidin-4-yl)-1H-pyrrolo[2,3-c]pyridin-1-yl)benzamide (Example 1, Step 1, 60 mg, 0.15 mmol, hydrochloride) and tert-butyl (trans-4-formylcyclohexyl)carbamate (35 mg, 0.15 mmol) in MeOH (2 mL, anhydrous) was added TEA (75 mg, 0.75 mmol). The resulting mixture was stirred at 2-18° C. for 20 min, then NaBH$_3$CN (29 mg, 0.45 mmol) was added. The resulting mixture was stirred at 2-18° C. for about 16 h. The mixture was concentrated, and the residue was purified by preparative RP-HPLC Method A to give tert-butyl ((1r,4r)-4-((4-(1-(4-fluoro-2-(isopropyl(methyl)carbamoyl)phenyl)-1H-pyrrolo[2,3-c]pyridin-3-yl)piperidin-1-yl)methyl)cyclohexyl)carbamate. Yield: 80 mg (88%); LCMS method E: R$_t$=0.816 min; (M+H)$^+$=606.5. $^1$H NMR (CD3OD): δ ppm 8.86-9.01 (m, 1H), 8.25-8.39 (m, 2H), 8.14 (d, J=11.6 Hz, 1H), 7.74 (dd, J=8.4, 4.0 Hz, 1H), 7.43-7.56 (m, 2H), 4.35-4.45 (s, 1H), 3.70-3.80 (m, 3H), 3.35-3.50 (m, 2H), 3.05-3.30 (m, 4H), 2.55-2.65 (m, 3H), 2.05-2.40 (m, 5H), 1.80-2.05 (m, 5H), 1.44 (s, 6H), 1.05-1.38 (m, 6H), 0.55-0.95 (m, 5H). $^{19}$F NMR (CD3OD): δ ppm −77.07, −110.41~−110.60.

Step 2: 2-(3-(1-(((1r,4r)-4-aminocyclohexyl)methyl)piperidin-4-yl)-1H-pyrrolo[2,3-c]pyridin-1-yl)-5-fluoro-N-isopropyl-N-methylbenzamide

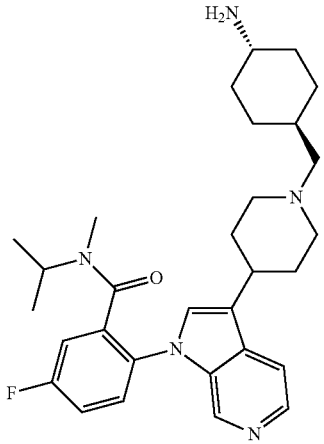 [SMILES: CC(C)N(C)C(=O)c1cc(F)ccc1-n1cc(C2CCN(C[C@H]3CC[C@H](N)CC3)CC2)c2ccncc21]

To a solution of tert-butyl (trans-4-((4-(1-(4-fluoro-2-(isopropyl(methyl)carbamoyl)phenyl)-1H-pyrrolo[2,3-c]pyridin-3-yl)piperidin-1-yl)methyl)cyclohexyl)carbamate (80 mg, 0.13 mmol) in DCM (3 mL) was added HCl-dioxane (0.6 mL, 4 M). The mixture was stirred at 5-18° C. for 4 h. The mixture was concentrated to give crude 2-(3-(1-((trans-4-aminocyclohexyl)methyl)piperidin-4-yl)-1H-pyrrolo[2,3-c]pyridin-1-yl)-5-fluoro-N-isopropyl-N-methylbenzamide (HCl salt) was directly used in the next step without purification. Yield: 80 mg (100% crude); LCMS method E: R$_t$=0.756 min; (M+H)$^+$=506.5

Step 3: 2-(3-(1-(((1r,4r)-4-acetamidocyclohexyl)methyl)piperidin-4-yl)-1H-pyrrolo[2,3-c]pyridin-1-yl)-5-fluoro-N-isopropyl-N-methylbenzamide (Example 20)

To a solution of 2-(3-(1-((trans-4-aminocyclohexyl)methyl)piperidin-4-yl)-1H-pyrrolo[2,3-c]pyridin-1-yl)-5-fluoro-N-isopropyl-N-methylbenzamide (80 mg, 0.16 mmol, HCl salt) in DCM (2 mL, anhydrous) was added pyridine (101 mg, 1.28 mmol) and Ac$_2$O (18 mg, 0.17 mmol). The mixture was stirred at RT for 16 h. The mixture was concentrated, and the residue was purified by preparative RP-HPLC Method A to give 2-(3-(1-(((trans-4-acetamidocyclohexyl)methyl)piperidin-4-yl)-1H-pyrrolo[2,3-c]pyridin-1-yl)-5-fluoro-N-isopropyl-N-methylbenzamide (TFA salt) as white solid. Yield: 15 mg (17%); LCMS method E: R$_t$=0.849 min; (M+H)$^+$=548.4. $^1$H NMR (CD3OD): δ ppm 8.85-9.04 (m, 1H), 8.30-8.40 (m, 2H), 8.10-8.21 (m, 1H), 7.76 (dd, J=8.8, 4.8 Hz, 1H), 7.43-7.58 (m, 2H), 4.33-4.45 (m, 1H), 3.70-3.85 (m, 2H), 3.55-3.70 (m, 1H), 3.40-3.50 (m, 1H), 3.15-3.25 (m, 2H), 3.10 (d, J=6.4 Hz, 2H), 2.58-2.68 (m, 3H), 2.12-2.40 (m, 4H), 1.87-2.04 (m, 8H), 1.07-1.40 (m, 6H), 0.49-1.01 (m, 4H). $^{19}$F NMR (CD3OD): δ ppm −76.92, −110.45~−110.63.

Example 21. 5-fluoro-N-isopropyl-N-methyl-2-(3-(1-(((trans-4-(methylsulfonamido)cyclohexyl)methyl)piperidin-4-yl)-1H-pyrrolo[2,3-c]pyridin-1-yl)benzamide

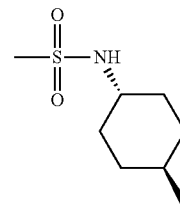

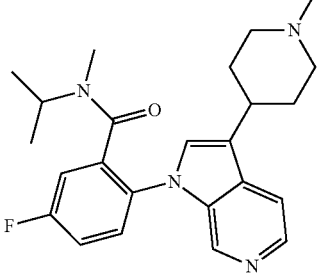

A mixture of 2-(3-(1-((trans-4-aminocyclohexyl)methyl)piperidin-4-yl)-1H-pyrrolo[2,3-c]pyridin-1-yl)-5-fluoro-N-isopropyl-N-methylbenzamide (Example 20, Step 2, 85 mg, 0.17 mmol) in CH$_2$Cl$_2$ (15 mL) was added Et$_3$N (86 mg, 0.85 mmol), (MeSO$_2$)$_2$O (89 mg, 0.51 mmol) stirred at RT for 0.5 h. The mixture was then concentrated under reduced pressure and the residue was purified by basic preparative RP-HPLC method G to give 5-fluoro-N-isopropyl-N- methyl-2-(3-(1-((trans-4-(methylsulfonamido)cyclohexyl)methyl)piperidin-4-yl)-1H-pyrrolo[2,3-c]pyridin-1-yl)benzamide as white solid. Yield: 38.3 mg (27%); LCMS method E: $R_t$=0.859 min; $(M+H)^+$=584.4. $^1$H NMR (CD$_3$OD): δ ppm 8.30-8.41 (m, 1H), 7.94-7.98 (m, 1H), 7.54 (d, J=5.2 Hz, 1H), 7.41-7.48 (m, 1H), 7.13-7.23 (m, 3H), 4.24-4.27 (m, 0.5H), 3.35-3.38 (m, 0.5H), 2.95-3.00 (m, 1H), 2.80-2.90 (m, 2H), 2.60-2.75 (m, 4H), 2.23-2.46 (m, 3H), 1.90-2.10 (m, 2H) 1.90-2.00 (m, 2H) 1.75-1.85 (m, 4H), 1.55-1.75 (d, J=13.2 Hz, 4H), 1.25-1.35 (m, 1H), 1.05-1.15 (m, 2H), 0.75-0.90 (m, 5H), 0.00-0.35 (m, 3H). $^{19}$F NMR (CD3OD): δ ppm −113.59~−113.32.

Example 22. 2-(3-(1-(4-acetamidobenzyl)piperidin-4-yl)-1H-pyrrolo[2,3-c]pyridin-1-yl)-5-fluoro-N-isopropyl-N-methylbenzamide

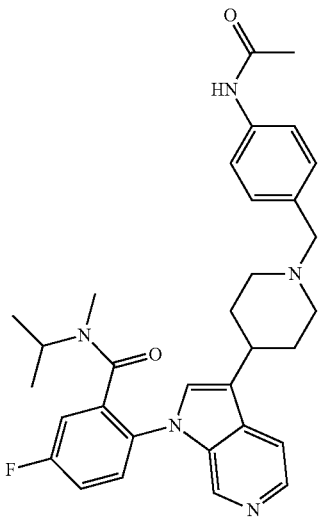 [SMILES: CC(=O)Nc1ccc(CN2CCC(c3cn(-c4ccc(F)cc4C(=O)N(C)C(C)C)c4cnccc34)CC2)cc1]

Step 1: tert-butyl (4-((4-(1-(4-fluoro-2-(isopropyl(methyl)carbamoyl)phenyl)-1H-pyrrolo[2,3-c]pyridin-3-yl)piperidin-1-yl)methyl)phenyl)carbamate

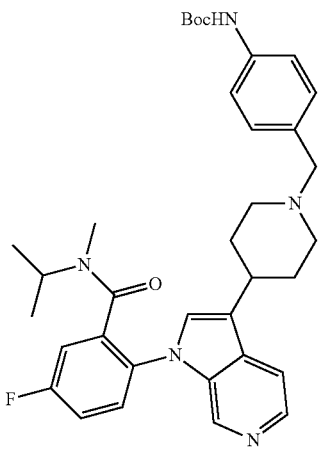 [SMILES: CC(C)N(C)C(=O)c1cc(F)ccc1-n1cc(C2CCN(Cc3ccc(NC(=O)OC(C)(C)C)cc3)CC2)c2ccncc21]

To a solution of 5-fluoro-N-isopropyl-N-methyl-2-(3-(piperidin-4-yl)-1H-pyrrolo[2,3-c]pyridin-1-yl)benzamide (Example 1, Step 1, 200 mg, 0.51 mmol, HCl salt), tert-butyl (4-formylphenyl)carbamate (244 mg, 1.01 mmol) and Et$_3$N (258 mg, 2.55 mmol) in anhydrous MeOH (20 mL) was stirred at RT for 0.5 h. NaBH$_3$CN (128 mg, 2.04 mmol) was added and then stirred at 60° C. for 18 h. The mixture was concentrated under reduced pressure. The residue was purified column chromatography on silica gel (eluting with DCM/MeOH=1/0 to 10/1) to afford tert-butyl (4-((4-(1-(4-fluoro-2-(isopropyl(methyl)carbamoyl)phenyl)-1H-pyrrolo[2,3-c]pyridin-3-yl)piperidin-1-yl)methyl)phenyl)carbamate as yellow oil. Yield: 110 mg (36%); LCMS method B: $R_t$=0.615 min; $(M+H)^+$=600.1

Step 2: 2-(3-(1-(4-aminobenzyl)piperidin-4-yl)-1H-pyrrolo[2,3-c]pyridin-1-yl)-5-fluoro-N-isopropyl-N-methylbenzamide

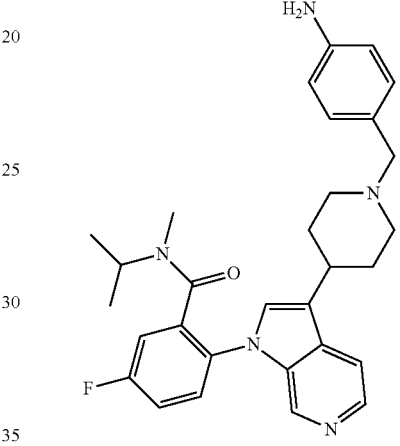

To a solution of tert-butyl (4-((4-(1-(4-fluoro-2-(isopropyl(methyl)carbamoyl)phenyl)-1H-pyrrolo[2,3-c]pyridin-3-yl)piperidin-1-yl)methyl)phenyl)carbamate (110 mg, 0.18 mmol) in anhydrous DCM (20 mL) was added HCl-dioxane (4 mL, 4 N) solution at 0° C. The reaction was stirred at RT for 2 h. The mixture was concentrated under reduced pressure to afford 2-(3-(1-(4-aminobenzyl)piperidin-4-yl)-1H-pyrrolo[2,3-c]pyridin-1-yl)-5-fluoro-N-isopropyl-N-methylbenzamide as white solid, which was used without further purification. Yield: 91 mg (100% crude).

Step 3: 2-(3-(1-(4-acetamidobenzyl)piperidin-4-yl)-1H-pyrrolo[2,3-c]pyridin-1-yl)-5-fluoro-N-isopropyl-N-methylbenzamide To a solution of 2-(3-(1-(4-aminobenzyl)piperidin-4-yl)-1H-pyrrolo[2,3-c]pyridin-1-yl)-5-fluoro-N-isopropyl-N-methylbenzamide (41 mg, 0.082 mmol, HCl salt), Ac$_2$O (25 mg, 0.25 mmol) and pyridine (32 mg, 0.41 mmol) in anhydrous DCM (20 mL) was stirred at 2-15° C. for 18 h. The mixture was concentrated under reduced pressure. The residue purified by basic preparative RP-HPLC Method D to afford 2-(3-(1-(4-acetamidobenzyl)piperidin-4-yl)-1H-pyrrolo[2,3-c]pyridin-1-yl)-5-fluoro-N-isopropyl-N-methylbenzamide. LCMS method E: $R_t$=1.806 min; $(M+H)^+$=542.3. $^1$H NMR (CD$_3$OD): δ ppm 8.53-8.62 (m, 1H), 8.19 (dd, J=5.6, 8.0 Hz, 1H), 7.76 (d, J=5.6 Hz, 1H), 7.63-7.69 (m, 1H), 7.56 (d, J=8.4 Hz, 2H), 7.40-7.47 (m, 2H), 7.33-7.36 (m, 3H), 4.45-4.48 (m, 0.5H), 3.61 (s, 2H), 3.50-3.60 (m, 0.6H), 3.06-3.09 (m, 2H), 2.90-3.00 (m, 1H), 2.40-2.60 (m, 3H), 2.25-2.35 (m, 2H), 2.17 (s, 3H), 2.00-2.07 (m, 2H), 1.80-1.95 (m, 2H), 0.95-1.05 (m, 3H), 0.22-0.52 (m, 3H).
$^{19}$F NMR (CD3OD): δ ppm −111.27~−113.55.

Example 23. 5-fluoro-N-isopropyl-N-methyl-2-(3-(1-(4-(methylsulfonamido)benzyl)piperidin-4-yl)-1H-pyrrolo[2,3-c]pyridin-1-yl)benzamide

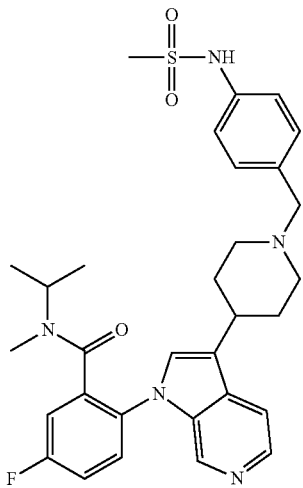 [SMILES: CC(C)N(C)C(=O)c1cc(F)ccc1-n1cc(C2CCN(Cc3ccc(NS(C)(=O)=O)cc3)CC2)c2ccncc21]

The title compound was prepared according to the method described in Example 22. Methanesulfonic anhydride was used instead of acetic anhydride in Step 3. LCMS method D: R$_t$=1.749 min; (M+H)$^+$=578.2. $^1$H NMR (CD3OD): δ ppm 8.54-8.63 (m, 1H), 8.18 (dd, J=5.6, 8.0 Hz, 1H), 7.76 (d, J=5.2 Hz, 1H), 7.60-7.70 (m, 1H), 7.34-7.45 (m, 5H), 7.26 (d, J=8.4 Hz, 1H), 4.40-4.50 (m, 0.5H), 3.62 (s, 2H), 3.50-3.60 (m, 0.5H), 3.06-3.09 (m, 2H), 2.97 (s, 3H), 2.90-2.95 (m, 1H), 2.40-2.70 (m, 3H), 2.25-2.35 (m, 2H), 2.00-2.07 (m, 2H), 1.80-1.95 (m, 2H), 0.95-1.10 (m, 3H), 0.22-0.60 (m, 3H). $^{19}$F NMR (CD3OD): δ ppm −113.24~113.53.

Example 24. 5-fluoro-N-isopropyl-N-methyl-2-(3-(1-(4-(methylsulfonyl)phenethyl)piperidin-4-yl)-1H-pyrrolo[2,3-c]pyridin-1-yl)benzamide

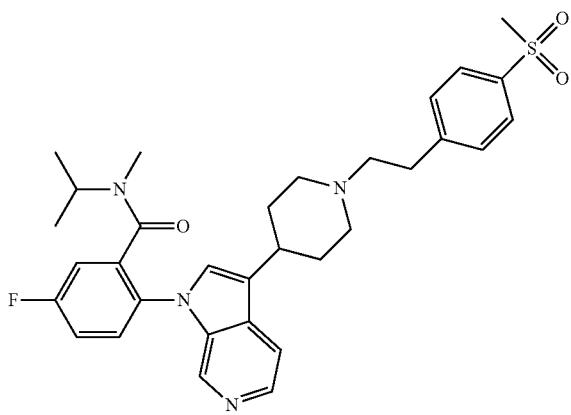 [SMILES: CC(C)N(C)C(=O)c1cc(F)ccc1-n1cc(C2CCN(CCc3ccc(S(C)(=O)=O)cc3)CC2)c2ccncc21]

Step 1:
1-(2-methoxyvinyl)-4-(methylsulfonyl)benzene

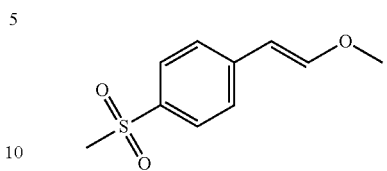

To a solution of MeOCH$_2$PPh$_3$Cl (1.9 g, 5.43 mmol) in anhydrous THF (40 mL) was added n-BuLi (2.2 mL, 5.43 mmol, 2.5 mol/L in hexane) dropwise at −78° C. under N$_2$. After 30 min, 4-(methylsulfonyl)benzaldehyde (500 mg, 2.71 mmol) dissolved in anhydrous THF (10 mL) was added dropwise. The reaction was stirred at −78° C. for 2 h and allowed warm to 7-22° C. for 18 h. The mixture was quenched with sat NH$_4$Cl (10 mL) solution. The mixture was diluted with H$_2$O (40 mL), extracted with EtOAc (3×50 mL). The combined organic layers were dried over anhydrous sodium sulfate, filtered, and the filtrate was concentrated under reduced pressure. The residue was purified by column chromatography on silica gel (eluting with petroleum ether/EtOAc=10/1 to 1/1) to afford (1-(2-methoxyvinyl)-4-(methylsulfonyl)benzene (about 90% purity, E & Z mixture, 1/1 ratio) as yellow solid. Yield: 200 mg (35%); $^1$H NMR (CDCl$_3$): δ ppm 7.80-7.85 (m, 4H), 7.73 (d, J=8.8 Hz, 2H), 7.39 (d, J=8.8 Hz, 2H), 7.22 (d, J=13.2 Hz, 1H), 6.32 (d, J=6.8 Hz, 1H), 5.85 (d, J=12.8 Hz, 1H), 5.29 (d, J=7.2 Hz, 1H), 3.86 (s, 3H), 3.74 (s, 3H), 3.04 (s, 6H).

Step 2: 2-(4-(methylsulfonyl)phenyl)acetaldehyde

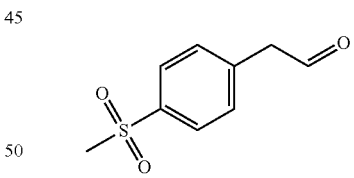

To a solution of 1-(2-methoxyvinyl)-4-(methylsulfonyl)benzene (200 mg, 0.94 mmol) in anhydrous THF (20 mL) was added aq. HCl (5 mL, 3N) solution. The reaction was stirred at 70° C. for 2 h. The mixture was diluted with H$_2$O (20 mL) and extracted with EtOAc (3×20 mL). The combined organic layers were dried over anhydrous sodium sulfate, filtered, and the filtrate was concentrated under reduced pressure to afford 2-(4-(methylsulfonyl)phenyl)acetaldehyde (150 mg, 80%, crude) as yellow solid, which was used for next step directly without further purification. Yield: 150 mg (80% crude);

Step 3: 5-fluoro-N-isopropyl-N-methyl-2-(3-(1-(4-(methylsulfonyl)phenethyl)piperidin-4-yl)-1H-pyrrolo[2,3-c]pyridin-1-yl)benzamide

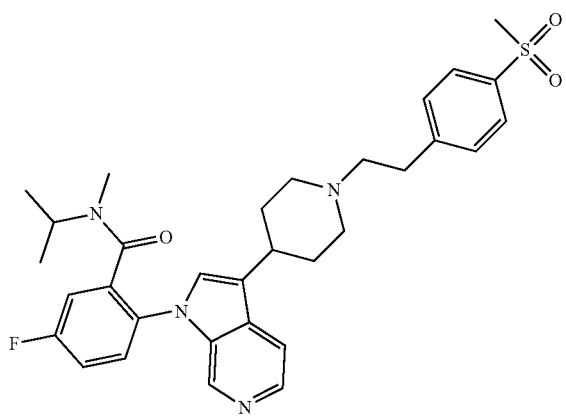 [SMILES: CC(C)N(C)C(=O)c1cc(F)ccc1-n1cc(C2CCN(CCc3ccc(S(C)(=O)=O)cc3)CC2)c2ccncc21]

To a solution of 5-fluoro-N-isopropyl-N-methyl-2-(3-(piperidin-4-yl)-1H-pyrrolo[2,3-c]pyridin-1-yl)benzamide (Example 1, Step 1, 50 mg, 0.13 mmol, HCl salt), 2-(4-(methylsulfonyl)phenyl)acetaldehyde (50 mg, 0.25 mmol, crude) and Et$_3$N (64 mg, 0.63 mmol) in anhydrous MeOH (20 mL) was stirred at 3-17° C. for 0.5 h. NaBH$_3$CN (33 mg, 0.52 mmol) was then added, and the reaction mixture was stirred at 60° C. for 18 h. The mixture was then concentrated under reduced pressure. The residue was purified preparative RP-HPLC Method D to afford 5-fluoro-N-isopropyl-N-methyl-2-(3-(1-(4-(methylsulfonyl)phenethyl)piperidin-4-yl)-1H-pyrrolo[2,3-c]pyridin-1-yl)benzamide as white solid. Yield: 20.0 mg (27%); LCMS method E: R$_t$=1.874 min; (M+H)$^+$=577.2. $^1$H NMR (CD$_3$OD): δ ppm 8.50-8.65 (m, 1H), 8.20 (dd, J=5.6, 8.0 Hz, 1H), 7.91 (d, J=8.4 Hz, 2H), 7.77 (d, J=5.6 Hz, 1H), 7.63-7.70 (m, 1H), 7.56 (d, J=8.0 Hz, 2H), 7.42-7.48 (m, 2H), 7.34-7.37 (m, 1H), 4.40-4.50 (m, 0.5H), 3.58-4.47 (m, 0.5H), 3.15-3.23 (m, 2H), 3.12 (s, 3H), 2.90-3.05 (m, 3H), 2.70-2.76 (m, 2H), 2.40-2.65 (m, 3H), 2.32-2.38 (m, 2H), 2.05-2.14 (m, 2H), 1.80-1.95 (m, 2H), 0.96-1.10 (m, 3H), 0.20-0.60 (m, 3H). $^{19}$F NMR (CD$_3$OD): δ ppm −113.25~−113.53.

Example 25. 2-(3-(1-(3-cyanophenethyl)piperidin-4-yl)-1H-pyrrolo[2,3-c]pyridin-1-yl)-5-fluoro-N-isopropyl-N-methylbenzamide

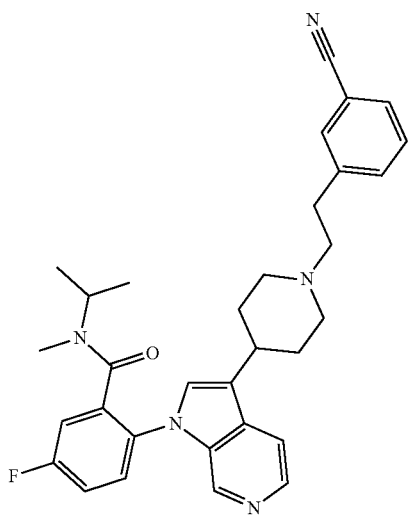 [SMILES: CC(C)N(C)C(=O)c1cc(F)ccc1-n1cc(C2CCN(CCc3cccc(C#N)c3)CC2)c2ccncc21]

The title compound was prepared according to the methods described in Example 24, starting with 3-cyanobenzaldehyde. LCMS method E: R$_t$=0.716 min; (M+H)$^+$=524.3. $^1$H NMR (CD$_3$OD): δ ppm 8.85-8.90 (m, 1H), 8.15-8.45 (m, 3H), 7.43-7.77 (m, 7H), 4.37 (s, 1H), 3.36-3.84 (m, 8H), 2.22-2.63 (m, 7H), 0.53-1.11 (m, 6H). $^{19}$F NMR (CD3OD): δ ppm −110.49~−110.67.

Example 26. 5-fluoro-N-isopropyl-N-methyl-2-(3-(1-(3-(methylcarbamoyl)phenethyl)piperidin-4-yl)-1H-pyrrolo[2,3-c]pyridin-1-yl)benzamide

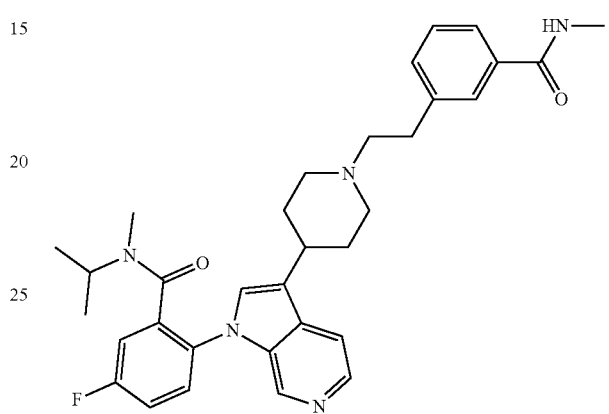

Step 1: methyl 3-(2-(4-(1-(4-fluoro-2-(isopropyl (methyl)carbamoyl)phenyl)-1H-pyrrolo[2,3-c]pyridin-3-yl)piperidin-1-yl)ethyl)benzoate

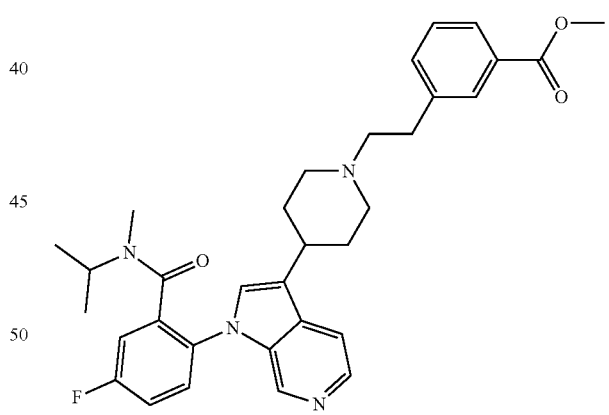

To a mixture of 5-fluoro-N-isopropyl-N-methyl-2-(3-(piperidin-4-yl)-1H-pyrrolo[2,3-c]pyridin-1-yl)benzamide (Example 1, Step 1, 100 mg, 0.25 mmol) in MeOH (10 mL) was added Et$_3$N (126 mg, 1.25 mmol) stirred at 7-19° C. for 10 min. Methyl 3-(2-oxoethyl)benzoate (90 mg, 0.51 mmol), which was prepared from methyl 4-formylbenzoate by a method similar to Steps 1-2 of Example 24 was added to the above mixture, followed by NaBH$_3$CN (62 mg, 1.00 mmol). The mixture was degassed and purged with N$_2$ for 3 times followed by heating under N$_2$ atmosphere at 70° C. for 17 h. The mixture was concentrated under reduced pressure. The residue was purified by column chromatograph on silica gel (eluting with DCM/MeOH=10/1) to give methyl 3-(2-(4-(1-

(4-fluoro-2-(isopropyl(methyl)carbamoyl)phenyl)-1H-pyrrolo[2,3-c]pyridin-3-yl)piperidin-1-yl)ethyl)benzoate as white oil. Yield: 135 mg (95%); LCMS method E: $R_f$=0.585 min; (M+H)$^+$=557.1 Step 2: 3-(2-(4-(1-(4-fluoro-2-(isopropyl(methyl)carbamoyl)phenyl)-1H-pyrrolo[2,3-c]pyridin-3-yl)piperidin-1-yl)ethyl)benzoic acid

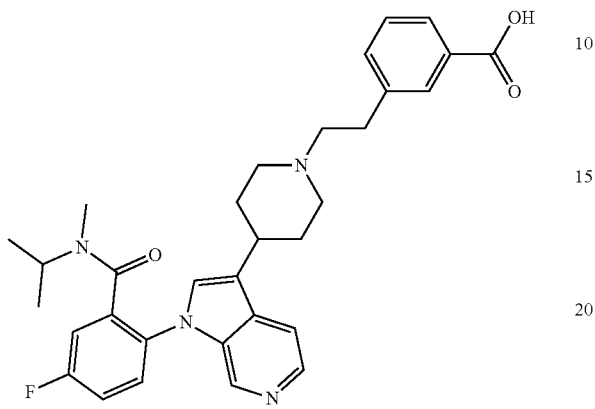

To a mixture of methyl 3-(2-(4-(1-(4-fluoro-2-(isopropyl(methyl)carbamoyl)phenyl)-1H-pyrrolo[2,3-c]pyridin-3-yl)piperidin-1-yl)ethyl)benzoate (50 mg, 0.09 mmol) in MeOH (5 mL) was added 10% NaOH solution (2 mL). The mixture was degassed and purged with $N_2$ for 3 times followed by heating under $N_2$ atmosphere at 8-18° C. for 17 h. The mixture was extracted with EtOAc (20 mL×3). To the aqueous solution was added 1N HCl to adjust pH=3-4. The aqueous solution was then extracted with EtOAc (20 mL×3). The combined organic layers were dried over anhydrous $Na_2SO_4$, filtered, and the filtrate was concentrated under reduced pressure to give 3-(2-(4-(1-(4-fluoro-2-(isopropyl(methyl)carbamoyl)phenyl)-1H-pyrrolo[2,3-c]pyridin-3-yl)piperidin-1-yl)ethyl)benzoic acid as yellow solid. Yield: 49 mg (100% crude); LCMS method E: $R_f$=0.578 min; (M+H)$^+$= 543.0

Step 3: 5-fluoro-N-isopropyl-N-methyl-2-(3-(1-(3-methylcarbamoyl)phenethyl)piperidin-4-yl)-1H-pyrrolo[2,3-c]pyridin-1-yl)benzamide To a mixture of 3-(2-(4-(1-(4-fluoro-2-(isopropyl(methyl)carbamoyl)phenyl)-1H-pyrrolo[2,3-c]pyridin-3-yl)piperidin-1-yl)ethyl)benzoic acid (49 mg, 0.09 mmol) in DMF (8 mL) was added HATU (103 mg, 0.27 mmol), MeNH$_2$ in THF (0.23 mL, 0.45 mmol) and Et$_3$N (36 mg, 0.36 mmol). The mixture was degassed and purged with $N_2$ 3 times followed by heating under $N_2$ atmosphere at 11-18° C. for 2 h. The mixture was then extracted with EtOAc (20 mL×3) and the combined organic layers were washed with water (20 mL×3). The combined organic layers were dried over anhydrous $Na_2SO_4$, filtered, and the filtrate was concentrated under reduced pressure. The residue was purified by basic preparative RP-HPLC Method D to give 5-fluoro-N-isopropyl-N-methyl-2-(3-(1-(3-(methylcarbamoyl)phenethyl)piperidin-4-yl)-1H-pyrrolo[2,3-c]pyridin-1-yl)benzamide as white solid. LCMS method E: $R_f$=0.873 min; (M+H)$^+$=556.4. $^1$H NMR (CD$_3$OD): δ ppm 8.55-8.64 (m, 1H), 8.20-8.25 (m, 1H), 7.65-7.79 (m, 4H), 7.35-7.50 (m, 5H), 4.47-4.64 (m, 0.5H), 3.54-3.62 (m, 0.5H), 3.19-3.26 (m, 2H) 2.94-3.04 (m, 3H), 2.94 (s, 3H), 2.75-2.84 (m, 2H), 2.47-2.69 (m, 3H), 2.38-2.47 (m, 2H), 2.11-2.15 (m, 2H), 1.91-1.96 (m, 2H), 0.90-1.09 (m, 3H), 0.12-0.59 (m, 3H). $^{19}$F NMR (CD3OD) δ ppm −113.23~−113.50.

Examples 27-27A. trans-(5-fluoro-2-(3-(1-((4-hydroxycyclohexyl)methyl)piperidin-4-yl)-1H-pyrrolo[2,3-c]pyridin-1-yl)-N-isopropyl-N-methylbenzamide) (Example 27) and cis-(5-fluoro-2-(3-(1-((4-hydroxycyclohexyl)methyl)piperidin-4-yl)-1H-pyrrolo[2,3-c]pyridin-1-yl)-N-isopropyl-N-methylbenzamide) (Example 27A)

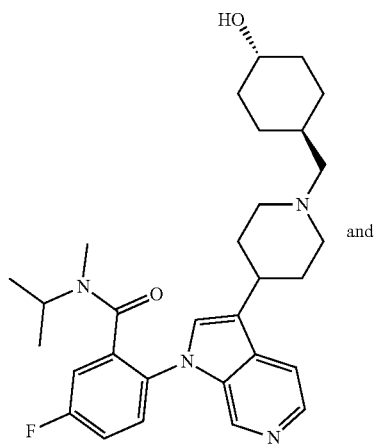

and

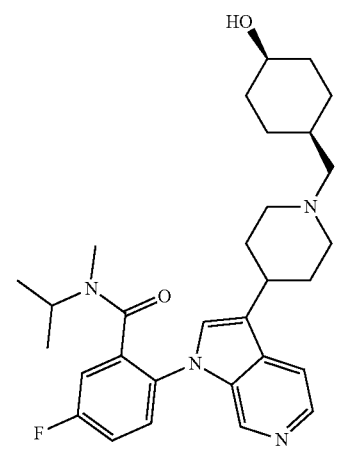

Step 1: 2-(3-(1-(1,4-dioxaspiro[4.5]decan-8-ylmethyl)piperidin-4-yl)-1H-pyrrolo[2,3-c]pyridin-1-yl)-5-fluoro-N-isopropyl-N-methylbenzamide

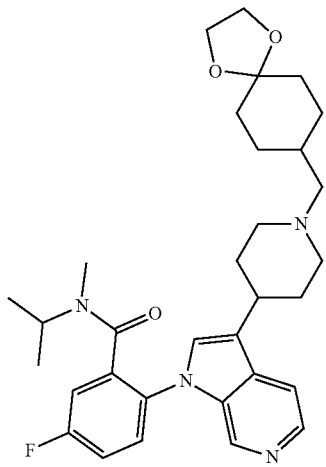 [SMILES: CC(C)N(C)C(=O)c1cc(F)ccc1-n1cc(C2CCN(CC3CCC4(CC3)OCCO4)CC2)c2ccncc21]

To a solution of 5-fluoro-N-isopropyl-N-methyl-2-(3-(piperidin-4-yl)-1H-pyrrolo[2,3-c]pyridin-1-yl)benzamide (Example 1, Step 1, 100 mg, 0.25 mmol) in MeOH (3 mL, anhydrous) was added 1,4-dioxaspiro[4.5]decane-8-carbaldehyde (65 mg, 0.38 mmol) and NaCNBH$_3$ (32 mg, 0.50 mmol). The resulting mixture was stirred at 6-10° C. under N$_2$ for 20 h. The reaction mixture was then concentrated under reduced pressure. The resulting residue was purified by basic preparative RP-HPLC Method D to give 2-(3-(1-(1,4-dioxaspiro[4.5]decan-8-ylmethyl)piperidin-4-yl)-1H-pyrrolo[2,3-c]pyridin-1-yl)-5-fluoro-N-isopropyl-N-methylbenzamide (40 mg, 28%) as white solid. Yield: 40 mg (28%); LCMS method D: R$_t$=1.567 min; (M+H)$^+$=549.3.

Step 2: 5-fluoro-N-isopropyl-N-methyl-2-(3-(1-((4-oxocyclohexyl)methyl)piperidin-4-yl)-1H-pyrrolo[2,3-c]pyridin-1-yl)benzamide

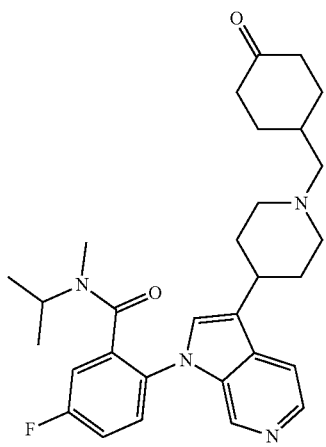 [SMILES: CC(C)N(C)C(=O)c1cc(F)ccc1-n1cc(C2CCN(CC3CCC(=O)CC3)CC2)c2ccncc21]

To a solution of 2-(3-(1-(1,4-dioxaspiro[4.5]decan-8-ylmethyl)piperidin-4-yl)-1H-pyrrolo[2,3-c]pyridin-1-yl)-5-fluoro-N-isopropyl-N-methylbenzamide (40 mg, 0.073 mmol) in THF (4 mL, anhydrous) was added aq. HCl (2 mL, 3 M in H$_2$O). The resulting mixture was stirred at 40° C. (oil temperature) under N$_2$ for 20 h. The reaction mixture was then neutralized by aq. NaOH (2 N in H$_2$O) and the aqueous layer was extracted with ethyl acetate (2×20 mL). The organic layers were washed with brine (2×30 mL), dried over anhydrous Na$_2$SO$_4$, filtered, and the filtrate was concentrated under reduced pressure to give 5-fluoro-N-isopropyl-N-methyl-2-(3-(1-((4-oxocyclohexyl)methyl)piperidin-4-yl)-1H-pyrrolo[2,3-c]pyridin-1-yl)benzamide (25 mg, 68% crude yield) as colorless oil, which was used for next step directly.

Step 3: trans-(5-fluoro-2-(3-(1-((4-hydroxycyclohexyl)methyl)piperidin-4-yl)-1H-pyrrolo[2,3-c]pyridin-1-yl)-N-isopropyl-N-methylbenzamide) and cis-(5-fluoro-2-(3-(1-((4-hydroxycyclohexyl)methyl)piperidin-4-yl)-1H-pyrrolo[2,3-c]pyridin-1-yl)-N-isopropyl-N-methylbenzamide)

To a solution of 5-fluoro-N-isopropyl-N-methyl-2-(3-(1-((4-oxocyclohexyl)methyl)piperidin-4-yl)-1H-pyrrolo[2,3-c]pyridin-1-yl)benzamide (25 mg, 0.050 mmol) in MeOH (3 mL, anhydrous) was added NaBH$_4$ (2.8 mg, 0.075 mmol), and the resulting mixture was stirred at RT for 30 min. The reaction mixture was then neutralized with 1N HCl (0.5 mL). The reaction mixture was purified by preparative RP-HPLC method A to give trans-(5-fluoro-2-(3-(1-((4-hydroxycyclohexyl)methyl)piperidin-4-yl)-1H-pyrrolo[2,3-c]pyridin-1-yl)-N-isopropyl-N-methylbenzamide (TFA salt) and cis-(5-fluoro-2-(3-(1-((4-hydroxycyclohexyl)methyl)piperidin-4-yl)-1H-pyrrolo[2,3-c]pyridin-1-yl)-N-isopropyl-N-methylbenzamide (TFA salt) both as colorless solid.

Example 27 (trans-isomer): LCMS method D: R$_t$=1.254 min; (M+H)$^+$=507.3. $^1$H NMR (CD3OD): δ ppm 8.81-9.12 (m, 1H), 8.32-8.42 (m, 2H), 8.14-8.18 (m, 1H), 7.74-7.78 (m, 1H), 7.43-7.57 (m, 2H), 4.33-4.44 (m, 0.5H), 3.68-3.84 (m, 2.5H), 3.52-3.58 (m, 1H), 3.40-3.45 (m, 1H), 3.22 (t, J=12.0 Hz, 2H), 3.08 (d, J=6.4 Hz, 2H), 2.59-2.67 (m, 3H), 2.15-2.38 (m, 4H), 1.87-2.07 (m, 5H), 1.30-1.40 (m, 2H), 1.08-1.26 (m, 4H), 0.51-1.05 (m, 4H). $^{19}$F NMR (CD3OD): δ ppm −110.67~−110.48, −76.88.

Example 27A (cis-isomer): LCMS method D: R$_t$=1.312 min; (M+H)$^+$=507.3. $^1$H NMR (CD3OD): δ ppm 8.90-8.99 (m, 1H), 8.33-8.38 (m, 2H), 8.12-8.18 (m, 1H), 7.74-7.78 (m, 1H), 7.46-7.58 (m, 2H), 4.40-4.42 (m, 0.5H), 3.95-4.01 (m, 0.5H), 3.60-3.80 (m, 2.0H), 3.43-3.50 (m, 1H), 3.15-3.30 (m, 4H), 3.11 (d, J=6.8 Hz, 1H), 2.56-2.69 (m, 3H), 2.09-2.45 (m, 5H), 1.74-2.08 (m, 3H), 1.53-1.69 (m, 4H), 0.34-1.32 (m, 7H). $^{19}$F NMR (CD3OD): δ ppm −110.71~−110.51, −76.90.

Example 28. 5-fluoro-N-isopropyl-N-methyl-2-(3-(1-(2-(1-(methylsulfonyl)piperidin-4-yl)ethyl)piperidin-4-yl)-1H-pyrrolo[2,3-c]pyridin-1-yl)benzamide

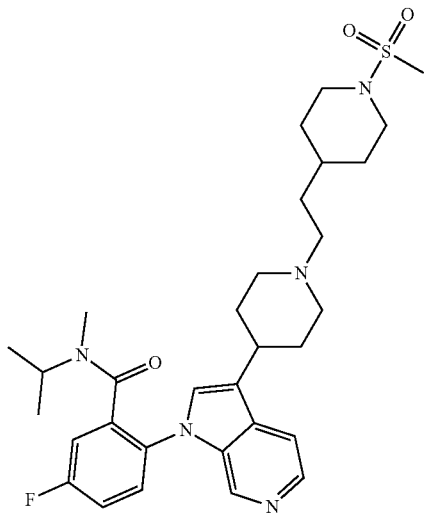 [SMILES: CC(C)N(C)C(=O)c1cc(F)ccc1-n1cc(C2CCN(CCC3CCN(S(C)(=O)=O)CC3)CC2)c2ccncc21]

Step 1: tert-butyl 4-(2-(4-(1-(4-fluoro-2-(isopropyl(methyl)carbamoyl)phenyl)-1H-pyrrolo[2,3-c]pyridin-3-yl)piperidin-1-yl)ethyl)piperidine-1-carboxylate

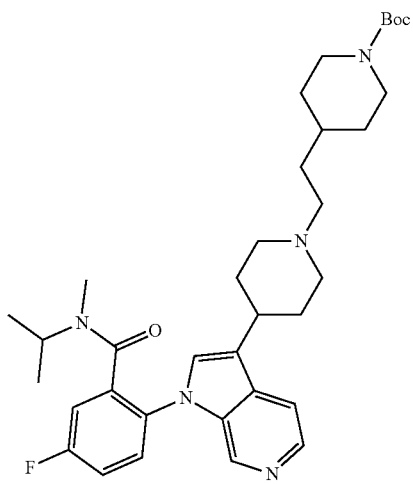 [SMILES: CC(C)N(C)C(=O)c1cc(F)ccc1-n1cc(C2CCN(CCC3CCN(C(=O)OC(C)(C)C)CC3)CC2)c2ccncc21]

A mixture of 5-fluoro-N-isopropyl-N-methyl-2-(3-(piperidin-4-yl)-1H-pyrrolo[2,3-c]pyridin-1-yl)benzamide (Example 1, Step 1, 120 mg, 0.28 mmol, HCl salt), tert-butyl 4-(2-oxoethyl)piperidine-1-carboxylate (95 mg, 0.42 mmol, HCl salt) and NaBH$_3$CN (70 mg, 1.12 mmol) in MeOH (5 mL) was stirred at 70° C. for 18 h. The mixture was then concentrated under reduced pressure. The residue was added to H$_2$O (20 mL) and extracted with EtOAc (2×50 mL). The combined organic layers were dried over anhydrous sodium sulfate, filtered, and the filtrate was concentrated under reduced pressure. The residue was purified by column chromatograph on silica gel (eluting with DCM/MeOH=10/1) to give tert-butyl 4-(2-(4-(1-(4-fluoro-2-(isopropyl(methyl)carbamoyl)phenyl)-1H-pyrrolo[2,3-c]pyridin-3-yl)piperidin-1-yl)ethyl)piperidine-1-carboxylate as yellow oil, which was used directly in the next step.

Step 2: 5-fluoro-N-isopropyl-N-methyl-2-(3-(1-(2-(piperidin-4-yl)ethyl)piperidin-4-yl)-1H-pyrrolo[2,3-c]pyridin-1-yl)benzamide

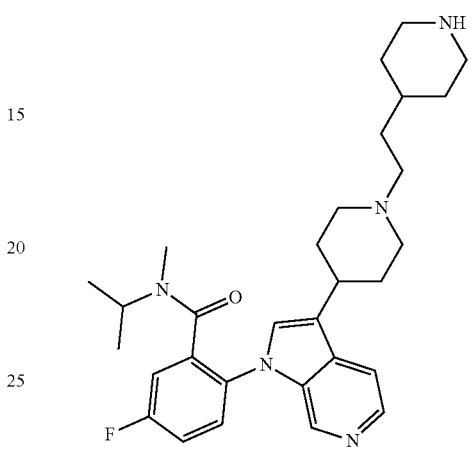

To a mixture of tert-butyl 4-(2-(4-(1-(4-fluoro-2-(isopropyl(methyl)carbamoyl)phenyl)-1H-pyrrolo[2,3-c]pyridin-3-yl)piperidin-1-yl)ethyl)piperidine-1-carboxylate (70 mg, 0.12 mmol) in anhydrous DCM (5 mL) was added HCl/dioxane (1 mL, 4 N), and the mixture was stirred at RT for 1 h. The mixture was then concentrated under reduced pressure to give crude 5-fluoro-N-isopropyl-N-methyl-2-(3-(1-(2-(piperidin-4-yl)ethyl)piperidin-4-yl)-1H-pyrrolo[2,3-c]pyridin-1-yl)benzamide (HCl salt) as white solid, which was used for the next step directly without further purification.

Step 3: 5-fluoro-N-isopropyl-N-methyl-2-(3-(1-(2-(1-(methylsulfonyl)piperidin-4-yl)ethyl)piperidin-4-yl)-1H-pyrrolo[2,3-c]pyridin-1-yl)benzamide To a mixture of 5-fluoro-N-isopropyl-N-methyl-2-(3-(1-(2-(piperidin-4-yl)ethyl)piperidin-4-yl)-1H-pyrrolo[2,3-c]pyridin-1-yl)benzamide (70 mg crude, 0.12 mmol, HCl salt) and Et$_3$N (61 mg, 0.08 mL, 0.6 mmol) in anhydrous DCM (5 mL) was added (MeSO$_2$)$_2$O (63 mg, 0.36 mmol), and the mixture was stirred at 6-20° C. for 30 min. The mixture was then concentrated under reduced pressure and the residue was purified by preparative RP-HPLC Method D to give 5-fluoro-N-isopropyl-N-methyl-2-(3-(1-(2-(1-(methylsulfonyl)piperidin-4-yl)ethyl)piperidin-4-yl)-1H-pyrrolo[2,3-c]pyridin-1-yl)benzamide as white solid. Yield: 14.6 mg (21%); LCMS method E: R$_t$=0.878 min; (M+H)$^+$=584.4. $^1$H NMR (CD$_3$OD): δ ppm 8.55-8.64 (m, 1H), 8.17-8.21 (m, 1H), 7.76-7.79 (m, 1H), 7.65-7.69 (m, 1H), 7.35-7.46 (m, 3H), 4.46-4.50 (m, 0.5H), 3.71-3.74 (m, 2H), 3.56-3.58 (m, 0.5H), 3.10-3.20 (m, 2H), 2.90-3.05 (m, 1H), 2.83-2.85 (m, 3H), 2.70-2.80 (m, 2H), 2.68 (s, 1.5H), 2.50-2.60 (m, 2H), 2.45 (s, 1.5H), 2.20-2.30 (m, 2H), 2.00-2.10 (m, 2H), 1.80-2.00 (m, 4H), 1.40-1.60 (m, 3H), 1.25-1.35 (m, 2H), 0.95-1.10 (m, 3H), 0.20-0.60 (m, 3H). $^{19}$F NMR (CD$_3$OD): δ ppm −115.84∼−113.23.

Example 29. 2-(3-(1-(4-(2-cyanopropan-2-yl)phenethyl)piperidin-4-yl)-1H-pyrrolo[2,3-c]pyridin-1-yl)-5-fluoro-N-isopropyl-N-methylbenzamide

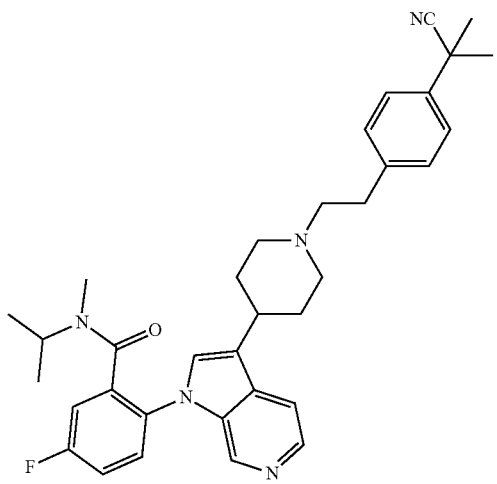 [SMILES: CC(C)N(C)C(=O)c1cc(F)ccc1-n1cc(C2CCN(CCc3ccc(C(C)(C)C#N)cc3)CC2)c2ccncc21]

Step 1: 2-(4-(bromomethyl)phenyl) ethanol

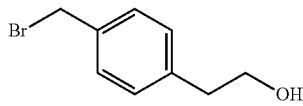

To solution of 2-(4-(bromomethyl)phenyl)acetic acid, 2-(4-(bromomethyl)phenyl)acetic acid (3.2 g, 13.9 mmol) in anhydrous THF (30 mL) was added dropwise BH$_3$-THF (20.7 mL, 20.7 mmol, 1 M) at 0° C. over 30 min. After addition, the mixture was stirred at 9-20° C. for 2 h. The mixture was added dropwise into aq. HCl (2 M, 30 mL) and stirred at 9-20° C. for 20 min. The mixture was then extracted with EtOAc (30 mL×2) and the combined organic was layers were washed with brine (50 mL×2), dried over Na$_2$SO$_4$, filtered, and the filtrate was concentrated. The resulting residue was purified by ISCO column (from 100% DCM to 5% MeOH in DCM) to give 2-(4-(bromomethyl)phenyl)ethanol as white solid. Yield: 3.1 g (100%); $^1$H NMR (CDCl$_3$): δ ppm 7.35 (d, J=8.0 Hz, 1H), 7.22 (d, J=8.0 Hz, 1H), 4.50 (s, 2H), 3.87 (t, J=6.4 Hz, 2H), 2.87 (t, J=6.4 Hz, 2H), 1.45 (brs, 1H).

Step 2. 2-(4-(2-hydroxyethyl)phenyl)acetonitrile

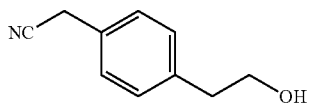 [SMILES: N#CCc1ccc(CCO)cc1]

To a solution of 2-(4-(bromomethyl)phenyl)ethanol (3.0 g, 13.8 mmol) in DMSO (30 mL) was added KCN (1.17 g, 18.0 mmol) and the solution was stirred at RT for 4 h. The mixture was then poured into tert-butyl methyl ether/NaHCO$_3$ (100 mL, 1/1) and stirred at 5-20° C. for 20 min. The organic layers were separated and washed with brine (50 mL×3), dried over Na$_2$SO$_4$, filtered, and the filtrate was concentrated to give 2-(4-(2-hydroxyethyl)phenyl)acetonitrile as yellow oil, which was used next step directly.

Step 3. 2-(4-(2-((tert-butyldimethylsilyl)oxy)ethyl)phenyl)acetonitrile

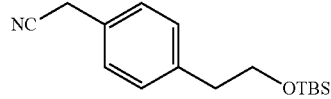 [SMILES: CC(C)(C)[Si](C)(C)OCCc1ccc(CC#N)cc1]

To a solution of 2-(4-(2-hydroxyethyl)phenyl)acetonitrile (1.5 g, 9.3 mmol) in anhydrous DMF (30 mL) was added TBSCl (1.68 g, 11.2 mmol) and imidazole (1.26 g, 18.6 mmol), and the mixture was stirred at 6-20° C. for 6 h. The mixture was then diluted with EtOAc (30 mL) and washed with brine (30 mL×2), dried over Na$_2$SO$_4$, filtered, and the filtrate was concentrated. The resulting residue was purified by ISCO column (from 100% petroleum ether to 10% EtOAc in petroleum ether) to give 2-(4-(2-((tert-butyldimethylsilyl)oxy)ethyl)phenyl)acetonitrile as colorless oil. Yield: 2.2 g (86%); $^1$H NMR (CDCl3): δ ppm 7.24-7.29 (m, 4H), 3.82 (t, J=7.2 Hz, 2H), 3.75 (s, 2H), 2.84 (t, J=6.8 Hz, 2H), 0.90 (s, 9H), 0.08 (s, 6H).

Step 4. 2-(4-(2-((tert-butyldimethylsilyl)oxy)ethyl)phenyl)-2-methylpropanenitrile

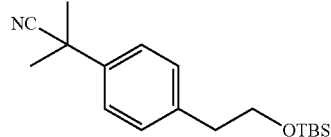 [SMILES: CC(C)(C#N)c1ccc(CCO[Si](C)(C)C(C)(C)C)cc1]

To a solution of 2-(4-(2-((tert-butyldimethylsilyl)oxy)ethyl)phenyl)acetonitrile (1.3 g, 4.7 mmol) in anhydrous DMF (10 mL) was added NaH (378 mg, 9.4 mmol) at 0° C. and stirred for 10 min. Then MeI (1.34 g, 9.4 mmol) was added dropwise into the mixture and stirred at RT for 2 h. The mixture was quenched with aq. NH$_4$Cl (20 mL) and extracted with EtOAc (20 mL×2). The combined organic layers were washed with brine (30 mL×3), dried over Na$_2$SO$_4$, filtered, and filtrate was concentrated to purify by ISCO column (10% EtOAc in petroleum ether) to give 2-(4-(2-((tert-butyldimethylsilyl)oxy)ethyl)phenyl)-2-methylpropanenitrile as colorless oil. Yield: 750 mg (53%); $^1$H NMR (CDCl3): δ ppm 7.40 (d, J=8.0 Hz, 2H), 7.26 (t, J=8.0 Hz, 2H), 3.82 (t, J=6.8 Hz, 2H), 2.84 (t, J=6.8 Hz, 2H), 1.73 (s, 6H), 0.88 (s, 9H), 0.00 (s, 6H).

Step 5: 2-(4-(2-hydroxyethyl)phenyl)-2-methylpropanenitrile

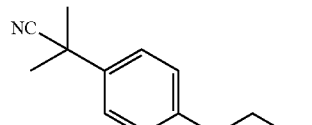

A solution of 2-(4-(2-((tert-butyldimethylsilyl)oxy)ethyl)phenyl)acetonitrile (750 mg, 2.5 mmol) in 1 M TBAF solution (THF solution, 3 mL) was stirred at 2-17° C. for 2 h. The mixture was then quenched with aq. NH₄Cl (10 mL) and extracted with EtOAc (10 mL×2). The combined organic layers were washed with brine (20 mL×2), dried over Na₂SO₄, filtered, and the filtrate was concentrated. The resulting residue was purified by acidic (TFA) preparative RP-HPLC Method A to give 2-(4-(2-hydroxyethyl)phenyl)-2-methylpropanenitrile (TFA salt) as yellow oil. Yield: 150 mg (33%); ¹H NMR (CDCl₃): δ ppm 7.41-7.44 (m, 2H), 7.25-7.28 (m, 2H), 3.90 (t, J=6.4 Hz, 2H), 3.06 (br s, 1H), 2.89 (t, J=6.4 Hz, 2H), 1.72 (s, 6H).

Step 6: 4-(2-cyanopropan-2-yl)phenethyl methanesulfonate

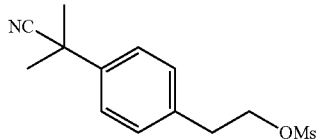 [SMILES: CC(C)(C#N)c1ccc(CCOS(C)(=O)=O)cc1]

To a solution of 2-(4-(2-hydroxyethyl)phenyl)-2-methylpropanenitrile (80 mg, 0.42 mmol) in anhydrous CH₂Cl₂ (5 mL) was added Et₃N (85 mg, 0.84 mmol) and MsCl (58 mg, 0.51 mmol), and the mixture was stirred at RT for 18 h. The mixture was diluted with DCM (10 mL) and washed with brine (10 mL×2), dried over Na₂SO₄, filtered, and the filtrate was concentrated to give 4-(2-cyanopropan-2-yl)phenethyl methanesulfonate as colorless oil. Yield: 70 mg (62%); %); LCMS method B: R_t=0.727 min; (M+H)⁺=285.0.

Step 7: 2-(3-(1-(4-(2-cyanopropan-2-yl)phenethyl)piperidin-4-yl)-1H-pyrrolo[2,3-c]pyridin-1-yl)-5-fluoro-N-isopropyl-N-methylbenzamide To solution of 4-(2-cyanopropan-2-yl)phenethyl methanesulfonate (70 mg, 0.26 mmol) in anhydrous DMF (2 mL) was added 5-fluoro-N-isopropyl-N-methyl-2-(7-(piperidin-4-yl)-5H-pyrrolo[3,2-d]pyrimidin-5-yl)benzamide (Example 63, Step 3, 52 mg, 0.13 mmol), Et₃N (66 mg, 0.65 mmol), and the mixture was stirred at 100° C. for 18 h. The mixture was then diluted with MeCN (3 mL) and purified by RP-HPLC Method D to give 2-(3-(1-(4-(2-cyanopropan-2-yl)phenethyl)piperidin-4-yl)-1H-pyrrolo[2,3-c]pyridin-1-yl)-5-fluoro-N-isopropyl-N-methylbenzamide as a white solid. Yield: 1.2 mg (1%); %); LCMS method D: R_t=1.747 min; (M+H)⁺=556.3. ¹H NMR (CD₃OD): δ ppm 8.83-9.91 (m, 1H), 8.34-8.39 (s, 1H), 8.30 (d, J=5.6 Hz, 1H), 8.05-8.15 (m, 1H), 7.70-7.80 (m, 1H), 7.44-7.57 (m, 4H), 7.40 (d, J=8.4 Hz, 2H), 3.85 (d, J=11.6 Hz, 2H), 3.42-3.50 (m, 3H), 3.10-3.20 (m, 2H), 2.57-2.66 (m, 3H), 2.38-2.41 (m, 2H), 2.00-2.20 (m, 3H), 1.72 (s, 6H), 1.30 (s, 3H), 1.02-1.18 (m, 2H), 0.55-0.95 (m, 3H). ¹⁹F NMR (CD₃OD): δ ppm −76.94, −110.51.

Example 30. 5-fluoro-N-isopropyl-N-methyl-2-(3-(1-(1-phenylethyl)piperidin-4-yl)-1H-pyrrolo[2,3-c]pyridin-1-yl)benzamide

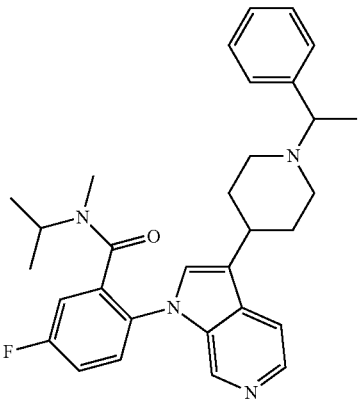 [SMILES: CC(c1ccccc1)N1CCC(c2cn(-c3ccc(F)cc3C(=O)N(C)C(C)C)c3cnccc23)CC1]

To a solution of 5-fluoro-N-isopropyl-N-methyl-2-(3-(piperidin-4-yl)-1H-pyrrolo[2,3-c]pyridin-1-yl)benzamide (Example 1, Step 1, 50 mg, 0.13 mmol) in DMF (3 mL) was added (1-bromoethyl)benzene (26 mg, 0.14 mmol) and K₂CO₃ (36 mg, 0.26 mmol), and the reaction mixture was stirred at 100° C. for 16 h. The mixture was then diluted with H₂O (100 mL) and extracted with EtOAc (30 mL×2). The combined organic layer was dried over anhydrous Na₂SO₄, filtered, and the filtrate was concentrated. The resulting residue was purified by acidic RP-HPLC to afford 5-fluoro-N-isopropyl-N-methyl-2-(3-(1-(1-phenylethyl)piperidin-4-yl)-1H-pyrrolo[2,3-c]pyridin-1-yl)benzamide (HCl salt) as white solid. Yield: 10.9 mg (17% crude); LCMS method E: R_t=0.743 min; (M+H)⁺=499.3. ¹H NMR (CD₃OD): δ ppm 8.80-9.00 (m, 1H), 8.25-8.40 (m, 2H), 8.05-8.20 (m, 1H), 7.70-7.80 (m, 1H), 7.40-7.60 (m, 7H), 4.50-4.60 (m, 1H), 4.30-4.40 (m, 0.5H), 3.85-3.95 (m, 1H), 3.60-3.75 (m, 0.5H), 3.45-3.55 (m, 1H), 3.30-3.40 (m, 1H), 3.00-3.25 (m, 2H), 2.55-2.65 (m, 3H), 2.25-2.40 (m, 2H), 2.00-2.20 (m, 2H), 1.75-1.90 (m, 3H), 0.50-1.20 (m, 6H). ¹⁹F NMR (CD₃OD): δ ppm −110.68~−110.50.

Example 31. 2-(3-(2-benzylpiperidin-4-yl)-1H-pyrrolo[2,3-c]pyridin-1-yl)-5-fluoro-N-isopropyl-N-methylbenzamide

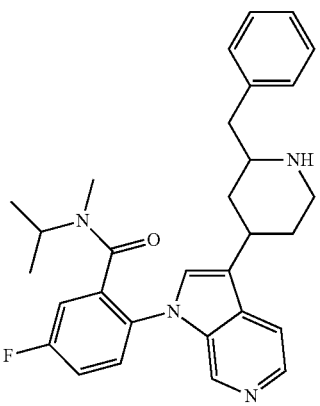 [SMILES: CC(C)N(C)C(=O)c1cc(F)ccc1-n1cc(C2CCNC(Cc3ccccc3)C2)c2ccncc21]

Step 1: tert-butyl 2-benzyl-4-(1-(4-fluoro-2-(isopropyl(methyl)carbamoyl)phenyl)-1H-pyrrolo[2,3-c]pyridin-3-yl)piperidine-1-carboxylate

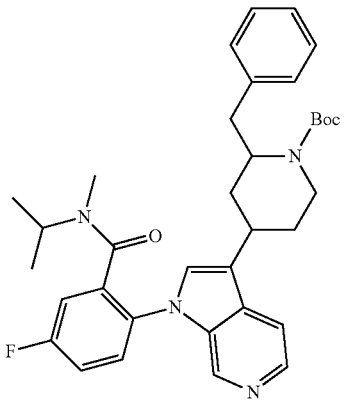 [SMILES: CC(C)N(C)C(=O)c1cc(F)ccc1-n1cc(C2CCN(C(=O)OC(C)(C)C)C(Cc3ccccc3)C2)c2ccncc21]

The title compound was prepared according to the method described for the synthesis of Intermediate 1, starting from tert-butyl 2-benzyl-4-oxopiperidine-1-carboxylate. LCMS method B: $R_t$=0.805 min; (M+H)$^+$=585.1.

Step 2: 2-(3-(2-benzylpiperidin-4-yl)-1H-pyrrolo[2,3-c]pyridin-1-yl)-5-fluoro-N-isopropyl-N-methylbenzamide To a solution of tert-butyl 2-benzyl-4-(1-(4-fluoro-2-(isopropyl(methyl)carbamoyl)phenyl)-1H-pyrrolo[2,3-c]pyridin-3-yl)piperidine-1-carboxylate (100 mg, 0.14 mmol) in DCM (3 mL) was added HCl/dioxane (1.0 mL), and the reaction mixture was stirred at RT for 16 h. The mixture was then concentrated, and the resulting residue was purified by acidic RP-HPLC Method A to afford 2-(3-(2-benzylpiperidin-4-yl)-1H-pyrrolo[2,3-c]pyridin-1-yl)-5-fluoro-N-isopropyl-N-methylbenzamide (HCl salt) as white solid. Yield: 31.1 mg (47%); LCMS method E: $R_t$=0.726 min; (M+H)$^+$=485.3. $^1$H NMR (CD$_3$OD): δ ppm 8.85-9.05 (m, 1H), 8.15-8.40 (m, 3H), 7.70-7.80 (m, 1H), 7.50-7.60 (m, 7H), 4.30-4.40 (m, 0.5H), 3.80-4.00 (m, 1H), 3.55-3.80 (m, 2.5H), 2.95-3.30 (m, 2H), 2.60 (s, 3H), 2.10-2.45 (m, 3H), 1.80-2.10 (m, 2H), 1.40-1.20 (m, 6H). $^{19}$F NMR (CD$_3$OD): δ ppm −110.64~−110.45 (m, 1F).

Example 32. 2-(3-(1-benzylpiperidin-4-yl)-1H-pyrrolo[2,3-c]pyridin-1-yl)-N-ethyl-5-fluoro-N-isopropylbenzamide

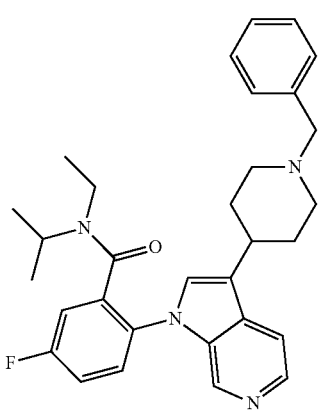 [SMILES: CCN(C(=O)c1cc(F)ccc1-n1cc(C2CCN(Cc3ccccc3)CC2)c2ccncc21)C(C)C]

The title compound was prepared from Intermediate 7 according to the method described in Example 1. LCMS method D: $R_t$=1.740 min; (M+H)$^+$=499.3. $^1$H NMR (CD$_3$OD): δ ppm 8.53-8.57 (m, 1H), 8.15-8.17 (m, 1H), 7.70-7.75 (m, 1H), 7.50-7.60 (m, 1H), 7.25-7.45 (m, 8H), 3.55-3.60 (m, 3H), 3.35-3.45 (m, 1H), 3.00-3.10 (m, 2H), 2.90-2.94 (m, 2H), 2.24 (t, J=12.0 Hz, 2H), 1.95-2.04 (m, 2H), 1.80-1.95 (m, 2H), 0.95-1.05 (m, 3H), 0.70-0.85 (m, 4H), 0.25-0.35 (m, 2H). $^{19}$F NMR (CD$_3$OD): δ ppm −113.26.

Example 33. 2-(3-(1-benzylpiperidin-4-yl)-1H-pyrrolo[2,3-c]pyridin-1-yl)-5-fluoro-N,N-diisopropylbenzamide

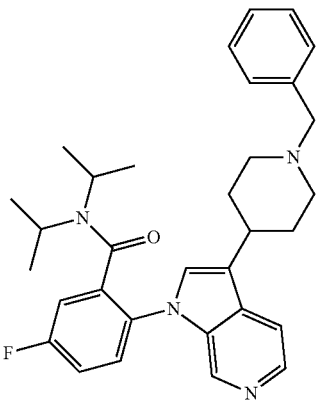 [SMILES: CC(C)N(C(=O)c1cc(F)ccc1-n1cc(C2CCN(Cc3ccccc3)CC2)c2ccncc21)C(C)C]

The title compound was prepared from Intermediate 8 according to the method described in Example 1. LCMS method D: $R_t$=2.341 min; (M+H)$^+$=5133. $^1$H NMR (CD30OD): δ ppm 8.58 (s, 1H), 8.16 (d, J=5.6 Hz, 1H), 7.76 (dd, J=0.8, 6.4 Hz, 1H), 7.55-7.74 (m, 1H), 7.44 (s, 1H), 7.30-7.44 (m, 5H), 7.20-7.30 (m, 2H), 3.60 (s, 2H), 3.50-3.60 (m, 1H), 3.35-3.35 (m, 1H), 3.04-3.08 (m, 2H), 2.85-2.95 (m, 1H), 2.22-2.28 (m, 2H), 2.00-2.10 (m, 2H), 1.80-1.95 (m, 2H), 1.44 (d, J=6.8 Hz, 3H), 1.02 (d, J=6.4 Hz, 6H), 0.28 (d, J=5.6 Hz, 3H). $^{19}$F NMR (CD30OD): δ ppm −113.37.

131

Example 34. N-(trans-4-(2-(4-(1-(2-(cyclopropyl-methoxy)-4-fluorophenyl)-1H-pyrrolo[2,3-c]pyridin-3-yl)piperidin-1-yl)ethyl)cyclohexyl)methanesulfonamide

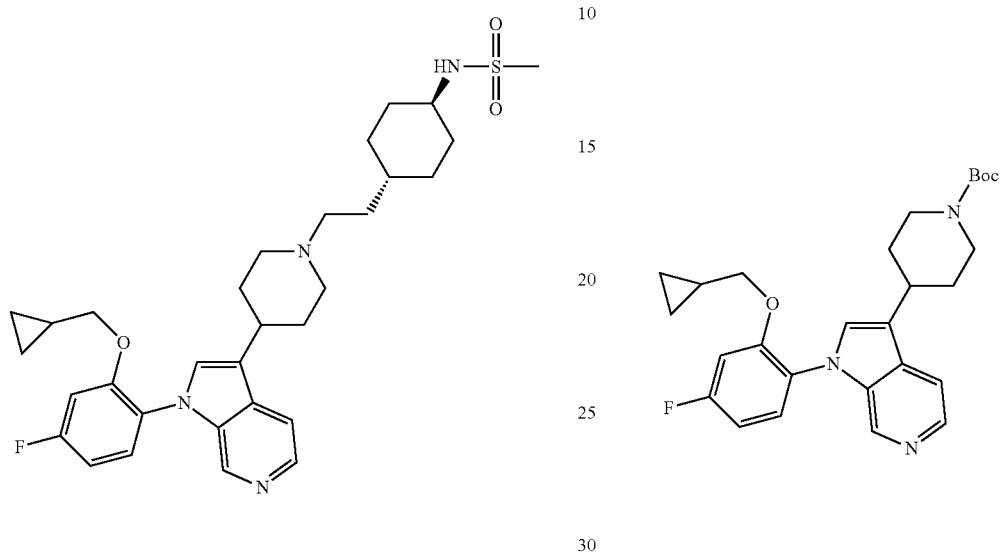

Step 1:
2-(cyclopropylmethoxy)-4-fluoro-1-iodobenzene

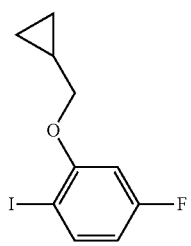 [SMILES: Fc1ccc(I)c(OCC2CC2)c1]

A mixture of 5-fluoro-2-iodophenol (200 mg, 0.84 mmol), (bromomethyl)cyclopropane (227 mg, 1.68 mmol) and $K_2CO_3$ (464 mg, 3.36 mmol) in $CH_3CN$ (5 mL) was stirred at reflux for 2 h. The mixture was filtered and the filtrate was concentrated under reduced pressure. The resulting residue was purified by column chromatograph on silica gel (eluting with petroleum ether) to give 2-(cyclopropylmethoxy)-4-fluoro-1-iodobenzene as colorless oil. Yield: 220 mg (90%); $^1$H NMR ($CDCl_3$): δ ppm 7.59-7.64 (m, 1H), 6.41-6.49 (m, 2H), 3.80 (d, J=6.4 Hz, 2H), 1.21-1.26 (m, 1H), 0.56-0.62 (m, 2H), 0.33-0.38 (m, 2H).

132

Step 2: tert-butyl 4-(1-(2-(cyclopropylmethoxy)-4-fluorophenyl)-1H-pyrrolo[2,3-c]pyridin-3-yl)piperidine-1-carboxylate A mixture of tert-butyl 4-(1H-pyrrolo[2,3-c]pyridin-3-yl)piperidine-1-carboxylate (Intermediate 1, Step 2, 150 mg, 0.5 mmol), 2-(cyclopropylmethoxy)-4-fluoro-1-iodobenzene (220 mg, 0.75 mmol), (1S,2S)—N1,N2-dimethylcyclohexane-1,2-diamine (28 mg, 0.2 mmol), CuI (10 mg, 0.05 mmol) and $K_3PO_4$ (317 mg, 1.5 mmol) in anhydrous DMF (5 mL) was stirred at 130° C. for 18 h. The mixture was cooled and then added to $H_2O$ (20 mL) and extracted with EtOAc (3×20 mL). The combined organic layers were washed with $H_2O$ (3×20 mL) and brine (20 mL), dried over anhydrous sodium sulfate, filtered, and the filtrate was concentrated under reduced pressure. The residue was purified by column chromatograph on silica gel (eluting with EtOAc) to give tert-butyl 4-(1-(2-(cyclopropylmethoxy)-4-fluorophenyl)-1H-pyrrolo[2,3-c]pyridin-3-yl)piperidine-1-carboxylate as yellow oil. Yield: 110 mg (36%); LCMS method E: $R_f$=1.029 min; (M+H)$^+$=466.3. $^1$H NMR ($CD_3OD$): δ ppm 7.76-8.27 (m, 3H), 7.43-7.47 (m, 2H), 7.04-7.08 (m, 1H), 6.86-6.89 (m, 1H), 4.22-4.26 (m, 2H), 3.90 (d, J=6.4 Hz, 2H), 3.01-3.16 (m, 3H), 2.09-2.13 (m, 2H), 1.65-1.77 (m, 2H), 1.50 (s, 9H), 1.04-1.07 (m, 1H), 0.42-0.46 (m, 2H), 0.17-0.22 (m, 2H). $^{19}$F NMR ($CD_3OD$): δ ppm −112.46.

Step 3: 1-(2-(cyclopropylmethoxy)-4-fluorophenyl)-3-(piperidin-4-yl)-1H-pyrrolo[2,3-c]pyridine

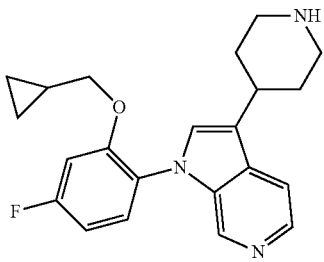 [SMILES: Fc1ccc(-n2cc(C3CCNCC3)c3ccncc32)c(OCC2CC2)c1]

To a mixture of tert-butyl 4-(1-(2-(cyclopropylmethoxy)-4-fluorophenyl)-1H-pyrrolo[2,3-c]pyridin-3-yl)piperidine-1-carboxylate (90 mg, 0.19 mmol) in CH$_2$Cl$_2$ (10 mL) was added HCl-dioxane (2 mL) under ice-cold water. The mixture was degassed and purged with N$_2$ 3 times. The mixture was stirred under N$_2$ atmosphere at RT for 2 h. The mixture was then concentrated under reduced pressure basified to pH=10-12 with 10% NaOH solution and extracted with CH$_2$Cl$_2$ (3×30 mL). The combined organic layers were dried over anhydrous sodium sulfate, filtered, and the filtrate was concentrated under reduced pressure to give the 1-(2-(cyclopropylmethoxy)-4-fluorophenyl)-3-(piperidin-4-yl)-1H-pyrrolo[2,3-c]pyridine as yellow oil, which was used for the next step directly without further purification. Yield: 70 mg (98% crude); LCMS method B: R$_t$=0.573 min; (M+H)$^+$=366.0

Step 4: N-(trans-4-(2-(4-(1-(2-(cyclopropylmethoxy)-4-fluorophenyl)-1H-pyrrolo[2,3-c]pyridin-3-yl)piperidin-1-yl)ethyl)cyclohexyl)methanesulfonamide The title compound was prepared according to the method described in steps 2 and 3 of Example 28. LCMS method D: R$_t$=2.395 min; (M+H)$^+$=569.3. $^1$H NMR (CD3OD): δ ppm 8.38 (s, 1H), 8.14 (d, J=6.0 Hz, 1H), 7.74 (d, J=6.0 Hz, 1H), 7.40-7.50 (m, 2H), 7.06 (d, J=10.0 Hz, 1H), 6.85-6.91 (m, 1H), 3.90 (d, J=6.8 Hz, 2H), 3.10-3.19 (m, 3H), 2.96 (s, 3H), 2.50-2.60 (m, 2H), 2.25-2.40 (m, 2H), 2.13-2.16 (m, 2H), 2.04-2.07 (m, 2H), 1.92-1.99 (m, 2H), 1.85-1.88 (m, 2H), 1.45-1.55 (m, 2H), 1.20-1.40 (m, 4H), 1.04-1.17 (m, 3H), 0.40-0.45 (m, 2H), 0.10-0.18 (m, 2H). $^{19}$F NMR (CD30OD): δ ppm −112.01.

Example 35. 1-(2-(cyclopropylmethoxy)-4-fluorophenyl)-3-(1-(4-fluorobenzyl)piperidin-4-yl)-1H-pyrrolo[2,3-c]pyridine

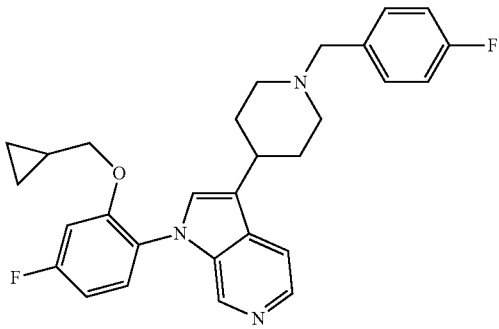 [SMILES: Fc1ccc(CN2CCC(c3cn(-c4ccc(F)cc4OCC4CC4)c4cnccc34)CC2)cc1]

To a mixture of 1-(2-(cyclopropylmethoxy)-4-fluorophenyl)-3-(piperidin-4-yl)-1H-pyrrolo[2,3-c]pyridine (Example 34, Step 3, 25 mg, 0.06 mmol, HCl salt) in MeOH (4 mL) was added 4-fluorobenzaldehyde (17 mg, 0.14 mmol) and NaBH$_3$CN (17 mg, 0.28 mmol). The mixture was degassed and purged with N$_2$ 3 times. The mixture was stirred under N$_2$ atmosphere at 70° C. for 17 h. The mixture was then concentrated under reduced pressure and the resulting residue was purified by preparative RP-HPLC method D to give 1-(2-(cyclopropylmethoxy)-4-fluorophenyl)-3-(1-(4-fluorobenzyl)piperidin-4-yl)-1H-pyrrolo[2,3-c]pyridine as white solid. Yield: 5.6 mg (18%); LCMS method E: R$_t$=0.999 min; (M+H)$^+$=474.3. $^1$H NMR (CD$_3$OD): δ ppm 8.37 (s, 1H), 8.13 (d, J=6.0 Hz, 1H), 7.73-7.74 (m, 1H), 7.40-7.50 (m, 4H), 7.04-7.12 (m, 3H), 6.86-6.90 (m, 1H), 3.89 (d, J=6.8 Hz, 2H), 3.63 (s, 2H), 3.00-3.09 (m, 2H), 2.90-2.99 (m, 1H), 2.25-2.32 (m, 2H), 2.05-2.11 (m, 2H), 1.85-1.97 (m, 2H), 0.95-1.06 (m, 1H), 0.40-0.46 (m, 2H), 0.15-0.20 (m, 2H). $^{19}$F NMR (CD$_3$OD): δ ppm −117.53, −112.06.

Example 36. 2-(3-(1-benzylpiperidin-4-yl)-1H-pyrrolo[2,3-c]pyridin-1-yl)-5-fluoro-N-(2-hydroxyethyl)-N-isopropylbenzamide

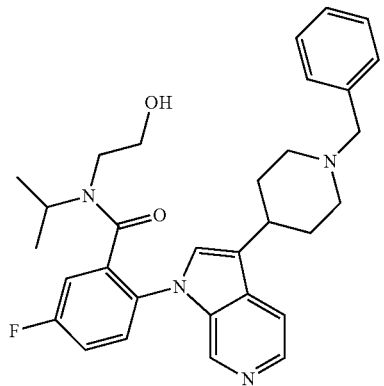 [SMILES: CC(C)N(CCO)C(=O)c1cc(F)ccc1-n1cc(C2CCN(Cc3ccccc3)CC2)c2ccncc21]

Step 1. tert-butyl 4-(1-(2-((2-((tert-butyldiphenylsilyl)oxy)ethyl) (isopropyl)carbamoyl)-4-fluorophenyl)-1H-pyrrolo[2,3-c]pyridin-3-yl)piperidine-1-carboxylate

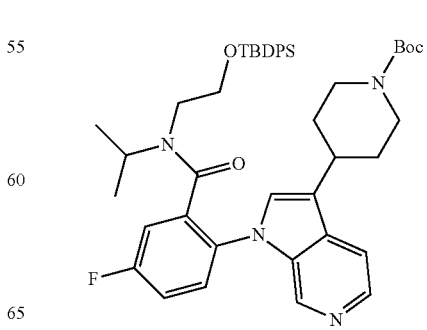

A mixture of 2-(3-(1-(tert-butoxycarbonyl)piperidin-4-yl)-1H-pyrrolo[2,3-c]pyridin-1-yl)-5-fluorobenzoic acid (Intermediate 1, Step 3, 100 mg, 0.23 mmol), N-(2-((tert-butyldiphenylsilyl)oxy)ethyl)propan-2-amine (as synthesized by method described in *European Journal of Organic Chemistry*, 2013(11), 2179-2187; 2013) (120 mg, 0.35 mmol), HATU (133 mg, 0.35 mmol) and Et₃N (116 mg, 0.16 mL, 1.15 mmol) in anhydrous DMF (8 mL) was stirred 10-15° C. for 18 h. The mixture was added to H₂O (20 mL) and extracted with ethyl acetate (3×30 mL). The combined organic layers were washed with H₂O (3×20 mL) and brine (20 mL), dried over anhydrous sodium sulfate, filtered, and the filtrate was concentrated under reduced pressure. The resulting residue was purified by column chromatograph on silica gel (eluting with ethyl acetate) to give tert-butyl 4-(1-(2-((2-((tert-butyldiphenylsilyl)oxy)ethyl)(isopropyl)carbamoyl)-4-fluorophenyl)-1H-pyrrolo[2,3-c]pyridin-3-yl)piperidine-1-carboxylate as yellow solid. Yield: 150 mg (86% crude); LCMS method B: $R_t$=0.883 min; (M+H)⁺= 763.3.

Step 2: 2-(3-(1-benzylpiperidin-4-yl)-1H-pyrrolo[2,3-c]pyridin-1-yl)-5-fluoro-N-(2-hydroxyethyl)-N-isopropylbenzamide The title compound was prepared according to the method described in step 2 of Example 1 to yield 2-(3-(1-benzylpiperidin-4-yl)-1H-pyrrolo[2,3-c]pyridin-1-yl)-5-fluoro-N-(2-hydroxyethyl)-N-isopropylbenzamide. LCMS method E: $R_t$=0.875 min; (M+H)⁺=515.4. ¹H NMR (CD₃OD): δ ppm 8.88-8.96 (m, 1H), 8.15-8.38 (m, 3H), 7.48-7.75 (m, 8H), 4.43 (s, 2H), 3.41-3.84 (m, 5H), 2.90-3.29 (m, 5H), 2.30-2.39 (m, 2H), 2.00-2.18 (m, 2H), 0.50-1.15 (m, 6H). ¹⁹F NMR (CD3OD): δ ppm −77.43~−76.65, −110.86~−110.48.

Example 37. 5-((4-(1-(4-fluorophenyl)-1H-pyrrolo[2,3-c]pyridin-3-yl)piperidin-1-yl)methyl)-4-methyl-1H-indole-2-carbonitrile

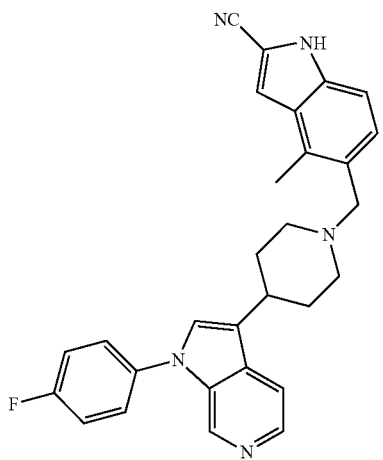 [SMILES: Cc1c(CN2CCC(c3cn(-c4ccc(F)cc4)c4cnccc34)CC2)ccc2[nH]c(C#N)cc12]

Step 1. tert-butyl 4-(1-(4-fluorophenyl)-1H-pyrrolo[2,3-c]pyridin-3-yl)piperidine-1-carboxylate

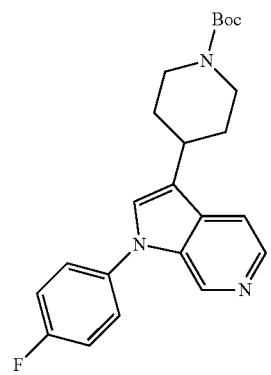 [SMILES: CC(C)(C)OC(=O)N1CCC(c2cn(-c3ccc(F)cc3)c3cnccc23)CC1]

To a solution of tert-butyl 4-(1H-pyrrolo[2,3-c]pyridin-3-yl)piperidine-1-carboxylate (Intermediate 1, Step 2, 200 mg, 0.66 mmmol) in anhydrous CH₂Cl₂ (5 mL) was added (4-fluorophenyl)boronic acid (85 mg, 1.32 mmol), Cu(OAc)₂ (240 mg, 1.32 mmol) and Et₃N (134 mg, 1.32 mmol) and the mixture was stirred at RT for 2 days. The mixture was filtered and the filtrate was concentrated and purified by Isco column (100% DCM to 15% MeOH in DCM) to afford tert-butyl 4-(1-(4-fluorophenyl)-1H-pyrrolo[2,3-c]pyridin-3-yl)piperidine-1-carboxylate as brown oil. Yield: 100 mg (38%); LCMS method B: $R_t$=0.739 min; (M+H)⁺=396.1.

Step 2. 5-((4-(1-(4-fluorophenyl)-1H-pyrrolo[2,3-c]pyridin-3-yl)piperidin-1-yl)methyl)-4-methyl-1H-indole-2-carbonitrile The title compound was prepared according to the methods described in steps 1 & 2 of Example 1 utilizing 5-formyl-4-methyl-1H-indole-2-carbonitrile to yield 5-((4-(1-(4-fluorophenyl)-1H-pyrrolo[2,3-c]pyridin-3-yl)piperidin-1-yl)methyl)-4-methyl-1H-indole-2-carbonitrile. LCMS method F: $R_t$=0.764 min; (M+H)⁺=464.3. ¹H NMR (CD3OD): δ ppm 9.06 (s, 1H), 8.34 (t, J=6.8 Hz, 2H), 8.27 (s, 1H), 7.68 (dd, J=8.0 5.6 Hz, 2H), 7.49 (t, J=8.8 Hz, 1H), 7.40-7.44 (m, 4H), 4.58 (s, 2H), 3.72 (d, J=12.4 Hz, 2H), 3.35-3.50 (m, 3H), 2.72 (s, 3H), 2.37 (d, J=15.2 Hz, 2H), 2.05-2.20 (m, 2H). ¹F NMR (CD3OD): δ ppm −77.04,−113.78.

Examples 38-40

The following Examples were synthesized by method described above for Example 37.

TABLE 4

| No. | Structural formula | Name | LC-MS method; Rt = Min; [M + H]+ |
|---|---|---|---|
| | NMR spectra details | | |

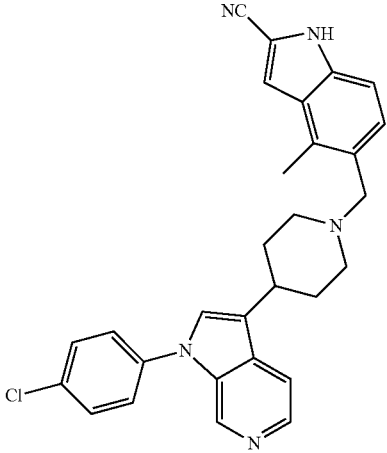 [SMILES: Cc1c(CN2CCC(c3cn(-c4ccc(Cl)cc4)c4cnccc34)CC2)ccc2[nH]c(C#N)cc12]

5-((4-(1-(4-chlorophenyl)-1H-pyrrolo[2,3-c]pyridin-3-yl)piperidin-1-yl)methyl)-4-methyl-1H-indole-2-carbonitrile

F; 2.212; 480.2

$^1$H NMR (DMSOd$_6$): δ ppm 12.27 (s, 1H), 8.87 (s, 1H), 8.21 (d, J = 5.2 Hz, 1H), 7.60-7.70 (m, 6H), 7.44 (s, 1H), 7.23-7.29 (m, 2H), 3.56 (s, 2H), 2.81-2.93 (m, 3H), 2.53 (s, 3H), 2.14-2.17 (m, 2H), 1.93-1.96 (m, 2H), 1.67-1.76 (m, 2H).

1-(4-fluorophenyl)-3-(1-isopentylpiperidin-4-yl)-1H-pyrrolo[2,3-c]pyridine

F; 1.335; 366.2

$^1$H NMR (CD3OD): δ ppm 8.70 (s, 1H), 8.15 (d, J = 5.2 Hz, 1H), 7.73 (d, J = 6.2 Hz, 1H), 7.54-7.59 (m, 3H), 7.30-7.34 (m, 2H), 3.10 (d, J = 12.0 Hz, 2H), 2.90-2.92 (m, 1H), 2.42-2.46 (m, 2H), 2.10-2.20 (m, 2H), 2.03-2.04 (m, 2H), 1.90-1.92 (m, 2H), 1.85-1.60 (m, 1H), 1.46-1.50 (m, 2H), 0.95 (d, J = 1.6 Hz, 6H). $^1$F NMR (DMSO-d$_6$): δ ppm −115.54.

| No. | Structural formula | Name | LC-MS method; Rt = Min; [M + H]+ |
|---|---|---|---|
| 40 | | 1-(4-fluorophenyl)-3-(1-phenethylpiperidin-4-yl)-1H-pyrrolo[2,3-c]pyridine | E; 1.138; 400.2 |

$^1$H NMR (CD3OD): δ ppm 8.71 (s, 1H), 8.17 (d, J = 5.6 Hz, 1H), 7.76 (d, J = 5.6 Hz, 1H), 7.57-7.60 (m, 3H), 7.19-7.33 (m, 7H), 3.19 (d, J = 12.0 Hz, 2H), 2.95-3.00 (m, 1H), 2.86-2.88 (m, 2H), 2.67-2.71 (m, 2H), 2.31-2.34 (m, 2H), 2.09-2.11 (m, 2H), 1.93-1.96 (m, 2H). $^{19}$F NMR (CD3OD): δ ppm −116.51.

Examples 41-41A. 5-fluoro-N-isopropyl-N-methyl-2-(3-(1-(((1r,4r)-4-(methylsulfonamido)cyclohexyl)methyl)azepan-4-yl)-1H-pyrrolo[2,3-c]pyridin-1-yl)benzamide and 2-(3-(azepan-4-yl)-1H-pyrrolo[2,3-c]pyridin-1-yl)-5-fluoro-N-isopropyl-N-methylbenzamide (Example 41A)

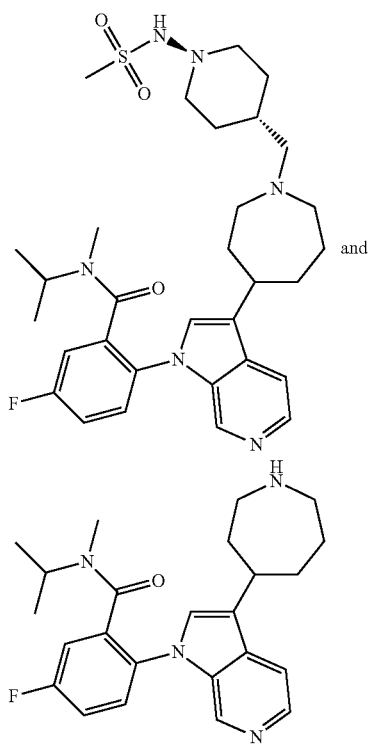

Step 1: 2-(3-(azepan-4-yl)-1H-pyrrolo[2,3-c]pyridin-1-yl)-5-fluoro-N-isopropyl-N-methylbenzamide (Example 41A)

A mixture of tert-butyl 4-(1-(4-fluoro-2-(isopropyl(methyl)carbamoyl)phenyl)-1H-pyrrolo[2,3-c]pyridin-3-yl)azepane-1-carboxylate (Intermediate 14, 40 mg, 0.07 mmol) in CH$_2$Cl$_2$ (1 mL, anhydrous) was added HCl-MeOH (1 mL). The resulting mixture was stirred at RT for 2 h to give 2-(3-(azepan-4-yl)-1H-pyrrolo[2,3-c]pyridin-1-yl)-5-fluoro-N-isopropyl-N-methylbenzamide) (TFA salt) as yellow oil. Yield: 4.5 mg (16%); LCMS method D: R$_t$=0.961 min; (M+H)$^+$=409.3. $^1$H NMR (CD$_3$OD): δ ppm 8.85-9.00 (m, 1H), 8.25-8.35 (m, 2H), 8.05-8.15 (m, 1H), 7.65-7.80 (m, 1H), 7.35-7.65 (m, 2H), 4.30-4.45 (m, 0.5H), 3.60-3.75 (m, 0.5H), 3.30-3.50 (m, 5H), 2.55-2.65 (m, 3H), 1.80-2.35 (m, 6H), 0.25-1.25 (m, 6H). $^{19}$F NMR (CD$_3$OD): δ ppm −76.94, −110.63.

Step 2: 5-fluoro-N-isopropyl-N-methyl-2-(3-(1-(((trans-4-(methylsulfonamido)cyclohexyl)methyl)azepan-4-yl)-1H-pyrrolo[2,3-c]pyridin-1-yl)benzamide (Example 41)

To a solution of 2-(3-(azepan-4-yl)-1H-pyrrolo[2,3-c]pyridin-1-yl)-5-fluoro-N-isopropyl-N-methylbenzamide (20 mg, 0.04 mmol, crude) and N-(trans-4-formylcyclohexyl)methanesulfonamide (Intermediate 21, 8 mg, 0.04 mmol) in anhydrous MeOH (3 mL) was added NaBH$_3$CN (10 mg, 0.16 mmol). The reaction was stirred at 23-28° C. for 16 h. The reaction mixture was concentrated and purified using preparative HPLC method D to give 5-fluoro-N-isopropyl-N-methyl-2-(3-(1-(((trans-4-(methylsulfonamido)cyclohexyl)methyl)azepan-4-yl)-1H-pyrrolo[2,3-c]pyridin-1-yl)benzamide as white solid. Yield: 6.9 mg (30%); LCMS method D: R$_t$=2.153 min; (M+H)$^+$=598.3. $^1$H NMR (CD$_3$OD): δ ppm 8.50-8.65 (m, 1H), 8.10-8.25 (m, 1H), 7.60-7.75 (m, 2H), 7.30-7.50 (m, 3H), 4.40-4.50 (m, 0.5H), 3.45-3.60 (m, 0.5H), 3.10-3.25 (m, 2H), 2.94 (s, 3H), 2.75-2.90 (m, 4H), 2.40-2.70 (m, 3H), 2.39 (d, J=6.4 Hz, 2H), 1.75-2.20 (m, 10H), 1.40-1.55 (m, 1H), 1.20-1.35 (m, 2H), 1.05-1.15 (m, 3H), 0.90-1.00 (m, 2H), 0.10-0.65 (m, 3H). $^{19}F$ NMR (CD$_3$OD): δ ppm −113.46.

Example 42. 5-((4-(1-(4-fluoro-2-isobutylphenyl)-1H-pyrrolo[2,3-c]pyridin-3-yl)piperidin-1-yl)methyl)-4-methyl-1H-indole-2-carbonitrile

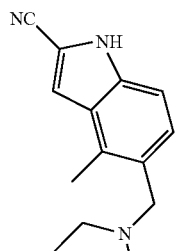

Step 1: tert-butyl 4-(1-(4-fluoro-2-formylphenyl)-1H-pyrrolo[2,3-c]pyridine-3-yl)piperidine-1-carboxylate

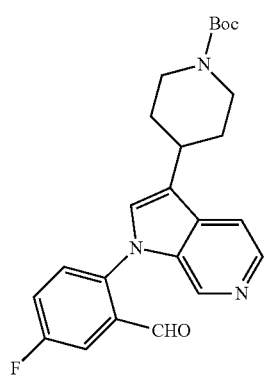 [SMILES: CC(C)(C)OC(=O)N1CCC(c2cn(-c3ccc(F)cc3C=O)c3cnccc23)CC1]

A mixture of tert-butyl 4-(1H-pyrrolo[2,3-c]pyridin-3-yl)piperidine-1-carboxylate (Intermediate 1, Step 2, 400 mg, 1.33 mmol), 2,5-difluorobenzaldehyde (378 mg, 2.66 mmol) and Cs$_2$CO$_3$ (1.73 g, 5.32 mmol) in CH$_3$CN (20 mL) was stirred at 50° C. for 18 h. Water (30 mL) was added and the mixture was extracted with EtOAc (3×30 mL). The combined organic layers were washed with H$_2$O (3×30 mL) and brine (30 mL), dried over anhydrous sodium sulfate, filtered, and the filtrate was concentrated under reduced pressure. The resulting residue was purified by column chromatograph on silica gel (eluting with petroleum ether/EtOAC=1/1) to give tert-butyl 4-(1-(4-fluoro-2-formylphenyl)-1H-pyrrolo[2,3-c]pyridin-3-yl)piperidine-1-carboxylate as brown solid. Yield: 320 mg (51%); LCMS method C: R$_t$=0.662 min; (M+H)$^+$=423.9. $^1$H NMR (CDCl$_3$): δ ppm 9.51 (s, 1H), 8.48 (s, 1H), 8.29 (d, J=6.0 Hz, 1H), 7.70-7.73 (m, 1H), 7.54-7.56 (m, 1H), 7.42-7.45 (m, 2H), 7.08 (s, 1H), 4.20-4.23 (m, 2H), 2.85-3.00 (m, 4H), 1.97-2.02 (m, 3H), 1.42 (s, 9H).

Step 2: tert-butyl 4-(1-(4-fluoro-2-(2-methylprop-1-en-1-yl)phenyl)-1H-pyrrolo[2,3-c]pyridin-3-yl)piperidine-1-carboxylate

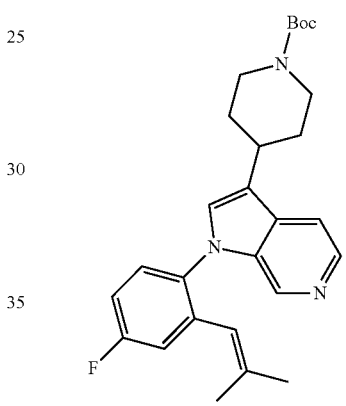

To a mixture of isopropyltriphenylphosphonium iodide (450 mg, 1.04 mmol) in anhydrous THF (10 mL) was added n-BuLi (0.42 mL, 1.04 mmol, 2.5 M in hexane) at −78° C. The mixture was stirred at −78° C. for 1 h. Tert-butyl 4-(1-(4-fluoro-2-formylphenyl)-1H-pyrrolo[2,3-c]pyridin-3-yl)piperidine-1-carboxylate (220 mg, 0.52 mmol) in anhydrous THF (5 mL) was added and the mixture was stirred at −78° C. for 2 h then at RT for 18 h. The mixture was quenched with saturated NH$_4$Cl solution (20 mL) at −30° C. and concentrated under reduced pressure to remove THF. The residue was then extracted with EtOAc (3×50 mL). The combined organic layers were dried over anhydrous sodium sulfate, filtered, and the filtrate was concentrated under reduced pressure. The residue was purified by column chromatograph on silica gel (eluting with petroleum ether/EtOAc=1/1) to give tert-butyl 4-(1-(4-fluoro-2-(2-methylprop-1-en-1-yl)phenyl)-1H-pyrrolo[2,3-c]pyridin-3-yl)piperidine-1-carboxylate as yellow oil. Yield: 200 mg (70%); LCMS method D: R$_t$=0.726 min; (M+H)$^+$=450.1.

143

Step 3: tert-butyl 4-(1-(4-fluoro-2-isobutylphenyl)-1H-pyrrolo[2,3-c]pyridin-3-yl)piperidine-1-carboxylate

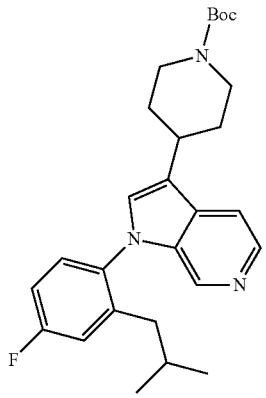 [SMILES: CC(C)Cc1cc(F)ccc1-n1cc(C2CCN(C(=O)OC(C)(C)C)CC2)c2ccncc21]

A mixture of tert-butyl 4-(1-(4-fluoro-2-(2-methylprop-1-en-1-yl)phenyl)-1H-pyrrolo[2,3-c]pyridin-3-yl)piperidine-1-carboxylate (60 mg, 0.13 mmol) and dry Pd—C (20 mg, 10%) in MeOH (6 mL) was stirred at RT for 3 h under $H_2$ (15 psi). The mixture was filtered through a pad of celite and the filtrate was concentrated under reduced pressure to give tert-butyl 4-(1-(4-fluoro-2-isobutylphenyl)-1H-pyrrolo[2,3-c]pyridin-3-yl)piperidine-1-carboxylate (60 mg, 100% crude) as colorless oil, which was used for the next step directly without further purification. Yield: 60 mg (100% crude); LCMS method C: $R_t$=0.740 min; (M+H)$^+$=452.1.

Step 4. 5-((4-(1-(4-fluoro-2-isobutylphenyl)-1H-pyrrolo[2,3-c]pyridin-3-yl)piperidin-1-yl)methyl)-4-methyl-1H-indole-2-carbonitrile The title compound was prepared according to the method described in steps 1 & 2 of Example 1 utilizing 5-formyl-4-methyl-1H-indole-2-carbonitrile to give 5-((4-(1-(4-fluoro-2-isobutylphenyl)-1H-pyrrolo[2,3-c]pyridin-3-yl)piperidin-1-yl)methyl)-4-methyl-1H-indole-2-carbonitrile. LCMS method E: $R_t$=1.782 min; (M+H)$^+$=520.3. $^1$H NMR (CD$_3$OD): δ ppm 8.11-8.19 (m, 2H), 7.74 (d, J=5.2 Hz, 1H), 7.12-7.35 (m, 7H), 3.67 (s, 2H), 3.06-3.09 (m, 2H), 2.92-2.98 (m, 1H), 2.58 (s, 3H), 2.28-2.34 (m, 3H), 2.01-2.10 (m, 3H), 1.84-1.91 (m, 2H), 1.16-1.48 (m, 1H), 0.62-0.66 (m, 6H). $^{19}$F NMR (CD$_3$OD): δ ppm −113.87~−116.24.

144

Example 43. 5-fluoro-N-isopropyl-N-methyl-2-(3-(1-((2-oxo-2,3-dihydro-1H-benzo[d]imidazol-5-yl)methyl)piperidin-3-yl)-1H-pyrrolo[2,3-c]pyridin-1-yl)benzamide (Mixture of Isomers)

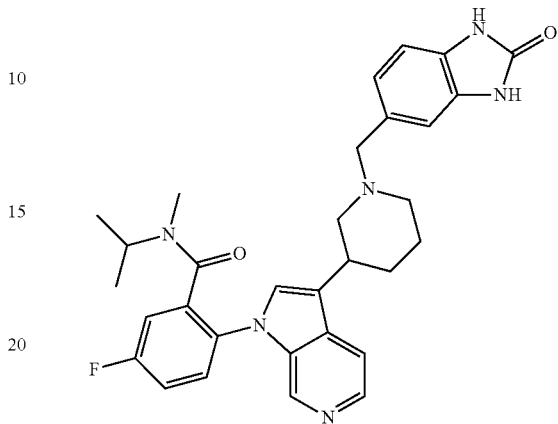

The title compound was synthesized as a mixture of isomers from Intermediate 2 according to the methods described in Example 1. In step 2,2-oxo-2,3-dihydro-1H-benzo[d]imidazole-5-carbaldehyde was utilized. LCMS method C: $R_t$=0.762 min; (M+H)$^+$=541.3.

Examples 43A-43B. 5-fluoro-N-isopropyl-N-methyl-2-(3-(1-((2-oxo-2,3-dihydro-1H-benzo[d]imidazol-5-yl)methyl)piperidin-3-yl)-1H-pyrrolo[2,3-c]pyridin-1-yl)benzamide (Isomers 1-2)

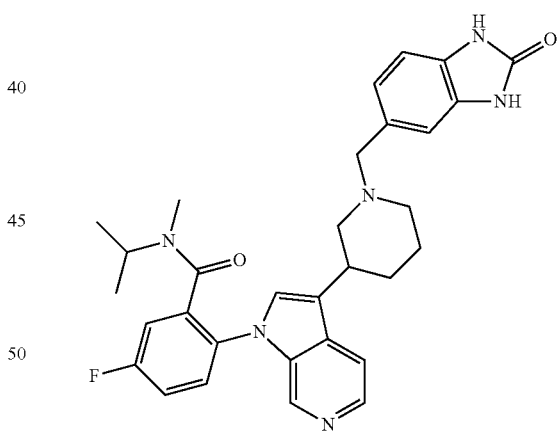

The compound of Example 43 was separated by SFC method A to give two isomers of 5-fluoro-N-isopropyl-N-methyl-2-(3-(1-((2-oxo-2,3-dihydro-1H-benzo[d]imidazol-5-yl)methyl)piperidin-3-yl)-1H-pyrrolo[2,3-c]pyridin-1-yl)benzamide.

Isomer 1: LCMS method D: $R_t$=0.998 min; (M+H)$^+$=541.2. $^1$H NMR (CD$_3$OD): δ ppm 8.53-8.62 (m, 1H), 8.12-8.19 (m, 1H), 7.63-7.70 (m, 2H), 7.34-7.50 (m, 3H), 6.95-7.15 (m, 3H), 4.30-4.40 (m, 0.5H), 3.52-3.70 (m, 2.5H), 2.85-3.30 (m, 3H), 2.30-2.60 (m, 3H), 2.05-2.25 (m, 3H), 1.75-1.90 (m, 2H), 1.45-1.65 (m, 1H), 0.95-1.10 (m, 3H), 0.10-0.45 (m, 3H). $^{19}$F NMR (CD$_3$OD): δ ppm −113.43~−113.08.

Isomer 2: LCMS method D: $R_t$=0.966 min; (M+H)$^+$ =541.2. $^1$H NMR (CD$_3$OD): δ ppm 8.53-8.62 (m, 1H), 8.12-8.19 (m, 1H), 7.63-7.70 (m, 2H), 7.34-7.50 (m, 3H), 6.95-7.15 (m, 3H), 4.30-4.40 (m, 0.5H), 3.52-3.70 (m, 2.5H), 2.85-3.30 (m, 3H), 2.30-2.60 (m, 3H), 2.05-2.25 (m, 3H), 1.75-1.90 (m, 2H), 1.45-1.65 (m, 1H), 0.95-1.10 (m, 3H), 0.10-0.45 (m, 3H). $^{19}$F NMR (CD$_3$OD): δ ppm −113.42~−113.07.

Example 44. 5-fluoro-2-(3-(1-((1-(2-hydroxyethyl)-2-oxo-2,3-dihydro-1H-benzo[d]imidazol-5-yl)methyl)piperidin-3-yl)-1H-pyrrolo[2,3-c]pyridin-1-yl)-N-isopropyl-N-methylbenzamide (Mixture of Isomers)

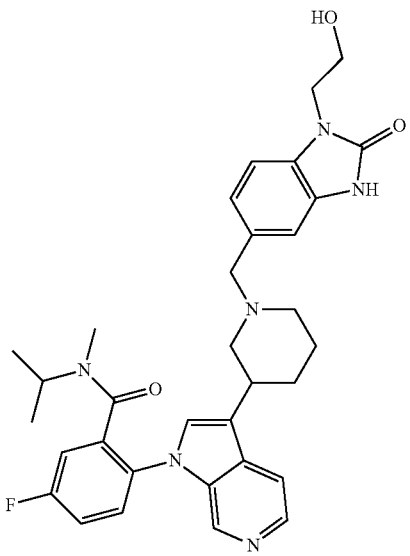 [SMILES: CC(C)N(C)C(=O)c1cc(F)ccc1-n1cc(C2CCCN(Cc3ccc4c(c3)[nH]c(=O)n4CCO)C2)c2ccncc21]

To a solution of 5-fluoro-N-isopropyl-N-methyl-2-(3-(piperidin-3-yl)-1H-pyrrolo[2,3-c]pyridin-1-yl)benzamide obtained by acid deprotection of Intermediate 2 (8.4 g, 21.29 mmol, crude, HCl salt) in MeOH (250 mL) was added Et$_3$N (6.5 g, 63.87 mmol). After stirring for 15 min, a mixture of 1-(2-hydroxyethyl)-2-oxo-2,3-dihydro-1H-benzo[d]imidazole-5-carbaldehyde and 2-(5-formyl-2-oxo-2,3-dihydro-1H-benzo[d]imidazol-1-yl)ethyl formate (Intermediates 24-24A, 8.8 g, 42.58 mmol) and NaBH$_3$CN (2.7 g, 42.58 mmol) was added in turn. The resulting mixture was stirred at 50° C. (oil temperature) under N$_2$ for 24 h. The reaction mixture was concentrated under reduced pressure to afford the crude product. The residue was diluted with H$_2$O (300 mL) and extracted with EtOAc (2×300 mL). The organic layers were washed with brine (2×400 mL), dried over anhydrous Na$_2$SO$_4$, filtered, and the filtrate was concentrated under reduced pressure to afford crude product. The residue was purified by column chromatography on silica gel (CH$_2$Cl$_2$/MeOH=30:1 to CH$_2$Cl$_2$/MeOH=6/1, contained 1% NH$_3$—H2O) to afford 5-fluoro-2-(3-(1-((1-(2-hydroxyethyl)-2-oxo-2,3-dihydro-1H-benzo[d]imidazol-5-yl)methyl)piperidin-3-yl)-1H-pyrrolo[2,3-c]pyridin-1-yl)-N-isopropyl-N-methylbenzamide as yellow solid. Yield: 6.5 g (52%); LCMS method B: $R_t$=0.566 min; (M+H)$^+$=585.2.

Examples 44A-44B. 5-fluoro-2-(3-(1-((1-(2-hydroxyethyl)-2-oxo-2,3-dihydro-1H-benzo[d]imidazol-5-yl)methyl)piperidin-3-yl)-1H-pyrrolo[2,3-c]pyridin-1-yl)-N-isopropyl-N-methylbenzamide (Isomers 1-2)

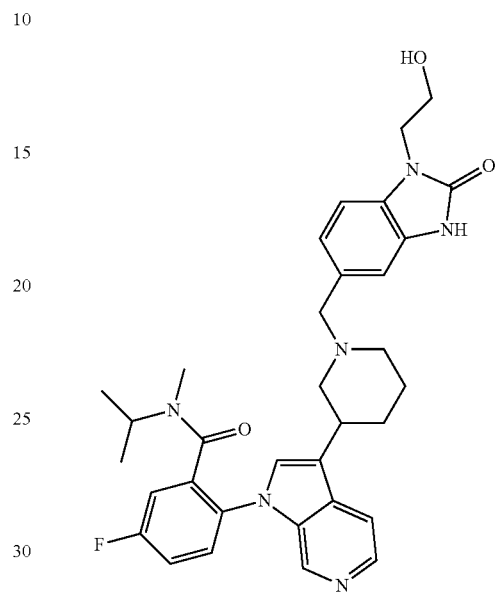

The compound of Example 44 was further purified by SFC method A to give two isomers of 5-fluoro-2-(3-(1-((1-(2-hydroxyethyl)-2-oxo-2,3-dihydro-1H-benzo[d]imidazol-5-yl)methyl)piperidin-3-yl)-1H-pyrrolo[2,3-c]pyridin-1-yl)-N-isopropyl-N-methylbenzamide.

Isomer 1: LCMS method D: $R_t$=1.644 min; (M+H)$^+$= 585.3. $^1$H NMR (CD$_3$OD): δ ppm 8.55-8.62 (m, 1H), 8.12-8.18 (m, 1H), 7.63-7.69 (m, 2H), 7.34-7.45 (m, 3H), 7.10-7.15 (m, 3H), 4.35-4.40 (m, 0.5H), 3.95-4.00 (m, 2H), 3.80-3.85 (m, 2H), 3.52-3.70 (m, 2.5H), 2.85-3.30 (m, 3H), 2.25-2.60 (m, 3H), 2.05-2.25 (m, 3H), 1.45-1.90 (m, 3H), 0.95-1.10 (m, 3H), 0.10-0.45 (m, 3H). $^{19}$F NMR (CD$_3$OD): δ ppm −113.34~−113.00.

Isomer 2: LCMS method B: $R_t$=1.638 min; (M+H)$^+$= 585.3. $^1$H NMR (CD$_3$OD): δ ppm 8.55-8.62 (m, 1H), 8.12-8.18 (m, 1H), 7.63-7.69 (m, 2H), 7.34-7.45 (m, 3H), 7.10-7.15 (m, 3H), 4.35-4.40 (m, 0.5H), 3.95-4.00 (m, 2H), 3.80-3.85 (m, 2H), 3.52-3.70 (m, 2.5H), 2.85-3.30 (m, 3H), 2.25-2.60 (m, 3H), 2.05-2.25 (m, 3H), 1.45-1.90 (m, 3H), 0.95-1.10 (m, 3H), 0.10-0.45 (m, 3H). $^{19}$F NMR (CD$_3$OD): δ ppm −113.41~−113.08.

Examples 45-50

The following Examples were synthesized by the method described for Example 1, steps 1 and 2, starting with Intermediate 2 and the appropriate starting materials.

TABLE 5

| Ex No. | Structural formula | Name | LC-MS method; Rt = Min; [M + H]+ |
|---|---|---|---|
|  | 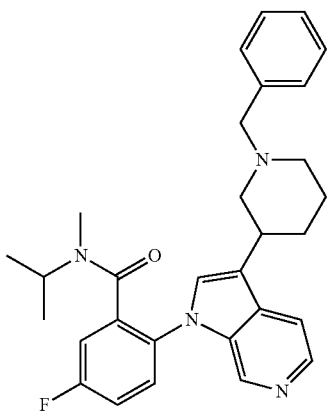 [SMILES: CC(C)N(C)C(=O)c1cc(F)ccc1-n1cc(C2CCCN(Cc3ccccc3)C2)c2ccncc21] | 2-(3-(1-benzylpiperidin-3-yl)-1H-pyrrolo[2,3-c]pyridin-1-yl)-5-fluoro-N-isopropyl-N-methylbenzamide (TFA salt) | E; 0.707; 485.3 |

NMR spectra details $^1$H NMR (CD$_3$OD): δ ppm 8.91-9.02 (m, 1H), 8.32-8.40 (m, 2H), 8.16-8.25 (m, 1H), 7.52-7.57 (m, 1H), 7.48-7.52 (m, 7H), 4.33-4.43 (m, 2.5H), 3.60-3.75 (m, 3.5H), 3.13-3.26 (m, 2H), 2.62 (s, 3H), 1.89-2.25 (m, 4H), 0.55-1.14 (m, 6H). $^{19}$F NMR (CD$_3$OD): δ ppm −110.46~110.28, −77.12.

| | 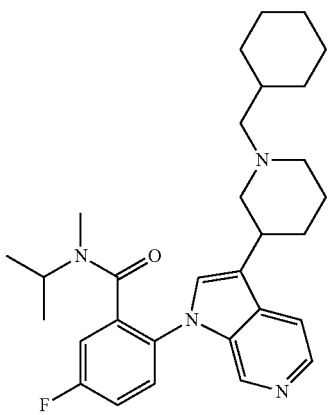 [SMILES: CC(C)N(C)C(=O)c1cc(F)ccc1-n1cc(C2CCCN(CC3CCCCC3)C2)c2ccncc21] | 2-(3-(1-(cyclohexylmethyl)piperidin-3-yl)-1H-pyrrolo[2,3-c]pyridin-1-yl)-5-fluoro-N-isopropyl-N-methylbenzamide | C; 0.764; 491.4 |

$^1$H NMR (CD$_3$OD): δ ppm 8.92-9.03 (m, 1H), 8.37-8.40 (m, 2H), 8.16-8.25 (m, 1H), 7.73-7.76 (m, 1H), 7.45-7.55 (m, 2H), 4.36-4.45 (m, 0.5H), 3.68-3.80 (m, 3.5H), 3.06-3.23 (m, 4H), 2.65-2.67 (d, J = 4.4 Hz, 3H), 2.13-2.22 (m, 3H), 1.71-1.96 (m, 7H), 0.45-1.39 (m, 11H). $^{19}$F NMR (CD$_3$OD): δ ppm −110.51~−110.34, −77.11.

TABLE 5-continued

| Ex No. | Structural formula | Name | LC-MS method; Rt = Min; [M + H]+ |
|---|---|---|---|
| 47 | 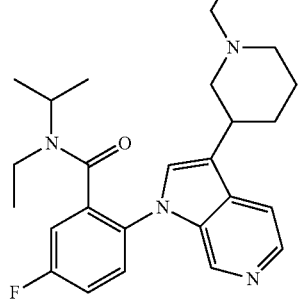 | N-ethyl-5-fluoro-N-isopropyl-2-(3-(1-((2-oxo-2,3-dihydro-1H-benzo[d]imidazol-5-yl)methyl)piperidin-3-yl)-1H-pyrrolo[2,3-c]pyridin-1-yl)benzamide | D; 0.664; 555.3 |

1H NMR (CD3OD): δ ppm 8.50-8.63 (m, 1 H), 8.10-8.25 (m, 1 H), 7.70-7.80 (m, 1 H), 7.55-7.65 (m, 1 H), 7.40-7.50 (m, 2 H), 7.25-7.35 (m, 1 H), 3.50-3.70 (m, 1 H), 3.35-3.45 (m, 1 H), 3.05-3.15 (m, 2 H), 2.90-3.00 (m, 1 H), 2.60-2.75 (m, 2 H), 2.10-2.20 (m, 1H), 1.60-1.90 (m, 3 H), 1.25-1.30 (m, 1 H), 0.95-1.05 (m, 3 H), 0.70-0.90 (m, 4 H), 0.30-0.40 (m, 2 H). 19F NMR (CD3OD): δ ppm −113.21.

| | 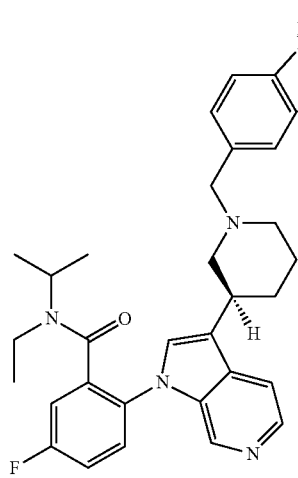 | (S)-N-ethyl-5-fluoro-N-isopropyl-2-(3-(1-((2-oxo-2,3-dihydro-1H-benzo[d]imidazol-5-yl)methyl)piperidin-3-yl)-1H-pyrrolo[2,3-c]pyridin-1-yl)benzamide | E; 1.126; 555.3 |

1H NMR (CD3OD): δ ppm 8.50-8.60 (m, 1 H), 8.10-8.20 (m, 1 H), 7.55-7.70 (m, 2 H), 7.30-7.45 (m, 3 H), 6.90-7.10 (m, 3H), 3.65-3.75 (m, 1 H), 3.45-3.60 (m, 3 H), 2.95-3.15 (m, 4 H), 2.70-2.90 (m, 1 H), 2.05-2.20 (m, 3 H), 1.75-18.5 (m, 2 H), 1.40-1.65 (m, 1 H), 0.98 (d, J = 6.8 Hz, 3 H), 0.60-0.90 (m, 4 H), 0.15-0.30 (m, 2 H). 19F NMR (CD3OD): δ ppm −113.24~−113.25.

TABLE 5-continued

| Ex No. | Structural formula | Name | LC-MS method; Rt = Min; [M + H]+ |
|---|---|---|---|
|  | 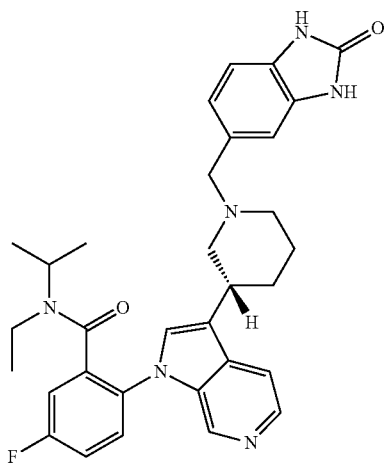 | (R)-N-ethyl-5-fluoro-N-isopropyl-2-(3-(1-((2-oxo-2,3-dihydro-1H-benzo[d]imidazol-5-yl)methyl)piperidin-3-yl)-1H-pyrrolo[2,3-c]pyridin-1-yl)benzamide | E; 1.127; 555.3 |

$^1$H NMR (CD$_3$OD): δ ppm 8.50-8.60 (m, 1 H), 8.10-8.20 (m, 1 H), 7.55-7.70 (m, 2 H), 7.30-7.45 (m, 3 H), 6.90-7.15 (m, 3 H), 3.65-3.75 (m, 1 H), 3.45-3.60 (m, 2 H), 2.95-3.20 (m, 4 H), 2.80-2.90 (m, 1 H), 2.05-2.25 (m, 3 H), 1.75-1.85 (m, 2 H), 1.45-1.60 (m, 1 H), 0.98 (d, J = 6.8 Hz, 3 H), 0.60-0.85 (m, 4 H), 0.15-0.25 (m, 2 H). $^{19}$F NMR (CD$_3$OD): δ ppm −113.19.

| 49 | 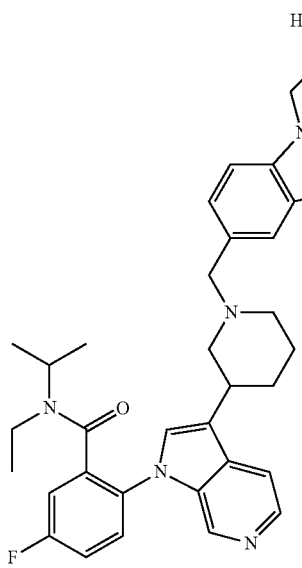 | N-ethyl-5-fluoro-2-(3-(1-((1-(2-hydroxyethyl)-2-oxo-2,3-dihydro-1H-benzo[d]imidazol-5-yl)methyl)piperidin-3-yl)-1H-pyrrolo[2,3-c]pyridin-1-yl)-N-isopropylbenzamide | E; 1.186; 599.3 |

TABLE 5-continued

| Ex No. | Structural formula | Name | LC-MS method; Rt = Min; [M + H]+ |
|---|---|---|---|
| | 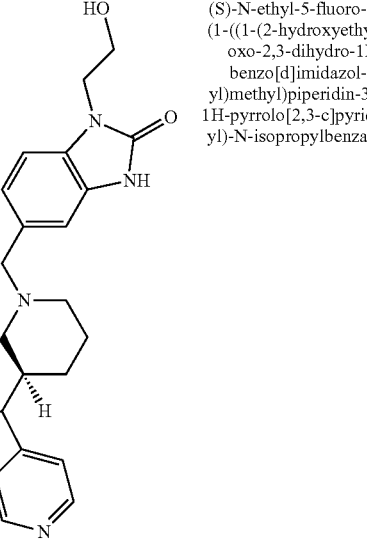 | (S)-N-ethyl-5-fluoro-2-(3-(1-((1-(2-hydroxyethyl)-2-oxo-2,3-dihydro-1H-benzo[d]imidazol-5-yl)methyl)piperidin-3-yl)-1H-pyrrolo[2,3-c]pyridin-1-yl)-N-isopropylbenzamide | E; 1.187; 599.3 |

1H NMR (CD3OD): δ ppm 8.58 (s, 1H), 8.13-8.19 (m, 1H), 7.55-7.71 (m, 2H), 7.30-7.49 (m, 3H), 7.05-7.18 (m, 3H), 3.96-4.02 (m, 2H), 3.79-3.87 (m, 2H), 3.60-3.70 (m, 1H), 3.51-3.62 (m, 2H), 3.34-3.41 (m, 1H), 3.08-3.23 (m, 2H), 2.95-3.02 (m, 1H), 2.80-2.90 (m, 1H), 2.06-2.24 (m, 3H), 1.84 (s, 2H), 1.57 (s, 1H), 0.90-1.02 (m, 3H), 0.90-0.61 (m, 4H), 0.27 (s, 2H). 19F NMR (CD3OD): δ ppm −113.18.

| 49B | 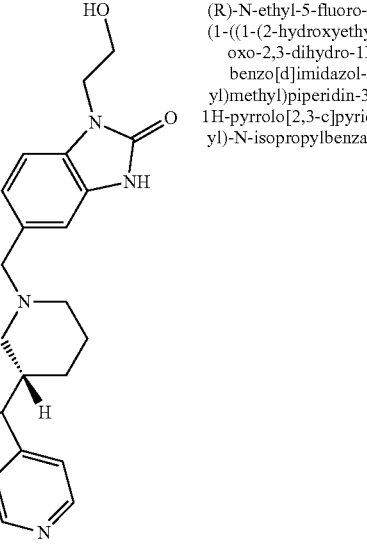 | (R)-N-ethyl-5-fluoro-2-(3-(1-((1-(2-hydroxyethyl)-2-oxo-2,3-dihydro-1H-benzo[d]imidazol-5-yl)methyl)piperidin-3-yl)-1H-pyrrolo[2,3-c]pyridin-1-yl)-N-isopropylbenzamide | E; 1.181; 599.3 |

1H NMR (CD3OD): δ ppm 8.50-8.58 (m, 1H), 8.12-8.20 (m, 1H), 7.59-7.70 (m, 2H), 7.33-7.48 (m, 3H), 7.05-7.18 (m, 3H), 3.95-4.02 (m, 2H), 3.75-3.83 (m, 2H), 3.65-3.74 (m, 1H), 3.52-3.62 (m, 2H), 3.34-3.42 (m, 1H), 3.08-3.23 (m, 2H), 2.84-3.06 (m, 2H), 2.05-2.25 (m, 3H), 1.75-1.95 (m, 2H), 1.50-1.60 (m, 1H), 0.90-1.01 (m, 3H), 0.61-0.88 (m, 4H), 0.20-0.35 (m, 2H). 19F NMR (CD3OD): δ ppm −113.17~−113.19.

Example 51. 2-(3-(2-azaspiro[3.5]nonan-7-yl)-1H-pyrrolo[2,3-c]pyridin-1-yl)-5-fluoro-N-isopropyl-N-methylbenzamide

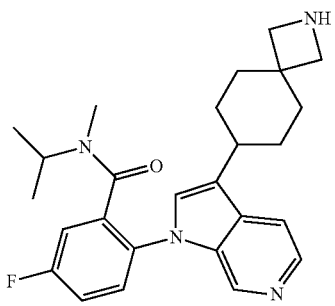 [SMILES: CC(C)N(C)C(=O)c1cc(F)ccc1-n1cc(C2CCC3(CC2)CNC3)c2ccncc21]

Example 51 was synthesized from Intermediate 3 by the method described in step 1 of Example 1. LCMS method C: $R_t$=0.773 min; $(M+H)^+$=435.3.

Example 51A. 5-fluoro-N-isopropyl-N-methyl-2-(3-(2-methyl-2-azaspiro[3.5]nonan-7-yl)-1H-pyrrolo[2,3-c]pyridin-1-yl)benzamide

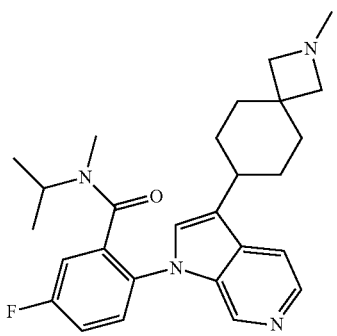 [SMILES: CC(C)N(C)C(=O)c1cc(F)ccc1-n1cc(C2CCC3(CC2)CN(C)C3)c2ccncc21]

The title compound was prepared according to the method described in Example 1, starting from Intermediate 3. In Step 2, formaldehyde was utilized. LCMS method C: $R_t$=0.893 min; $(M+H)^+$=449.3. $^1$H NMR (CD$_3$OD): δ ppm 8.80-9.00 (m, 1H), 8.20-8.35 (m, 2H), 8.00-8.10 (m, 1H), 7.65-7.75 (m, 1H), 7.35-7.55 (m, 2H), 4.35-4.45 (m, 0.5H), 4.20-4.30 (m, 1H), 4.00-4.10 (m, 1H), 3.80-3.95 (m, 2H), 3.60-3.75 (m, 0.5H), 3.00-3.10 (m, 1H), 2.96 (s, 3H), 2.50-2.65 (m, 3H), 2.05-2.30 (m, 4H), 1.75-1.95 (m, 2H), 1.45-1.70 (m, 2H), 0.35-1.20 (m, 6H). $^{19}$F NMR (CD$_3$OD): δ ppm −76.96, −110.73~−110.88.

Example 52. 5-fluoro-N-isopropyl-N-methyl-2-(3-(2-methyl-1,2,3,4-tetrahydroisoquinolin-6-yl)-1H-pyrrolo[2,3-c]pyridin-1-yl)benzamide

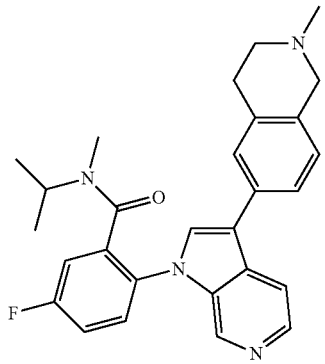 [SMILES: CC(C)N(C)C(=O)c1cc(F)ccc1-n1cc(-c2ccc3c(c2)CCN(C)C3)c2ccncc21]

A solution of 5-fluoro-N-isopropyl-N-methyl-2-(3-(1,2,3,4-tetrahydroisoquinolin-6-yl)-1H-pyrrolo[2,3-c]pyridin-1-yl)benzamide (Intermediate 17b, 50 mg, 0.11 mmol, HCl salt), paraformaldehyde (34 mg, 1.13 mmol) and Et$_3$N (57 mg, 0.56 mmol) in anhydrous MeOH (10 mL) was stirred at RT for 0.5 h. Then, NaBH$_3$CN (28 mg, 0.45 mmol) was added and the reaction mixture was stirred at 60° C. for 18 h. The reaction mixture was concentrated under reduced pressure and the residue was purified by basic preparative HPLC method D to give 5-fluoro-N-isopropyl-N-methyl-2-(3-(2-methyl-1,2,3,4-tetrahydroisoquinolin-6-yl)-1H-pyrrolo[2,3-c]pyridin-1-yl)benzamide as white solid. Yield: 28.3 mg (55%); LCMS method B: $R_t$=1.930 min; $(M+H)^+$=457.2. $^1$H NMR (CD$_3$OD): δ ppm 8.59-8.65 (m, 1H), 8.20-8.30 (m, 1H), 7.93 (d, J=5.6 Hz, 1H), 7.78 (s, 1H), 7.70-7.75 (m, 1H), 7.35-7.50 (m, 4H), 7.18 (d, J=8.8 Hz, 1H), 4.40-4.50 (m, 0.5H), 3.60-3.70 (m, 2H), 3.03 (t, J=5.6 Hz, 2H), 2.79 (t, J=6.0 Hz, 2H), 2.40-2.65 (m, 6H), 0.95-1.05 (m, 3H), 0.25-0.55 (m, 3H). $^{19}$F NMR (CD$_3$OD): δ ppm −112.79.

Examples 53-53A. 5-fluoro-2-(3-(4-hydroxycyclohexyl)-1H-pyrrolo[2,3-c]pyridin-1-yl)-N-isopropyl-N-methylbenzamide (Isomers 1-2)

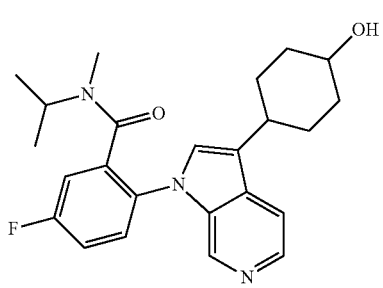 [SMILES: CC(C)N(C)C(=O)c1cc(F)ccc1-n1cc(C2CCC(O)CC2)c2ccncc21]

To a solution of 5-fluoro-N-isopropyl-N-methyl-2-(3-(4-oxocyclohexyl)-1H-pyrrolo[2,3-c]pyridin-1-yl)benzamide (Intermediate 17B, 50 mg, 0.12 mmol) in MeOH (3 mL, anhydrous) was added NaBH$_4$ (7 mg, 0.18 mmol). The resulting mixture was stirred at RT for 30 min. The reaction mixture was neutralized by 6N HCl to pH=7.0 and the mixture was concentrated under reduced pressure. The resulting residue was purified by preparative RP-HPLC method A to give 5-fluoro-2-(3-(trans-4-hydroxycyclohexyl)-1H-pyrrolo[2,3-c]pyridin-1-yl)-N-isopropyl-N-methylbenzamide 15 mg and 5-fluoro-2-(3-(cis-4-hydroxycyclohexyl)-1H-pyrrolo[2,3-c]pyridin-1-yl)-N-isopropyl-N-methylbenzamide Example 53 (Isomer 1): Yield: 9.50 mg; LCMS method D: $R_t$=0.799 min; (M+H)$^+$=410.2. $^1$H NMR (CD3OD): δ ppm 8.54-8.62 (m, 1H), 8.16-8.21 (m, 1H), 7.73-7.75 (m, 1H), 7.65-7.73 (m, 1H), 7.40-7.50 (m, 1H), 7.35-7.40 (m, 2H), 4.44-4.52 (m, 0.5H), 3.55-3.70 (m, 1.6H), 2.70-2.85 (m, 1H), 2.44-2.67 (m, 3H), 2.05-2.15 (m, 4H), 1.40-1.65 (m, 4H), 0.95-1.10 (m, 3H), 0.20-0.55 (m, 3H). $^{19}$F NMR (CD3OD): δ ppm −113.61~−113.36.

Example 53A (Isomer 2): Yield: 1.80 mg (4%); LCMS method D: $R_t$=0.851 min; (M+H)$^+$=410.2. $^1$H NMR (CD$_3$OD): δ ppm 8.54-8.64 (m, 1H), 8.16-8.21 (m, 1H), 7.60-7.75 (m, 2H), 7.34-7.45 (m, 3H), 4.44-4.53 (m, 0.5H), 4.00-4.05 (m, 1H), 3.55-3.60 (m, 0.5H), 2.90-3.00 (m, 1H), 2.45-2.70 (m, 3H), 1.76-1.86 (m, 6H), 1.30-1.49 (m, 2H), 1.00-1.20 (m, 3H), 0.21-0.55 (m, 3H). $^{19}$F NMR (CD$_3$OD): δ ppm −113.73~−113.45.

Examples 54-54A. 2-(3-(4-(dimethylamino)cyclohexyl)-1H-pyrrolo[2,3-c]pyridin-1-yl)-5-fluoro-N-isopropyl-N-methylbenzamide (Isomers 1-2, TFA salt)

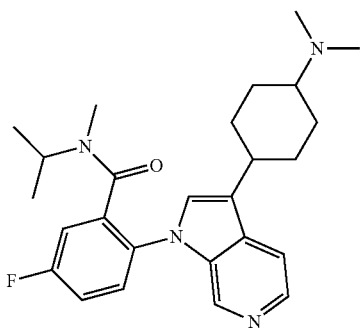 [SMILES: CC(C)N(C)C(=O)c1cc(F)ccc1-n1cc(C2CCC(N(C)C)CC2)c2ccncc21]

To a solution of 5-fluoro-N-isopropyl-N-methyl-2-(3-(4-oxocyclohexyl)-1H-pyrrolo[2,3-c]pyridin-1-yl)benzamide (Intermediate 17B, 40 mg, 0.10 mmol) in 5 mL of anhydrous MeOH was added dimethylamine hydrochloride (10 mg, 0.12 mmol), Et$_3$N (30 mg, 0.30 mmol) and NaBH$_3$CN (12 mg, 0.20 mmol). The resulting mixture was stirred at 50° C. for 18 h. The mixture was purified by preparative RP-HPLC Method A to give 2-(3-(trans-4-(dimethylamino)cyclohexyl)-1H-pyrrolo[2,3-c]pyridin-1-yl)-5-fluoro-N-isopropyl-N-methylbenzamide and 2-(3-(cis-4-(dimethylamino)cyclohexyl)-1H-pyrrolo[2,3-c]pyridin-1-yl)-5-fluoro-N-isopropyl-N-methylbenzamide as white solids.

Example 54 (Isomer 1): Yield: 5.0 mg (11%); LCMS method D: $R_t$=2.192 min; (M+H)$^+$=437.2. $^1$H NMR (CD$_3$OD): δ ppm 8.83-8.93 (m, 1H), 8.26-8.32 (m, 2H), 8.06 (d, J=11.2 Hz 1H), 7.65-7.75 (m, 1H), 7.42-7.55 (m, 2H), 4.36-4.40 (m 0.5H), 3.65-3.75 (m 0.5H), 3.35-3.45 (m 2H), 2.55-3.20 (m, 9H), 2.23-2.35 (m, 3H), 1.65-1.85 (m, 3H), 0.45-1.15 (m, 8H). $^{19}$F NMR (CD3OD): δ ppm −111.17~−110.73, −76.64~−76.93.

Example 54A (Isomer 2): Yield: 6.4 mg (14%); LCMS method D: $R_t$=2.145 min; (M+H)$^+$=437.2. $^1$H NMR (CD$_3$OD): δ ppm 8.90-9.00 (m, 1H), 8.24-8.33 (m, 3H), 7.76-7.77 (m, 1H), 7.44-7.53 (m, 2H), 4.35-4.41 (m, 0.5H), 3.70-3.72 (m, 0.5H), 3.35-3.53 (m, 2H), 2.59-2.62 (m, 9H), 2.02-2.20 (m, 8H), 050-1.11 (m, 6H). $^{19}$F NMR (CD$_3$OD): δ ppm −110.72~−110.60, −76.94.

Examples 55-58

The following Examples were synthesized according to the method described for Examples 54-54A.

TABLE 6

| | | NMR spectra details | |
|---|---|---|---|
| No. | Structural formula | Name | LCMS method; Rt = min; [M + H]$^+$ |
| | (structure shown) | 5-fluoro-N-isopropyl-N-methyl-2-(3-(trans-4-(pyrrolidin-1-yl)cyclohexyl)-1H-pyrrolo[2,3-c]pyridin-1-yl)benzamide | D; 0.560; 463.1 |

$^1$H NMR (CD$_3$OD): δ ppm 8.50-8.61 (m, 1H), 8.15-8.19 (m, 1H), 7.60-7.73 (m, 2H), 7.25-7.44 (m, 3H), 4.43-4.50 (m, 0.5H), 3.54-3.58 (m, 0.5H), 3.11-3.14 (m, 0.6H), 2.86-2.92 (m, 5.5H), 2.43-2.80 (m, 3H), 2.15-2.23 (m, 4H), 1.80-1.95 (m, 4H), 1.45-1.58 (m, 4H), 0.95-1.04 (m, 3H), 0.15-0.55 (m, 3H).
$^{19}$F NMR (CD$_3$OD): δ ppm −15.27 ~ −114.85.

TABLE 6-continued

| | | | LCMS method; Rt = min; |
|---|---|---|---|
| No. | Structural formula | Name | [M + H]+ |

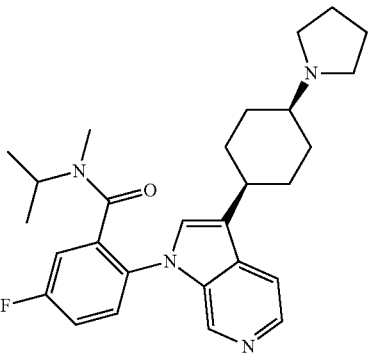 [SMILES: CC(C)N(C)C(=O)c1cc(F)ccc1-n1cc([C@H]2CC[C@@H](N3CCCC3)CC2)c2ccncc21]

5-fluoro-N-isopropyl-N-methyl-2-(3-(cis-4-(pyrrolidin-1-yl)cyclohexyl)-1H-pyrrolo[2,3-c]pyridin-1-yl)benzamide

C; 0.671; 576.1

$^1$H NMR (CD$_3$OD): δ ppm 8.54-8.62 (m, 1H), 8.17-8.20 (m, 1H), 7.60-7.75 (m, 2H), 7.40-7.50 (m, 1H), 7.30-7.40 (m, 2H), 4.46-4.51 (m, 0.5H), 3.54-3.59 (m, 0.5H), 2.81-2.90 (m, 5H), 2.44-2.67 (m, 3H), 2.15-2.40 (m, 5H), 1.85-4.95 (m, 4H), 1.51-1.65 (m, 4H), 0.95-1.06 (m, 3H), 0.15-0.55 (m, 3H).
$^{19}$F NMR (CD$_3$OD): δ ppm −13.11 ~ −113.55.

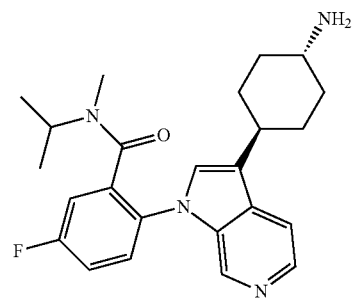 [SMILES: CC(C)N(C)C(=O)c1cc(F)ccc1-n1cc([C@H]2CC[C@H](N)CC2)c2ccncc21]

2-(3-(trans-4-aminocyclohexyl)-1H-pyrrolo[2,3-c]pyridin-1-yl)-5-fluoro-N-isopropyl-N-methylbenzamide

F; 0.814; 409.4

$^1$H NMR (CD$_3$OD): δ ppm 8.54-8.63 (m, 1H), 8.15-8.55 (m, 1H), 7.66-7.75 (m, 2H), 7.38-7.46 (m, 1H), 7.35-7.38 (m, 2H), 4.44-4.52 (m, 0.5H), 3.55-3.62 (m, 0.5H), 2.82-2.93 (m, 2H), 2.46-2.68 (m, 3H), 2.06-2.16 (m, 4H), 1.60-1.65 (m, 2H), 1.40-1.48 (m, 2H), 1.00-1.28 (m, 3H), 0.20-0.60 (m, 3H).
$^{19}$F NMR (CD$_3$OD): δ ppm −13.33 ~ −113.58.

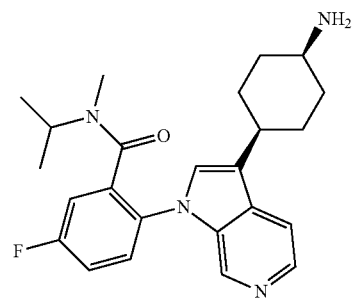 [SMILES: CC(C)N(C)C(=O)c1cc(F)ccc1-n1cc([C@H]2CC[C@@H](N)CC2)c2ccncc21]

2-(3-(cis-4-aminocyclohexyl)-1H-pyrrolo[2,3-c]pyridin-1-yl)-5-fluoro-N-isopropyl-N-methylbenzamide

F; 0.814; 409.4

$^1$H NMR (CD$_3$OD): δ ppm 8.54-8.63 (m, 1H), 8.16-8.23 (m, 1H), 7.65-7.78 (m, 2H), 7.38-7.50 (m, 2H), 7.36-7.38 (m, 1H), 4.45-4.51 (m, 0.5H), 3.55-3.62 (m, 0.5H), 3.10-3.25 (m, 2H), 2.46-2.69 (m, 3H), 1.70-2.01 (m, 8H), 1.01-1.08 (m, 3H), 0.18-0.55 (m, 3H). $^{19}$F NMR (CD$_3$OD): δ ppm −113.21 ~ −113.44.

Example 59. 5-fluoro-N-isopropyl-N-methyl-2-(3-(4-phenoxycyclohexyl)-1H-pyrrolo[2,3-c]pyridin-1-yl)benzamide

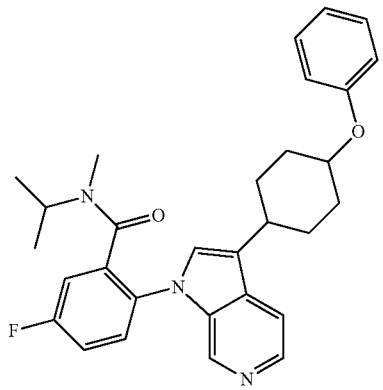 [SMILES: CC(C)N(C)C(=O)c1cc(F)ccc1-n1cc(C2CCC(Oc3ccccc3)CC2)c2ccncc21]

Step 1: 5-fluoro-2-(3-(4-hydroxycyclohexyl)-1H-pyrrolo[2,3-c]pyridin-1-yl)-N-isopropyl-N-methylbenzamide

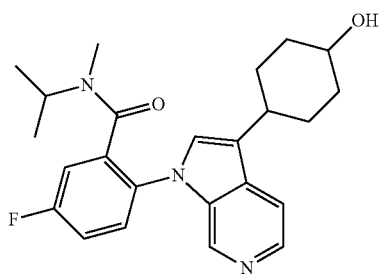 [SMILES: CC(C)N(C)C(=O)c1cc(F)ccc1-n1cc(C2CCC(O)CC2)c2ccncc21]

To a solution of 5-fluoro-N-isopropyl-N-methyl-2-(3-(4-oxocyclohexyl)-1H-pyrrolo[2,3-c]pyridin-1-yl)benzamide (Intermediate 17B, 100 mg, 0.25 mmol) in MeOH (5 mL, anhydrous) was added NaBH$_4$ (15 mg, 0.37 mmol), and the resulting mixture was stirred at 14-20° C. for 15 min. The reaction mixture was then concentrated under reduced pressure. The resulting residue was purified by preparative TLC on silica gel (EtOAc) to give 5-fluoro-2-(3-(4-hydroxycyclohexyl)-1H-pyrrolo[2,3-c]pyridin-1-yl)-N-isopropyl-N-methylbenzamide as colorless solid. Yield: 60 mg (59%); LCMS method B: R$_t$=0.625 min; (M+H)$^+$=410.1

Step 2: 5-fluoro-N-isopropyl-N-methyl-2-(3-(4-phenoxycyclohexyl)-1H-pyrrolo[2,3-c]pyridin-1-yl)benzamide To a solution of 5-fluoro-2-(3-(4-hydroxycyclohexyl)-1H-pyrrolo[2,3-c]pyridin-1-yl)-N-isopropyl-N-methylbenzamide (60 mg, 0.15 mmol) and phenol (71 mg, 0.75 mmol) in THF (6 mL, anhydrous) was added a solution of PPh$_3$ (197 mg, 0.75 mmol) in THF (2 mL, anhydrous) and DIAD (152 mg, 0.75 mmol) via syringe, dropwise under N$_2$. The resulting mixture was stirred at 13-22° C. under N$_2$ for about 4 h. The reaction mixture was then concentrated under reduced pressure to remove THF. The resulting residue was purified by preparative TLC on silica gel (petroleum ether/ethyl acetate=1/3) to give crude 5-fluoro-N-isopropyl-N-methyl-2-(3-(4-phenoxycyclohexyl)-1H-pyrrolo[2,3-c]pyridin-1-yl)benzamide (80 mg), which was re-purified by RP-HPLC method D to give 5-fluoro-N-isopropyl-N-methyl-2-(3-(4-phenoxycyclohexyl)-1H-pyrrolo[2,3-c]pyridin-1-yl)benzamide as white solid. Yield: 18.5 mg (25%); LCMS method D: R$_t$=1.801 min; (M+H)$^+$=486.3. $^1$H NMR (CD$_3$OD): δ ppm 8.33-8.42 (m, 1H), 7.95-8.00 (m, 1H), 7.41-7.55 (m, 2H), 7.03-7.25 (m, 5H), 6.67-6.77 (m, 3H), 4.39-4.50 (m, 1H), 4.14-4.32 (m, 0.5H), 3.31-3.37 (m, 0.5H), 2.75-2.85 (m, 1H), 2.22-2.49 (m, 3H), 1.42-2.08 (m, 8H), 0.74-0.92 (m, 3H), 0.04-0.46 (m, 3H). $^{19}$F NMR (CD$_3$OD): δ ppm −113.71~−113.45.

Examples 60-60A. 5-fluoro-N-isopropyl-N-methyl-2-(3-(4-(((2-oxo-2,3-dihydro-1H-benzo[d]imidazol-5-yl)methyl)amino)cyclohexyl)-1H-pyrrolo[2,3-c]pyridin-1-yl)benzamide (Isomers 1-2)

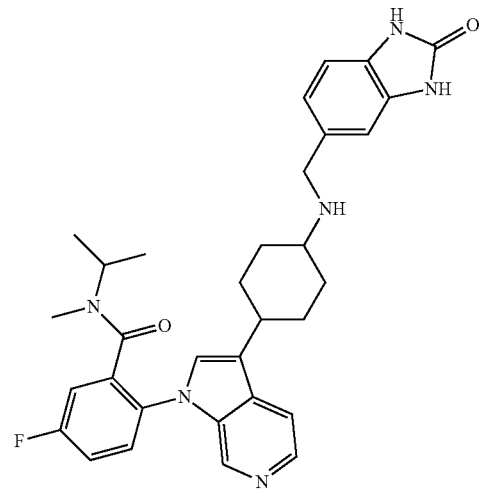 [SMILES: CC(C)N(C)C(=O)c1cc(F)ccc1-n1cc(C2CCC(NCc3ccc4[nH]c(=O)[nH]c4c3)CC2)c2ccncc21]

Step 1: 2-(3-(4-aminocyclohexyl)-1H-pyrrolo[2,3-c]pyridin-1-yl)-5-fluoro-N-isopropyl-N-methylbenzamide

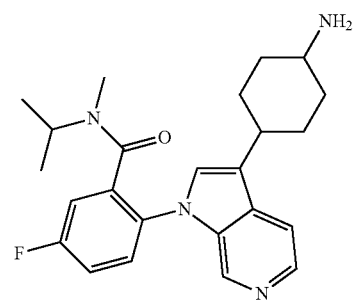 [SMILES: CC(C)N(C)C(=O)c1cc(F)ccc1-n1cc(C2CCC(N)CC2)c2ccncc21]

To a solution of 5-fluoro-N-isopropyl-N-methyl-2-(3-(4-oxocyclohexyl)-1H-pyrrolo[2,3-c]pyridin-1-yl)benzamide (Intermediate 17B, 220 mg, 0.54 mmol) in MeOH (10 mL, dry) was added NH₄OAc (83 mg, 1.08 mmol) and NaBH₃CN (68 mg, 1.08 mmol), and the resulting mixture was stirred at 50° C. under N₂ for 20 h. The mixture was purified by preparative RP-HPLC method A to give 2-(3-(4-aminocyclohexyl)-1H-pyrrolo[2,3-c]pyridin-1-yl)-5-fluoro-N-isopropyl-N-methylbenzamide (TFA salt) as white solid. Yield: 110 mg (50%); LCMS method E: $R_t$=0.494 min; (M+H)⁺=409.1 ¹H NMR (CD₃OD): δ ppm 8.80-9.10 (m, 1H), 8.25-8.40 (m, 2H), 8.05-8.20 (m, 1H), 7.70-7.80 (m, 1H), 7.40-7.60 (m, 2H), 4.30-4.45 (m, 0.5H), 3.70-3.80 (m, 0.5H), 3.20-3.30 (m, 1H), 3.05-3.15 (m, 1H), 2.55-2.70 (m, 3H), 2.15-2.30 (m, 3H), 1.90-2.10 (m, 2H), 1.60-1.80 (m, 3H), 0.35-1.20 (m, 6H). ¹⁹F NMR (CD₃OD): δ ppm −110.86~−110.60.

Step 2. 5-fluoro-N-isopropyl-N-methyl-2-(3-(trans-4-(((2-oxo-2,3-dihydro-1H-benzo[d]imidazol-5-yl)methyl)amino)cyclohexyl)-1H-pyrrolo[2,3-c]pyridin-1-yl)benzamide The title compound was prepared according to the method described in Example 45 and separated by SFC method A to give two isomers of 5-fluoro-N-isopropyl-N-methyl-2-(3-(4-(((2-oxo-2,3-dihydro-1H-benzo[d]imidazol-5-yl)methyl)amino)cyclohexyl)-1H-pyrrolo[2,3-c]pyridin-1-yl)benzamide.

Example 60 (Isomer 1): LCMS method D: $R_t$=1.164 min; (M+H)⁺=555.3. ¹H NMR (CD₃OD): δ ppm 8.54-8.62 (m, 1H), 8.17-8.21 (m, 1H), 7.66-7.74 (m, 2H), 7.35-7.50 (m, 3H), 7.04-7.15 (m, 3H), 4.44-4.51 (m, 0.5H), 3.89 (s, 2H), 3.51-3.60 (m, 0.5H), 2.89-2.95 (m, 1H), 2.44-2.67 (m, 4H), 2.06-2.17 (m, 4H), 1.45-1.58 (m, 4H), 0.95-1.06 (m, 3H), 0.15-0.54 (m, 3H). ¹⁹F NMR (CD₃OD): δ ppm −113.58~−113.35.

Example 60A (Isomer 2): LCMS method D: $R_t$=1.231 min; (M+H)⁺=555.3. ¹H NMR (CD₃OD): δ ppm 8.53-8.61 (m, 1H), 8.16-8.18 (m, 1H), 7.66-7.73 (m, 2H), 7.34-7.47 (m, 3H), 7.00-7.12 (m, 3H), 4.43-4.47 (m, 0.5H), 3.84 (s, 2H), 3.52-3.58 (m, 0.5H), 3.05-3.15 (m, 1H), 2.90-2.95 (m, 1H), 2.43-2.66 (m, 3H), 1.75-2.05 (m, 8H), 0.95-1.05 (m, 3H), 0.15-0.50 (m, 3H). ¹⁹F NMR (CD₃OD): δ ppm −113.56~−113.33.

Examples 61-62

The following Examples were synthesized by method described above for Example 60-60A.

TABLE 7

| Ex No. | Structural | Name | LCMS method; Rt = min; [M + H]⁺ |
|---|---|---|---|
| | 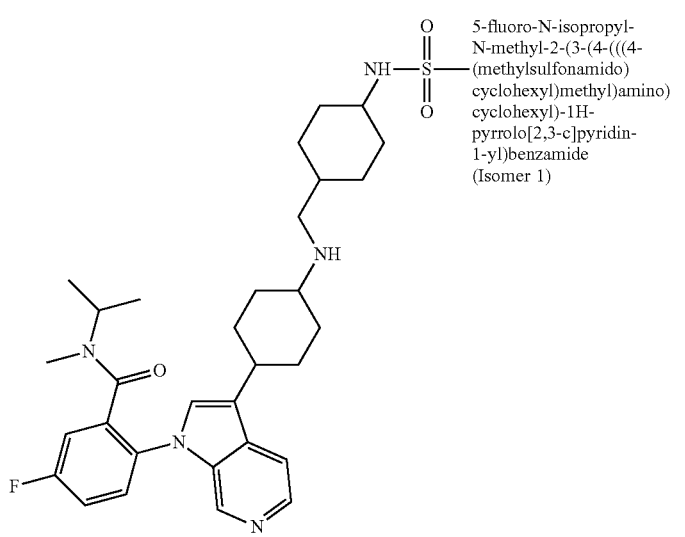 | 5-fluoro-N-isopropyl-N-methyl-2-(3-(4-(((4-(methylsulfonamido)cyclohexyl)methyl)amino)cyclohexyl)-1H-pyrrolo[2,3-c]pyridin-1-yl)benzamide (Isomer 1) | E; 1.906; 598.3 |

¹H NMR (CD₃OD): δ ppm 8.54-8.63 (m, 1H), 8.16-8.25 (m, 1H), 7.66-7.75 (m, 2H), 7.35-7.50 (m, 3H), 4.44-4.51 (m, 0.5H), 3.55-3.57 (m, 0.5H), 3.10-3.20 (m, 1H), 2.85-3.00 (m, 4H), 2.44-2.65 (m, 6H), 2.06-2.20 (m, 6H), 1.85-1.92 (m, 2H), 1.30-1.70 (m, 8H), 0.95-1.15 (m, 4H), 0.15-0.65 (m, 3H).
¹⁹F NMR (CD₃OD): δ ppm −13.33 ~ −113.58.

| Ex No. | Structural | Name | LCMS method; Rt = min; [M + H]+ |
|---|---|---|---|
| | | 5-fluoro-N-isopropyl-N-methyl-2-(3-(4-(((4-(methylsulfonamido)cyclohexyl)methyl)amino)cyclohexyl)-1H-pyrrolo[2,3-c]pyridin-1-yl)benzamide (Isomer 2) | E; 1.832; 598.3 |

1H NMR (CD3OD): δ ppm 8.54-8.62 (m, 1H), 8.16-8.20 (m, 1H), 7.67-7.74 (m, 2H), 7.30-7.48 (m, 3H), 4.46-4.49 (m, 0.5H), 3.50-3.55 (m, 0.5H), 3.10-3.21 (m, 2H), 2.80-2.95 (m, 4H), 2.54-2.68 (m, 2H), 2.45-2.53 (m, 3H), 1.95-2.08 (m, 4H), 1.60-1.95 (m, 8H), 1.40-1.50 (m, 1H), 1.25-1.35 (m, 2H), 0.95-1.15 (m, 5H), 0.15-0.55 (m, 3H). 19F NMR (CD3OD): δ ppm −113.29 ~ −113.53.

Example 63. 2-(7-(1-((2-cyano-4-methyl-1H-indol-5-yl)methyl)piperidin-4-yl)-5H-pyrrolo[3,2-d]pyrimidin-5-yl)-5-fluoro-N-isopropyl-N-methylbenzamide Step 1: tert-butyl 4-(5-(4-fluoro-2-(methoxycarbonyl)phenyl)-5H-pyrrolo[3,2-d]pyrimidin-7-yl)piperidine-1-carboxylate and 2-(7-(1-(tert-butoxycarbonyl)piperidin-4-yl)-5H-pyrrolo[3,2-d]pyrimidin-5-yl)-5-fluorobenzoic acid

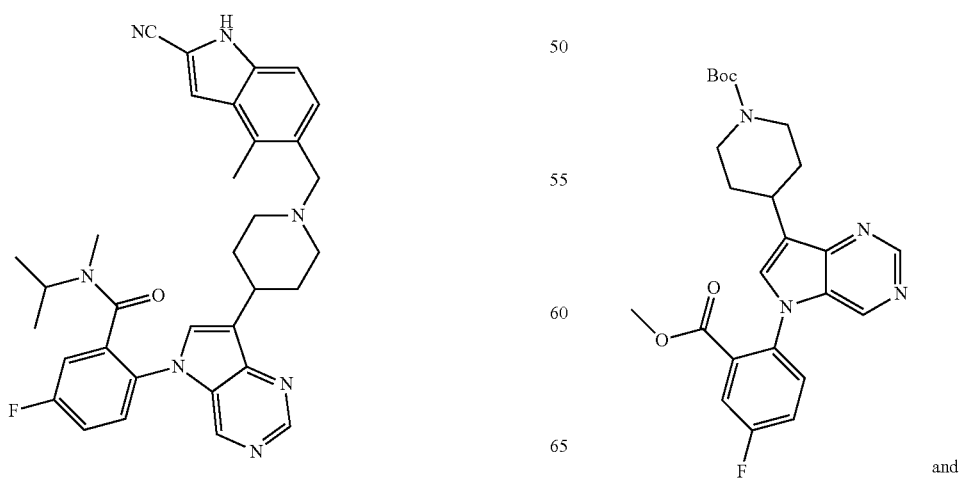

and

-continued

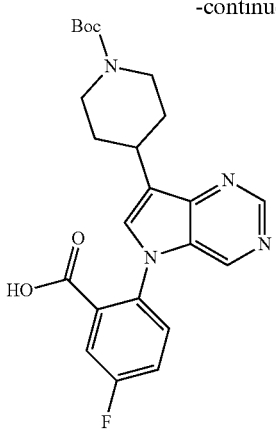

To a solution of tert-butyl 4-(5H-pyrrolo[3,2-d]pyrimidin-7-yl)piperidine-1-carboxylate (Intermediate 18, 300 mg, 0.99 mmol), methyl 2,5-difluorobenzoate (205 mg, 1.19 mmol) and Cs$_2$CO$_3$ (646 mg, 1.98 mmol) in anhydrous DMF (20 mL) was stirred at 100° C. for 18 h. The mixture was then concentrated under high vacuum. The resulting residue was diluted with 1 N HCl (50 mL), extracted with DCM (50 mL×3) and DCM/propanol (v/v, 80/20 mL). The combined organic layers were dried over anhydrous Na$_2$SO$_4$, filtered, and the filtrate was concentrated under reduced pressure. The residue was purified by acidic preparative RP-HPLC method A to afford 2-(7-(1-(tert-butoxycarbonyl)piperidin-4-yl)-5H-pyrrolo[3,2-d]pyrimidin-5-yl)-5-fluorobenzoic acid (TFA salt) and tert-butyl 4-(5-(4-fluoro-2-(methoxycarbonyl)phenyl)-5H-pyrrolo[3,2-d]pyrimidin-7-yl)piperidine-1-carboxylate, both as yellow solid. Yield: 211 mg (48% yield); LCMS method C: R$_t$=0.725 min; (M+H)$^+$=441.0.

Step 2: tert-butyl 4-(5-(4-fluoro-2-(isopropyl (methyl)carbamoyl)phenyl)-5H-pyrrolo[3,2-d]pyrimidin-7-yl)piperidine-1-carboxylate

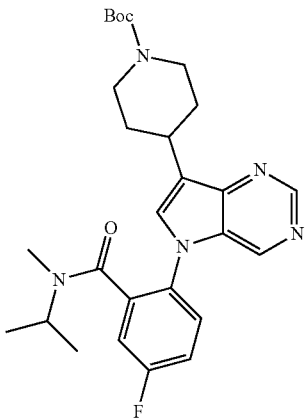 [SMILES: CC(C)N(C)C(=O)c1cc(F)ccc1-n1cc(C2CCN(C(=O)OC(C)(C)C)CC2)c2ncncc21]

To a solution of 2-(7-(1-(tert-butoxycarbonyl)piperidin-4-yl)-5H-pyrrolo[3,2-d]pyrimidin-5-yl)-5-fluorobenzoic acid (80 mg, 0.16 mmol, 88.6% purity), N-methylpropan-2-amine (18 mg, 0.24 mmol), HATU (92 mg, 0.24 mmol) and DIEA (103 mg, 0.80 mmol) in anhydrous DMF (20 mL) was stirred at RT for 18 h. The mixture was concentrated under high vacuum, the residue was diluted with H$_2$O (20 mL) solution and extracted with DCM (3×20 mL). The combined organic layers were dried over anhydrous sodium sulfate, filtered, and the filtrate was concentrated under reduced pressure. The crude residue was purified by column chromatography on silica gel (eluting with petroleum ether/EtOAc=1/1 to 0/1) to afford tert-butyl 4-(5-(4-fluoro-2-(isopropyl(methyl)carbamoyl)phenyl)-5H-pyrrolo[3,2-d]pyrimidin-7-yl)piperidine-1-carboxylate as yellow oil. Yield: 55 mg (54%); LCMS method C: R$_t$=0.774 min; (M+H)$^+$=496.1.

Step 3: 5-fluoro-N-isopropyl-N-methyl-2-(7-(piperidin-4-yl)-5H-pyrrolo[3,2-d]pyrimidin-5-yl)benzamide

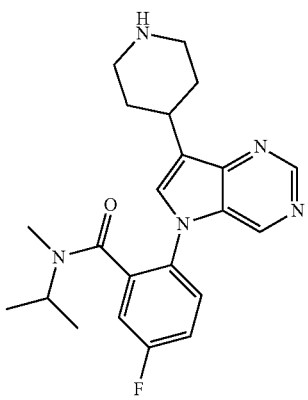 [SMILES: CC(C)N(C)C(=O)c1cc(F)ccc1-n1cc(C2CCNCC2)c2ncncc21]

To a solution of tert-butyl 4-(5-(4-fluoro-2-(isopropyl (methyl)carbamoyl)phenyl)-5H-pyrrolo[3,2-d]pyrimidin-7-yl)piperidine-1-carboxylate (55 mg, 0.11 mmol) in anhydrous DCM (10 mL) was added HCl/dioxane (3 mL, 4 N) at 0° C. The reaction mixture was stirred at RT for 2 h. The mixture was then concentrated under reduced pressure. The resulting residue was diluted with 1 N NaOH (20 mL) solution and extracted with CH$_2$Cl$_2$ (3×20 mL). The combined organic layers were dried over anhydrous sodium sulfate, filtered, and the filtrate was concentrated under reduced pressure to afford 5-fluoro-N-isopropyl-N-methyl-2-(7-(piperidin-4-yl)-5H-pyrrolo[3,2-d]pyrimidin-5-yl)benzamide (40 mg, 91%, crude) as yellow oil, which was used without further purification. Yield: 55 mg (91% crude);

Step 4: 2-(7-(1-((2-cyano-4-methyl-1H-indol-5-yl) methyl)piperidin-4-yl)-5H-pyrrolo[3,2-d]pyrimidin-5-yl)-5-fluoro-N-isopropyl-N-methylbenzamide To a solution of 5-fluoro-N-isopropyl-N-methyl-2-(7-(piperidin-4-yl)-5H-pyrrolo[3,2-d]pyrimidin-5-yl)benzamide (40 mg, 0.10 mmol, crude), 5-formyl-4-methyl-1H-indole-2-carbonitrile (37 mg, 0.20 mmol) and HOAc (10 uL) in anhydrous MeOH (10 mL) was stirred at 6-20° C. for 0.5 h. NaBH$_3$CN (25 mg, 0.40 mmol) was then added and the reaction mixture was stirred at 55° C. for 4 h. The mixture was concentrated under reduced pressure. The residue was purified by preparative RP-HPLC method D to afford 2-(7-(1-((2-cyano-4-methyl-1H-indol-5-yl)methyl)piperidin-4-yl)-5H-pyrrolo[3,2-d]pyrimidin-5-yl)-5-fluoro-N-isopropyl-N-methylbenzamide as white solid. Yield: 14.7 mg (26%); LCMS method E: R$_t$=2.140 min; (M+H)$^+$=564.3. $^1$H NMR (CD$_3$OD): δ ppm 8.87 (d, J=6.0 Hz, 1H), 8.70-8.85 (m, 1H), 7.60-7.75 (m, 2H), 7.40-7.50 (m, 1H), 7.30-7.40 (m, 2H), 7.31 (s, 1H), 7.27 (d, J=8.4 Hz, 1H), 4.42-4.45 (m, 0.5H), 3.75 (s, 2H), 3.59-3.66 (m, 0.5H), 3.05-3.15 (m, 3H), 2.45-2.70 (m, 6H), 2.30-2.45 (m, 2H), 2.05-2.20 (m, 2H), 1.80-1.95 (m, 2H), 1.05 (d, J=6.8 Hz, 3H), 0.35-0.65 (m, 3H).

$^{19}$F NMR (CD$_3$OD): δ ppm −112.50~112.80.

Example 64. 2-(7-(1-((2-cyano-4-methyl-1H-indol-5-yl)methyl)piperidin-4-yl)-5H-pyrrolo[3,2-d]pyrimidin-5-yl)-5-fluoro-N,N-dimethylbenzamide

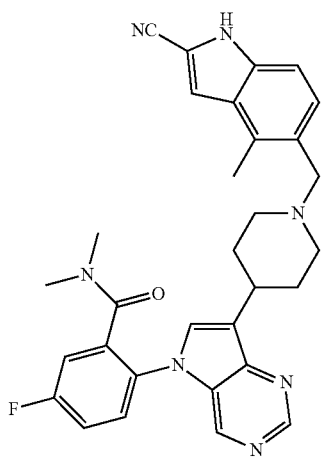 [SMILES: Cc1c(CN2CCC(c3cn(-c4ccc(F)cc4C(=O)N(C)C)c4cncnc34)CC2)ccc2[nH]c(C#N)cc12]

The title compound was prepared according to a method similar to Example 63. In Step 2, dimethylamine was utilized. LCMS method E: R$_t$=2.008 min; (M+H)$^+$=536.3. $^1$H NMR (CD$_3$OD): δ ppm 8.85 (s, 1H), 8.72 (s, 1H), 7.66-7.71 (m, 2H), 7.45-7.50 (m, 1H), 7.36-7.41 (m, 2H), 7.26-7.31 (m, 2H), 3.69 (s, 2H), 3.00-3.10 (m, 3H), 2.73 (s, 3H), 2.62 (s, 3H), 2.57 (s, 3H), 2.25-35 (m, 2H), 2.10-2.10 (m, 2H), 1.75-1.90 (m, 2H). $^{19}$F NMR (CD$_3$OD): δ ppm −112.92.

Example 65. 5-(4-fluorophenyl)-7-(1-((tetrahydro-2H-pyran-4-yl)methyl)piperidin-4-yl)-5H-pyrrolo[3,2-d]pyrimidine

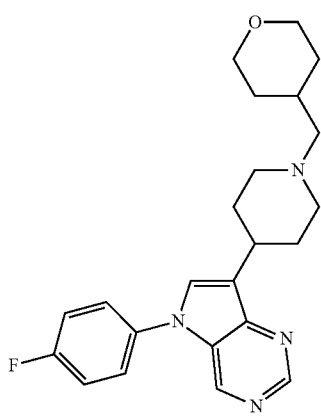 [SMILES: Fc1ccc(-n2cc(C3CCN(CC4CCOCC4)CC3)c3ncncc32)cc1]

Step 1: tert-butyl 4-(5-(4-fluorophenyl)-5H-pyrrolo[3,2-d]pyrimidin-7-yl)piperidine-1-carboxylate

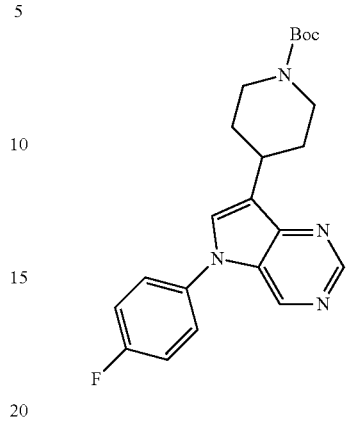

To a solution of tert-butyl 4-(5H-pyrrolo[3,2-d]pyrimidin-7-yl)piperidine-1-carboxylate (Intermediate 18, 300 mg, 1.0 mmmol) in anhydrous CH$_2$Cl$_2$ (5 mL) was added (4-fluorophenyl)boronic acid (280 mg, 2.0 mmol), Cu(OAc)$_2$ (305 mg, 2.0 mmol) and Et$_3$N (202 mg, 2.0 mmol) and the mixture was stirred at RT for 3 days. The mixture was filtered and the filtrate was concentrated and purified by ISCO column (DCM/MeOH=10/1) to afford tert-butyl 4-(5-(4-fluorophenyl)-5H-pyrrolo[3,2-d]pyrimidin-7-yl)piperidine-1-carboxylate (60 mg, 15% yield) as brown oil. Yield: 60 mg (15%); LCMS method E: R$_t$=2.126 min; (M+H)$^+$= 397.2. $^1$H NMR (CD$_3$OD): δ ppm 8.80-9.00 (m, 2H), 7.88 (s, 1H), 7.58-7.62 (m, 2H), 7.29-7.33 (m, 2H), 4.20 (d, J=13.2 Hz, 2H), 3.16-3.22 (m, 1H), 2.85-3.00 (m, 2H), 2.09 (d, J=12.0 Hz, 2H), 1.65-1.84 (m, 2H), 1.46 (s, 9H). $^1$F NMR (CD$_3$OD): δ ppm −115.84~115.87.

Step 2: 5-(4-fluorophenyl)-7-(piperidin-4-yl)-5H-pyrrolo[3,2-d]pyrimidine

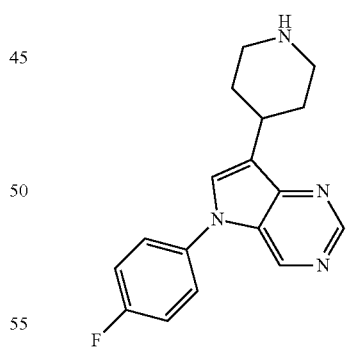

To solution of tert-butyl 4-(5-(4-fluorophenyl)-5H-pyrrolo[3,2-d]pyrimidin-7-yl)piperidine-1-carboxylate (60 mg, 0.15 mmol) in anhydrous CH$_2$Cl$_2$ (2 mL) was added HCl-dioxane (1 mL) and the mixture was stirred at RT for 2 h. The mixture was concentrated and adjusted to pH=10 by NH$_3$—H$_2$O and then lyophilized to give 5-(4-fluorophenyl)-7-(piperidin-4-yl)-5H-pyrrolo[3,2-d]pyrimidine as white solid. Yield: 45 mg (99% crude yield); LCMS method C: R$_t$=0.865 min; (M+H)$^+$=297.1. $^1$H NMR (CD$_3$OD): δ ppm 8.85-9.00 (m, 2H), 8.00 (s, 1H), 7.64-7.68 (m, 2H), 7.35-

7.40 (m, 2H), 3.55 (d, J=13.2 Hz, 2H), 3.35-3.45 (m, 1H), 3.15-3.25 (m, 2H), 2.38 (t, J=13.6 Hz, 2H), 2.13-2.24 (m, 2H). $^{19}$F NMR (CD$_3$OD): δ ppm −115.75.

Step 3: 5-(4-fluorophenyl)-7-(1-((tetrahydro-2H-pyran-4-yl)methyl)piperidin-4-yl)-5H-pyrrolo[3,2-d]pyrimidine To solution of 5-(4-fluorophenyl)-7-(piperidin-4-yl)-5H-pyrrolo[3,2-d]pyrimidine (25 mg, 0.084 mmmol) in anhydrous MeOH (2 mL) was added tetrahydro-2H-pyran-4-carbaldehyde (10 mg, 0.084 mmol), NaBH$_3$CN (16 mg, 0.25 mol). The mixture was stirred at RT for 16 h. The mixture was purified by preparative RP-HPLC method A to afford 5-(4-fluorophenyl)-7-(1-((tetrahydro-2H-pyran-4-yl)methyl)piperidin-4-yl)-5H-pyrrolo[3,2-d]pyrimidine (TFA salt) as white solid. Yield: 19 mg (57%); LCMS method C: R$_t$=0.629 min; (M+H)$^+$=395.3. $^1$H NMR (CD$_3$OD z): δ ppm 9.23 (s, 1H), 9.09 (s, 1H), 8.39 (s, 1H), 7.71 (q, J=4.4 Hz, 2H), 7.41 (t, J=8.4 Hz, 2H), 3.97 (dd, J=7.2 3.6 Hz, 2H), 3.79 (d, J=12.4 Hz, 2H), 3.46-3.51 (m, 3H), 3.23 (t, J=6.4 Hz, 2H), 3.11 (d, J=7.2 Hz, 2H), 2.41-2.47 (m, 4H), 2.33-2.40 (m, 1H), 1.76 (d, J=12.8 Hz, 2H), 1.40-1.46 (m, 2H). $^{19}$F NMR (CD$_3$OD): δ ppm −77.19, −114.33.

Examples 66-73

The following Examples were synthesized by method described above for Example 65.

TABLE 8

| Ex No. | Structural formula | Name | LCMS Method; Rt = min; [M + H]$^+$ |
|---|---|---|---|
|  |  | 5-((4-(5-(4-fluorophenyl)-5H-pyrrolo[3,2-d]pyrimidin-7-yl)piperidin-1-yl)methyl)-4-methyl-1H-indole-2-carbonitrile | C; 0.678; 465.2 |

$^1$H NMR (CD$_3$OD): δ ppm 9.30 (s, 1H), 9.14 (s, 1H), 8.60 (s, 1H), 7.31 (dd, J = 4.8, 8.8 Hz, 2H), 7.54 (d, J = 8.0 Hz, 1H), 7.41-7.44 (m, 4H), 4.60 (s, 2H), 3.68-3.71 (m, 2H), 3.37-3.51 (m, 3H), 2.72 (s, 3H), 2.44-2.48 (m, 2H), 2.20-2.40 (m, 2H). $^{19}$F NMR (CD$_3$OD): δ ppm −113.70.

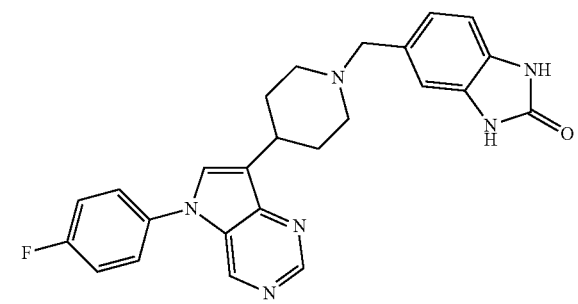 [SMILES: O=c1[nH]c2ccc(CN3CCC(c4cn(-c5ccc(F)cc5)c5cncnc45)CC3)cc2[nH]1]

| | | 5-((4-(5-(4-fluorophenyl)-5H-pyrrolo[3,2-d]pyrimidin-7-yl)piperidin-1-yl)methyl)-1H-benzo[d]imidazol-2(3H)-one | C; 0.771; 443.2 |

$^1$H NMR (CD$_3$OD): δ ppm 9.12 (s, 1H), 9.01 (s, 1H), 8.22 (s, 1H), 7.67 (dd, J = 8.8 4.8 Hz, 2H), 7.38 (t, J = 8.8 Hz, 2H), 7.21-7.29 (m, 2H), 7.15 (d, J = 8.0 Hz, 1H), 4.33-4.45 (m, 2H), 3.65 (d, J = 12.4 Hz, 2H), 3.41 (t, J = 12.4 Hz, 1H), 3.15-3.30 (m, 2H), 2.44 (d, J = 13.6 Hz, 2H), 2.15-2.32 (m, 2H). $^{19}$F NMR (CD$_3$OD): δ ppm −77.01, −114.74.

TABLE 8-continued

NMR spectra details

| Ex No. | Structural formula | Name | LCMS Method; Rt = min; [M + H]+ |
|---|---|---|---|
| 68 | | 7-(1-((1H-indol-6-yl)methyl)piperidin-4-yl)-5-(4-fluorophenyl)-5H-pyrrolo[3,2-d]pyrimidine | E; 1.646; 426.4 |

¹H NMR (CD₃OD): δ ppm 8.91 (s, 1H), 8.87 (s, 1H), 7.88 (s, 1H), 7.57-7.66 (m, 2H), 7.52 (d, J = 8.4 Hz, 1H), 7.40 (s, 1H), 7.34 (t, J = 8.8 Hz, 2H), 7.23 (d, J = 3.2 Hz, 1H), 6.98-7.08 (m, 1H), 6.42 (d, J = 3.2 Hz, 1H), 3.74 (s, 2H), 3.03-3.18 (m, 3H), 2.34 (t, J = 11.2 Hz, 2H), 2.10-2.21 (m, 2H), 1.84-1.98 (m, 2H). ¹⁹F NMR (CD₃OD): δ ppm −116.06 ~ −116.09.

| | | 7-(1-((1H-indol-5-yl)methyl)piperidin-4-yl)-5-(4-fluorophenyl)-5H-pyrrolo[3,2-d]pyrimidine | E; 1.662; 426.2 |

¹H NMR (CD₃OD): δ ppm 9.34 (s, 1 H), 9.16 (s, 1 H), 8.68 (s, 1 H), 7.70-7.82 (m, 4 H), 7.50-7.55 (m, 1 H), 7.40-7.50 (m, 3 H), 7.25-7.35 (m, 2H), 4.47 (s, 2 H), 3.60-3.70 (m, 2 H), 3.45-3.50 (m, 1 H), 3.25-3.30 (m, 2 H), 2.40-2.50 (m, 2 H), 2.25-2.35 (m, 2 H). ¹⁹F NMR (CD₃OD): δ ppm −113.57.

| | | 5-((4-(5-(4-fluoro-2-methylphenyl)-5H-pyrrolo[3,2-d]pyrimidin-7-yl)piperidin-1-yl)methyl)-4-methyl-1H-indole-2-carbonitrile | D; 0.868; 479.3 |

¹H NMR (CD₃OD): δ ppm 9.17 (s, 1 H), 9.07 (s, 1 H), 8.55 (s, 1 H), 7.55-7.60 (m, 1 H), 7.45-7.55 (m, 1 H), 7.35-7.45 (m, 2 H), 7.30-7.35 (m, 1H), 7.15-7.25 (m, 1 H), 4.58 (s, 2H), 3.65-3.75 (m, 2H), 3.45-3.60 (m, 1 H), TABLE 8-continued NMR spectra details

| Ex No. | Structural formula | Name | LCMS Method; Rt = min; [M + H]+ |
|---|---|---|---|
| | | 5-((4-(5-(3-fluorophenyl)-5H-pyrrolo[3,2-d]pyrimidin-7-yl)piperidin-1-yl)methyl)-4-methyl-1H-indole-2-carbonitrile (TFA salt) | D; 0.869; 465.3 |

3.35-3.45 (m, 2 H), 2.73 (s, 3 H), 2.40-2.45 (m, 2 H), 2.25-2.40 (m, 2 H), 2.11 (s, 3 H). 19F NMR (CD$_3$OD): δ ppm −112.42.

$^1$H NMR (CD$_3$OD): δ ppm$^1$ 9.16 (s, 1 H), 8.99 (s, 1 H), 8.16 (s, 1 H), 7.61-7.72 (m, 1 H), 7.36-7.59 (m, 5 H), 7.23-7.31 (m, 1 H), 4.57 (s, 2 H), 3.70 (d, J = 12.4 Hz, 2 H), 3.35-3.53 (m 3 H), 2.67-2.80 (m, 3 H), 2.44 (d, J = 14.4 Hz, 2 H), 2.17-2.28 (m, 2 H). $^{19}$F NMR (CD$_3$OD): δ ppm −77.30, −111.75.

| | | 4-methyl-5-((4-(5-phenyl-5H-pyrrolo[3,2-d]pyrimidin-7-yl)piperidin-1-yl)methyl)-1H-indole-2-carbonitrile | C; 0.663; 447.2 |

$^1$H NMR (CD$_3$OD): δ ppm 9.11 (s, 1H), 8.99 (s, 1H), 8.19 (s, 1H), 7.35-7.74 (m, 8H), 4.57 (s, 2H), 3.70 (d, J = 12.4 Hz, 2H), 3.34-3.52 (m, 3H), 2.72 (s, 3H), 2.44 (d, J = 13.6 Hz, 2H), 2.17-2.31 (m, 2H).

| | | 5-((4-(5-phenyl-5H-pyrrolo[3,2-d]pyrimidin-7-yl)piperidin-1-yl)methyl)-1H-benzo[d]imidazol-2(3H)-one | C; 0.573; 425.0 |

$^1$H NMR (CD$_3$OD): δ ppm 8.85-9.00 (m, 2H), 7.93 (s, 1H), 7.56-7.65 (m, 4H), 7.43-7.50 (m, 1H), 7.11 (s, 1H), 7.04-7.08 (m, 1H), 6.95-7.03 (m, 1H), 3.63 (s, 2H), 3.02-3.15 (m, 3H), 2.28 (t, J = 11.6 Hz, 2H), 2.15 (d, J = 12.8 Hz, 2H), 1.82-1.98 (m, 2H).

Example 74. 5-fluoro-N-isopropyl-N-methyl-2-(1-(1-((2-oxo-2,3-dihydro-1H-benzo[d]imidazol-5-yl)methyl)piperidin-3-yl)-1H-pyrrolo[3,2-c]pyridin-3-yl)benzamide

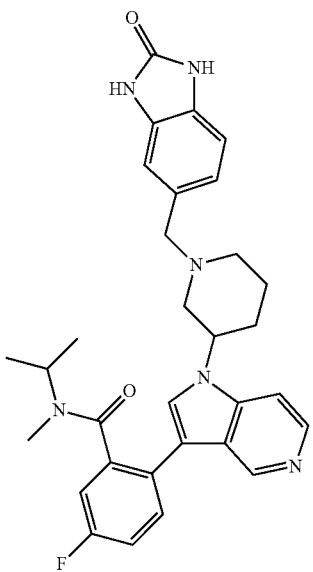 [SMILES: CC(C)N(C)C(=O)c1cc(F)ccc1-c1cn(C2CCCN(Cc3ccc4[nH]c(=O)[nH]c4c3)C2)c2ccncc12]

Step 1: tert-butyl 3-(3-iodo-1H-pyrrolo[3,2-c]pyridin-1-yl)piperidine-1-carboxylate

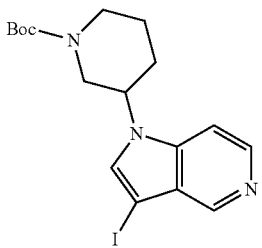 [SMILES: CC(C)(C)OC(=O)N1CCCC(n2cc(I)c3cnccc32)C1]

To a solution of 3-iodo-1H-pyrrolo[3,2-c]pyridine (150 mg, 0.62 mmol) in DMF (3 mL) was added NaH (26 mg, 0.65 mmol, 60% in mineral oil) at RT. The suspension stirred at RT for 15 min followed by the addition of tert-butyl 3-((methylsulfonyl)oxy)piperidine-1-carboxylate (273 mg, 0.98 mmol) at RT. The reaction mixture was then heated at 80° C. for 5 hours. After cooling to RT, a saturated aq. solution of NH$_4$Cl (5 mL) was added followed by EtOAc (10 mL). The aq. layer was separated and extracted with EtOAc (2×5 mL). The organic layers were combined, washed with brine, dried over Na$_2$SO$_4$, and evaporated. Purification of the crude product using ISCO flash column chromatography (100% Hexane to 100% EtOAc) gave tert-butyl 3-(3-iodo-1H-pyrrolo[3,2-c]pyridin-1-yl)piperidine-1-carboxylate (53 mg, 20%). LCMS Method C: t$_R$=5.194; [M+H]$^+$=428.40.

Step 2: 2-(1-(1-(tert-butoxycarbonyl)piperidin-3-yl)-1H-pyrrolo[3,2-c]pyridin-3-yl)-5-fluorobenzoic Acid

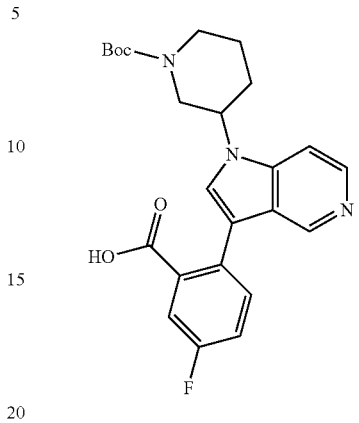

A suspension of tert-butyl 3-(3-iodo-1H-pyrrolo[3,2-c]pyridin-1-yl)piperidine-1-carboxylate (90 mg, 0.21 mmol), (5-fluoro-2-(methoxycarbonyl)phenyl)boronic acid (83 mg, 0.42 mmol), Pd(PPh$_3$)$_4$ (20 mg, 10 mol %) and 2M aq. Na$_2$CO$_3$ (1 mL) in dioxane (3 mL) were heated at 70° C. for 5 h. After cooling to RT, a standard workup was performed using EtOAc and water. The EtOAc layer was dried over Na$_2$SO$_4$ and evaporated to afford crude tert-butyl 3-(3-(4-fluoro-2-(methoxycarbonyl)phenyl)-1H-pyrrolo[3,2-c]pyridin-1-yl)piperidine-1-carboxylate. This crude material was taken up in 2 mL of THF and 1 mL of MeOH. A 4 N NaOH solution (1 mL) was added at RT and the reaction mixture stirred for 4 h. The reaction mixture was diluted with 5 mL of water and washed with EtOAc. The aqueous layer was cooled to 0° C. and acidified to pH=~4 using 2N HCl. The product was extracted from the acidified aqueous layer using EtOAc (3×5 mL). The EtOAc layer was dried over Na$_2$SO$_4$ and evaporated to afford nearly pure 2-(1-(1-(tert-butoxycarbonyl)piperidin-3-yl)-1H-pyrrolo[3,2-c]pyridin-3-yl)-5-fluorobenzoic acid (40 mg, 42% over 2 steps). LCMS Method C: t$_R$=5.489 min; [M+H]$^+$=440.50.

Step 3: tert-butyl 3-(3-(4-fluoro-2-(isopropyl(methyl)carbamoyl)phenyl)-1H-pyrrolo[3,2-c]pyridin-1-yl)piperidine-1-carboxylate

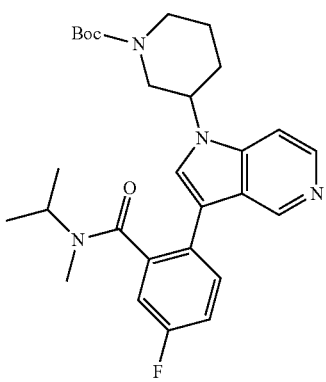 [SMILES: CC(C)N(C)C(=O)c1cc(F)ccc1-c1cn(C2CCCN(C(=O)OC(C)(C)C)C2)c2ccncc12]

To a solution of 2-(1-(1-(tert-butoxycarbonyl)piperidin-3-yl)-1H-pyrrolo[3,2-c]pyridin-3-yl)-5-fluorobenzoic acid (40 mg, 0.091 mmol), N-methylpropan-2-amine (20 mg, 0.27 mmol) and iPr₂NEt (0.05 mL, 0.29 mmol) in DMF (2 mL) was added HATU (58 g, 0.18 mmol) at RT. The reaction stirred for 1 h at RT. H₂O (3 mL) and EtOAc (5 mL) were added and the aqueous layer was extracted with EtOAc (2×2 mL). The organic layers were combined, washed with H₂O, dried over Na₂SO₄, and evaporated. Purification using ISCO flash column chromatography (eluting with 10% MeOH in DCM) gave tert-butyl 3-(3-(4-fluoro-2-(isopropyl(methyl) carbamoyl)phenyl)-1H-pyrrolo[3,2-c]pyridin-1-yl)piperidine-1-carboxylate (16 mg, 36%). LCMS Method B: $t_R$=1.035 min; [M+H]⁺=495.32.

Step 4: 5-fluoro-N-isopropyl-N-methyl-2-(1-(1-((2-oxo-2,3-dihydro-1H-benzo[d]imidazol-5-yl)methyl) piperidin-3-yl)-1H-pyrrolo[3,2-c]pyridin-3-yl)benzamide The title compound was prepared according to the method described in Example 4 utilizing 2-oxo-2,3-dihydro-1H-benzo[d]imidazole-5-carbaldehyde. LCMS method C: $t_R$=2.661 min; [M+H]⁺=541.58. ¹H NMR (CD₃OD): mixture of rotamers δ 9.03 (s, 1H), 8.45 (d, J=6.8, 1H), 8.16 (d, J=6.6 Hz, 1H), 8.05-8.01 (m, 1H), 7.71-7.60 (m, 1H), 7.39-7.35 (m, 1H), 7.25-7.30 (m, 1H), 7.18-7.16 (m, 2H), 7.13-7.02 (m, 1H), 5.19-5.10 (m, 1H), 4.84-4.79 (m, 1H), 4.52-4.48 (m, 1H), 4.30-4.17 (m, 2H), 3.58-3.40 (m, 3H), 3.15-2.90 (m, 2H), 2.67 (s, 3H), 2.25-2.02 (m, 2H), 1.33-1.29 (m, 3H), 1.02-0.99 (m, 3H).

Example 78. 5-fluoro-N-isopropyl-N-methyl-2-(1-(1-(2-((1r,4r)-4-(methylsulfonamido)cyclohexyl) ethyl)piperidin-4-yl)-2-oxo-1,2-dihydro-3H-imidazo [4,5-c]pyridin-3-yl)benzamide

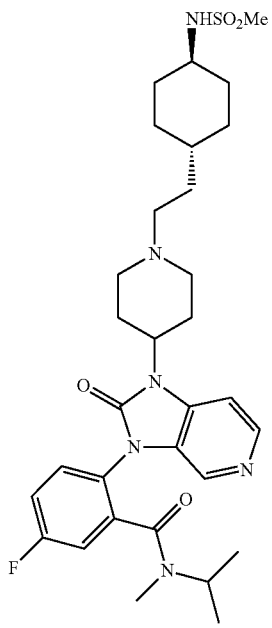

Step 1: tert-butyl 4-(2-oxo-2,3-dihydro-1H-imidazo [4,5-c]pyridin-1-yl)piperidine-1-carboxylate and tert-butyl 1-(1-(tert-butoxycarbonyl)piperidin-4-yl)-2-oxo-1,2-dihydro-3H-imidazo[4,5-c]pyridine-3-carboxylate

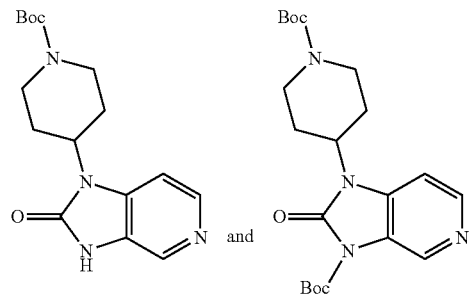 [SMILES: CC(C)(C)OC(=O)N1CCC(n2c(=O)[nH]c3cnccc32)CC1 ; CC(C)(C)OC(=O)N1CCC(n2c(=O)n(C(=O)OC(C)(C)C)c3cnccc32)CC1]

To a suspension of 1-(piperidin-4-yl)-1,3-dihydro-2H-imidazo[4,5-c]pyridin-2-one (4.23 g, 16.62 mmol, synthesized by a method described in BMCL, 16(19), 5052-5056; 2006) in MeOH (30 mL) was added Et₃N (4.5 mL, 33.24 mmol). The mixture was gently heated until complete dissolution of starting material was observed. The solvent was then evaporated and the material was thoroughly dried under high vacuum. The material was taken up in MeOH (30 mL) and Boc₂O (4.34 g, 19.92 mmol) was added at RT and the reaction mixture was stirred at RT for 5 h. Evaporation of the solvent gave crude tert-butyl 4-(2-oxo-2,3-dihydro-1H-imidazo[4,5-c]pyridin-1-yl)piperidine-1-carboxylate (5.3 grams, >95%) containing ~20% of tert-butyl 1-(1-(tert-butoxycarbonyl)piperidin-4-yl)-2-oxo-1,2-dihydro-3H-imidazo[4,5-c]pyridine-3-carboxylate. This crude material was used directly for the next step without further purification. LCMS method B: $t_R$=0.748 min; [M+H]⁺=319.29. ¹H NMR (CD₃OD): δ 8.41-8.36 (m, 2H), 7.72 (d, J=6.0 Hz, 1H), 4.58-4.50 (m, 1H), 4.30-4.26 (m, 2H), 3.02-2.85 (m, 2H), 2.41-2.30 (m, 2H), 1.88-1.84 (m, 2H), 1.49 (s, 9H).

Step 2. 2-(1-(1-(tert-butoxycarbonyl)piperidin-4-yl)-2-oxo-1,2-dihydro-3H-imidazo[4,5-c]pyridin-3-yl)-5-fluorobenzoic acid

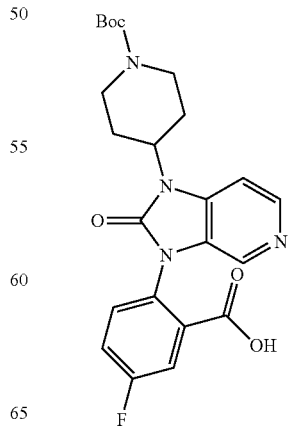

A suspension of crude tert-butyl 4-(2-oxo-2,3-dihydro-1H-imidazo[4,5-c]pyridin-1-yl)piperidine-1-carboxylate containing ~20% of tert-butyl 1-(1-(tert-butoxycarbonyl)piperidin-4-yl)-2-oxo-1,2-dihydro-3H-imidazo[4,5-c]pyridine-3-carboxylate (1 g, 3.14 mmol), 2-bromo-5-fluorobenzoic acid (800 mg, 3.65 mmol), CuI (200 mg, 1.04 mmol), Cs$_2$CO$_3$ (1.5 g, 4.6 mmol) and 1,10-phenanthroline (50 mg, 10 mol %) in DMF (8 mL) was heated at 70° C. for 24 h. The reaction mixture was cooled to RT and filtered through a plug of celite with EtOAc washings. The solvent was removed to afford crude 2-(1-(1-(tert-butoxycarbonyl)piperidin-4-yl)-2-oxo-1,2-dihydro-3H-imidazo[4,5-c]pyridin-3-yl)-5-fluorobenzoic acid which was used directly for the next step without further purification. LCMS method C: t$_R$=4.658 min; [M+H]$^+$=457.52.

Step 3. tert-butyl 4-(3-(4-fluoro-2-(isopropyl(methyl)carbamoyl)phenyl)-2-oxo-2,3-dihydro-1H-imidazo[4,5-c]pyridin-1-yl)piperidine-1-carboxylate

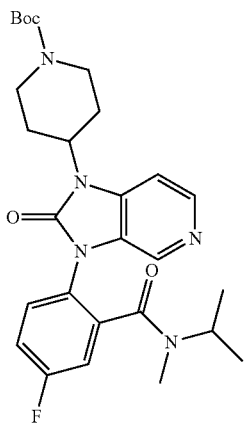 [SMILES: CC(C)N(C)C(=O)c1cc(F)ccc1-n1c(=O)n(C2CCN(C(=O)OC(C)(C)C)CC2)c2ccncc21]

To a solution of the above crude 2-(1-(1-(tert-butoxycarbonyl)piperidin-4-yl)-2-oxo-1,2-dihydro-3H-imidazo[4,5-c]pyridin-3-yl)-5-fluorobenzoic acid, N-methylpropan-2-amine (459 mg, 6.30 mmol) and iPr$_2$NEt (1.6 mL, 9.2 mmol) in DMF (10 mL) was added HATU (1.8 g, 4.5 mmol) at RT. The reaction mixture was stirred at RT for 12 h. H$_2$O (10 mL) and EtOAc (20 mL) were then added to the reaction mixture. The EtOAc layer was separated, dried over Na$_2$SO$_4$, and evaporated. The crude material was purified by ISCO flash column chromatography (eluting with 10% MeOH in DCM) to afford tert-butyl 4-(3-(4-fluoro-2-(isopropyl(methyl)carbamoyl)phenyl)-2-oxo-2,3-dihydro-1H-imidazo[4,5-c]pyridin-1-yl)piperidine-1-carboxylate (610 mg, 54% over 2 steps). $^1$H NMR (CDCl$_3$): mixture of rotamers δ 8.32 (d, J=5.2 Hz, 1H), 8.18 (s, 1H), 7.49-7.43 (m, 1H), 7.29-7.25 (m, 1H), 7.20-7.17 (m, 1H), 7.08 (d, J=5.2 Hz, 1H), 4.64-4.57 (m, 1H), 4.45-4.22 (m, 3H), 2.86-2.80 (m, 2H), 2.79 (s, 3H), 2.37-2.22 (m, 2H), 1.90-1.72 (m, 2H), 1.51 (s, 9H), 1.15-1.04 (m, 3H), 0.91 (d, J=6.4 Hz, 3H).

Step 4: 5-fluoro-N-isopropyl-N-methyl-2-(2-oxo-1-(piperidin-4-yl)-1,2-dihydro-3H-imidazo[4,5-c]pyridin-3-yl)benzamide hydrochloride salt

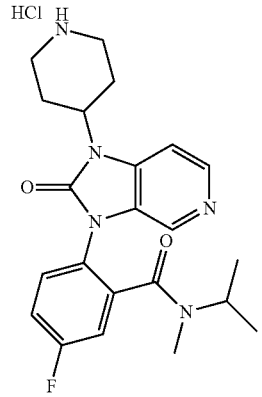 [SMILES: Cl ; CC(C)N(C)C(=O)c1cc(F)ccc1-n1c(=O)n(C2CCNCC2)c2ccncc21]

A 5N HCl solution in iPrOH (5 mL) was added to tert-butyl 4-(3-(4-fluoro-2-(isopropyl(methyl)carbamoyl)phenyl)-2-oxo-2,3-dihydro-1H-imidazo[4,5-c]pyridin-1-yl)piperidine-1-carboxylate (610 mg, 1.19 mmol) at RT. After stirring at RT for 2 h, the solvent was evaporated to afford crude 5-fluoro-N-isopropyl-N-methyl-2-(2-oxo-1-(piperidin-4-yl)-1,2-dihydro-3H-imidazo[4,5-c]pyridin-3-yl)benzamide HCl salt. This material was used directly for the next step without further purification.

Step 5: tert-butyl ((1r,4r)-4-(2-(4-(3-(4-fluoro-2-(isopropyl(methyl)carbamoyl)phenyl)-2-oxo-2,3-dihydro-1H-imidazo[4,5-c]pyridin-1-yl)piperidin-1-yl)ethyl)cyclohexyl)carbamate

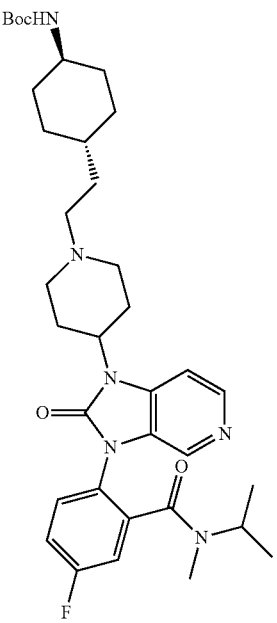 [SMILES: CC(C)N(C)C(=O)c1cc(F)ccc1-n1c(=O)n(C2CCN(CC[C@H]3CC[C@H](NC(=O)OC(C)(C)C)CC3)CC2)c2ccncc21]

To a solution of 5-fluoro-N-isopropyl-N-methyl-2-(2-oxo-1-(piperidin-4-yl)-1,2-dihydro-3H-imidazo[4,5-c]pyridin-3-yl)benzamide HCl salt (20 mg, 0.044 mmol), Et$_3$N (0.02 mL, 0.13 mmol) and tert-butyl (trans)-4-(2-oxoethyl)(cyclohexyl)carbamate (21 mg, 0.088 mmol) in MeOH was added NaBH₃CN (6 mg, 0.088 mmol) at RT and the reaction mixture was stirred at RT for 24 h. Evaporation of the solvent and purification using ISCO flash column chromatography (eluting with 15% MeOH in DCM) gave tert-butyl ((trans)-4-(2-(4-(3-(4-fluoro-2-(isopropyl(methyl)carbamoyl)phenyl)-2-oxo-2,3-dihydro-1H-imidazo[4,5-c]pyridin-1-yl)piperidin-1-yl)ethyl)cyclohexyl)carbamate (30 mg, >95%). LCMS Method C: t$_R$=4.842 min; [M+H]⁺=637.70

Step 6: 2-(1-(1-(2-((1r,4r)-4-aminocyclohexyl)ethyl)piperidin-4-yl)-2-oxo-, 2-dihydro-3H-imidazo[4,5-c]pyridin-3-yl)-5-fluoro-N-isopropyl-N-methylbenzamide

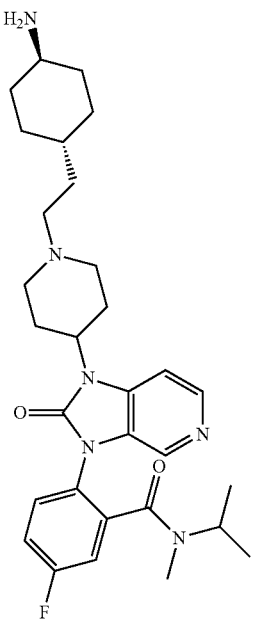 [SMILES: CC(C)N(C)C(=O)c1cc(F)ccc1-n1c(=O)n(C2CCN(CC[C@H]3CC[C@H](N)CC3)CC2)c2ccncc21]

The title compound was prepared according to a method similar to the method described in Step 4 of Example 1, and was used directly in the next step. LCMS: Method A: t$_R$=0.438 min; [M+H]⁺=537.39.

Step 7: 5-fluoro-N-isopropyl-N-methyl-2-(1-(1-(2-((1r,4r)-4-(methylsulfonamido)cyclohexyl)ethyl)piperidin-4-yl)-2-oxo-1,2-dihydro-3H-imidazo[4,5-c]pyridin-3-yl)benzamide The title compound was synthesized by a method similar to Example 21. LCMS method C: t$_R$=3.161 min; [M+H]⁺=615.53. ¹H NMR (CD₃OD): mixture of rotamers δ 8.56 (d, J=6.4 Hz, 1H), 8.35 (s, 1H), 7.93 (d, J=6.4, 1H), 7.72-7.68 (m, 1H), 7.52-7.43 (m, 2H), 4.83-4.75 (m, 1H), 4.58-4.51 (m, 1H), 3.81-3.70 (m, 2H), 3.22-3.14 (m, 5H), 2.94 (s, 3H), 2.94-2.80 (m, 2H), 2.87 (s, 3H), 2.30-2.18 (m, 2H), 2.06-2.02 (m, 2H), 1.87-1.80 (m, 2H), 1.72-1.66 (m, 2H), 1.36-1.09 (m, 8H), 1.04 (d, J=6.8 Hz, 3H).

Example 79. 5-fluoro-N-isopropyl-N-methyl-2-(2-oxo-1-(1-((2-oxo-2,3-dihydro-1H-benzo[d]imidazol-5-yl)methyl)piperidin-4-yl)-1,2-dihydro-3H-imidazo[4,5-c]pyridin-3-yl)benzamide

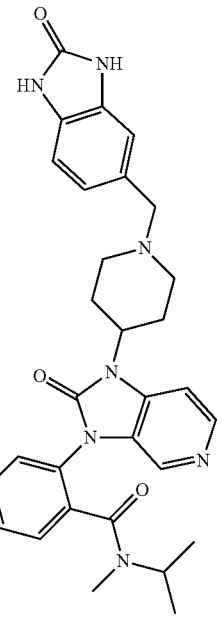

The title product was synthesized by the method described in Example 74. In step 1, tert-butyl 4-((methylsulfonyl)oxy)piperidine-1-carboxylate was utilized. LCMS method C: t$_R$=2.421 min in 16 min; [M+H]⁺=558.62. ¹H NMR (CD₃OD): mixture of rotamers δ 8.35 (bs, 1H), 8.14 (bs, 1H), 7.66-7.62 (m, 1H), 7.58-7.50 (m, 1H), 7.49-7.38 (m, 2H), 7.23-7.06 (m, 3H), 4.69-4.60 (m, 1H), 4.52-4.46 (m, 1H), 4.38 (s, 2H), 3.69-3.60 (m, 2H), 3.27-3.20 (m, 4H), 2.90-2.84 (m, 2H), 2.84 (s, 3H), 2.21-2.10 (m, 2H), 1.33-1.13 (m, 3H), 0.97 (d, J=6.0 Hz, 3H).

Example 80. 5-((4-(3-(4-fluorophenyl)-2-oxo-2,3-dihydro-1H-imidazo[4,5-c]pyridin-1-yl)piperidin-1-yl)methyl)-4-methyl-1H-indole-2-carbonitrile

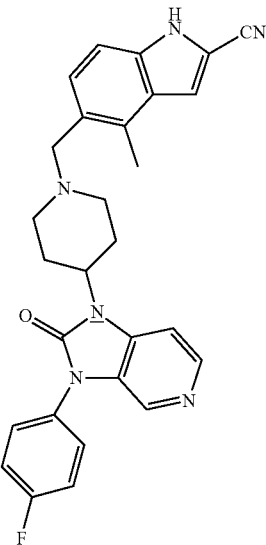 [SMILES: Cc1c(CN2CCC(n3c(=O)n(-c4ccc(F)cc4)c4cnccc43)CC2)ccc2[nH]c(C#N)cc12]

185

Step 1: tert-butyl 4-(3-(4-fluorophenyl)-2-oxo-2,3-dihydro-1H-imidazo[4,5-c]pyridin-1-yl)piperidine-1-carboxylate

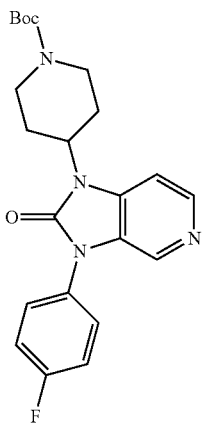 [SMILES: CC(C)(C)OC(=O)N1CCC(n2c(=O)n(-c3ccc(F)cc3)c3cnccc32)CC1]

A suspension of crude tert-butyl 4-(2-oxo-2,3-dihydro-1H-imidazo[4,5-c]pyridin-1-yl)piperidine-1-carboxylate (Example 78, Step 1, 100 mg, 0.31 mmol), (4-fluorophenyl) boronic acid (100 mg, 0.71 mmol), Cu(OAc)$_2$ (165 mg, 0.92 mmol), Et$_3$N (0.15 ml, 1.07 mmol) and 4 Å molecular sieve (150 mg) in DCM (3 mL) was stirred at RT for 24 h. The reaction mixture was filtered through a plug of celite with DCM washings. The DCM solution was washed with a sat. aq. NH$_4$Cl solution, dried over Na$_2$SO$_4$, and evaporated. The crude material was purified by ISCO flash column chromatography (eluting with 10% MeOH in DCM) to give tert-butyl 4-(3-(4-fluorophenyl)-2-oxo-2,3-dihydro-1H-imidazo[4,5-c]pyridin-1-yl)piperidine-1-carboxylate (56 mg, 44%). LCMS method C: t$_R$=5.508; [M+H]$^+$=413.58.

Step 2. 5-((4-(3-(4-fluorophenyl)-2-oxo-2,3-dihydro-1H-imidazo[4,5-c]pyridin-1-yl)piperidin-1-yl)methyl)-4-methyl-1H-indole-2-carbonitrile The title compound was prepared according to the method described in Example 74. In the final step, 5-formyl-1H-indole-2-carbonitrile was utilized. LCMS method C: t$_R$=3.623 min; [M+H]$^+$=481.56 $^1$H NMR (CD$_3$OD): δ 8.54 (d, J=6.0 Hz, 1H), 8.47 (s, 1H), 7.92 (d, J=6.0 Hz, 1H), 7.64-7.61 (m, 2H), 7.50-7.36 (m, 5H), 4.89-4.90 (m, 1H), 4.57 (s, 2H), 3.76-3.72 (m, 2H), 3.42-3.31 (m, 2H), 2.90-2.84 (m, 2H), 2.71 (s, 3H), 2.27-2.22 (m, 2H).

Example 81. 2-(1-(1-(cyclohexylmethyl)piperidin-4-yl)-2-oxo-1,2-dihydro-3H-imidazo[4,5-c]pyridin-3-yl)-5-fluoro-N-isopropyl-N-methylbenzamide

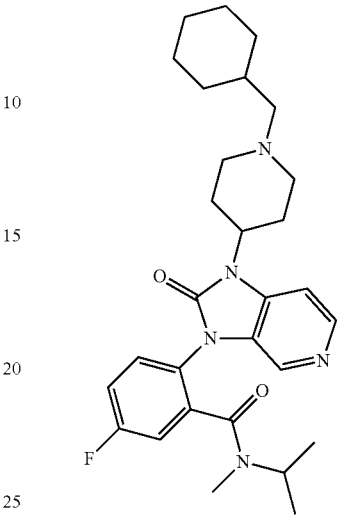

The title compound was synthesized by the method described in Example 79. In final Step 5, 1-cyclohexane aldehyde was utilized. LC-M Method C: t$_R$=4.159 min, [M+H]$^+$=508.2. $^1$H NMR (CD$_3$OD,): mixture of rotamers δ 8.41 (d, J=6.0 Hz, 1H), 8.19 (s, 1H), 7.69-7.63 (m, 2H), 7.51-7.40 (m, 2H), 4.74-4.71 (m, 1H), 4.55-4.50 (m, 1H), 3.80-3.75 (m, 2H), 3.28-3.17 (m, 2H), 3.03 (d, J=6.8 Hz, 2H), 2.92-2.81 (m, 2H), 2.84 (s, 3H), 2.22-2.12 (m, 2H), 1.90-1.72 (m, 6H), 1.43-1.05 (m, 8H), 1.00 (d, J=6.4 Hz, 3H).

Example 82. 2-(1-(1-((2-cyano-4-methyl-1H-indol-5-yl)methyl)piperidin-4-yl)-2-oxo-1,2-dihydro-3H-imidazo[4,5-c]pyridin-3-yl)-5-fluoro-N-isopropyl-N-methylbenzamide

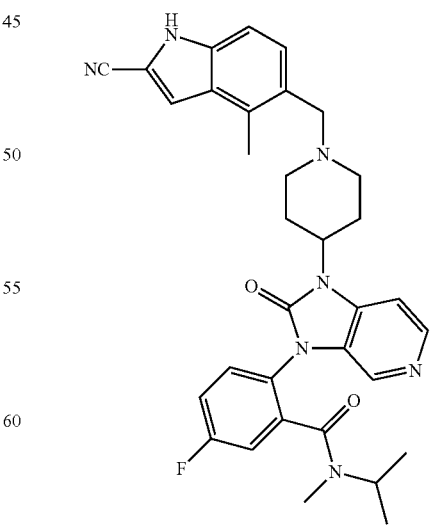

The title compound was synthesized by the method described in Example 79. In the final step, 5-formyl-4- methyl-1H-indole-2-carbonitrile was utilized. LCMS method C: $t_R$=4.251 min; [M+H]$^+$=580.60, $^1$H NMR (CD$_3$OD): mixture of rotamers δ 8.53 (d, J=6.4 Hz, 1H), 8.32-8.29 (m, 1H), 7.88-7.85 (m, 1H), 7.70-7.66 (m, 1H), 7.50-7.40 (m, 5H), 4.82-4.76 (m, 1H), 4.56 (s, 2H), 4.56-4.49 (m, 1H), 3.74-3.70 (m, 2H), 3.40-3.31 (m, 2H), 2.90-2.80 (m, 2H), 2.84 (s, 3H), 2.69 (s, 3H), 2.22-2.17 (m, 2H), 1.14-1.11 (m, 3H), 1.00 (d, J=6.8 Hz, 3H).

Example 83. 5-fluoro-2-(1-(1-(4-fluorobenzyl)piperidin-4-yl)-2-oxo-1,2-dihydro-3H-imidazo[4,5-c]pyridin-3-yl)-N-isopropyl-N-methylbenzamide

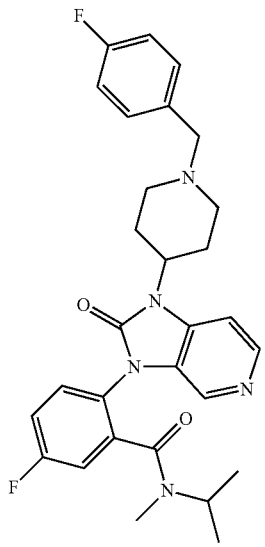 [SMILES: CC(C)N(C)C(=O)c1cc(F)ccc1-n1c(=O)n(C2CCN(Cc3ccc(F)cc3)CC2)c2ccncc21]

The title compound was synthesized by the method described in Example 79. In the final step 4-fluorobenzaldehyde was utilized. LCMS method C: $t_R$=3.660; [M+H]$^+$=520.65. $^1$H NMR (CD$_3$OD): mixture of rotamers δ 8.60-8.50 (m, 1H), 8.32-8.28 (m, 1H), 7.85-7.81 (m, 1H), 7.69-7.66 (m, 1H), 7.60-7.57 (m, 2H), 7.50-7.45 (m, 2H), 7.29-7.24 (m, 2H), 4.87-4.70 (m, 1H), 4.55-4.51 (m, 1H), 4.39 (s, 2H), 3.70-3.65 (m, 2H), 3.26-3.20 (m, 2H), 2.86-2.75 (m, 2H), 2.85 (s, 3H), 2.22-2.10 (m, 2H), 1.16-1.13 (m, 3H), 1.01 (d, J=6.4 Hz, 3H).

Example 84. 5-fluoro-2-(3-(1-((1-(2-hydroxyethyl)-2-oxo-2,3-dihydro-1H-benzo[d]imidazol-5-yl)methyl)piperidin-3-yl)-1H-pyrrolo[2,3-c]pyridin-1-yl)-N,N-diisopropylbenzamide

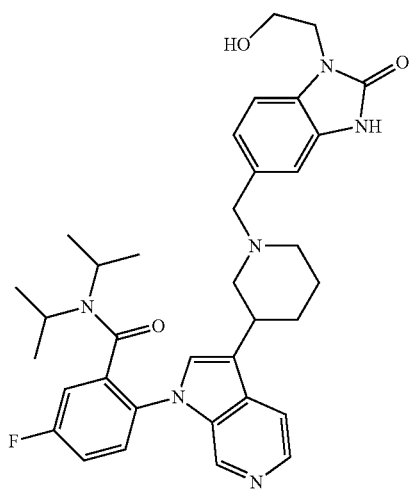 [SMILES: CC(C)N(C(=O)c1cc(F)ccc1-n1cc(C2CCCN(Cc3ccc4c(c3)[nH]c(=O)n4CCO)C2)c2ccncc21)C(C)C]

Step 1: 5-fluoro-2-(1H-pyrrolo[2,3-c]pyridin-1-yl)benzoic acid

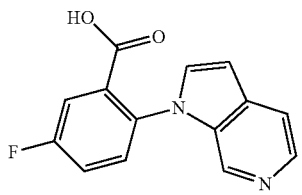 [SMILES: O=C(O)c1cc(F)ccc1-n1ccc2ccncc21]

A 500 mL flask was charged with 6-aza-indole (10.0 g, 84.65 mmol), 5-fluoro-2-iodobenzoic acid (24.77 g, 93.12 mmol), Cu powder (5.38 g, 84.65 mmol), K$_2$CO$_3$ (29.2 g, 211.6 mmol, 2.5 eq.) and N-methyl pyrrolidone (NMP) (200 mL). The mixture was degassed 3 times and refilled with N$_2$ before heating to 150° C. for 2 h. The reaction mixture was cooled to RT and filtered through a short pad of Celite and washed with MeCN and EtOAc (50 mL each). The filtrate was concentrated to remove MeCN and EtOAc. Aq. 6M HCl (28 mL) was added slowly with stirring, to a final pH=6. The resulting precipitate was collected by filtration and washed with H$_2$O to yield 43.3 g of the product. LCMS method B: $R_t$=0.58 min, 257 (M+H)$^+$=257.1

Step 2. 5-fluoro-N,N-diisopropyl-2-(1H-pyrrolo[2,3-c]pyridin-1-yl)benzamide

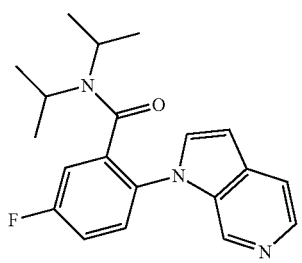 [SMILES: CC(C)N(C(=O)c1cc(F)ccc1-n1ccc2ccncc21)C(C)C]

To a suspension of 5-fluoro-2-(1H-pyrrolo[2,3-c]pyridin-1-yl)benzoic acid (0.200 g, 0.78 mmol), benzotriazol-1-yloxytripyrrolidinophosphonium hexafluorophosphate (PyBOP) (489 mg, 0.94 mmol, 1.2 eq.) in DMF (2 mL) was added iPr$_2$NH (0.55 mL, 3.90 mmol, 5 eq.) and a clear dark solution formed. The mixture was then stirred for 6 h. The reaction mixture was diluted with EtOAc and washed with saturated aqueous NaHCO$_3$ solution. The combined organic phases were washed with brine, dried over over anhydrous Na$_2$SO$_4$, and filtered. The filtrate was concentrated to dryness. The resulting residue was purified by flash chromatography to afford 165 mg of the desired product which was directly used in the next step.

Step 3: 2-(3-bromo-1H-pyrrolo[2,3-c]pyridin-1-yl)-5-fluoro-N,N-diisopropylbenzamide

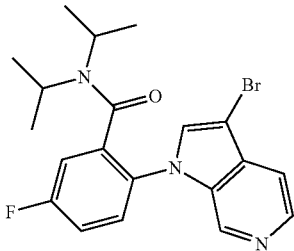 [SMILES: CC(C)N(C(=O)c1cc(F)ccc1-n1cc(Br)c2ccncc21)C(C)C]

To a solution of 5-fluoro-N,N-diisopropyl-2-(1H-pyrrolo[2,3-c]pyridin-1-yl)benzamide (700 mg, 2.06 mmol) in EtOAc (15 mL) cooled to 0° C. was added N-bromosuccinimide (NBS) (441 mmog, 2.48 mmol), 1.2 eq.) in one portion and the reaction mixture was stirred at RT for 2 h. The reaction mixture was cooled to 0° C., quenched with aqueous $Na_2S_2O_3$ solution, and extracted with EtOAc. The organic phase was washed with with brine, dried over anhydrous $Na_2SO_4$, and filtered. The filtrate was concentrated to dryness and the resulting residue was purified by flash chromatography to afford 0.873 g of the desired product. LCMS method B: $t_R$: 0.97 min; (M+H)$^+$=418.1.

Step 4: tert-butyl 5-(1-(2-(diisopropylcarbamoyl)-4-fluorophenyl)-1H-pyrrolo[2,3-c]pyridin-3-yl)-3,6-dihydropyridine-1 (2H)-carboxylate

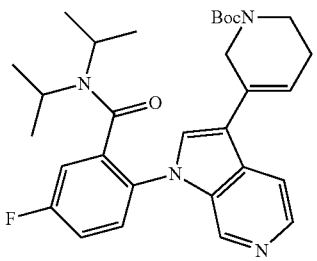 [SMILES: CC(C)N(C(=O)c1cc(F)ccc1-n1cc(C2=CCCN(C(=O)OC(C)(C)C)C2)c2ccncc21)C(C)C]

A 10 mL CEM microwave test tube charged with 2-(3-bromo-1H-pyrrolo[2,3-c]pyridin-1-yl)-5-fluoro-N,N-diisopropylbenzamide (305 mg, 0.73 mmol), tert-butyl 5-(4,4,5,5-tetramethyl-1,3,2-dioxaborolan-2-yl)-3,6-dihydropyridine-1(2H)-carboxylate (248 mg, 0.80 mmol), $K_3PO_4$ (310 mg, 1.46 mmol), SPhos-Pd-G2 (16 mg, 0.022 mmol), dioxane (3 mL), and $H_2O$ (1 mL) under $N_2$ atmosphere was heated to 110° C. for 15 min. The reaction mixture was diluted with EtOAc, washed with $H_2O$, brine, dried over anhydrous $Na_2SO_4$, and filtered. The filtrate was concentrated to dryness and the resulting residue was purified by flash chromatography to afford 342 mg of tert-butyl 5-(1-(2-(diisopropylcarbamoyl)-4-fluorophenyl)-1H-pyrrolo[2,3-c]pyridin-3-yl)-3,6-dihydropyridine-1(2H)-carboxylate. LCMS method B: $t_R$: 1.18 min; (M+H)$^+$=521.1

Step 5: tert-butyl 3-(1-(2-(diisopropylcarbamoyl)-4-fluorophenyl)-1H-pyrrolo[2,3-c]pyridin-3-yl)piperidine-1-carboxylate

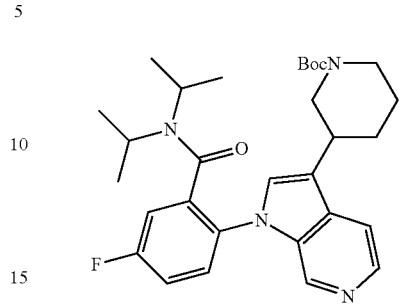

Tert-butyl 5-(1-(2-(diisopropylcarbamoyl)-4-fluorophenyl)-1H-pyrrolo[2,3-c]pyridin-3-yl)-3,6-dihydropyridine-1 (2H)-carboxylate (336 mg, 0.645 mmol) was hydrogenated under 50 psi of $H_2$ in MeOH (30 mL) with 10% Pd/C (100 mg) for 24 h. The reaction mixture was then filtered through a celite pad. The resulting residue was concentrated to dryness and purified by flash chromatography on silica gel with hexane/EtOAc to afford 263 mg of tert-butyl 3-(1-(2-(diisopropylcarbamoyl)-4-fluorophenyl)-1H-pyrrolo[2,3-c]pyridin-3-yl)piperidine-1-carboxylate. LCMS method B: $t_R$: 1.17 min; (M+H)$^+$=523.1.

Step 6: 5-fluoro-N,N-diisopropyl-2-(3-(piperidin-3-yl)-1H-pyrrolo[2,3-c]pyridin-1-yl)benzamide

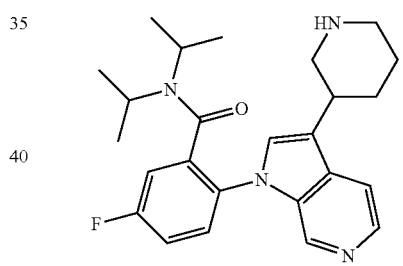

To a solution of tert-butyl 3-(1-(2-(diisopropylcarbamoyl)-4-fluorophenyl)-1H-pyrrolo[2,3-c]pyridin-3-yl)piperidine-1-carboxylate (260 mg, 0.50 mmol) in MeOH (2 mL) was added 4 M HCl/dioxane (2 mL) and the mixture was stirred for 30 min at RT. The reaction mixture was concentrated to dryness to afford 247 mg of 5-fluoro-N,N-diisopropyl-2-(3-(piperidin-3-yl)-1H-pyrrolo[2,3-c]pyridin-1-yl)benzamide as bis HCl salt. LCMS method B: $t_R$: 0.60 min; (M+H)$^+$=423.1.

Step 7: 5-fluoro-2-(3-(1-((1-(2-hydroxyethyl)-2-oxo-2,3-dihydro-1H-benzo[d]imidazol-5-yl)methyl)piperidin-3-yl)-1H-pyrrolo[2,3-c]pyridin-1-yl)-N,N-diisopropylbenzamide To a solution of 5-fluoro-N,N-diisopropyl-2-(3-(piperidin-3-yl)-1H-pyrrolo[2,3-c]pyridin-1-yl)benzamide as bis HCl salt (50 mg, 0.10 mmol) in MeOH (2.5 mL) was added TEA (30 μL), HOAc (1 drop), 2-(5-formyl-2-oxo-2,3-dihydro-1H-benzo[d]imidazol-1-yl)ethyl formate (Intermediate 24, 35 mg, 0.14 mmol) and NaBH$_3$CN (70 mg, 1.11 mmol). The mixture was heated at 40° C. for 24 h. The reaction mixture was concentrated under reduced pressure, and the residue was purified by preparative HPLC method A to afford 43.5 mg of the desired product as TFA salt. LCMS method B: $t_R$: 0.62 min; (M+H)$^+$=613.1. $^1$H NMR (CD$_3$OD) δ: 8.58 (s, 1H), 8.18 (d, J=5.6 Hz, 1H), 7.72 (d, J=5.6 Hz, 1H), 7.62 (m, 1H), 7.46 (m, 1H), 7.40 (td, J=8.4, 2.8 Hz, 1H), 7.30 (dd, J=8.4, 2.8 Hz, 1H), 3.54 (m, 1H), 3.36 (m, 1H), 3.21-3.10 (m, 3H), 2.95 (m, 1H), 2.93 (s, 3H), 2.22 (m, 2H), 2.13-1.81 (m, 10H), 1.52 (m, 2H), 1.45 (d, J=6.4 Hz, 3H), 1.29 (m, 2H), 1.07-1.01 (m, 8H), 0.25 (m, 2H).

Example 84A. 5-fluoro-N,N-diisopropyl-2-(3-(1-((2-oxo-2,3-dihydro-1H-benzo[d]imidazol-5-yl)methyl)piperidin-3-yl)-1H-pyrrolo[2,3-c]pyridin-1-yl)benzamide

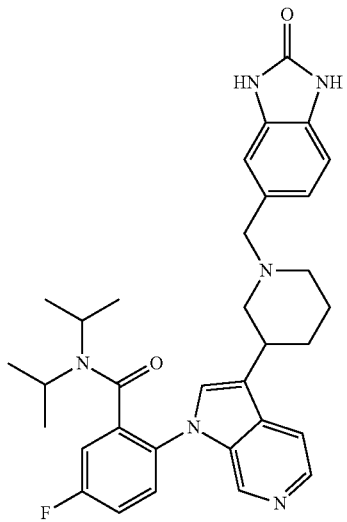 [SMILES: CC(C)N(C(=O)c1cc(F)ccc1-n1cc(C2CCCN(Cc3ccc4[nH]c(=O)[nH]c4c3)C2)c2ccncc21)C(C)C]

This compound was synthesized by a method similar to Example 84. In Step 7, 2-oxo-2,3-dihydro-1H-benzo[d]imidazole-5-carbaldehyde was used. LCMS method B: $t_R$: 0.61 min; (M+H)$^+$=569.2. $^1$H NMR (CD$_3$OD) δ: 8.99 (brs, 1H), 8.37 (d, J=6.4 Hz, 1H), 8.31 (d, J=6.4 Hz, 1H), 8.20 (s, 1H), 7.71 (m, 1H), 7.48 (td, J=8.4, 2.8 Hz, 1H), 7.41 (td, J=8.0, 2.8 Hz, 1H), 7.23-7.16 (m, 2H), 7.10 (m, 1H), 4.45 (m, 1H), 4.36 (m, 1H), 3.61 (m, 4H), 3.30-3.14 (m, 3H), 2.95 (s, 1H), 2.20-1.87 (m, 4H), 1.38 (m, 3H), 1.09 (m, 3H), 0.90-0.51 (m, 6H).

Example 84B. 5-fluoro-N,N-diisopropyl-2-(3-(piperidin-4-yl)-1H-pyrrolo[2,3-c]pyridin-1-yl)benzamide

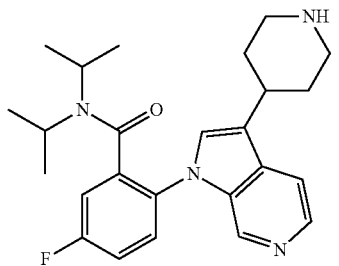 [SMILES: CC(C)N(C(=O)c1cc(F)ccc1-n1cc(C2CCNCC2)c2ccncc21)C(C)C]

The title compound was synthesized by the method described in Example 84 from steps 1 through 6. In step 4, tert-butyl 4-(4,4,5,5-tetramethyl-1,3,2-dioxaborolan-2-yl)-3,6-dihydropyridine-1(2H)-carboxylate was utilized. LCMS method B: $t_R$: 0.58 min; (M+H)$^+$=423.2.

Example 85. (R)-2-(5-((3-(1-(4-fluoro-2-(isopropyl(methyl)carbamoyl)phenyl)-1H-pyrrolo[2,3-c]pyridin-3-yl)piperidin-1-yl)methyl)-2-oxo-2,3-dihydro-1H-benzo[d]imidazol-1-yl)ethyl acetate

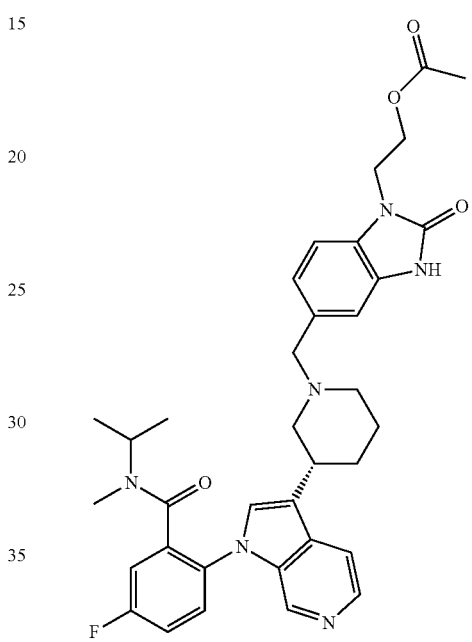

To a solution of 5-fluoro-2-(3-(1-((1-(2-hydroxyethyl)-2-oxo-2,3-dihydro-1H-benzo[d]imidazol-5-yl)methyl)piperidin-3-yl)-1H-pyrrolo[2,3-c]pyridin-1-yl)-N-isopropyl-N-methylbenzamide (Example 44, 50 mg, 0.085 mmol) in DCM (2 mL) at 0° C. was added pyridine (3 drops) followed by Ac$_2$O (3 drops). The mixture was stirred for 30 min and MeOH (1 mL) was added to quench the reaction. The mixture was stirred for another additional 20 min, then the reaction mixture was concentrated to dryness. The residue was extracted with EtOAc, washed with aqueous NaHCO$_3$ and brine successively. The organic phase was dried over anhydrous Na$_2$SO$_4$ and filtered. The filtrate was concentrated to dryness and the resulting residue was purified by flash chromatography to afford 36 mg of (R)-2-(5-((3-(1-(4-fluoro-2-(isopropyl(methyl)carbamoyl)phenyl)-1H-pyrrolo[2,3-c]pyridin-3-yl)piperidin-1-yl)methyl)-2-oxo-2,3-dihydro-1H-benzo[d]imidazol-1-yl)ethyl acetate. LCMS method B: $t_R$: 0.61 min; (M+H)$^+$=627.1. $^1$H NMR (CD$_3$OD) δ: 8.62 and 8.54 (brs, 1H), 8.17 (brs, 1H), 7.67 (m, 2H), 7.45-7.37 (m, 3H), 7.15 (m, 3H), 4.84-4.74 (m, 2H), 4.37 (m, 2H), 4.15 (m, 2H), 3.77-3.52 (m, 2H), 3.24-3.03 (m, 4H), 2.60 and 2.57 (m, 1H), 2.38 (m, 1H), 2.22-2.10 (m, 2H), 1.90-1.73 (m, 5H), 1.58 (m, 1H), 0.98 (m, 3H), 0.40 (m, 1H), 0.14 (m, 1H).

Example 86. (R)-2-(5-((3-(1-(4-fluoro-2-(isopropyl (methyl)carbamoyl)phenyl)-1H-pyrrolo[2,3-c]pyridin-3-yl)piperidin-1-yl)methyl)-2-oxo-2,3-dihydro-1H-benzo[d]imidazol-1-yl)ethyl stearate

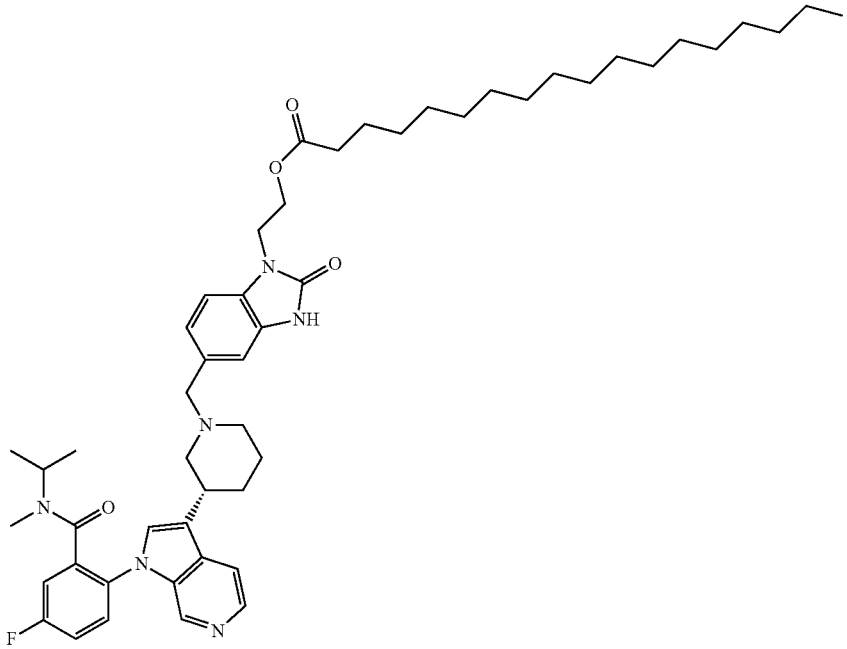 [SMILES: CCCCCCCCCCCCCCCCCC(=O)OCCn1c(=O)[nH]c2cc(CN3CCC[C@H](c4cn(-c5ccc(F)cc5C(=O)N(C)C(C)C)c5cnccc45)C3)ccc21]

Step 1: Stearoyl Chloride

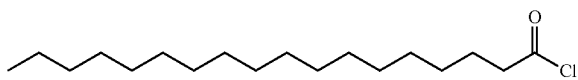 [SMILES: CCCCCCCCCCCCCCCCCC(=O)Cl]

To a suspension of stearic acid (409 mg, 1.44 mmol) in dry DCM 6 mL) cooled to 0° C. was added oxalyl chloride (0.21 mL, 2.88 mmol), followed by a small drop of DMF, and the mixture was stirred at RT for 16 h. The reaction mixture was evaporated to dryness, and the resulting residue was dissolved in dry DCM (10 mL) to afford stearoyl chloride solution in DCM (ca. 0.144 M).

Step 2. (R)-2-(5-((3-(1-(4-fluoro-2-(isopropyl (methyl)carbamoyl)phenyl)-1H-pyrrolo[2,3-c]pyridin-3-yl)piperidin-1-yl)methyl)-2-oxo-2,3-dihydro-1H-benzo[d]imidazol-1-yl)ethyl stearate To a solution of (R)-5-fluoro-2-(3-(1-((1-(2-hydroxyethyl)-2-oxo-2,3-dihydro-1H-benzo[d]imidazol-5-yl)methyl)piperidin-3-yl)-1H-pyrrolo[2,3-c]pyridin-1-yl)-N-isopropyl-N-methylbenzamide (Example 44A, 50 mg, 0.085 mmol) chilled to 0° C. was added above stearoyl chloride solution (0.6 mL, ca. 0.086 mmol) dropwise. The mixture was stirred for 10 min before it was quenched with MeOH (0.2 mL). The reaction mixture was diluted with EtOAc (10 mL) and washed with aqueous NaHCO₃ and brine successively. The organic phase was dried over anhydrous Na₂SO₄ and filtered. The filtrate was concentrated to dryness, and the resulting residue was purified by flash chromatography to afford 47 mg of (R)-2-(5-((3-(1-(4-fluoro-2-(isopropyl (methyl)carbamoyl)phenyl)-1H-pyrrolo[2,3-c]pyridin-3-yl)piperidin-1-yl)methyl)-2-oxo-2,3-dihydro-1H-benzo[d]imidazol-1-yl)ethyl stearate. LCMS method B: $t_R$: 1.48 min; (M+H)⁺=851.2. ¹H NMR (CD₃OD) δ: 8.60 and 8.52 (brs, 1H), 8.15 (m, 1H), 7.67 (m, 2H), 7.67-7.45 (m, 3H), 7.13-7.09 (m, 3H), 4.37 (m, 2H), 4.13 (m, 2H), 3.71-3.51 (m, 2H), 3.17-2.99 (m, 4H), 2.57 (m, 1H), 2.36 (m, 1H), 2.21-2.08 (m, 5H), 1.82 (m, 2H), 1.52-1.14 (m, 34H), 0.98 (d, J=7.2 Hz, 3H), 0.88 (d, J=7.2 Hz, 1H), 0.40 (m, 1H), 0.11 (m, 1H).

Example 87. 5-fluoro-N,N-diisopropyl-2-(3-(1-(((1r,4r)-4-(methylsulfonamido)cyclohexyl)methyl)piperidin-3-yl)-1H-pyrrolo[2,3-c]pyridin-1-yl)benzamide

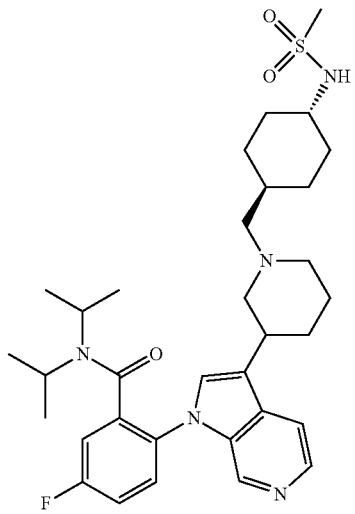 [SMILES: CC(C)N(C(=O)c1cc(F)ccc1-n1cc(C2CCCN(C[C@H]3CC[C@H](NS(C)(=O)=O)CC3)C2)c2ccncc21)C(C)C]

The title compound was synthesized by a method similar to Example 72 utilizing 5-fluoro-N,N-diisopropyl-2-(3-(piperidin-4-yl)-1H-pyrrolo[2,3-c]pyridin-1-yl)benzamide (Example 84B) and N-((1r,4r)-4-formylcyclohexyl)methanesulfonamide. LCMS method B: $t_R$: 0.67 min; (M+H)$^+$= 612.2. $^1$H NMR (CD$_3$OD) δ: 8.58 (s, 1H), 8.18 (d, J=5.6 Hz, 1H), 7.72 (d, J=5.6 Hz, 1H), 7.62 (m, 1H), 7.46 (m, 1H), 7.40 (td, J=8.4, 2.8 Hz, 1H), 7.30 (dd, J=8.4, 2.8 Hz, 1H), 3.54 (m, 1H), 3.36 (m, 1H), 3.21-3.10 (m, 3H), 2.95 (m, 1H), 2.93 (s, 3H), 2.22 (m, 2H), 2.13-1.81 (m, 10H), 1.52 (m, 2H), 1.45 (d, J=6.4 Hz, 3H), 1.29 (m, 2H), 1.07-1.01 (m, 8H), 0.25 (m, 2H).

Example 88. 2-(3-(1-((3-cyano-3-methyl-2-oxoindolin-6-yl)methyl)piperidin-3-yl)-1H-pyrrolo[2,3-c]pyridin-1-yl)-5-fluoro-N-isopropyl-N-methylbenzamide

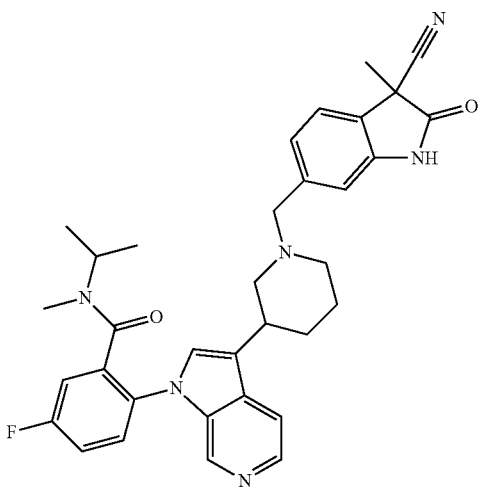 [SMILES: CC(C)N(C)C(=O)c1cc(F)ccc1-n1cc(C2CCCN(Cc3ccc4c(c3)NC(=O)C4(C)C#N)C2)c2ccncc21]

The title compound was prepared from 6-formyl-3-methyl-2-oxoindoline-3-carbonitrile (Intermediate 20) by a method similar to Example 84A. LCMS method B: $t_R$: 0.68 min; (M+H)$^+$=579.2. $^1$H NMR (CD$_3$OD) δ: 8.58 (s, 1H), 8.18 (d, J=5.6 Hz, 1H), 7.72 (d, J=5.6 Hz, 1H), 7.62 (m, 1H), 7.46 (m, 1H), 7.40 (td, J=8.4, 2.8 Hz, 1H), 7.30 (dd, J=8.4, 2.8 Hz, 1H), 3.54 (m, 1H), 3.36 (m, 1H), 3.21-3.10 (m, 3H), 2.95 (m, 1H), 2.93 (s, 3H), 2.22 (m, 2H), 2.13-1.81 (m, 10H), 1.52 (m, 2H), 1.45 (d, J=6.4 Hz, 3H), 1.29 (m, 2H), 1.07-1.01 (m, 8H), 0.25 (m, 2H).

Example 89. 5-fluoro-N-isopropyl-N-methyl-2-(3-(2-(((trans-3-(methylsulfonamido)cyclobutyl)methyl)octahydrocyclopenta[c]pyrrol-5-yl)-1H-pyrrolo[2,3-c]pyridin-1-yl)benzamide

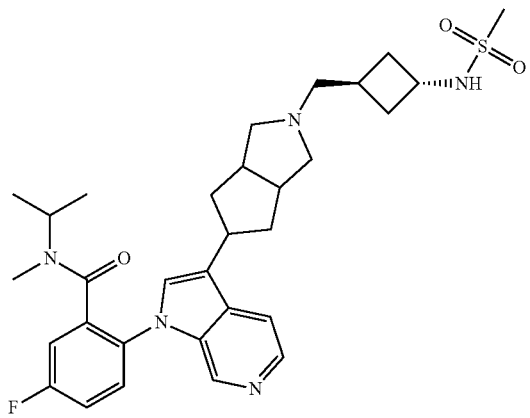 [SMILES: CC(C)N(C)C(=O)c1cc(F)ccc1-n1cc(C2CC3CN(C[C@H]4C[C@H](NS(C)(=O)=O)C4)CC3C2)c2ccncc21]

Step 1: 5-fluoro-N-isopropyl-N-methyl-2-(3-(octahydrocyclopenta[c]pyrrol-5-yl)-1H-pyrrolo[2,3-c]pyridin-1-yl)benzamide

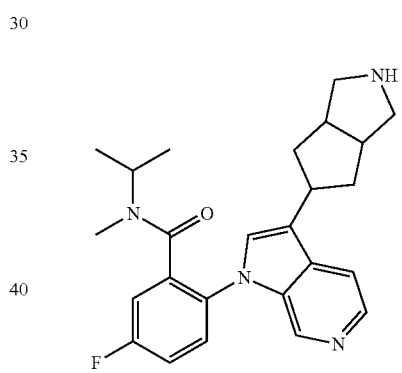

To a mixture of tert-butyl 5-(1-(4-fluoro-2-(isopropyl(methyl)carbamoyl)phenyl)-1H-pyrrolo[2,3-c]pyridine-3-yl)hexahydrocyclopenta[c]pyrrole-2(1H)-carboxylate (Intermediate 15, 300 mg, 0.58 mmol) in anhydrous DCM (6 mL) was added HCl/dioxane (2 mL, 4 N), and the mixture was stirred at RT for 1 h. The mixture was concentrated under reduced pressure and the residue was basified to pH=12-14 with 10% NaOH solution, and then extracted with DCM/i-PrOH (v/v=10/1, 3×80 mL). The combined organic layers were dried over anhydrous sodium sulfate, filtered, and concentrated under reduced pressure to give 5-fluoro-N-isopropyl-N-methyl-2-(3-(octahydrocyclopenta[c]pyrrol-5-yl)-1H-pyrrolo[2,3-c]pyridin-1-yl)benzamide as white solid, which was used for the next step directly without further purification. Yield: 240 mg (99% crude); LCMS method B: $t_R$: 0.86 min; (M+H)$^+$=421.3. $^1$H NMR (CD$_3$OD,): δ ppm 8.50-8.65 (m, 1H), 8.15-8.25 (m, 1H), 7.76 (d, J=5.2 Hz, 1H), 7.65-7.70 (m, 1H), 7.35-7.50 (m, 3H), 4.40-4.55 (m, 0.5H), 3.55-3.65 (m, 0.5H), 3.25-3.30 (m, 1H), 2.90-3.00 (m, 6H), 2.40-2.70 (m, 5H), 1.00-1.50 (m, 5H), 0.20-0.55 (m, 3H). $^{19}$F NMR (CD$_3$OD): δ ppm −113.35.

Step 2: tert-butyl (trans-3-((5-(1-(4-fluoro-2-(isopropyl(methyl)carbamoyl)phenyl)-1H-pyrrolo[2,3-c]pyridin-3-yl)hexahydrocyclopenta[c]pyrrol-2(1H)-yl)methyl)cyclobutyl) Carbamate

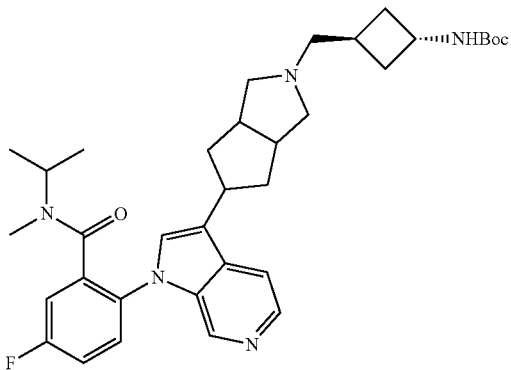 [SMILES: CC(C)N(C)C(=O)c1cc(F)ccc1-n1cc(C2CC3CN(C[C@H]4C[C@H](NC(=O)OC(C)(C)C)C4)CC3C2)c2ccncc21]

A mixture of 5-fluoro-N-isopropyl-N-methyl-2-(3-(octahydrocyclopenta[c]pyrrol-5-yl)-1H-pyrrolo[2,3-c]pyridin-1-yl)benzamide (60 mg, 0.14 mmol), tert-butyl (trans-3-formylcyclobutyl)carbamate (Intermediate 22, 56 mg, 0.28 mmol) and NaBH$_3$CN (44 mg, 0.7 mmol) in anhydrous MeOH (4 mL) was stirred at 70° C. for 18 h. The mixture was concentrated under reduced pressure and H$_2$O (20 mL) was added to the residue, and then extracted with EtOAc (3×30 mL). The combined organic layers were dried over anhydrous sodium sulfate, filtered, and concentrated under reduced pressure. The residue was purified by column chromatography on silica gel (eluting with DCM/MeOH=10/1) to give tert-butyl (trans-3-((5-(1-(4-fluoro-2-(isopropyl(methyl)carbamoyl)phenyl)-1H-pyrrolo[2,3-c]pyridin-3-yl)hexahydrocyclopenta[c]pyrrol-2(1H)-yl)methyl)cyclobutyl)carbamate as colourless oil. Yield: 65 mg (76%); LCMS method B: $t_R$: 0.620 min; (M+H)$^+$=604.3.

Step 3: 2-(3-(2-((trans-3-aminocyclobutyl)methyl)octahydrocyclopenta[c]pyrrol-5-yl)-1H-pyrrolo[2,3-c]pyridin-1-yl)-5-fluoro-N-isopropyl-N-methylbenzamide

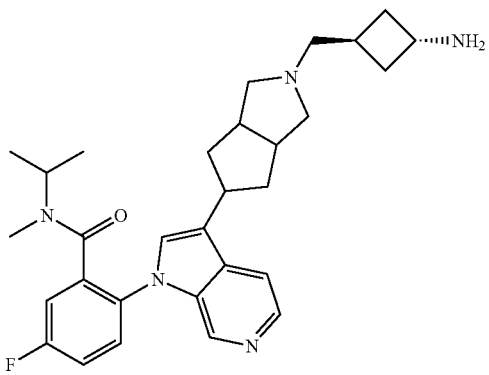 [SMILES: CC(C)N(C)C(=O)c1cc(F)ccc1-n1cc(C2CC3CN(C[C@H]4C[C@H](N)C4)CC3C2)c2ccncc21]

To tert-butyl (trans-3-((5-(1-(4-fluoro-2-(isopropyl(methyl)carbamoyl)phenyl)-1H-pyrrolo[2,3-c]pyridin-3-yl)hexahydrocyclopenta[c]pyrrol-2(1H)-yl)methyl)cyclobutyl) carbamate (65 mg, 0.11 mmol) in DCM (4 mL, anhydrous) was added TFA (1 mL) at 0° C., and the mixture was stirred at 22-27° C. for 2 h. The mixture was basified to pH=12-14 with 10% NaOH solution, extracted with DCM/i-PrOH (v/v=10/1.4×30 mL). The combined organic layers were dried over anhydrous sodium sulfate, filtered, and concentrated under reduced pressure to give 2-(3-(2-((trans-3-aminocyclobutyl)methyl)octahydrocyclopenta[c]pyrrol-5-yl)-1H-pyrrolo[2,3-c]pyridin-1-yl)-5-fluoro-N-isopropyl-N-methylbenzamide as colourless oil, which was used for the next step directly without further purification. Yield: 40 mg (74% crude);

Step 4: 5-fluoro-N-isopropyl-N-methyl-2-(3-(2-((trans-3-(methylsulfonamido)cyclobutyl)methyl)octahydrocyclopenta[c]pyrrol-5-yl)-1H-pyrrolo[2,3-c]pyridin-1-yl)benzamide To a mixture of 2-(3-(2-((trans-3aminocyclobutyl)methyl)octahydrocyclopenta[c]pyrrol-5-yl)-1H-pyrrolo[2,3-c]pyridin-1-yl)-5-fluoro-N-isopropyl-N-methylbenzamide (40 mg, 0.08 mmol) and Et$_3$N (40 mg, 0.56 mL, 0.4 mmol) in anhydrous DCM (3 mL) was added (MeSO$_2$)$_2$O (38 mg, 0.24 mmol) at 0° C. and the mixture was stirred at RT for 1 h. The mixture was added to H$_2$O (20 mL), and extracted with DCM (3×30 mL). The combined organic layers were dried over anhydrous sodium sulfate, filtered, concentrated, and the residue was purified by basic preparative HPLC method D to give 5-fluoro-N-isopropyl-N-methyl-2-(3-(2-((trans-3-(methylsulfonamido)cyclobutyl)methyl)octahydrocyclopenta[c]pyrrol-5-yl)-1H-pyrrolo[2,3-c]pyridin-1-yl)benzamide as white solid. Yield: 6.3 mg (14%); LCMS method D: $t_R$: 1.965 min; (M+H)$^+$=582.2. $^1$H NMR (CD$_3$OD): δ ppm 8.50-8.65 (m, 1H), 8.15-8.20 (m, 1H), 7.76 (d, J=5.2 Hz, 1H), 7.65-7.70 (m, 1H), 7.35-7.50 (m, 3H), 4.45-4.55 (m, 0.5H), 3.90-4.00 (m, 1H), 3.55-3.65 (m, 0.5H), 3.25-3.30 (m, 1H), 2.90 (s, 3H), 2.75-2.85 (m, 2H), 2.40-2.70 (m, 12H), 2.15-2.25 (m, 4H), 1.55-1.65 (m, 2H), 1.00-1.10 (m, 3H), 0.20-0.60 (m, 3H). $^{19}$F NMR (CD$_3$OD): δ ppm −113.53.

Examples 90-91

The following Examples were synthesized by method described above for Example 89.

TABLE 10

NMR spectra details

| Ex No. | Structural formula | Name | LCMS Method; Rt = min; [M + H]+ |
|---|---|---|---|
| | | 5-fluoro-N-isopropyl-N-methyl-2-(3-(2-((trans-4-(methylsulfonamido)cyclohexyl)methyl)octahydrocyclopenta[c]pyrrol-5-yl)-1H-pyrrolo[2,3-c]pyridin-1-yl)benzamide | E; 2.185 min; 610.3 |

1H NMR (CD3OD): δ ppm 8.55-8.70 (m, 1H), 8.15-8.20 (m, 1H), 7.76 (d, J = 5.6 Hz, 1H), 7.65-7.70 (m, 1H), 7.30-7.50 (m, 3H), 4.45-4.55 (m, 0.5H), 3.55-3.60 (m, 0.5H), 3.15-3.30 (m, 2H), 2.95 (s, 3H), 2.30-2.75 (m, 13H), 2.00-2.10 (m, 4H), 1.90-1.95 (m, 3H), 1.60-1.65 (m, 2H), 1.00-1.10 (m, 5H), 0.20-0.60 (m, 3H). 19F NMR (CD3OD): δ ppm −113.53.

| | | 5-fluoro-N-isopropyl-N-methyl-2-(3-(2-((1-(methylsulfonyl)piperidin-4-yl)methyl)octahydrocyclopenta[c]pyrrol-5-yl)-1H-pyrrolo[2,3-c]pyridin-1-yl)benzamide (TFA salt) | D; 0.921 min; 596.4 |

1H NMR (CD3OD): δ ppm 8.80-9.00 (m, 1H), 8.30-8.35 (m, 2H), 8.10-8.15 (m, 1H), 7.70-7.75 (m, 1H), 7.45-7.55 (m, 2H), 4.35-4.45 (m, 0.5H), 3.60-4.00 (m, 5H), 3.40-3.55 (m, 0.5H), 3.00-3.35 (m, 6H), 2.50-2.90 (m, 10H), 1.65-2.05 (m, 5H), 1.30-1.45 (m, 2H), 0.45-1.15 (m, 6H). 19F NMR (CD3OD): δ ppm −110.71, −76.99.

Example 92. 5-fluoro-N-isopropyl-N-methyl-2-(3-(1-((cis-3-(methylsulfonamido)cyclobutyl)methyl)piperidin-4-yl)-1H-pyrrolo[2,3-c]pyridin-1-yl)benzamide

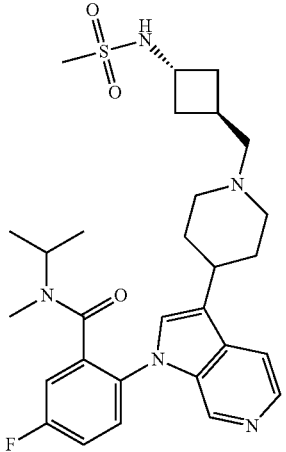 [SMILES: CC(C)N(C)C(=O)c1cc(F)ccc1-n1cc(C2CCN(C[C@H]3C[C@H](NS(C)(=O)=O)C3)CC2)c2ccncc21]

The title compound was synthesized by the method described for Example 1, from starting from 5-fluoro-N-isopropyl-N-methyl-2-(3-(piperidin-4-yl)-1H-pyrrolo[2,3-c]pyridin-1-yl)benzamide (Example 1, Step 1) and N-((1r,3r)-3-formylcyclobutyl)methanesulfonamide. LCMS method D: $t_R$: 1.757 min; $(M+H)^+=556.2$. $^1$H NMR (CD$_3$OD): δ ppm 8.50-8.70 (m, 1H), 8.15-8.25 (m, 1H), 7.75-7.80 (m, 1H), 7.60-7.70 (m, 1H), 7.30-7.50 (m, 3H), 4.35-4.55 (m, 0.5H), 3.70-3.85 (m, 1H), 3.55-3.65 (m, 0.5H), 3.00-3.10 (m, 2H), 2.92-3.00 (m, 1H), 2.91 (s, 3H), 2.70-2.95 (m, 3H), 2.40-2.70 (m, H), 2.20-2.35 (m, 3H), 2.00-2.10 (m, 2H), 1.80-2.00 (m, 2H), 1.65-1.80 (m, 2H), 0.95-1.15 (m, 3H), 0.15-0.60 (m, 3H). $^{19}$F NMR (CD$_3$OD): δ ppm −113.39.

Example 93. 5-fluoro-N-isopropyl-N-methyl-2-(3-(1-(2-(4-(methylsulfonamido)piperidin-1-yl)ethyl)piperidin-4-yl)-1H-pyrrolo[2,3-c]pyridin-1-yl)benzamide

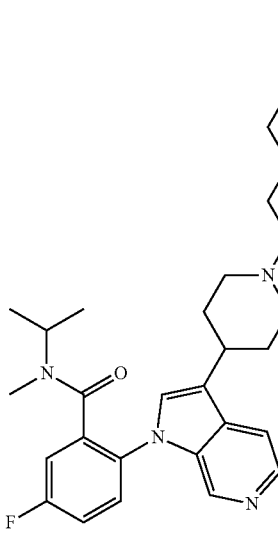

Step 1: 2-(3-(1-(2,2-dimethoxyethyl)piperidin-4-yl)-1H-pyrrolo[2,3-c]pyridin-1-yl)-5-fluoro-N-isopropyl-N-methylbenzamide

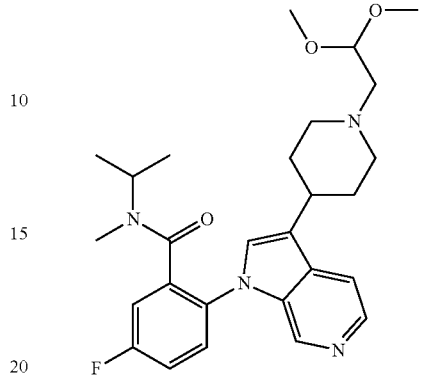

To a mixture of 5-fluoro-N-isopropyl-N-methyl-2-(3-(piperidin-4-yl)-1H-pyrrolo[2,3-c]pyridin-1-yl)benzamide (Example 1, Step 1, 200 mg, 0.51 mmol, HCl salt) in DMF (10 mL) was added 2-bromo-1,1-dimethoxyethane (171 mg, 1.01 mmol) and K$_2$CO$_3$ (211 mg, 1.53 mmol). The mixture was degassed and purged with N$_2$ 3 times and then heated under N$_2$ at 110° C. for 17 h. The mixture was added to water (30 mL) and extracted with EtOAc (3×30 mL). The combined organic layers were dried over anhydrous sodium sulfate, filtered, and concentrated under reduced pressure. The residue was purified by column chromatography on silica gel (eluting with DCM/MeOH=10/1) to give 2-(3-(1-(2,2-dimethoxyethyl)piperidin-4-yl)-1H-pyrrolo[2,3-c]pyridin-1-yl)-5-fluoro-N-isopropyl-N-methylbenzamide as red oil. Yield: 115 mg (47%); LCMS method B: $t_R$: 0.528 min; $(M+H)^+=483.1$.

Step 2: 5-fluoro-N-isopropyl-N-methyl-2-(3-(1-(2-oxoethyl)piperidin-4-yl)-1H-pyrrolo[2,3-c]pyridin-1-yl)benzamide

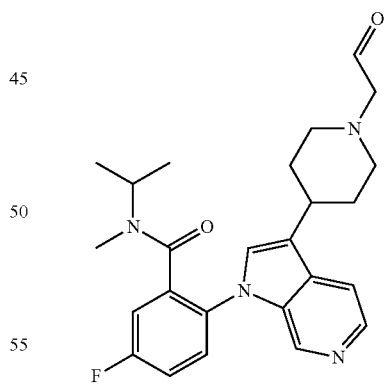

To a mixture of 2-(3-(1-(2,2-dimethoxyethyl)piperidin-4-yl)-1H-pyrrolo[2,3-c]pyridin-1-yl)-5-fluoro-N-isopropyl-N-methylbenzamide (115 mg, 0.24 mmol) in THF (10 mL) was added aq. HCl (4 mL, 3 M). The mixture was degassed and purged with N$_2$ 3 times and then heated under N$_2$ at 70° C. for 17 h. The mixture was concentrated under reduced pressure to give 5-fluoro-N-isopropyl-N-methyl-2-(3-(1-(2-oxoethyl)piperidin-4-yl)-1H-pyrrolo[2,3-c]pyridin-1-yl)benzamide (211 mg crude, 100% yield crude) (HCl salt) as red solid. Yield: 211 mg (100% crude); LCMS method B: $t_R$: 0.474 min; $(M+H)^+=455.1$.

Step 3: tert-butyl (1-(2-(4-(1-(4-fluoro-2-(isopropyl (methyl)carbamoyl)phenyl)-1H-pyrrolo[2,3-c]pyridin-3-yl)piperidin-1-yl)ethyl)piperidin-4-yl)carbamate

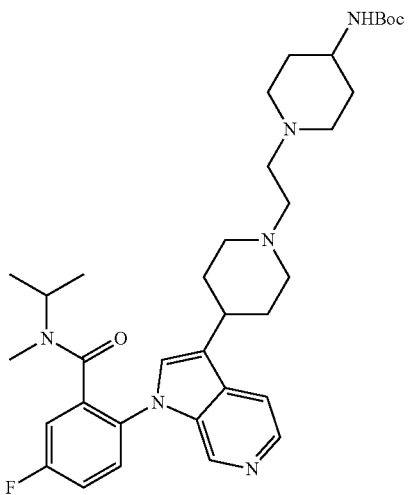 [SMILES: CC(C)N(C)C(=O)c1cc(F)ccc1-n1cc(C2CCN(CCN3CCC(NC(=O)OC(C)(C)C)CC3)CC2)c2ccncc21]

To a mixture of 5-fluoro-N-isopropyl-N-methyl-2-(3-(1-(2-oxoethyl)piperidin-4-yl)-1H-pyrrolo[2,3-c]pyridin-1-yl)benzamide (211 mg, 0.48 mmol, HCl salt) in MeOH (15 mL) was added Et₃N (146 mg, 1.44 mmol), tert-butyl piperidin-4-ylcarbamate (194 mg, 0.97 mmol) and NaBH₃CN (119 mg, 1.92 mmol). The mixture was degassed and purged with N₂ 3 times and then heated under N₂ at 70° C. for 15 h. The mixture was concentrated under reduced pressure and the residue was purified by column chromatography on silica gel (eluting with DCM/MeOH=10/1) to give tert-butyl (1-(2-(4-(1-(4-fluoro-2-(isopropyl(methyl)carbamoyl)phenyl)-1H-pyrrolo[2,3-c]pyridin-3-yl)piperidin-1-yl)ethyl)piperidin-4-yl)carbamate as red solid. Yield: 156 mg (51%); LCMS method B: $t_R$: 0.572 min; (M+H)⁺=621.3.

Step 4: 2-(3-(1-(2-(4-aminopiperidin-1-yl)ethyl)piperidin-4-yl)-1H-pyrrolo[2,3-c]pyridin-1-yl)-5-fluoro-N-isopropyl-N-methylbenzamide

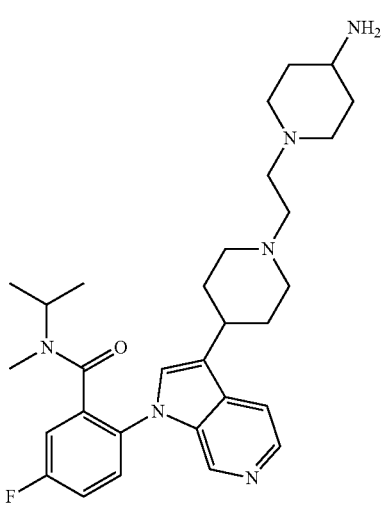 [SMILES: CC(C)N(C)C(=O)c1cc(F)ccc1-n1cc(C2CCN(CCN3CCC(N)CC3)CC2)c2ccncc21]

To a mixture of tert-butyl (1-(2-(4-(1-(4-fluoro-2-(isopropyl(methyl)carbamoyl)phenyl)-1H-pyrrolo[2,3-c]pyridin-3-yl)piperidin-1-yl)ethyl)piperidin-4-yl)carbamate (156 mg, 0.25 mmol) in CH₂Cl₂ (15 mL) was added HCl-dioxane (3 mL) at 0° C. The mixture was degassed and purged with N₂ followed by stirring under N₂ at RT for 2 h. The mixture was concentrated under reduced pressure and the residue was purified by preparative HPLC method A to give 2-(3-(1-(2-(4-aminopiperidin-1-yl)ethyl)piperidin-4-yl)-1H-pyrrolo[2,3-c]pyridin-1-yl)-5-fluoro-N-isopropyl-N-methylbenzamide (TFA salt) as red solid. Yield: 118 mg (90%); LCMS method B: $t_R$: 0.790 min; (M+H)⁺=521.5.

Step 5: 5-fluoro-N-isopropyl-N-methyl-2-(3-(1-(2-(4-(methylsulfonamido)piperidin-1-yl)ethyl) piperidin-4-yl)-1H-pyrrolo[2,3-c]pyridin-1-yl)benzamide To a mixture of 2-(3-(1-(2-(4-aminopiperidin-1-yl)ethyl)piperidin-4-yl)-1H-pyrrolo[2,3-c]pyridin-1-yl)-5-fluoro-N-isopropyl-N-methylbenzamide (80 mg, 0.15 mmol, TFA salt) in CH₂Cl₂ (10 mL) was added Et₃N (76 mg, 0.75 mmol) and (MeSO₂)₂O (80 mg, 0.46 mmol). The mixture was degassed and purged with N₂ 3 times and then stirred under N₂ atmosphere at RT for 0.5 h. The mixture was concentrated under reduced pressure and the residue was purified by basic preparative HPLC method D to give 5-fluoro-N-isopropyl-N-methyl-2-(3-(1-(2-(4-(methylsulfonamido)piperidin-1-yl)ethyl)piperidin-4-yl)-1H-pyrrolo[2,3-c]pyridin-1-yl)benzamide) as white solid. Yield: 19.3 mg (21%); LCMS method D: $t_R$: 0.820 min; (M+H)⁺=599.3. ¹H NMR (CD₃OD): δ ppm 8.50-8.65 (m, 1H), 8.15-8.25 (m, 1H), 7.75-7.80 (m, 1H), 7.60-7.70 (m, 1H), 7.30-7.50 (m, 3H), 4.40-4.55 (m, 0.5H), 3.50-3.65 (m, 0.5H), 3.20-3.30 (m, 2H), 3.05-3.20 (m, 2H), 2.98 (s, 3H), 2.90-2.96 (m, 2H), 2.40-2.70 (m, 7H), 2.15-2.40 (m, 4H), 2.05-2.15 (m, 2H), 1.95-2.05 (m, 2H), 1.80-1.95 (m, 2H), 1.55-1.70 (m, 2H), 0.95-1.10 (m, 3H), 0.15-0.60 (m, 3H). ¹⁹F NMR (CD₃OD): δ ppm −113.37.

Example 94. 5-fluoro-N-isopropyl-N-methyl-2-(3-(1-(pyridin-2-yl)piperidin-4-yl)-1H-pyrrolo[2,3-c]pyridin-1-yl)benzamide

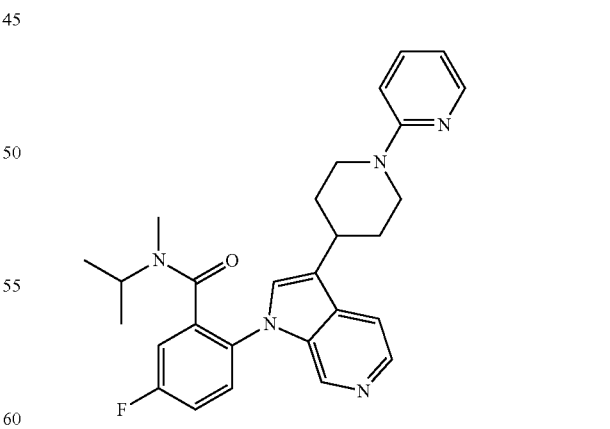

A solution of 5-fluoro-N-isopropyl-N-methyl-2-(3-(piperidin-4-yl)-1H-pyrrolo[2,3-c]pyridin-1-yl)benzamide (Example 1, Step 1, 50 mg, 0.13 mmol, HCl salt), 2-fluoropyridine (49 mg, 0.25 mmol) and Cs₂CO₃ (330 mg, 1.01 mmol) in anhydrous DMF (3 mL) was stirred at 80° C. for 36 h. The mixture was concentrated under reduced pressure and the residue was purified by basic preparative HPLC method D to give 5-fluoro-N-isopropyl-N-methyl-2-(3-(1-(pyridin-2-yl)piperidin-4-yl)-1H-pyrrolo[2,3-c]pyridin-1-yl)benzamide as white solid. Yield: 12.4 mg (21%); LCMS method D: $t_R$: 1.978 min; (M+H)$^+$=472.2. $^1$H NMR (CD$_3$OD): δ ppm 8.61, 8.53 (s, 1H), 8.19 (d, J=5.6 Hz, 1H), 8.08 (d, J=4.0 Hz, 1H), 7.75 (d, J=2.0 Hz, 1H), 7.35-7.70 (m, 5H), 6.89 (d, J=8.8 Hz, 1H), 6.66 (d, J=5.2 Hz, 1H), 4.35-4.45 (m, 2.5H), 3.50-3.60 (m, 0.5H), 3.00-3.10 (m, 3H), 2.62, 2.43 (s, 3H), 2.05-2.15 (m, 2H), 1.70-1.80 (m, 2H), 0.95-1.05 (m, 3H), 0.20-0.55 (m, 3H). $^{19}$F NMR (CD$_3$OD): δ ppm –113.40.

Examples 95A-95B. 5-fluoro-2-(3-(4-(3-hydroxypyrrolidin-1-yl)cyclohexyl)-1H-pyrrolo[2,3-c]pyridin-1-yl)-N-isopropyl-N-methylbenzamide (Isomers 1-2)

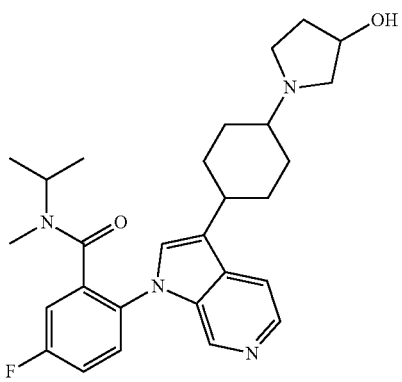 [SMILES: CC(C)N(C)C(=O)c1cc(F)ccc1-n1cc(C2CCC(N3CCC(O)C3)CC2)c2ccncc21]

To a solution of 5-fluoro-N-isopropyl-N-methyl-2-(3-(4-oxocyclohexyl)-1H-pyrrolo[2,3-c]pyridin-1-yl)benzamide (Intermediate 17B, 60 mg, 0.15 mmol) in 5 mL of anhydrous MeOH was added pyrrolidin-3-ol (16 mg, 0.18 mmol) and NaBH$_3$CN (19 mg, 0.30 mmol). The resulting mixture was stirred at 45-50° C. (oil temperature) for 18 h. The mixture was purified by preparative HPLC method D to give two isomers of 5-fluoro-2-(3-(4-(3-hydroxypyrrolidin-1-yl)cyclohexyl)-1H-pyrrolo[2,3-c]pyridin-1-yl)-N-isopropyl-N-methylbenzamide as white solid.

Example 95A (Isomer 1): Yield: 22.4 mg (32%); LCMS method D: $t_R$: 1.171 min; (M+H)$^+$=479.2. $^1$H NMR (CD$_3$OD): δ ppm 8.50-8.70 (m, 1H), 8.10-8.25 (m, 1H), 7.60-7.80 (m, 2H), 7.30-7.50 (m, 3H), 4.35-4.55 (m, 1.5H), 3.50-3.65 (m, 0.5H), 2.95-3.05 (m, 1H), 2.80-2.95 (m, 2H), 2.70-2.80 (m, 1H), 2.35-2.70 (m, 4H), 2.05-2.30 (m, 6H), 1.40-1.85 (m, 5H), 0.95-1.15 (m, 3H), 0.10-0.65 (m, 3H). $^{19}$F NMR (CD$_3$OD): δ ppm–113.46.

Example 95B (Isomer 2): Yield: 14.1 mg (20%); LCMS method D: $t_R$: 1.119 min; (M+H)$^+$=479.2. $^1$H NMR (CD$_3$OD): δ ppm 8.50-8.65 (m, 1H), 8.10-8.20 (m, 1H), 7.60-7.80 (m, 2H), 7.30-7.50 (m, 3H), 4.30-4.55 (m, 1.5H), 3.55-3.65 (m, 0.5H), 3.05-3.15 (m, 1H), 2.75-2.95 (m, 2H), 2.40-2.70 (m, 5H), 2.05-2.40 (m, 4H), 1.70-2.00 (m, 7H), 0.95-1.10 (m, 3H), 0.20-0.60 (m, 3H). $^{19}$F NMR (CD$_3$OD): δ ppm –113.59.

Examples 96-120

The following Examples were synthesized by method described above for Examples 95A-95B.

TABLE 11

| | | | |
|---|---|---|---|
| | | | NMR spectra details |
| Ex No. | Structure | Name | LCMS Method; Rt = min; [M + H]$^+$ |
| | | 5-fluoro-2-(3-(trans-4-((S)-2-(hydroxymethyl)pyrrolidin-1-yl)cyclohexyl)-1H-pyrrolo[2,3-c]pyridin-1-yl)-N-isopropyl-N-methylbenzamide | D; 1.479; 493.2 |

$^1$H NMR (CD$_3$OD): δ ppm 8.50-8.65 (m, 1H), 8.10-8.25 (m, 1H), 7.60-7.80 (m, 2H), 7.30-7.50 (m, 3H), 4.40-4.55 (m, 0.5H), 3.50-3.60 (m, 1.5H), 3.35-3.40 (m, 1H), 3.00-3.10 (m, 2H), 2.80-2.95 (m, 1H), 2.40-2.75 (m, 5H), 2.05-2.25 (m, 4H), 1.45-1.90 (m, 8H), 0.95-1.10 (m, 3H), 0.15-0.60 (m, 3H).
$^{19}$F NMR (CD$_3$OD): δ ppm –113.48.

TABLE 11-continued

NMR spectra details

| Ex No. | Structure | Name | LCMS Method; Rt = min; [M + H]+ |
|---|---|---|---|
| | | 5-fluoro-2-(3-(cis-4-((S)-2-(hydroxymethyl)pyrrolidin-1-yl)cyclohexyl)-1H-pyrrolo[2,3-c]pyridin-1-yl)-N-isopropyl-N-methylbenzamide | D; 1.687; 493.2 |

¹H NMR (CD₃OD): δ ppm 8.50-8.65 (m, 1H), 8.10-8.20 (m, 1H), 7.60-7.80 (m, 2H), 7.30-7.50 (m, 3H), 4.30-4.55 (m, 1.5H), 3.55-3.65 (m, 0.5H), 3.05-3.15 (m, 1H), 2.75-2.95 (m, 2H), 2.40-2.70 (m, 5H), 2.05-2.40 (m, 4H), 1.70-2.00 (m, 7H), 0.95-1.10 (m, 3H), 0.20-0.60 (m, 3H). ¹⁹F NMR (CD₃OD): δ ppm -113.49.

| | | 5-fluoro-2-(3-(trans-4-(3-(hydroxymethyl)azetidin-1-yl)cyclohexyl)-1H-pyrrolo[2,3-c]pyridin-1-yl)-N-isopropyl-N-methylbenzamide (TFA salt) | D; 0.876; 479.4 |

¹H NMR (CD₃OD): δ ppm 8.95-9.05 (m, 1H), 8.30-8.35 (m, 2H), 8.05-8.15 (m, 1H), 7.70-7.80 (m, 1H), 7.40-7.55 (m, 2H), 4.05-4.45 (m, 4.5H), 3.60-3.80 (m, 2.5H), 3.30-3.35 (m, 1H), 2.85-3.20 (m, 2H), 2.60-2.65 (m, 3H), 2.00-2.30 (m, 4H), 1.45-1.75 (m, 4H), 0.55-1.15 (m, 6H). ¹⁹F NMR (CD₃OD): δ ppm -110.75, -76.86.

| 99 | | 5-fluoro-2-(3-(cis-4-(3-(hydroxymethyl)azetidin-1-yl)cyclohexyl)-1H-pyrrolo[2,3-c]pyridin-1-yl)-N-isopropyl-N-methylbenzamide (TFA salt) | D; .870; 479.4 |

¹H NMR (CD₃OD): δ ppm 8.95-9.05 (m, 1H), 8.30-8.35 (m, 2H), 8.05-8.15 (m, 1H), 7.70-7.80 (m, 1H), 7.40-7.55 (m, 2H), 4.05-4.45 (m, 4.5H), 3.60-3.80 (m, 2.5H), 3.30-3.35 (m, 1H), 2.85-3.20 (m, 2H), 2.60-2.65 (m, 3H), 2.00-2.30 (m, 4H), 1.45-1.75 (m, 4H), 0.55-1.15 (m, 6H). ¹⁹F NMR (CD₃OD): δ ppm -110.75, -76.86.

TABLE 11-continued

NMR spectra details

| Ex No. | Structure | Name | LCMS Method; Rt = min; [M + H]+ |
|---|---|---|---|
| | | 5-fluoro-2-(3-(trans-4-((R)-2-(hydroxymethyl)pyrrolidin-1-yl)cyclohexyl)-1H-pyrrolo[2,3-c]pyridin-1-yl)-N-isopropyl-N-methylbenzamide | D; 1.469; 493.2 |

$^1$H NMR (CD$_3$OD): δ ppm 8.50-8.65 (m, 1H), 8.10-8.20 (m, 1H), 7.60-7.75 (m, 2H), 7.30-7.50 (m, 3H), 4.40-4.55 (m, 0.5H), 3.50-3.60 (m, 1.5H), 3.35-3.45 (m, 1H), 3.00-3.20 (m, 2H), 2.70-3.00 (m, 3H), 2.35-2.70 (m, 3H), 2.05-2.25 (m, 4H), 1.50-2.00 (m, 8H), 0.90-1.15 (m, 3H), 0.15-0.60 (m, 3H). $^{19}$F NMR (CD$_3$OD): δ ppm −113.49.

| | | 5-fluoro-2-(3-(cis-4-((R)-2-(hydroxymethyl)pyrrolidin-1-yl)cyclohexyl)-1H-pyrrolo[2,3-c]pyridin-1-yl)-N-isopropyl-N-methylbenzamide | D; 1.768; 493.3 |

$^1$H NMR (CD$_3$OD): δ ppm 8.50-8.70 (m, 1H), 8.10-8.25 (m, 1H), 7.60-7.80 (m, 2H), 7.30-7.55 (m, 3H), 4.40-4.55 (m, 0.5H), 3.50-3.65 (m, 1.5H), 3.35-3.45 (m, 1H), 3.20-3.30 (m, 1H), 3.05-3.20 (m, 2H), 2.75-2.90 (m, 1H), 2.40-2.75 (m, 4H), 2.05-2.25 (m, 2H), 1.90-2.00 (m, 2H), 1.70-1.90 (m, 8H), 0.95-1.10 (m, 3H), 0.15-0.65 (m, 3H). $^{19}$F NMR (CD$_3$OD): δ ppm −113.32.

| 102 | | 5-fluoro-2-(3-(trans-4-((R)-3-(hydroxymethyl)pyrrolidin-1-yl)cyclohexyl)-1H-pyrrolo[2,3-c]pyridin-1-yl)-N-isopropyl-N-methylbenzamide | D; 0.880; 493.3 |

$^1$H NMR (CD$_3$OD): δ ppm 8.50-8.65 (m, 1H), 8.10-8.20 (m, 1H), 7.70-7.75 (m, 1H), 7.60-7.70 (m, 1H), 7.40-7.50 (m, 1H), 7.30-7.35 (m, 2H), 4.40-4.50 (m, 0.5H), 3.40-3.65 (m, 2.5H), 2.95-3.05 (m, 1H), 2.80-2.90 (m, 2H), 2.40-2.70 (m, 6H), 2.10-2.30 (m, 5H), 1.90-2.05 (m, 1H), 1.40-1.70 (m, 5H), 0.90-1.10 (m, 3H), 0.10-0.60 (m, 3H). $^{19}$F NMR (CD$_3$OD): δ ppm −113.44.

TABLE 11-continued

NMR spectra details

| Ex No. | Structure | Name | LCMS Method; Rt = min; [M + H]+ |
|---|---|---|---|
| | | 5-fluoro-2-(3-(cis-4-((R)-3-(hydroxymethyl)pyrrolidin-1-yl)cyclohexyl)-1H-pyrrolo[2,3-c]pyridin-1-yl)-N-isopropyl-N-methylbenzamide | D; 0.876; 493.4 |

$^1$H NMR (CD$_3$OD): δ ppm 8.50-8.65 (m, 1H), 8.10-8.20 (m, 1H), 7.70-7.75 (m, 1H), 7.60-7.70 (m, 1H), 7.40-7.50 (m, 2H), 7.30-7.35 (m, 1H), 4.40-4.50 (m, 0.5H), 3.40-3.65 (m, 2.5H), 3.05-3.20 (m, 1H), 2.75-2.85 (m, 2H), 2.40-2.70 (m, 6H), 2.30-2.35 (m, 2H), 1.70-2.25 (m, 9H), 1.45-1.60 (m, 1H), 0.90-1.10 (m, 3H), 0.10-0.60 (m, 3H). $^{19}$F NMR (CD$_3$OD): δ ppm −113.59.

| | | 5-fluoro-2-(3-(trans-4-((S)-3-(hydroxymethyl)pyrrolidin-1-yl)cyclohexyl)-1H-pyrrolo[2,3-c]pyridin-1-yl)-N-isopropyl-N-methylbenzamide | D; 0.880 493.4 |

$^1$H NMR (CD$_3$OD): δ ppm 8.50-8.65 (m, 1H), 8.10-8.20 (m, 1H), 7.70-7.75 (m, 1H), 7.60-7.65 (m, 1H), 7.40-7.50 (m, 1H), 7.30-7.35 (m, 2H), 4.40-4.50 (m, 0.5H), 3.40-3.65 (m, 2.5H), 2.95-3.05 (m, 1H), 2.75-2.90 (m, 2H), 2.40-2.70 (m, 6H), 2.10-2.30 (m, 5H), 1.90-2.05 (m, 1H), 1.40-1.70 (m, 5H), 0.90-1.10 (m, 3H), 0.10-0.60 (m, 3H). $^{19}$F NMR (CD$_3$OD): δ ppm −113.46.

| 105 | | 5-fluoro-2-(3-(cis-4-((S)-3-(hydroxymethyl)pyrrolidin-1-yl)cyclohexyl)-1H-pyrrolo[2,3-c]pyridin-1-yl)-N-isopropyl-N-methylbenzamide | D; 0.874; 493.3 |

$^1$H NMR (CD$_3$OD): δ ppm 8.50-8.65 (m, 1H), 8.10-8.20 (m, 1H), 7.70-7.75 (m, 1H), 7.60-7.65 (m, 1H), 7.40-7.50 (m, 2H), 7.30-7.35 (m, 1H), 4.40-4.50 (m, 0.5H), 3.40-3.65 (m, 2.5H), 3.05-3.20 (m, 1H), 2.75-2.85 (m, 2H), 2.40-2.70 (m, 6H), 2.30-2.35 (m, 2H), 1.70-2.25 (m, 9H), 1.45-1.60 (m, 1H), 0.90-1.10 (m, 3H), 0.10-0.60 (m, 3H). $^{19}$F NMR (CD$_3$OD): δ ppm −113.51.

TABLE 11-continued

NMR spectra details

| Ex No. | Structure | Name | LCMS Method; Rt = min; [M + H]+ |
|---|---|---|---|
| | | 5-fluoro-N-isopropyl-N-methyl-2-(3-(trans-4-(piperidin-1-yl)cyclohexyl)-1H-pyrrolo[2,3-c]pyridin-1-yl)benzamide | D; 0.914; 477.4 |

¹H NMR (CD₃OD): δ ppm 8.50-8.65 (m, 1H), 8.10-8.20 (m, 1H), 7.60-7.75 (m, 2H), 7.30-7.45 (m, 3H), 4.40-4.50 (m, 0.5H), 3.55-3.65 (m, 0.5H), 2.80-2.90 (m, 1H), 2.40-2.70 (m, 8H), 2.05-2.20 (m, 4H), 1.50-1.70 (m, 10H), 0.95-1.05 (m, 3H), 0.15-0.55 (m, 3H). ¹⁹F NMR (CD₃OD): δ ppm −113.49.

| | | 5-fluoro-N-isopropyl-N-methyl-2-(3 1-yl)cyclohexyl)-1H-pyrrolo[2,3-c]pyridin-1-yl)benzamide | D; 0.914; 477.4 |

¹H NMR (CD₃OD): δ ppm 8.50-8.65 (m, 1H), 8.15-8.20 (m, 1H), 7.60-7.75 (m, 2H), 7.30-7.55 (m, 3H), 4.40-4.55 (m, 0.5H), 3.55-3.65 (m, 0.5H), 2.40-2.70 (m, 8H), 2.05-2.20 (m, 2H), 1.45-1.95 (m, 13H), 0.95-1.05 (m, 3H), 0.15-0.60 (m, 3H). ¹⁹F NMR (CD₃OD): δ ppm −113.40.

| 108 | | 5-fluoro-2-(3-(trans-4-(4-hydroxypiperidin-1-yl)cyclohexyl)-1H-pyrrolo[2,3-c]pyridin-1-yl)-N-isopropyl-N-methylbenzamide (TFA salt) | D; 0.621; 493.4 |

¹H NMR (CD₃OD): δ 8.93-9.02 (m, 1H), 8.23-8.33 (m, 1H), 8 34-8.35 (m, 2H), 7.78-7.80 (m, 1H), 7.45-7.52 (m, 2H), 4.37-4.41 (m, 0.5H), 4.08-4.09 (m, 0.5H), 3.70-3.81 (m, 1H), 3.59-3.62 (m, 2H), 3.39 (s, 3H), 3.12-3.15 (m, 1H), 2.60-2.63 (m, 3H), 1.74-2.29 (m, 12H), 0.50-1.11 (m, 6H). ¹⁹F NMR (CD₃OD): δ −76.75, −110.60.

TABLE 11-continued

NMR spectra details

| Ex No. | Structure | Name | LCMS Method; Rt = min; [M + H]⁺ |
|---|---|---|---|
| | | 5-fluoro-2-(3-(cis-4-(4-hydroxypiperidin-1-yl)cyclohexyl)-1H-pyrrolo[2,3-c]pyridin-1-yl)-N-isopropyl-N-methylbenzamide (TFA salt) | D; 0.561; 493.4 |

$^1$H NMR (CD$_3$OD): δ 8.85-8 95 (m, 1H), 8.32-8.34 (m, 2H), 8 09-8.11 (m, 1H), 7.71-7.74 (m, 1H), 7.44-7.51 (m, 2H), 4.36-4.38 (m, 0.5H), 4.11-4.12 (m, 0.5H), 3.71-3.84 (m, 1H), 3.57-3.60 (m, 2H), 3.40-3.43 (s, 3H), 3.11-3.22 (m, 1H), 2.61-2.63 (m, 3H), 1.75-2.31 (m, 12H), 0.58-1.10 (m, 6H). $^{19}$F NMR (CD$_3$OD): δ −76.99, −110.70.

| | | 2-(3-(trans-4-(4,4-difluoropiperidin-1-yl)cyclohexyl)-1H-pyrrolo[2,3-c]pyridin-1-yl)-5-fluoro-N-isopropyl-N-methylbenzamide | D; 0.928; 513.3 |

$^1$H NMR (CD$_3$OD): δ ppm 8.50-8.65 (m, 1H), 8.15-8.20 (m, 1H), 7.65-7.75 (m, 2H), 7.35-7.50 (m, 3H), 4.40-4.55 (m, 0.5H), 3.50-3.60 (m, 0.5H), 2.70-2.85 (m, 5H), 2.40-2.70 (m, 4H), 1.95-2.30 (m, 8H), 1.50-1.70 (m, 4H), 0.95-1.10 (m, 3H), 0.10-0.65 (m, 3H). $^{19}$F NMR (CD$_3$OD): δ ppm −113.60, −99.27.

TABLE 11-continued

| Ex No. | Structure | Name | LCMS Method; Rt = min; [M + H]+ |
|---|---|---|---|
| | 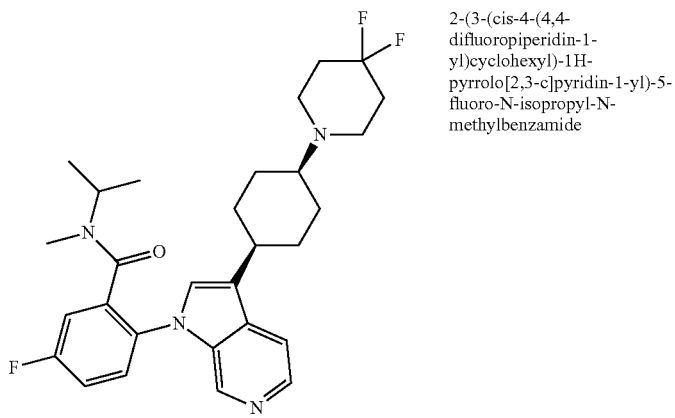 | 2-(3-(cis-4-(4,4-difluoropiperidin-1-yl)cyclohexyl)-1H-pyrrolo[2,3-c]pyridin-1-yl)-5-fluoro-N-isopropyl-N-methylbenzamide | D; 0.931; 513.3 |

$^1$H NMR (CD$_3$OD): δ ppm 8.50-8.65 (m, 1H), 8.15-8.25 (m, 1H), 7.60-7.75 (m, 2H), 7.45-7.55 (m, 2H), 7.35-7.40 (m, 1H), 4.40-4.55 (m, 0.5H), 3.55-3.65 (m, 0.5H), 3.20-3.30 (m, 1H), 2.60-2.75 (m, 6H), 2.45-2.55 (m, 1H), 2.35-2.45 (m, 1H), 2.05-2.20 (m, 2H), 1.75-2.05 (m, 10H), 1.00-1.10 (m, 3H), 0.10-0.55 (m, 3H). $^{19}$F NMR (CD$_3$OD): δ ppm −113.39, −99.43.

| | 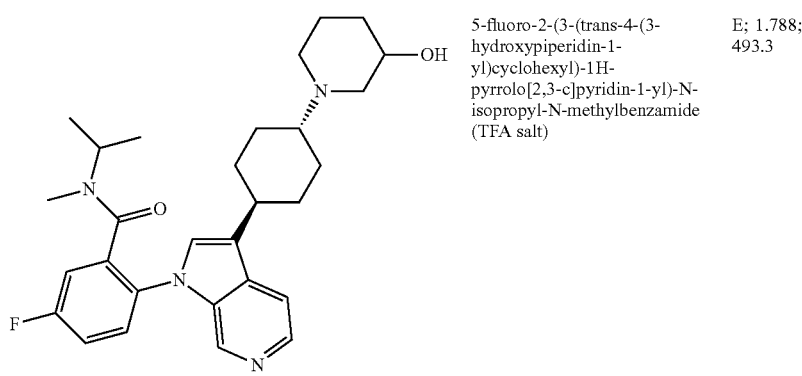 | 5-fluoro-2-(3-(trans-4-(3-hydroxypiperidin-1-yl)cyclohexyl)-1H-pyrrolo[2,3-c]pyridin-1-yl)-N-isopropyl-N-methylbenzamide (TFA salt) | E; 1.788; 493.3 |

$^1$H NMR (CD$_3$OD): δ ppm 8.85-9.00 (m, 1H), 8.30-8.35 (m, 2H), 8.05-8.15 (m, 1H), 7.70-7.80 (m, 1H), 7.45-7.55 (m, 2H), 4.40-4.45 (m, 0.5H), 4.38-4.40 (m, 1H), 3.70-3.80 (m, 1H), 3.33-3.45 (m, 2H), 3.15-3.35 (m, 3H), 2.70-2.85 (m, 0.5H), 2.60-2.65 (m, 3H), 2.30-2.35 (m, 5H), 1.75-1.95 (m, 7H), 0.35-1.15 (m, 6H). $^{19}$F NMR (CD$_3$OD): δ ppm −110.74, −76.89.

TABLE 11-continued

NMR spectra details

| Ex No. | Structure | Name | LCMS Method; Rt = min; [M + H]+ |
|---|---|---|---|
| | 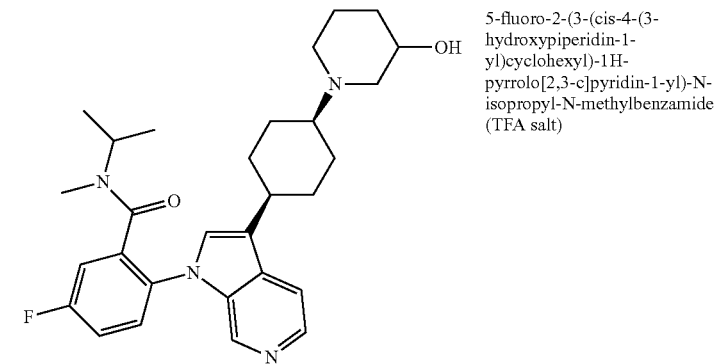 | 5-fluoro-2-(3-(cis-4-(3-hydroxypiperidin-1-yl)cyclohexyl)-1H-pyrrolo[2,3-c]pyridin-1-yl)-N-isopropyl-N-methylbenzamide (TFA salt) | E; 1.842; 493.3 |

¹H NMR (CD₃OD): δ ppm 8.85-9.05 (m, 1H), 8.25-8.40 (m, 3H), 7.75-7.85 (m, 1H), 7.45-7.60 (m, 2H), 4.20-4.50 (m, 1H), 3.35-3.75 (m, 5H), 2.90-3.30 (m, 2H), 2.60-2.70 (m, 3H), 1.65-2.40 (m, 12H), 0.35-1.15 (m, 6H).
¹⁹F NMR (CD₃OD): δ ppm −110.62, −76.81.

| | 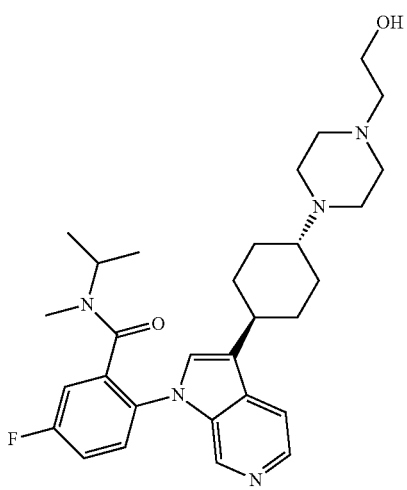 [SMILES: CC(C)N(C)C(=O)c1cc(F)ccc1-n1cc([C@H]2CC[C@H](N3CCN(CCO)CC3)CC2)c2ccncc21] | 5-fluoro-2-(3-(trans-4-(4-(2-hydroxyethyl)piperazin-1-yl)cyclohexyl)-1H-pyrrolo[2,3-c]pyridin-1-yl)-N-isopropyl-N-methylbenzamide | E; 1.592; 522.3 |

¹H NMR (CD₃OD): δ ppm 8.50-8.65 (m, 1H), 8.10-8.20 (m, 1H), 7.70-7.75 (m, 1H), 7.60-7.65 (m, 1H), 7.40-7.50 (m, 1H), 7.30-7.35 (m, 2H), 4.40-4.50 (m, 0.5H), 3.65-3.75 (m, 2H), 3.50-3.60 (m, 0.5H), 2.85-2.95 (m, 1H), 2.70-2.80 (m, 4H), 2.60-2.65 (m, 4H), 2.50-2.55 (m, 2H), 2.40-2.45 (m, 2H), 2.10-2.35 (m, 4H), 1.50-1.70 (m, 4H), 1.20-1.35 (m, 2H), 0.95-1.10 (m, 3H), 0.45-0.55 (m, 1H), 0.10-0.20 (m, 2H).
¹⁹F NMR (CD₃OD): δ ppm −113.42.

TABLE 11-continued

| Ex No. | Structure | Name | LCMS Method; Rt = min; [M + H]+ |
|---|---|---|---|
|  |  | 5-fluoro-2-(3-(cis-4-(4-(2-hydroxyethyl)piperazin-1-yl)cyclohexyl)-1H-pyrrolo[2,3-c]pyridin-1-yl)-N-isopropyl-N-methylbenzamide (TFA salt) | E; 0.988; 522.4 |

1H NMR (CD3OD): δ ppm 8.85-9.05 (m, 1H), 8.25-8.35 (m, 2H), 8.19 (s, 1H), 7.70-7.85 (m, 1H), 7.40-7.55 (m, 2H), 4.35-4.45 (m, 0.5H), 3.80-3.90 (m, 2H), 3.65-3.75 (m, 0.5H), 3.30-3.50 (m, 8H), 3.00-3.20 (m, 4H), 2.55-2.65 (m, 3H), 2.15-2.25 (m, 2H), 1.80-2.20 (m, 6H), 0.30-1.30 (m, 6H). 19F NMR (CD3OD): δ ppm −77.06, −110.71.

| 116 |  | 5-fluoro-N-isopropyl-N-methyl-2-(3-(4-(3-oxopiperazin-1-yl)cyclohexyl)-1H-pyrrolo[2,3-c]pyridin-1-yl)benzamide (HCl salt) | E; 0.851; 492.4 |

1H NMR (CD3OD): δ 8.80-9.05 (m, 1H), 8.10-8.40 (m, 3H), 7.75-7.90 (m, 1H), 7.40-7.60 (m, 2H), 4.30-4.45 (m, 0.5H), 3.80-4.05 (m, 2H), 3.45-3.80 (m, 4.5H), 3.10-3.25 (m, 1H), 2.55-2.70 (m, 3H), 2.25-2.45 (m, 4H), 2.05-2.25 (m, 2H), 1.70-2.00 (m, 3H), 0.50-1.20 (m, 6H). 19F NMR (CD3OD): δ −110.78.

TABLE 11-continued

| | NMR spectra details | | |
|---|---|---|---|
| Ex No. | Structure | Name | LCMS Method; Rt = min; [M + H]+ |

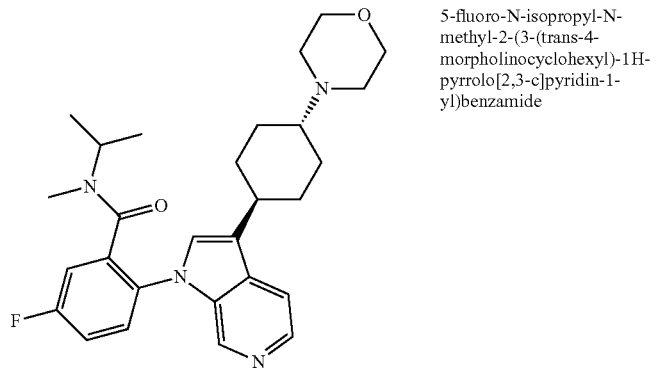

5-fluoro-N-isopropyl-N-methyl-2-(3-(trans-4-morpholinocyclohexyl)-1H-pyrrolo[2,3-c]pyridin-1-yl)benzamide

E; 1.092; 479.3

$^1$H NMR (CD$_3$OD): δ ppm 8.53-8.62 (m, 1H), 8.15-8.18 (m, 1H), 7.72-7.73 (m, 1H), 7.65-7.69 (m, 1H), 7.44-7.45 (m, 1H), 7.33-7.37 (m, 2H), 4.44-4.50 (m, 0.5H), 3.72-3.75 (m, 4H), 3.52-3.59 (m, 0.5H), 2.84-2.90 (m, 1H), 2.38-2.67 (m, 8H), 2.11-2.18 (m, 4H), 1.47-1.60 (m, 4H), 0.98-1.04 (m, 3H), 0.19-0.53 (m, 3H).
$^{19}$F NMR (CD$_3$OD): δ ppm −113.48.

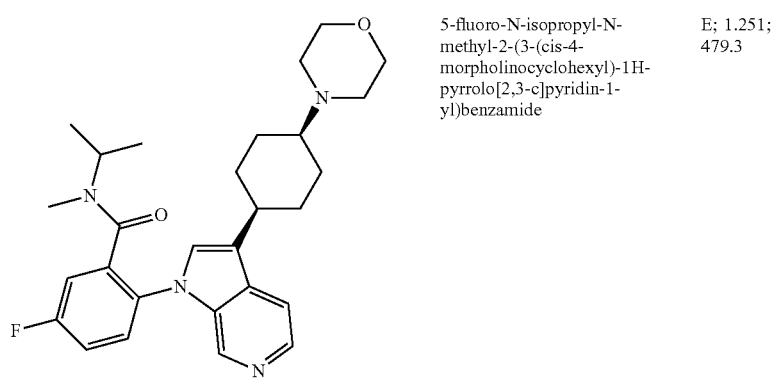

5-fluoro-N-isopropyl-N-methyl-2-(3-(cis-4-morpholinocyclohexyl)-1H-pyrrolo[2,3-c]pyridin-1-yl)benzamide

E; 1.251; 479.3

$^1$H NMR (CD$_3$OD): δ ppm 8.54-8.62 (m, 1H), 8.15-8.19 (m, 1H), 7.73-7.67 (m, 2H), 7.45-7.46 (m, 2H), 7.34-7.35 (m, 1H), 4.45-4.52 (m, 0.5H), 3.74 (s, 4H), 3.54-3.61 (m, 0.5H), 3.17-3.18 (m, 1H), 2.32-3.69 (m, 8H), 2.01-2.13 (m, 2H), 1.70-2.18 (m, 6H), 0.99-1.05 (m, 3H), 0.20-0.53 (m, 3H). $^{19}$F NMR (CD$_3$OD): δ ppm −113.50.

TABLE 11-continued

| Ex No. | Structure | Name | LCMS Method; Rt = min; [M + H]+ |
|---|---|---|---|
| | | 1-(trans-4-(1-(4-fluoro-2-(isopropyl(methyl)carbamoyl)phenyl)-1H-pyrrolo[2,3-c]pyridin-3-yl)cyclohexyl)piperidine-4-carboxylic acid | E; 1.178; 521.3 |

$^1$H NMR (CD$_3$OD): δ 8.53-8 61 (m, 1H), 8.16-8.18 (s, 1H), 7.38-7.51 (d, J = 5.2 Hz, 2H), 7.65-7.66 (m, 1H), 7.40-7.44 (m, 1H), 7.37-7.40 (m, 1H), 7.34-7.36 (m, 1H), 4.42-4.49 (m, 0.5H), 3.50-3.56 (m, 0.5H), 3.29-3.47 (m, 2H), 3.28-3.29 (m, 1H), 3.03-3.11 (m, 2H), 2.93-2.96 (m, 1H), 2.43-2.66 (m, 4H), 1.99-2.40 (m, 8H), 1.70-1.82 (m, 4H), 0.99-1.04 (m, 3H), 0.18-0.52 (m, 3H). $^{19}$F NMR (CD$_3$OD, 376 MHz): δ −113.25.

| | | 1-(cis-4-(1-(4-fluoro-2-(isopropyl(methyl)carbamoyl)phenyl)-1H-pyrrolo[2,3-c]pyridin-3-yl)cyclohexyl)piperidine-4-carboxylic acid | E; 1.190; 521.3 |

$^1$H NMR (CD$_3$OD): δ 8.53-8 60 (m, 1H), 8.18 (s, 1H), 7.60-7.71 (m, 2H), 7.58-7.60 (m, 1H), 7.46-7.48 (m, 1H), 7.37-7.39 (m, 1H), 4.43-4.48 (m, 0.5H), 3.60-3.63 (m, 0.5H), 3.43-2.44 (m, 3H), 3.25-3.26 (m, 1H), 3.02-3.08 (m, 2H), 2.47-2.65 (m, 3H), 2.26-2.33 (m, 3H), 1.79-2.11 (m, 10H), 0.88-1.04 (m, 3H), 0.18-0.25 (m, 3H).
$^{19}$F NMR (CD$_3$OD): δ −112.84.

Example 121. 5-((3-(1-(2-(3-cyclopropyl-5-methyl-4H-1,2,4-triazol-4-yl)-4-fluorophenyl)-1H-pyrrolo[2,3-c]pyridin-3-yl)piperidin-1-yl)methyl)-1H-benzo[d]imidazol-2(3H)-one

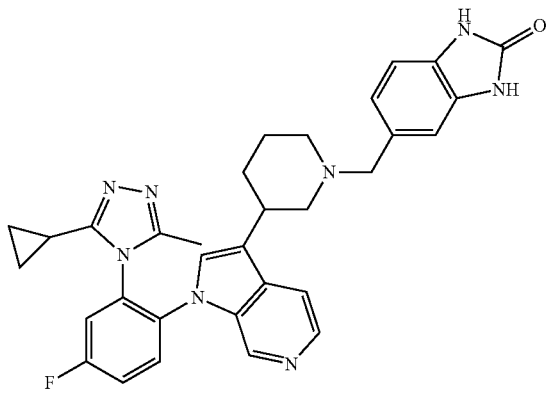 [SMILES: Cc1nnc(C2CC2)n1-c1cc(F)ccc1-n1cc(C2CCCN(Cc3ccc4[nH]c(=O)[nH]c4c3)C2)c2ccncc21]

Step 1: tert-butyl 5-(1H-pyrrolo[2,3-c]pyridin-3-yl)-3,4-dihydropyridine-1(2H)-carboxylate

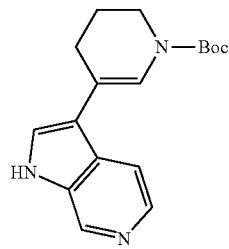 [SMILES: CC(C)(C)OC(=O)N1C=C(c2c[nH]c3cnccc23)CCC1]

To a solution of 1H-pyrrolo[2,3-c]pyridine (500 mg, 4.23 mmol) in MeOH/H₂O (30 mL, v/v=2/1) was added tert-butyl 3-oxopiperidine-1-carboxylate (4.225 g, 21.15 mmol), KOH (2.375 g, 42.3 mmol). The resulting mixture was degassed with N₂ and stirred at 75° C. for 48 h. The mixture was concentrated under reduced pressure and H₂O (50 mL) was added and extracted with EtOAc (3×30 mL). The combined organic layers were dried over anhydrous Na₂SO₄, filtered and concentrated under reduced pressure. The residue was purified by ISCO column on silica gel (eluting with dichloromethane/methanol=1/0 to 10/1) to give tert-butyl 5-(1H-pyrrolo[2,3-c]pyridin-3-yl)-3,4-dihydropyridine-1(2H)-carboxylate as brown solid. Yield: 1.1 g (87%); LCMS method D: $t_R$: 0.636 min; (M+H)⁺=300.1. ¹H NMR (CD₃OD): δ ppm 8.67-8.69 (m, 1H), 8.09-8.15 (m, 1H), 7.84 (d, J=5.6 Hz, 0.5H), 7.10 (d, J=5.6 Hz, 0.5H), 7.55 (s, 1H), 7.36-7.43 (m, 1H), 3.62-3.67 (m, 2H), 2.50-2.53 (m, 2H), 1.98-2.03 (m, 2H), 1.51-1.56 (m, 9H).

Step 2: tert-butyl 3-(1H-pyrrolo[2,3-c]pyridin-3-yl)piperidine-1-carboxylate

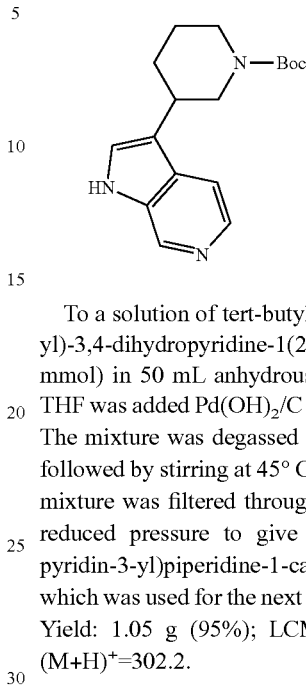

To a solution of tert-butyl 5-(1H-pyrrolo[2,3-c]pyridin-3-yl)-3,4-dihydropyridine-1(2H)-carboxylate (1.1 g, 3.67 mmol) in 50 mL anhydrous MeOH and 50 mL anhydrous THF was added Pd(OH)₂/C (110 mg, 0.156 mmol, 20 wt %). The mixture was degassed and purged with H₂ three times followed by stirring at 45° C. for 48 h under H₂ (50 psi). The mixture was filtered through celite and concentrated under reduced pressure to give tert-butyl 3-(1H-pyrrolo[2,3-c]pyridin-3-yl)piperidine-1-carboxylate as yellow solid, which was used for the next step without further purification. Yield: 1.05 g (95%); LCMS method D: $t_R$: 0.669 min; (M+H)⁺=302.2.

Step 3: tert-butyl 3-(1-(4-fluoro-2-nitrophenyl)-1H-pyrrolo[2,3-c]pyridin-3-yl)piperidine-1-carboxylate

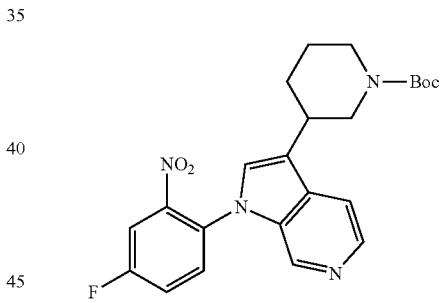

To a solution of tert-butyl 3-(1H-pyrrolo[2,3-c]pyridin-3-yl)piperidine-1-carboxylate (500 mg, 1.66 mmol) in 16 mL anhydrous DMF was added 2,5-difluoronitrobenzene (396 mg, 2.49 mmol) under N₂ and the mixture was stirred at 75° C. for 17 h. The mixture was then quenched with water (50 mL) and extracted with EtOAc (3×30 mL). The combined organic layers were dried over anhydrous Na₂SO₄, filtered, and concentrated under reduced pressure. The resulting residue was purified by flash column on silica gel (ISCO) (eluting with petroleum ether: ethyl acetate=1/0 to 1/1) to give tert-butyl 3-(1-(4-fluoro-2-nitrophenyl)-1H-pyrrolo[2,3-c]pyridin-3-yl)piperidine-1-carboxylate as brown oil. Yield: 450 mg (62%); LCMS method D: $t_R$: 0.773 min; (M+H)⁺=441.2. ¹H NMR (CDCl₃): δ ppm 8.4 (s, 1H), 8.35 (d, J=5.2 Hz, 1H), 8.01 (s, 1H), 7.85 (dd, J=7.6, 2.8 Hz, 1H), 7.59-7.63 (m, 1H), 7.50-7.54 (m, 1H), 7.05 (s, 2H), 2.95-2.96 (m, 4H), 2.88-2.92 (m, 5H), 1.49 (m, 9H).

Step 4: tert-butyl 3-(1-(2-amino-4-fluorophenyl)-1H-pyrrolo[2,3-c]pyridin-3-yl)piperidine-1-carboxylate

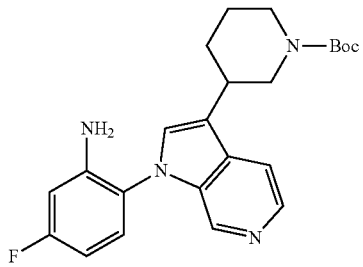 [SMILES: CC(C)(C)OC(=O)N1CCCC(c2cn(-c3ccc(F)cc3[N+](=O)[O-])c3cnccc23)C1]

To a solution of tert-butyl 3-(1-(4-fluoro-2-nitrophenyl)-1H-pyrrolo[2,3-c]pyridin-3-yl)piperidine-1-carboxylate (400 mg, 908.13 μmol) in 8 mL H$_2$O and 16 mL CH$_3$CH$_2$OH were added Fe (253.6 mg, 4.54 mmol) and NH$_4$Cl (485.8 mg, 9.08 mmol). The mixture was stirred at 90° C. for 16 h. The mixture was filtered through celite and concentrated under reduced pressure. The resulting residue was dissolved in H$_2$O (20 mL) and extracted with EtOAc (3×20 mL). The combined organic layers were washed with brine (20 mL), dried over anhydrous Na$_2$SO$_4$, filtered, and concentrated under reduced pressure to give crude tert-butyl 3-(1-(2-amino-4-fluorophenyl)-1H-pyrrolo[2,3-c]pyridin-3-yl)piperidine-1-carboxylate as brown solid. Yield: 360 mg (86%); LCMS method D: t$_R$: 0.734 min; (M+H)$^+$=411.2.

Step 5: tert-butyl 3-(1-(2-acetamido-4-fluorophenyl)-1H-pyrrolo[2,3-c]pyridin-3-yl)piperidine-1-carboxylate

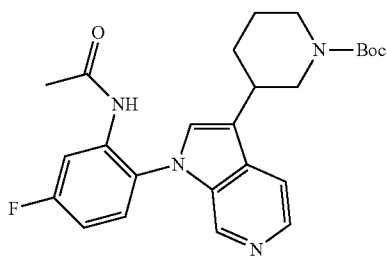 [SMILES: CC(=O)Nc1cc(F)ccc1-n1cc(C2CCCN(C(=O)OC(C)(C)C)C2)c2ccncc21]

To a solution of tert-butyl 3-(1-(2-amino-4-fluorophenyl)-1H-pyrrolo[2,3-c]pyridin-3-yl)piperidine-1-carboxylate (180 mg, 438.51 μmol) in 5 mL anhydrous CH$_2$Cl$_2$ was added Ac$_2$O (223.8 mg, 2.19 mmol) and pyridine (173.4 mg, 2.19 mmol) and the mixture was stirred at 20° C. for 16 h. The mixture was then concentrated under reduced pressure and the resulting residue was purified by ISCO column on silica gel (eluting with petroleum ether/EtOAc=1/0 to 0/1) to give tert-butyl 3-(1-(2-acetamido-4-fluorophenyl)-1H-pyrrolo[2,3-c]pyridin-3-yl)piperidine-1-carboxylate as brown solid. Yield: 63 mg (32%); LCMS method E: t$_R$: 0.710 min; (M+H)$^+$=453.2. $^1$H NMR (CDCl$_3$): δ 8.37 (m, 1H), 8.23-8.25 (m, 2H), 7.61 (m, 1H), 7.32 (m, 1H), 7.21-7.26 (m, 1H), 7.10 (s, 1H), 6.91-6.96 (m, 1H), 2.91-3.04 (m, 4H), 1.49 (m, 13H).

Step 6: tert-butyl 3-(1-(2-ethanethioamido-4-fluorophenyl)-1H-pyrrolo[2,3-c]pyridin-3-yl)piperidine-1-carboxylate

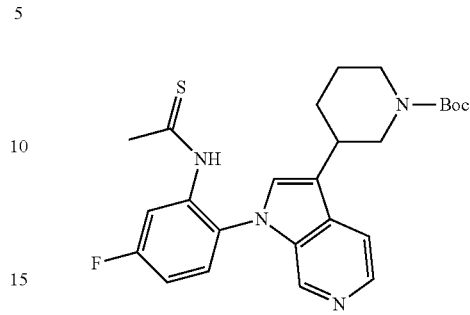

To a solution of tert-butyl 3-(1-(2-acetamido-4-fluorophenyl)-1H-pyrrolo[2,3-c]pyridin-3-yl)piperidine-1-carboxylate (63 mg, 139.22 μmol) in 5 mL anhydrous toluene was added Lawesson's reagent (61.9 mg, 153.14 μmol). The mixture was degassed and purged with N$_2$ 3 times followed by stirring at 125° C. for 16 h under N$_2$. The solvent was removed under reduced pressure and the resulting residue was purified by flash column on silica gel (ISCO) (eluting with DCM:MeOH=1:0 to 10:1) to give tert-butyl 3-(1-(2-ethanethioamido-4-fluorophenyl)-1H-pyrrolo[2,3-c]pyridin-3-yl)piperidine-1-carboxylate as brown solid. Yield: 30 mg (46%); LCMS method E: t$_R$: 0.745 min; (M+H)$^+$=469.2.

Step 7: tert-butyl 3-(1-(2-(3-cyclopropyl-5-methyl-4H-1,2,4-triazol-4-yl)-4-fluorophenyl)-1H-pyrrolo[2,3-c]pyridin-3-yl)piperidine-1-carboxylate

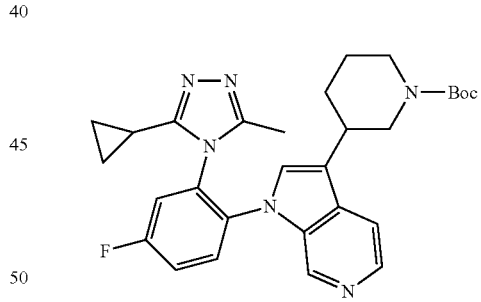

To a solution of tert-butyl 3-(1-(2-ethanethioamido-4-fluorophenyl)-1H-pyrrolo[2,3-c]pyridin-3-yl)piperidine-1-carboxylate (20 mg, 42.68 μmol) in 2 mL anhydrous dioxane was added cyclopropanecarbohydrazide (8.6 mg, 85.36 μmol). The mixture was degassed and purged with N$_2$ 3 times followed by stirring at 120° C. for 12 h under N$_2$. The mixture was concentrated under reduced pressure, the residue was purified by preparative TLC (CH$_2$Cl$_2$/MeOH=10/1) to give tert-butyl 3-(1-(2-(3-cyclopropyl-5-methyl-4H-1,2,4-triazol-4-yl)-4-fluorophenyl)-1H-pyrrolo[2,3-c]pyridin-3-yl)piperidine-1-carboxylate as brown solid. Yield: 5 mg (23%); LCMS method E: t$_R$: 0.667 min; (M+H)$^+$=517.1.

Step 8: 1-(2-(3-cyclopropyl-5-methyl-4H-1,2,4-triazol-4-yl)-4-fluorophenyl)-3-(piperidin-3-yl)-1H-pyrrolo[2,3-c]pyridine

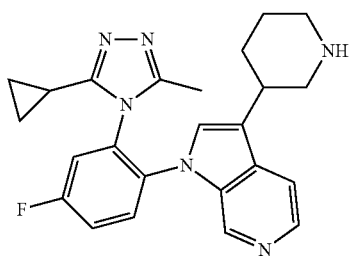 [SMILES: Cc1nnc(C2CC2)n1-c1cc(F)ccc1-n1cc(C2CCCNC2)c2ccncc21]

To a solution of tert-butyl 3-(1-(2-(3-cyclopropyl-5-methyl-4H-1,2,4-triazol-4-yl)-4-fluorophenyl)-1H-pyrrolo[2,3-c]pyridin-3-yl)piperidine-1-carboxylate (5 mg, 9.68 mol) in 4 mL anhydrous $CH_2Cl_2$ was added HCl-dioxane (1 mL, 4 N) and the mixture was stirred at 20° C. for 2 h. The mixture was then concentrated under reduced pressure to give 1-(2-(3-cyclopropyl-5-methyl-4H-1,2,4-triazol-4-yl)-4-fluorophenyl)-3-(piperidin-3-yl)-1H-pyrrolo[2,3-c]pyridine as yellow oil, which was used for the next step directly. Yield: 4 mg (crude, 100%); LCMS method D: $t_R$: 2.070 min; $(M+H)^+$=417.2.

Step 9: 5-((3-(1-(2-(3-cyclopropyl-5-methyl-4H-1,2,4-triazol-4-yl)-4-fluorophenyl)-1H-pyrrolo[2,3-c]pyridin-3-yl)piperidin-1-yl)methyl)-1H-benzo[d]imidazol-2(3H)-one To a solution of 1-(2-(3-cyclopropyl-5-methyl-4H-1,2,4-triazol-4-yl)-4-fluorophenyl)-3-(piperidin-3-yl)-1H-pyrrolo[2,3-c]pyridine (4 mg, 9.6 μmol) in 1 mL anhydrous MeOH was added pyridine (3.8 mg, 48.02 μmol), 2-oxo-2,3-dihydro-1H-benzo[d]imidazole-5-carbaldehyde (2.3 mg, 14.41 μmol) and $NaBH_3CN$ (3 mg, 48.02 μmol) and the mixture was stirred at 50° C. for 16 h under $N_2$. The solvent was removed under reduced pressure and the resulting residue was purified by preparative HPLC method E followed by lyophilization to give 5-((3-(1-(2-(3-cyclopropyl-5-methyl-4H-1,2,4-triazol-4-yl)-4-fluorophenyl)-1H-pyrrolo[2,3-c]pyridin-3-yl)piperidin-1-yl)methyl)-1H-benzo[d]imidazol-2(3H)-one as white solid. Yield: 1.60 mg (30%); LCMS method D: $t_R$: 1.517 min; $(M+H)^+$=563.2. $^1H$ NMR ($CD_3OD$): δ ppm 8.59 (d, J=3.2 Hz, 1H), 8.16-8.18 (m, 1H), 7.92-7.96 (m, 1H), 7.60-7.71 (m, 3H), 7.05 (s, 1H), 6.99-7.00 (m, 2H), 6.90 (d, J=9.2 Hz, 1H), 3.60 (s, 2H), 2.88-3.08 (m, 3H). 1.93-2.15 (m, 6H), 1.74-1.75 (m, 2H). 1.34-1.40 (m, 2.5H), 0.86-0.95 (m, 2.5H). $^{19}F$ NMR ($CD_3OD$): δ ppm −110.97.

Example 122. 5-fluoro-N-isopropyl-N-methyl-2-(3-(1-((2-oxo-2,3-dihydro-1H-benzo[d]imidazol-5-yl)methyl)pyrrolidin-3-yl)-1H-pyrrolo[2,3-c]pyridin-1-yl)benzamide

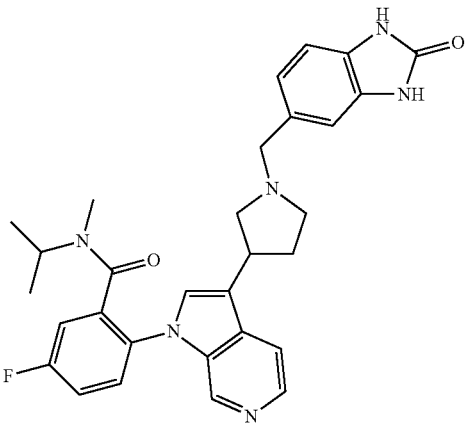 [SMILES: CC(C)N(C)C(=O)c1cc(F)ccc1-n1cc(C2CCN(Cc3ccc4[nH]c(=O)[nH]c4c3)C2)c2ccncc21]

The title compound was synthesized by the method described in Example 1, starting from Intermediate 4 and 2-oxo-2,3-dihydro-1H-benzo[d]imidazole-5-carbaldehyde. LCMS method D: $t_R$: 1.627 min; $(M+H)^+$=527.2. $^1H$ NMR ($CD_3OD$): δ ppm 8.54-8.61 (m, 1H), 8.17-8.20 (m, 1H), 7.75 (d, J=5.6 Hz, 1H), 7.64-7.69 (m, 1H), 7.42-7.48 (m, 2H), 7.35-7.38 (m, 1H), 7.01-7.14 (m, 3H), 4.42-4.47 (m, 0.5H), 3.66-3.83 (m, 3H), 3.50-3.61 (m, 0.5H), 3.14-3.24 (m, 1H), 2.77-2.96 (m, 2H), 2.60-2.69 (m, 2H), 2.42-2.49 (m, 3H), 1.95-2.06 (m, 1H), 1.01 (t, J=6.8 Hz, 3H), 0.21-0.54 (m, 3H). $^{19}F$ NMR ($CD_3OD$): δ ppm −113.34.

Examples 123-127

The following Examples were synthesized by method described above for Example 122.

TABLE 12

NMR spectra details

| Ex No. | Structural formula | Name | LCMS Method; Rt = min; [M + H]+ |
|---|---|---|---|
|  | 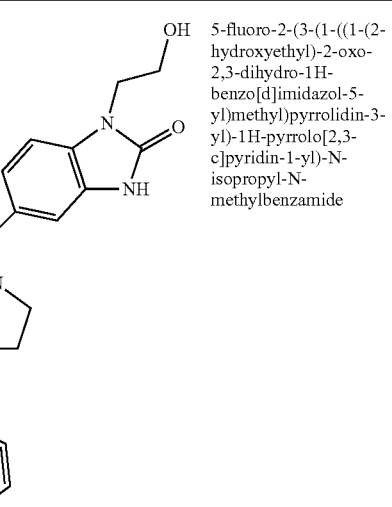 | 5-fluoro-2-(3-(1-((1-(2-hydroxyethyl)-2-oxo-2,3-dihydro-1H-benzo[d]imidazol-5-yl)methyl)pyrrolidin-3-yl)-1H-pyrrolo[2,3-c]pyridin-1-yl)-N-isopropyl-N-methylbenzamide | D; 1.600; 571.2 |

1H NMR (CD3OD): δ 8.54-8.61 (m, 1H), 8.17-8.20 (m, 1H), 7.75 (d, J = 5.2 Hz, 1H), 7.64-7.69 (m, 1H), 7.42-7.48 (m, 2H), 7.35-7.38 (m, 1H), 7.12-7.18 (m, 3H), 4.44-4.47 (m, 0.5H), 3.98-4.01 (m, 2H), 3.76-3.85 (m, 4H), 3.56-3.72 (m, 1.5H), 3.14-3.20 (m, 1H), 2.79-2.92 (m, 2H), 2.60-2.69 (m, 2H), 2.40-2.52 (m, 3H), 1.95-2.06 (m, 1H), 1.01 (t, J = 6.4 Hz, 3H), 0.21-0.54 (m, 3H). 19F NMR (CD3OD): δ -113.34.

| 124 | 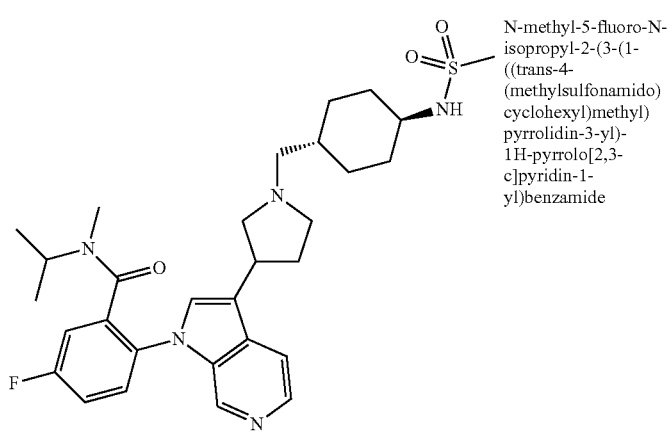 | N-methyl-5-fluoro-N-isopropyl-2-(3-(1-((trans-4-(methylsulfonamido)cyclohexyl)methyl)pyrrolidin-3-yl)-1H-pyrrolo[2,3-c]pyridin-1-yl)benzamide | E; 1.855; 570.3 |

| Ex No. | Structural formula | Name | LCMS Method; Rt = min; [M + H]+ |
|---|---|---|---|
| | 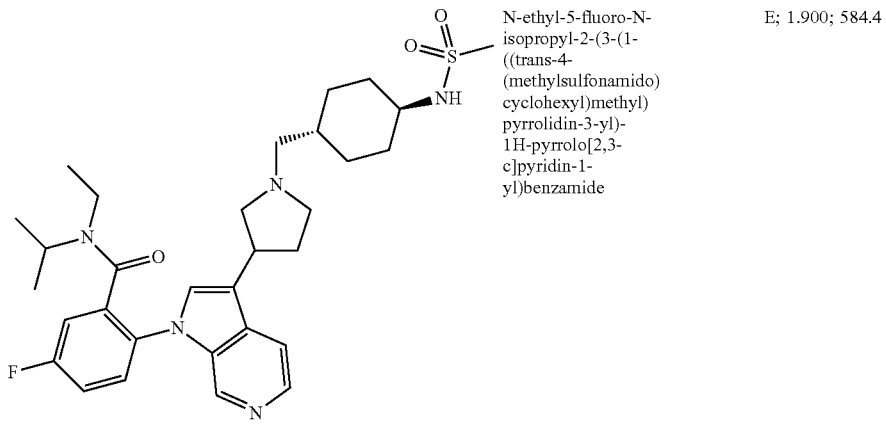 | N-ethyl-5-fluoro-N-isopropyl-2-(3-(1-((trans-4-(methylsulfonamido)cyclohexyl)methyl)pyrrolidin-3-yl)-1H-pyrrolo[2,3-c]pyridin-1-yl)benzamide | E; 1.900; 584.4 |

$^{1}$H NMR (CD$_3$OD): δ 8.60 (s, 1H), 8.19 (d, J = 5.2 Hz, 1H), 7.79-7.82 (m, 1H), 7.63-7.68 (m, 1H), 7.43-7.47 (m, 2H), 7.34-7.39 (m, 1H), 3.66-3.70 (m, 1H), 3.55-3.61 (m, 1H), 3.43-3.48 (m, 1H), 3.13-3.22 (m, 2H), 2.88-2.98 (m, 5H), 2.70-2.76 (m, 1H), 2.58-2.65 (m, 1H), 2.37-2.49 (m, 3H), 1.95-2.08 (m, 5H), 1.47-1.53 (m, 1H), 1.27-1.37 (m, 2H), 0.98-1.13 (m, 5H), 0.76-0.90 (m, 3.5H), 0.31-0.34 (m, 2.5H). $^{19}$F NMR (CD$_3$OD): δ −113.21.

| | 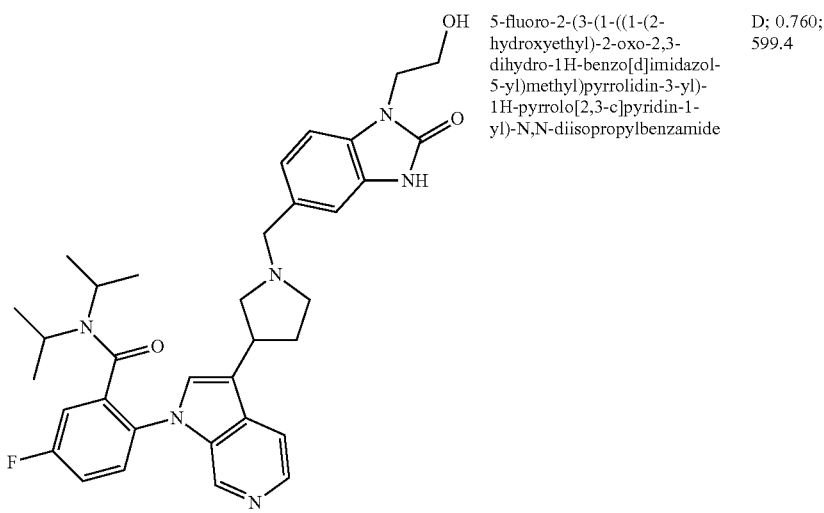 | 5-fluoro-2-(3-(1-((1-(2-hydroxyethyl)-2-oxo-2,3-dihydro-1H-benzo[d]imidazol-5-yl)methyl)pyrrolidin-3-yl)-1H-pyrrolo[2,3-c]pyridin-1-yl)-N,N-diisopropylbenzamide | D; 0.760; 599.4 |

$^{1}$H NMR (CD$_3$OD): δ 8.60 (s, 1 H), 8.19 (d, J = 5.6 Hz, 1H), 7.75-7.77 (m, 1H), 7.62-7.66 (m, 1H), 7.49 (s, 1H), 7.39-7.44 (m, 1H), 7.29-7.32 (m, 1H), 7.11-7.18 (m, 3H), 3.98-4.00 (m, 2H), 3.83-3.87 (m, 2H), 3.64-3.78 (m, 3H), 3.50-3.56 (m, 1H), 3.28-3.31 (m, 1H), 3.14-3.20 (m, 1H), 2.90-2.95 (m, 1H), 2.72-2.83 (m, 1H), 2.60-2.67 (m, 1H), 2.39-2.48 (m, 1H), 1.98-2.07 (m, 1H), 1.45 (d, J = 6.8 Hz, 3H), 1.01 (d, J = 11.6, 6.4 Hz, 6H), 0.15-0.25 (m, 3H). $^{19}$F NMR (CD$_3$OD): δ −113.21.

TABLE 12-continued

NMR spectra details

| Ex No. | Structural formula | Name | LCMS Method; Rt = min; [M + H]+ |
|---|---|---|---|
| | 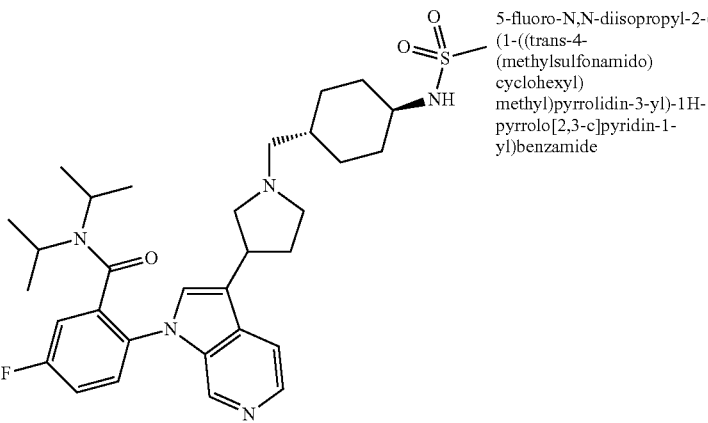 | 5-fluoro-N,N-diisopropyl-2-(3-(1-((trans-4-(methylsulfonamido)cyclohexyl)methyl)pyrrolidin-3-yl)-1H-pyrrolo[2,3-c]pyridin-1-yl)benzamide | D; 0.765; 598.4 |

$^1$H NMR (CD$_3$OD): δ 8.61 (s, 1H), 8.19 (d, J = 5.6 Hz, 1H), 7.79-7.82 (m, 1H), 7.64-7.68 (m, 1H), 7.51 (s, 1H), 7.40-7.45 (m, 1H), 7.30-7.33 (m, 1H), 3.66-3.71 (m, 1H), 3.51-3.58 (m, 1H), 3.33-3.37 (m, 1H), 3.15-3.22 (m, 2H), 2.89-2.96 (m, 4H), 2.58-2.76 (m, 2H), 2.37-2.50 (m, 3H), 1.95-2.07 (m, 5H), 1.45-1.54 (m, 4H), 1.27-1.38 (m, 2H), 1.02-1.14 (m, 8H), 0.22-0.24 (m, 3H).
$^{19}$F NMR (CD$_3$OD): δ −113.33.

Examples 128-128A. 5-fluoro-N-isopropyl-N-methyl-2-(3-(4-(methyl((4-(methylsulfonamido)cyclohexyl)methyl)amino)cyclohexyl)-1H-pyrrolo[2,3-c]pyridin-1-yl)benzamide (Isomers 1-2)

Step 1: 5-fluoro-N-isopropyl-N-methyl-2-(3-(4-(methylamino)cyclohexyl)-1H-pyrrolo[2,3-c]pyridin-1-yl)benzamide

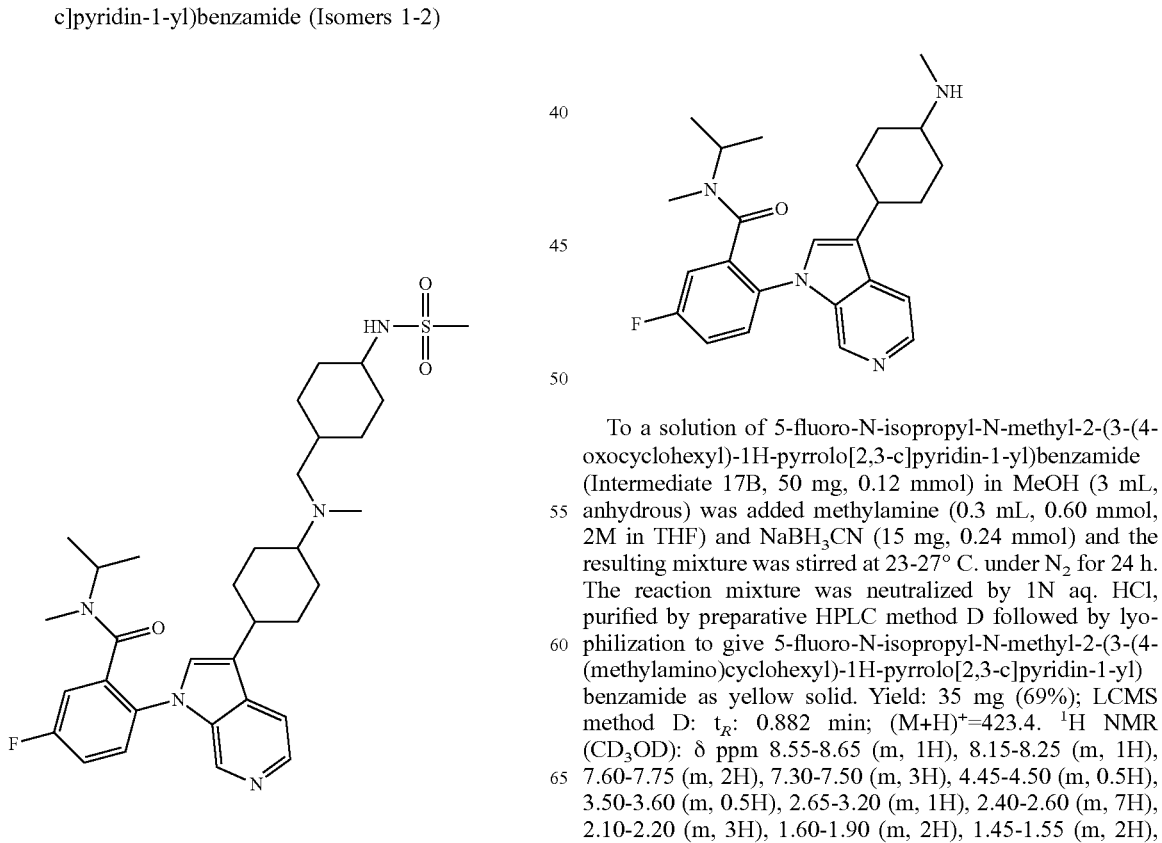

To a solution of 5-fluoro-N-isopropyl-N-methyl-2-(3-(4-oxocyclohexyl)-1H-pyrrolo[2,3-c]pyridin-1-yl)benzamide (Intermediate 17B, 50 mg, 0.12 mmol) in MeOH (3 mL, anhydrous) was added methylamine (0.3 mL, 0.60 mmol, 2M in THF) and NaBH$_3$CN (15 mg, 0.24 mmol) and the resulting mixture was stirred at 23-27° C. under N$_2$ for 24 h. The reaction mixture was neutralized by 1N aq. HCl, purified by preparative HPLC method D followed by lyophilization to give 5-fluoro-N-isopropyl-N-methyl-2-(3-(4-(methylamino)cyclohexyl)-1H-pyrrolo[2,3-c]pyridin-1-yl)benzamide as yellow solid. Yield: 35 mg (69%); LCMS method D: t$_R$: 0.882 min; (M+H)$^+$=423.4. $^1$H NMR (CD$_3$OD): δ ppm 8.55-8.65 (m, 1H), 8.15-8.25 (m, 1H), 7.60-7.75 (m, 2H), 7.30-7.50 (m, 3H), 4.45-4.50 (m, 0.5H), 3.50-3.60 (m, 0.5H), 2.65-3.20 (m, 1H), 2.40-2.60 (m, 7H), 2.10-2.20 (m, 3H), 1.60-1.90 (m, 2H), 1.45-1.55 (m, 2H), 1.35-1.40 (m, 1H), 0.95-1.10 (m, 3H), 0.10-0.60 (m, 3H). $^{19}$F NMR (CD$_3$OD): δ ppm −113.48.

Step 2: tert-butyl (trans-4-(((4-(1-(4-fluoro-2-(isopropyl(methyl)carbamoyl)phenyl)-1H-pyrrolo[2,3-c]pyridin-3-yl)cyclohexyl)(methyl)amino)methyl)cyclohexyl)carbamate

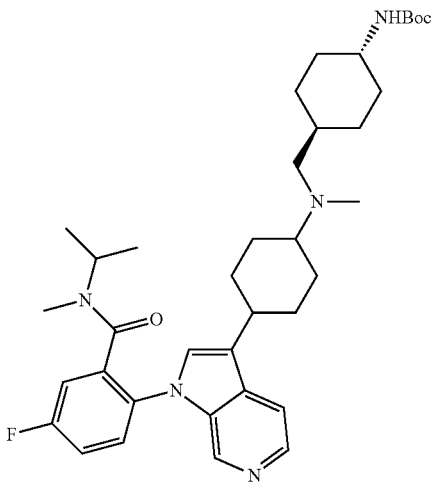 [SMILES: CC(C)N(C)C(=O)c1cc(F)ccc1-n1cc(C2CCC(N(C)C[C@H]3CC[C@H](NC(=O)OC(C)(C)C)CC3)CC2)c2ccncc21]

To a solution of 5-fluoro-N-isopropyl-N-methyl-2-(3-(4-(methylamino)cyclohexyl)-1H-pyrrolo[2,3-c]pyridin-1-yl)benzamide (25 mg, 0.059 mmol) in MeOH (2 mL, anhydrous) was added tert-butyl (trans-4-formylcyclohexyl)carbamate (20 mg, 0.088 mmol) and NaBH$_3$CN (8 mg, 0.118 mmol) and the resulting mixture was stirred at 40° C. (oil remperature) under N$_2$ for 20 h. The reaction mixture was concentrated and purified by preparative TLC on silica gel (CH$_2$Cl$_2$/MeOH=10/1) to give tert-butyl (trans-4-(((4-(1-(4-fluoro-2-(isopropyl(methyl)carbamoyl)phenyl)-1H-pyrrolo[2,3-c]pyridin-3-yl)cyclohexyl)(methyl)amino)methyl)cyclohexyl)carbamate as colorless solid. Yield: 40 mg (100% yield, 80% purity); LCMS method C: t$_R$: 0.678 min; (M+H)$^+$=634.2.

Step 3: 2-(3-(4-(((trans-4-aminocyclohexyl)methyl)(methyl)amino)cyclohexyl)-1H-pyrrolo[2,3-c]pyridin-1-yl)-5-fluoro-N-isopropyl-N-methylbenzamide

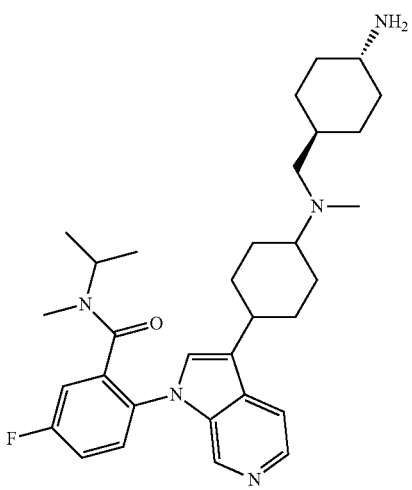 [SMILES: CC(C)N(C)C(=O)c1cc(F)ccc1-n1cc(C2CCC(N(C)C[C@H]3CC[C@H](N)CC3)CC2)c2ccncc21]

To a solution of tert-butyl (trans-4-(((4-(1-(4-fluoro-2-(isopropyl(methyl)carbamoyl)phenyl)-1H-pyrrolo[2,3-c]pyridin-3-yl)cyclohexyl)(methyl)amino)methyl)cyclohexyl)carbamate (40 mg, 0.063 mmol, 80% purity) in CH$_2$Cl$_2$ (6 mL, anhydrous) was added HCl-dioxane (2 mL, 4 M) and the resulting mixture was stirred at 18-25° C. for 2 h. The reaction mixture was concentrated under reduced pressure to give 2-(3-(4-(((trans-4-aminocyclohexyl)methyl)(methyl)amino)cyclohexyl)-1H-pyrrolo[2,3-c]pyridin-1-yl)-5-fluoro-N-isopropyl-N-methylbenzamide as yellow oil. Yield: 40 mg (100% crude); LCMS method F: t$_R$: 0.838 min; (M+H)$^+$=534.4.

Step 4. 5-fluoro-N-isopropyl-N-methyl-2-(3-(4-(methyl((4-(methylsulfonamido)cyclohexyl)methyl)amino)cyclohexyl)-1H-pyrrolo[2,3-c]pyridin-1-yl)benzamide To a solution of 2-(3-(4-(((trans-4-aminocyclohexyl)methyl)(methyl)amino)cyclohexyl)-1H-pyrrolo[2,3-c]pyridin-1-yl)-5-fluoro-N-isopropyl-N-methylbenzamide (40 mg, 0.075 mmol, HCl salt) in CH$_2$Cl$_2$ (5 mL, anhydrous) was added (MeSO$_2$)$_2$O (13 mg, 0.075 mmol) and Et$_3$N (38 mg, 0.375 mmol) and the resulting mixture was stirred at RT under N$_2$ for 20 h. The reaction mixture was concentrated under reduced pressure and purified by preparative HPLC method D to give two isomers of 5-fluoro-N-isopropyl-N-methyl-2-(3-(4-(methyl((4-(methylsulfonamido)cyclohexyl)methyl)amino)cyclohexyl)-1H-pyrrolo[2,3-c]pyridin-1-yl)benzamide as white solid.

Example 128 (Isomer 1): Yield: 3.4 mg (7%); LCMS method D: t$_R$: 2.229 min; (M+H)$^+$=612.3. $^1$H NMR (CD$_3$OD): δ ppm 8.50-8.65 (m, 1H), 8.15-8.25 (m, 1H), 7.60-7.75 (m, 2H), 7.40-7.50 (m, 1H), 7.30-7.40 (m, 2H), 4.40-4.55 (m, 0.5H), 3.50-3.60 (m, 0.5H), 3.10-3.20 (m, 1H), 2.96 (s, 3H), 2.70-2.85 (m, 1H), 2.40-2.52 (m, 4H), 2.25-2.40 (m, 5H), 2.15-2.25 (m, 2H), 1.95-2.15 (m, 6H), 1.25-2.65 (m, 7H), 1.00-1.10 (m, 5H), 0.15-0.60 (m, 3H). $^{19}$F NMR (CD$_3$OD): δ ppm−113.48.

Example 128A (Isomer 2): Yield: 10.60 mg (23%); LCMS method D: t$_R$: 1.927 min; (M+H)$^+$=612.3. $^1$H NMR (CD$_3$OD): δ ppm 8.50-8.65 (m, 1H), 8.15-8.25 (m, 1H), 7.65-7.75 (m, 2H), 7.35-7.50 (m, 3H), 4.40-4.55 (m, 0.5H), 3.50-3.60 (m, 0.5H), 3.10-3.40 (m, 2H), 2.95 (s, 3H), 2.40-2.65 (m, 4H), 2.20-2.40 (m, 5H), 2.00-2.20 (m, 4H), 1.60-1.95 (m, 8H), 1.40-1.55 (m, 1H), 1.25-1.40 (m, 2H), 0.95-1.10 (m, 5H), 0.15-0.60 (m, 3H). $^{19}$F NMR (CD$_3$OD): δ ppm −113.35.

Example 129. 2-(3-(trans-4-benzamidocyclohexyl)-1H-pyrrolo[2,3-c]pyridine-1-yl)-5-fluoro-N-isopropyl-N-methylbenzamide

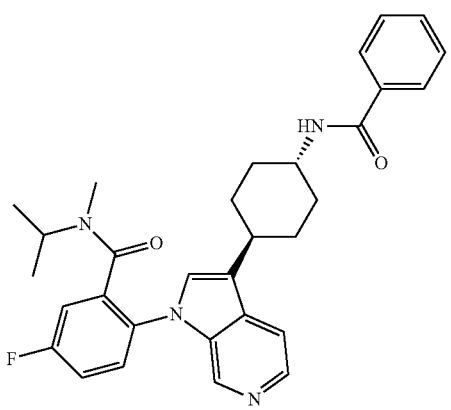 [SMILES: CC(C)N(C)C(=O)c1cc(F)ccc1-n1cc([C@H]2CC[C@H](NC(=O)c3ccccc3)CC2)c2ccncc21]

To a solution of 2-(3-(trans-4-aminocyclohexyl)-1H-pyrrolo[2,3-c]pyridin-1-yl)-5-fluoro-N-isopropyl-N-methylbenzamide (Example 57, 20 mg, 0.05 mmol) and HATU (23 mg, 0.06 mmol) in $CH_2Cl_2$ (3 mL, anhydrous) was added DIEA (19 mg, 0.15 mmol) and benzoic acid (10 mg, 0.08 mmol) and the resulting mixture was stirred at RT for 18 h. The reaction mixture was concentrated and the residue was purified by preparative HPLC Method B to give 2-(3-(trans-4-benzamidocyclohexyl)-1H-pyrrolo[2,3-c]pyridine-1-yl)-5-fluoro-N-isopropyl-N-methylbenzamide (TFA salt) as white solid. Yield: 23.9 mg (80%); LCMS method C: $t_R$: 0.707 min; $(M+H)^+=513.1$. $^1$H NMR ($CD_3OD$): δ ppm 8.80-8.95 (m, 1H), 8.10-8.35 (m, 3H), 7.70-7.90 (m, 3H), 7.40-7.50 (m, 5H), 4.35-4.50 (m, 0.5H), 3.95-4.10 (m, 1H), 3.70-3.85 (m, 0.5H), 3.05-3.20 (m, 1H), 2.66 (s, 3H), 2.15-2.30 (m, 4H), 1.60-1.90 (m, 4H), 0.45-1.25 (m, 6H). $^{19}$F NMR ($CD_3OD$): δ ppm −110.82, −76.98.

Example 130-133

The following Examples were synthesized by method described above for Example 129.

TABLE 13

| Ex No. | Structure | Name | LCMS Method; Rt = min; [M + H]+ |
|---|---|---|---|
| | | NMR spectra details | |
| | | 2-(3-(trans-4-(cyclohexanecarboxamido)cyclohexyl)-1H-pyrrolo[2,3-c]pyridin-1-yl)-5-fluoro-N-isopropyl-N-methylbenzamide | C; 0.730; 519.1 |

$^1$H NMR ($CD_3OD$): δ ppm 8.50-8.65 (m, 1H), 8.15-8.25 (m, 1H), 7.60-7.80 (m, 2H), 7.30-7.50 (m, 3H), 4.40-4.55 (m, 0.5H), 3.70-3.80 (m, 1H), 3.50-3.65 (m, 0.5H), 2.85-2.95 (m, 1H), 2.40-2.70 (m, 3H), 2.00-2.25 (m, 5H), 1.75-1.90 (m, 4H), 1.60-1.75 (m, 3H), 1.40-1.55 (m, 4H), 1.20-1.40 (m, 3H), 0.95-1.10 (m, 3H), 0.15-0.65 (m, 3H). $^{19}$F NMR ($CD_3OD$): δ ppm −113.43.

TABLE 13-continued

| Ex No. | Structure | Name | LCMS Method; Rt = min; [M + H]+ |
|---|---|---|---|
|  |  | 2-(3-(trans-4-benzamidocyclohexyl)-1H-pyrrolo[2,3-c]pyridine-1-yl)-5-fluoro-N-isopropyl-N-methylbenzamide (TFA salt) | C; 0.694; 520.1 |

¹H NMR (CD₃OD): δ ppm 8.80-8.95 (m, 1H), 8.10-8.40 (m, 3H), 7.70-8.05 (m, 3H), 7.40-7.60 (m, 2H), 4.35-4.45 (m, 0.5H), 3.95-4.10 (m, 1H), 3.70-3.85 (m, 0.5H), 2.65 (s, 3H), 2.10-2.30 (m, 4H), 1.70-1.90 (m, 4H), 0.50-1.20 (m, 6H). ¹⁹F NMR (CD₃OD): δ ppm −110.86, −76.92.

| Ex No. | Structure | Name | LCMS Method; Rt = min; [M + H]+ |
|---|---|---|---|
| 132 | 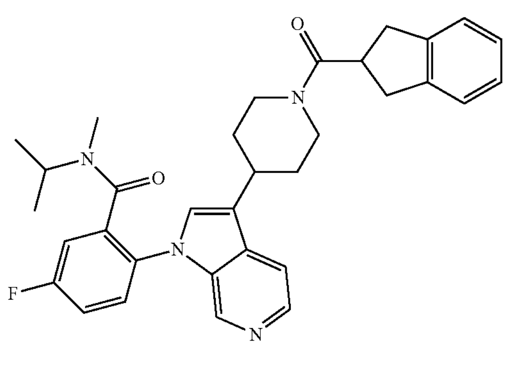 [SMILES: CC(C)N(C)C(=O)c1cc(F)ccc1-n1cc(C2CCN(C(=O)C3Cc4ccccc4C3)CC2)c2ccncc21] | 2-(3-(1-(2,3-dihydro-1H-indene-2-carbonyl)piperidin-4-yl)-1H-pyrrolo[2,3-c]pyridin-1-yl)-5-fluoro-N-isopropyl-N-methylbenzamide | E; 2.016; 539.2 |

¹H NMR (CD₃OD): δ ppm 8.55-8.70 (m, 1H), 8.15-8.25 (m, 1H), 7.75-7.85 (m, 1H), 7.60-7.75 (m, 1H), 7.40-7.50 (m, 2H), 7.30-7.40 (m, 1H), 7.15-7.25 (m, 2H), 7.10-7.15 (m, 2H), 7.65-7.80 (m, 1H), 4.65-4.80 (m, 1H), 4.40-4.55 (m, 0.5H), 4.25-4.35 (m, 1H), 3.70-3.85 (m, 1H), 3.55-3.65 (m, 0.5H), 3.35-3.50 (m, 1H), 3.15-3.30 (m, 5H), 2.85-3.00 (m, 1H), 2.40-2.75 (m, 3H), 2.10-2.30 (m, 2H), 1.60-1.85 (m, 2H), 0.95-1.15 (m, 3H), 0.20-0.65 (m, 3H). ¹⁹F NMR (CD₃OD): δ ppm −113.27.

TABLE 13-continued

NMR spectra details

| Ex No. | Structure | Name | LCMS Method; Rt = min; [M + H]+ |
|---|---|---|---|
| | 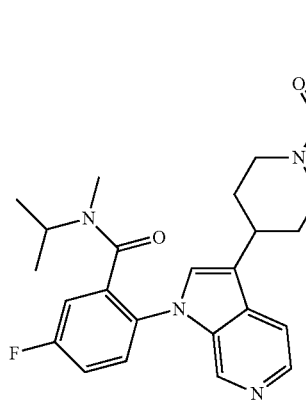 | 5-fluoro-N-isopropyl-N-methyl-2-(3-(1-(2-phenylacetyl)piperidin-4-yl)-1H-pyrrolo[2,3-c]pyridin-1-yl)benzamide | E; 1.837; 513.2 |

$^1$H NMR (CD$_3$OD): δ ppm 8.50-8.60 (m, 1H), 8.10-8.20 (m, 1H), 7.60-7.70 (m, 2H), 7.20-7.50 (m, 8H), 4.65-4.75 (m, 1H), 4.35-4.50 (m, 0.5H), 4.05-4.20 (m, 1H), 3.75-3.95 (m, 2H), 3.45-3.60 (m, 0.5H), 3.20-3.30 (m, 1H), 3.10-3.20 (m, 1H), 2.80-2.95 (m, 1H), 2.40-2.65 (m, 3H), 2.00-2.10 (m, 1H), 1.90-2.00 (m, 1H), 1.55-1.70 (m, 1H), 1.30-1.45 (m, 1H), 0.95-1.10 (m, 3H), 0.10-0.55 (m, 3H). $^{19}$F NMR (CD$_3$OD): δ ppm −113.29.

Example 134. 5-fluoro-2-(3-(1-((1-(2-hydroxyethyl)-2-oxo-2,3-dihydro-1H-benzo[d]imidazol-5-yl)methyl)piperidin-3-yl)-1H-pyrrolo[2,3-c]pyridin-1-yl)-N,N-diisopropylbenzamide

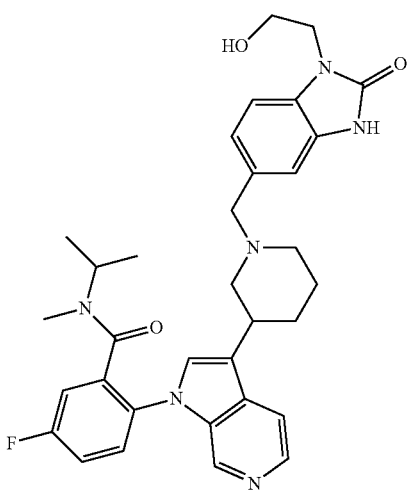 [SMILES: CC(C)N(C)C(=O)c1cc(F)ccc1-n1cc(C2CCCN(Cc3ccc4c(c3)[nH]c(=O)n4CCO)C2)c2ccncc21]

Step 1. 5-fluoro-2-hydrazinylbenzoic acid (HCl salt)

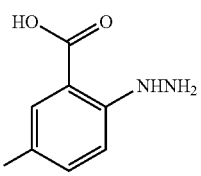

To a suspension of 2-amino-5-fluorobenzoic acid (7.00 g, 45.13 mmol) in conc. HCl (50 mL) and H$_2$O (30 mL) chilled to −15° C. was added a solution of sodium nitrite (3.11 g, 45.13 mmol) dropwise, at such a speed to maintain the reaction temperature below −5° C. After the addition, it was stirred for another 30 min. A freshly prepared solution of tin(II) chloride (25.67 g, 135.39 mmol) in conc. HCl (13 mL) was added slowly while maintaining the temperature below −5° C. After the addition, it was stirred for another 2 h at −5° C. The precipitate was collected by filtration, washed with cold water and ethyl acetate, dried over vacuum to afford 6.64 g of 5-fluoro-2-hydrazinylbenzoic acid HCl salt as off-white solid. LCMS method B: t$_R$: 0.41 min; (M+H)$^+$=171.1

Step 2: tert-butyl 3-(3-fluoroisonicotinoyl)piperidine-1-carboxylate

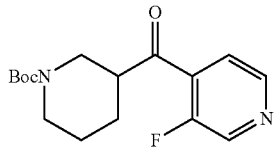 [SMILES: CC(C)(C)OC(=O)N1CCCC(C(=O)c2ccncc2F)C1]

To freshly prepared LDA solution in THF (30.0 mmol, 60 mL) at −78° C. under N₂ atmosphere was added 3-fluoropyridine (2.43 g, 25 mmol) dropwise and stirred for 30 min at −78° C. Then a solution of tert-butyl 3-(methoxy(methyl)carbamoyl)piperidine-1-carboxylate (5.99 g, 22.0 mmol) in dry THF (40 mL) was added. The resulting mixture was allowed to warm to RT slowly overnight before quenching with aq NH₄Cl solution. It was extracted with EA, washed with H₂O, brine successively, and dried over anhydrous Na₂SO₄, and filtered, and evaporated to dry. The residue was purified by flash chromatography to afford 4.91 g of tert-butyl 3-(3-fluoroisonicotinoyl)piperidine-1-carboxylate. LCMS method D: $t_R$: 1.45 min; (M+H)⁺=309.1

Step 3. 2-(3-(1-(tert-butoxycarbonyl)piperidin-3-yl)-1H-pyrazolo[3,4-c]pyridin-1-yl)-5-fluorobenzoic acid

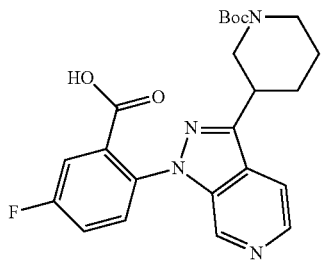 [SMILES: CC(C)(C)OC(=O)N1CCCC(c2nn(-c3ccc(F)cc3C(=O)O)c3cnccc23)C1]

A mixture of 5-fluoro-2-hydrazinylbenzoic acid HCl salt (1.18 g, 5.71 mmol), tert-butyl 3-(3-fluoroisonicotinoyl)piperidine-1-carboxylate (1.76 mmol, 5.71 mmol) and K₂CO₃ (2.36 g, 17.13 mmol) in DMF (20 ml) was heated at 130° C. for 48 h. The reaction mixture was neutralized with aqueous 1 M HCl solution and extracted with EtOAc twice. The combined organic phases were washed with brine and dried over anhydrous Na₂SO₄, and filtered, and evaporated to afford the crude product 2-(3-(1-(tert-butoxycarbonyl)piperidin-3-yl)-1H-pyrazolo[3,4-c]pyridin-1-yl)-5-fluorobenzoic acid, 1.87 g. it was used for next step without further purification. LCMS method B: $t_R$: 1.19 min; (M+H)⁺= 441.1

Step 4. tert-butyl 3-(1-(4-fluoro-2-(isopropyl(methyl)carbamoyl)phenyl)-1H-pyrazolo[3,4-c]pyridin-3-yl)piperidine-1-carboxylate

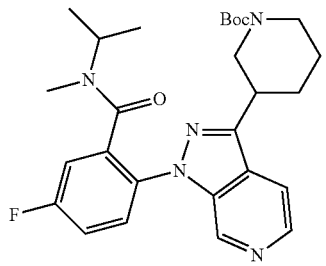 [SMILES: CC(C)N(C)C(=O)c1cc(F)ccc1-n1nc(C2CCCN(C(=O)OC(C)(C)C)C2)c2ccncc21]

To a solution of 2-(3-(1-(tert-butoxycarbonyl)piperidin-3-yl)-1H-pyrazolo[3,4-c]pyridin-1-yl)-5-fluorobenzoic acid (1.01 g, 2.29 mmol) in DMF (12 mL) was added TEA (0.7 mL, 5.05 mmol) isopropylmethyl amine (0.35 mmol), 3.44 mmol), and BOP (1.22 g, 2.75 mmol). The resulting mixture was stirred for 30 min and diluted with EtOAc, and washed with H₂O, brine, dried over anhydrous Na₂SO₄, filtered, and evaporated. The residue was purified by flash chromatography to afford 0.617 g of the desired product. LCMS method B: $t_R$: 1.134 min; (M+H)⁺=496.

Steps 5-6: 5-fluoro-2-(3-(1-((1-(2-hydroxyethyl)-2-oxo-2,3-dihydro-1H-benzo[d]imidazol-5-yl)piperidin-3-yl)-1H-pyrazolo[3,4-c]pyridin-1-yl)-N-isopropyl-N-methylbenzamide The title compound was synthesized by the method described in Example 1 utilizing Steps 1 and 2. In step 2, 2-(5-formyl-2-oxo-2,3-dihydro-1H-benzo[d]imidazol-1-yl) ethyl formate (Intermediate 24) was utilized.

LCMS method B: $t_R$: 0.67 min; (M+H)⁺=586.1. ¹H NMR (CD₃OD) δ: 9.30 (brs, 1H), 8.48 (s, 1H), 8.32 (s, 1H), 7.81 (m, 1H), 7.52-7.45 (m, 2H), 7.29-7.27 (m, 3H), 4.54-4.30 (m, 2H), 4.00 (m, 2H), 3.98-3.68 (m, 5H), 3.49-3.31 (m, 3H), 3.13 (m, 1H), 2.76-2.57 (m, 3H), 2.38 (m, 1H), 2.16-1.88 (m, 3H), 1.15 (m, 1H), 0.9-0.68 (m, 5H).

Example 135. 5-fluoro-N-isopropyl-N-methyl-2-(1-(1-((2-oxo-2,3-dihydro-1H-benzo[d]imidazol-5-yl)methyl)piperidin-3-yl)-2-thioxo-1,2-dihydro-3H-imidazo[4,5-c]pyridin-3-yl)benzamide

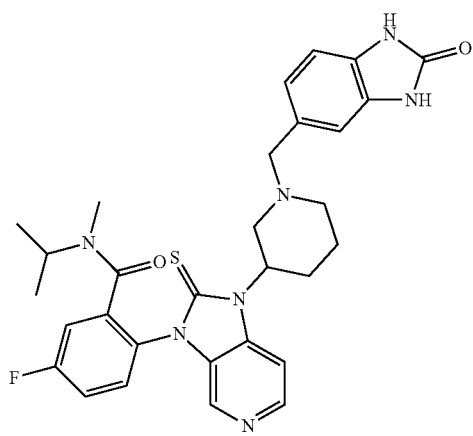 [SMILES: CC(C)N(C)C(=O)c1cc(F)ccc1-n1c(=S)n(C2CCCN(Cc3ccc4[nH]c(=O)[nH]c4c3)C2)c2ccncc21]

Step 1: tert-butyl 3-((3-nitropyridin-4-yl)amino)piperidine-1-carboxylate

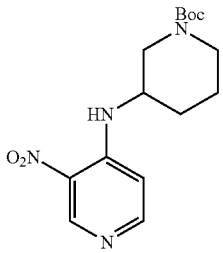 [SMILES: CC(C)(C)OC(=O)N1CCCC(Nc2ccncc2[N+](=O)[O-])C1]

A CEM 10 mL tube was charged with 4-chloro-3-nitropyridine (0.36 g, 2.3 mmol), tert-butyl 3-aminopiperidine-1-carboxylate (0.46 g, 2.3 mmol) and trimethylamine (1 mL). The resulting solution was heated in the microwave reactor at 100° C. for 90 min. Upon cooling to RT, the mixture was transferred to a separate funnel with EtOAc (~50 mL), washed with water (4×10 mL), brine (10 mL), and dried over $Na_2SO_4$. After filtration, the solvent was removed under vacuum to obtain the crude product tert-butyl 3-((3-nitropyridin-4-yl)amino)piperidine-1-carboxylate (0.7 g, 95%); LCMS method B: $R_t$=0.95 min; $(M+H)^+$=323.1.

Step 2: tert-butyl 3-((3-aminopyridin-4-yl)amino)piperidine-1-carboxylate

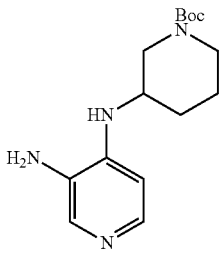

To a solution of tert-butyl 3-((3-nitropyridin-4-yl)amino)piperidine-1-carboxylate (0.7 g, 2.17 mmol) in MeOH (10 mL), was added Pd—C (50 mg); the mixture was stirred under a $H_2$ balloon at RT for 1.5 h, filtered through a Celite pad, and the filtrate was evaporated to dryness under vacuum to give tert-butyl 3-((3-aminopyridin-4-yl)amino)piperidine-1-carboxylate (0.72 g), which was used for the next step without purification. LCMS method B: $R_t$=0.75 min; $(M+H)^+$=293.3.

Step 3: tert-butyl 3-(2-thioxo-2,3-dihydro-1H-imidazo[4,5-c]pyridin-1-yl)piperidine-1-carboxylate

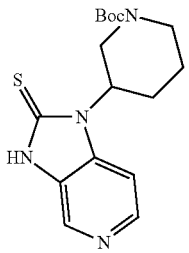 [SMILES: CC(C)(C)OC(=O)N1CCCC(n2c(=S)[nH]c3cnccc32)C1]

To a solution of tert-butyl 3-((3-aminopyridin-4-yl)amino)piperidine-1-carboxylate (167.5 mg, 0.57 mmol) in THF (6 mL), was added $Et_3N$ (250 uL) followed by di(1H-imidazol-1-yl)methanethione (123 mg, 0.68 mmol), and the resulting solution was stirred at RT overnight. The reaction mixture was then diluted with EtOAc (10 mL) and washed with water (4×10 mL). The solvent was removed and the residue was purified on a flash column to give tert-butyl 3-(2-thioxo-2,3-dihydro-1H-imidazo[4,5-c]pyridin-1-yl)piperidine-1-carboxylate (74.9 mg, 45%); LCMS method B: $R_t$=0.88 min; $(M+H)^+$=335.2.

Step 4: 2-(1-(1-(tert-butoxycarbonyl)piperidin-3-yl)-2-thioxo-1,2-dihydro-3H-imidazo[4,5-c]pyridin-3-yl)-5-fluorobenzoic acid

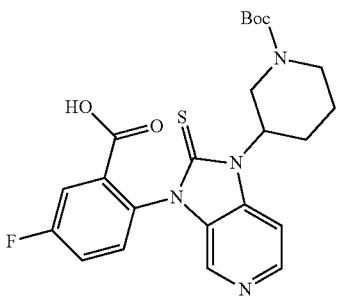 [SMILES: CC(C)(C)OC(=O)N1CCCC(n2c(=S)n(-c3ccc(F)cc3C(=O)O)c3cnccc32)C1]

To a mixture of tert-butyl 3-(2-thioxo-2,3-dihydro-1H-imidazo[4,5-c]pyridin-1-yl)piperidine-1-carboxylate (74.9 mg, 0.22 mmol), 2-bromo-5-fluorobenzoic acid (59 mg, 0.26 mmol), $Cs_2CO_3$ (110 mg, 0.33 mmol), 1,10-phenanthroline (5 mg), CuI (20 mg) in a septa sealed vial, was added DMF (2 mL) under nitrogen, and the resulting mixture was degassed for 10 min, and heated in the sealed vial at 70° C. overnight. The solvent was removed under high vacuum, the residue was slurried in EtOAc, filtered through Celite, and the Celite pad was washed with MeOH. The combined organic solvents were removed to give the crude product, which was used for the next step. LC-MS $t_R$=0.97 min.

Step 5. tert-butyl 3-(3-(4-fluoro-2-(isopropyl(methyl)carbamoyl)phenyl)-2-thioxo-2,3-dihydro-1H-imidazo[4,5-c]pyridin-1-yl)piperidine-1-carboxylate

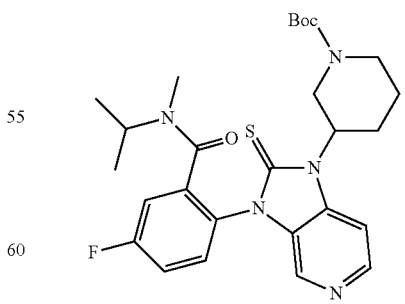

To the crude product from Step 4 was added N-methylpropan-2-amine (100 uL) and $Et_3N$ (200 uL) followed by coupling reagent BOP (50 mg), and the resulting solution was stirred at RT overnight. EtOAc was then added and the mixture was washed with water. The organic layer was evaporated under vacuum, the residue was purified through a flash column, and the product was eluted out under 10% MeOH in DCM to give tert-butyl 3-(3-(4-fluoro-2-(isopropyl(methyl)carbamoyl)phenyl)-2-thioxo-2,3-dihydro-1H-imidazo[4,5-c]pyridin-1-yl)piperidine-1-carboxylate (34.7 mg, ~30% yield from Step 4); LCMS method B: $R_t$=1.03 min; $(M+H)^+$=528.3.

Step 6. 5-fluoro-N-isopropyl-N-methyl-2-(1-(piperidin-3-yl)-2-thioxo-, 2-dihydro-3H-imidazo[4,5-c]pyridin-3-yl)benzamide

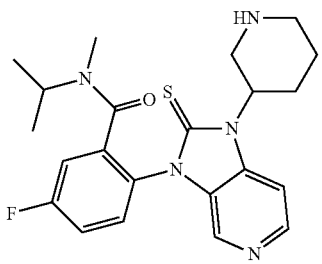 [SMILES: CC(C)N(C)C(=O)c1cc(F)ccc1-n1c(=S)n(C2CCCNC2)c2ccncc21]

To a solution of tert-butyl 3-(3-(4-fluoro-2-(isopropyl (methyl)carbamoyl)phenyl)-2-thioxo-2,3-dihydro-1H-imidazo[4,5-c]pyridin-1-yl)piperidine-1-carboxylate (34.7 mg, 0.066 mmol) in DCM (1 mL), was added TFA (200 uL); the solution was stirred at RT for 30 min, the solvent was removed and the crude product was used for the next step without purification; LCMS method B: $R_t$=0.52 min; $(M+H)^+$=428.1.

Step 7: 5-fluoro-N-isopropyl-N-methyl-2-(1-(1-((2-oxo-2,3-dihydro-1H-benzo[d]imidazol-5-yl)methyl)piperidin-3-yl)-2-thioxo-1,2-dihydro-3H-imidazo[4,5-c]pyridin-3-yl)benzamide To the solution of the crude product from Step 6 in MeOH (2 mL) was added NaOAc (14 mg), and 2-oxo-2,3-dihydro-1H-benzo[d]imidazole-5-carbaldehyde (21 mg). The resulting mixture was stirred at RT for 15 min, at which point NaCNBH$_3$ (15 mg) was added to the solution. The resulting mixture was heated at 50° C. overnight to give a clear solution, which was purified directly by preparative RP-HPLC method E to give 5-fluoro-N-isopropyl-N-methyl-2-(1-(1-((2-oxo-2,3-dihydro-1H-benzo[d]imidazol-5-yl)methyl)piperidin-3-yl)-2-thioxo-1,2-dihydro-3H-imidazo[4,5-c]pyridin-3-yl)benzamide as a TFA salt (1.20 mg); LCMS method B: $R_t$=0.54 min; $(M+H)^+$=574.6; $^1$H NMR (MeOH-d4): δ 9.01 (br, 1H), 8.51 (s, 1H), 8.21 (s, 1H), 7.74 (s, 1H), 7.38-7.04 (m, 5H), 4.65 (m, 1H), 4.48 (m, 1H), 4.31 (m, 2H), 3.83 (m, 4H), 2.87 (m, 2H), 2.52 (m, 1H), 2.15 (m, 3H), 1.99 (m, 1H), 1.32-0.82 (m, 6H).

Example 136. tert-butyl ((1r,4r)-4-(2-(3-(1-(2-(diisopropylcarbamoyl)-4-fluorophenyl)-1H-pyrrolo[2,3-c]pyridin-3-yl)azetidin-1-yl)ethyl)cyclohexyl)carbamate

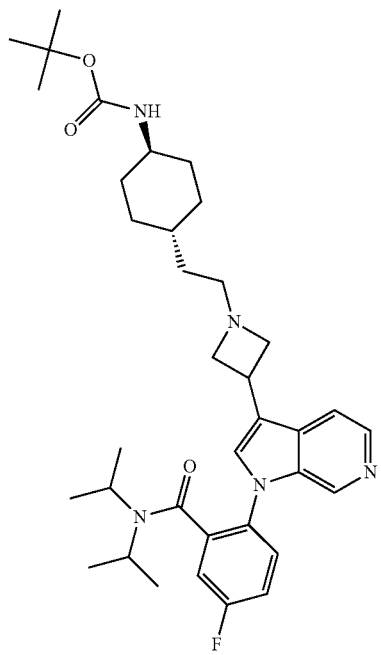 [SMILES: CC(C)N(C(=O)c1cc(F)ccc1-n1cc(C2CN(CC[C@H]3CC[C@H](NC(=O)OC(C)(C)C)CC3)C2)c2ccncc21)C(C)C]

Step 1: tert-butyl 3-(1-(2-(diisopropylcarbamoyl)-4-fluorophenyl)-1H-pyrrolo[2,3-c]pyridin-3-yl) azetidine-1-carboxylate

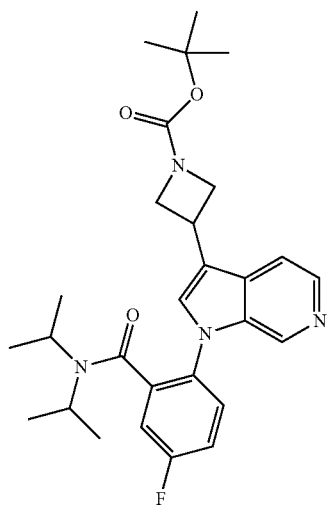 [SMILES: CC(C)N(C(=O)c1cc(F)ccc1-n1cc(C2CN(C(=O)OC(C)(C)C)C2)c2ccncc21)C(C)C]

A sealed 25 mL vial was charged with 2-(3-bromo-1H-pyrrolo[2,3-c]pyridin-1-yl)-5-fluoro-N,N-diisopropylbenzamide (Example 84, Step 3) (0.58 g, 1.39 mmol), potassium (1-(tert-butoxycarbonyl)azetidin-3-yl)trifluoroborate (0.46 g, 1.81 mmol), Ru-Phos-Pd (50.5 mg, 0.07 mmol), and K$_3$PO$_4$ (1.47 g, 6.95 mmol), and the vial was sealed and purged with nitrogen. A degassed mixture of 1,4-dioxane/ water (6 mL:2.2 mL) was added under a nitrogen atmosphere. The vial was heated at 120° C. overnight. LC-MS showed ~20 percent conversion. After cooling to RT, the mixture was transferred to a separate funnel with EtOAc (~50 mL), and washed with water (4×10 mL) and brine (10 mL). The solvent was removed under vacuum and the residue was purified by flash column (10% MeOH/DCM) to obtain tert-butyl 3-(1-(2-(diisopropylcarbamoyl)-4-fluorophenyl)-1H-pyrrolo[2,3-c]pyridin-3-yl)azetidine-1-carboxylate (120 mg, 17%), with the recovery of starting material. LCMS method B: $R_t$=1.07 min; $(M+H)^+$=495.5; $^1$H NMR (MeOH-d4): δ 8.94 (br, 1H), 8.32 (d, J=6.4 Hz, 1H), 8.31 (s, 1H), 8.18 (d, J=6.4 Hz, 1H), 7.72 (dd, J=8.4, 4.4 Hz, 1H), 7.45 (ddd, J=8.4, 8.0, 2.8 Hz, 1H), 7.37 (dd, J=8.0, 2.8 Hz, 1H), 4.47 (m, 2H), 4.19 (m, 1H), 4.04 (m, 2H), 3.64 (m, 1H), 3.34 (m, 1H), 1.44 (s, 9H), 1.37 (d, J=6.4 Hz, 3H), 1.08 (d, J=6.4 Hz, 3H), 0.79, 0.61 (two br, 6H).

Step 2: 2-(3-(azetidin-3-yl)-1H-pyrrolo[2,3-c]pyridin-1-yl)-5-fluoro-N,N-diisopropylbenzamide

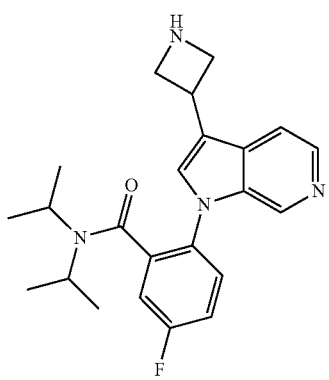 [SMILES: CC(C)N(C(=O)c1cc(F)ccc1-n1cc(C2CNC2)c2ccncc21)C(C)C]

To a solution of tert-butyl 3-(1-(2-(diisopropylcarbamoyl)-4-fluorophenyl)-1H-pyrrolo[2,3-c]pyridin-3-yl)azetidine-1-carboxylate (Example 136, 120 mg, 0.24 mmol) in DCM (2 mL), there was added TFA (100 µL). The solution was stirred at RT overnight, solvent was removed and the crude product was used for the next step without purification; LCMS method B: $R_t$=0.54 min; $(M+H)^+$=395.5.

Step 3: tert-butyl ((1r,4r)-4-(2-(3-(1-(2-(diisopropylcarbamoyl)-4-fluorophenyl)-1H-pyrrolo[2,3-c]pyridin-3-yl) azetidin-1-yl)ethyl)cyclohexyl)carbamate To the solution of the above crude product (~0.10 mmol) in MeOH (1 mL), there was added NaOAc (24 mg), tert-butyl ((1r,4r)-4-(2-oxoethyl)cyclohexyl)carbamate (36 mg, 0.15 mmol), and the resulting mixture was stirred at RT for 15 min, at which point NaCNBH$_3$ (15 mg) was added into the solution. The resulting mixture was stirred at RT for 1 h to give a clear solution, which was purified directly by preparative RP-HPLC method E to give tert-butyl ((1r,4r)-4-(2-(3-(1-(2-(diisopropylcarbamoyl)-4-fluorophenyl)-1H-pyrrolo[2,3-c]pyridin-3-yl)azetidin-1-yl)ethyl)cyclohexyl) carbamate as a TFA salt (26.3 mg); LCMS method B: $R_t$=0.87 min; $(M+H)^+$=620.7.

Example 137. 5-fluoro-N,N-diisopropyl-2-(3-(1-(2-((1r,4r)-4-(methylsulfonamido)cyclohexyl)ethyl) azetidin-3-yl)-1H-pyrrolo[2,3-c]pyridin-1-yl)benzamide

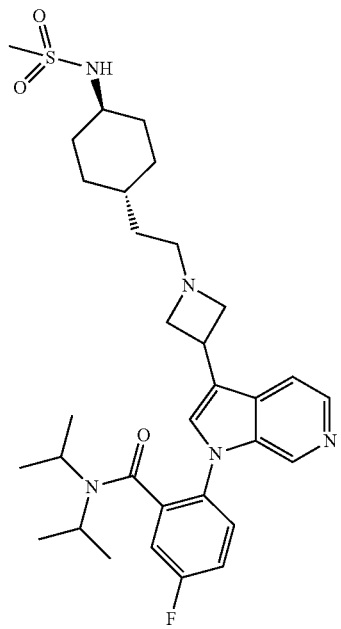 [SMILES: CC(C)N(C(=O)c1cc(F)ccc1-n1cc(C2CN(CC[C@H]3CC[C@H](NS(C)(=O)=O)CC3)C2)c2ccncc21)C(C)C]

Step 1: 2-(3-(1-(2-((1r,4r)-4-aminocyclohexyl)ethyl) azetidin-3-yl)-1H-pyrrolo[2,3-c]pyridin-1-yl)-5-fluoro-N,N-diisopropylbenzamide

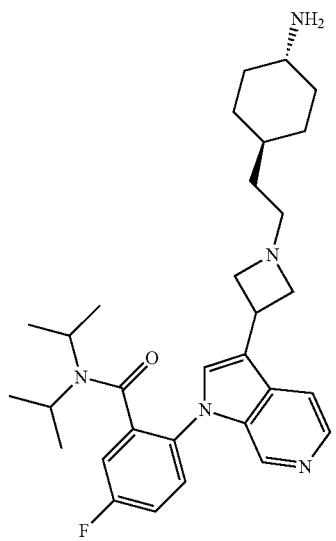 [SMILES: CC(C)N(C(=O)c1cc(F)ccc1-n1cc(C2CN(CC[C@H]3CC[C@H](N)CC3)C2)c2ccncc21)C(C)C]

To a solution of tert-butyl ((1r,4r)-4-(2-(3-(1-(2-(diisopropylcarbamoyl)-4-fluorophenyl)-1H-pyrrolo[2,3-c]pyridin-3-yl)azetidin-1-yl)ethyl)cyclohexyl)carbamate (24 mg, 0.038 mmol) in DCM (1 mL), there was added TFA (50 µL). The solution was stirred at RT overnight, the solvent was removed and the residue was dissolved in DCM (5 mL) and washed with 1 N NaOH aqueous solution. The organic layer was dried over Na$_2$SO$_4$, and concentrated in vacuum to give 2-(3-(1-(2-((1r,4r)-4-aminocyclohexyl)ethyl)azetidin-3-yl)-1H-pyrrolo[2,3-c]pyridin-1-yl)-5-fluoro-N,N-diisopropylbenzamide as a free amine, which was used for the next step without purification; LCMS method B: R$_t$=0.50 min; (M+H)$^+$=520.5.

Step 2: 5-fluoro-N,N-diisopropyl-2-(3-(1-(2-((1r,4r)-4-(methylsulfonamido)cyclohexyl)ethyl)azetidin-3-yl)-1H-pyrrolo[2,3-c]pyridin-1-yl)benzamide To a solution of the above 2-(3-(1-(2-((1r,4r)-4-aminocyclohexyl)ethyl)azetidin-3-yl)-1H-pyrrolo[2,3-c]pyridin-1-yl)-5-fluoro-N,N-diisopropylbenzamide (~18 mg) in DCM (1 mL), there was added Et$_3$N (50 μL). The resulting solution was cooled to −30° C. and methanesulfonic anhydride was added. The solution was warmed up to RT and stirred overnight. After removing the solvent, the residue was purified by preparative RP-HPLC method E to give 5-fluoro-N,N-diisopropyl-2-(3-(1-(2-((1r,4r)-4-(methylsulfonamido)cyclohexyl)ethyl)azetidin-3-yl)-1H-pyrrolo[2,3-c]pyridin-1-yl)benzamide as a TFA salt; LCMS method B: R$_t$=0.67 min; (M+H)$^+$=598.7.

Example 138. 5-fluoro-N,N-diisopropyl-2-(3-(1-(((1r,4r)-4-(methylsulfonamido)cyclohexyl)methyl)azetidin-3-yl)-1H-pyrrolo[2,3-c]pyridin-1-yl)benzamide

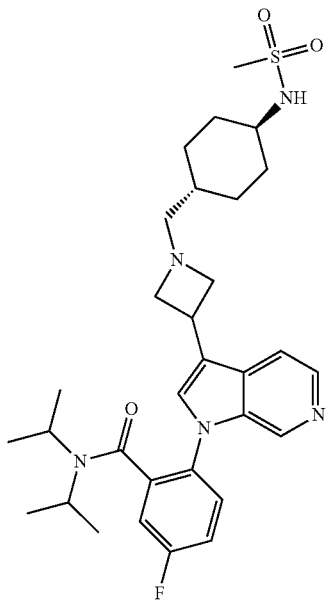 [SMILES: CC(C)N(C(=O)c1cc(F)ccc1-n1cc(C2CN(C[C@H]3CC[C@H](NS(C)(=O)=O)CC3)C2)c2ccncc21)C(C)C]

The title compound was synthesized according to the method described in Example 136, Step 3, starting with 2-(3-(azetidin-3-yl)-1H-pyrrolo[2,3-c]pyridin-1-yl)-5-fluoro-N,N-diisopropylbenzamide (0.05 mmol) and tert-butyl ((1r,4r)-4-formylcyclohexyl)carbamate (14 mg). The product was purified by preparative RP-HPLC method E to give 5-fluoro-N,N-diisopropyl-2-(3-(1-(((1r,4r)-4-(methylsulfonamido)cyclohexyl)methyl)azetidin-3-yl)-1H-pyrrolo[2,3-c]pyridin-1-yl)benzamide as a TFA salt; LCMS method B: R$_t$=0.63 min; (M+H)$^+$=584.6.

Examples 139-139A. 5-fluoro-N,N-diisopropyl-2-(3-(4-(2-(methylsulfonamido)-6-azaspiro[3.4]octan-6-yl)cyclohexyl)-1H-pyrrolo[2,3-c]pyridin-1-yl)benzamide (Isomers 1-2)

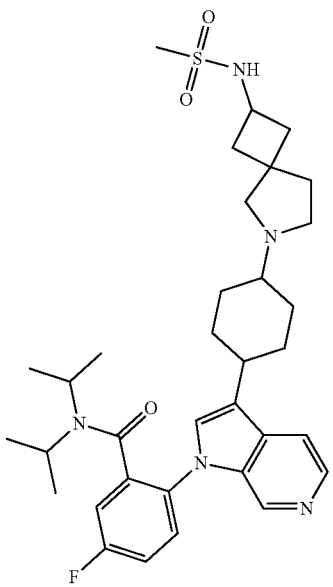 [SMILES: CC(C)N(C(=O)c1cc(F)ccc1-n1cc(C2CCC(N3CCC4(CC(NS(C)(=O)=O)C4)C3)CC2)c2ccncc21)C(C)C]

Step 1: N-((2s, 4r)-6-azaspiro[3.4]octan-2-yl)methanesulfonamide

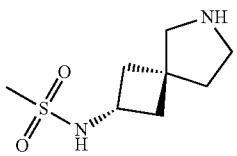

1.0 mmol of tert-butyl (2s,4r)-2-amino-6-azaspiro[3.4]octane-6-carboxylate was reacted with methanesulfonic anhydride (1.0 mmol) in pyridine/DCM (5 mL, 1:10) at RT for 30 min. Water was added and the product was separated into DCM, washed with brine and dried over anhydrous sodium sulfate and the solvent was removed under reduced pressure. The crude product was treated with 1.0 mL of TFA at RT for 2 h and excess TFA was removed.

Step 2. 5-fluoro-N,N-diisopropyl-2-(3-(4-(2-(methylsulfonamido)-6-azaspiro[3.4]octan-6-yl)cyclohexyl)-1H-pyrrolo[2,3-c]pyridin-1-yl)benzamide (Isomers 1-2)

The title compound was synthesized by the method described in step 2 of Example 1, starting from Intermediate 17B and N-((2s,4r)-6-azaspiro[3.4]octan-2-yl)methanesulfonamide. The two isomers were separated by SFC method A.

Example 139 (Isomer 1): LCMS method D: R$_t$=1.254 min; (M+H)$^+$=624.3.

Example 139A (Isomer 2): LCMS method D: R$_t$=1.284 min; (M+H)$^+$=624.3.

Example 140. 5-fluoro-N,N-diisopropyl-2-(3-(1-((2-oxo-2,3-dihydrobenzo[d]oxazol-5-yl)methyl)pyrrolidin-3-yl)-1H-pyrrolo[2,3-c]pyridin-1-yl)benzamide

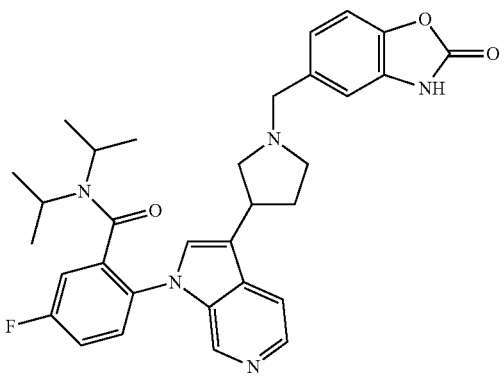 [SMILES: CC(C)N(C(=O)c1cc(F)ccc1-n1cc(C2CCN(Cc3ccc4oc(=O)[nH]c4c3)C2)c2ccncc21)C(C)C]

The title compound was synthesized by the method described in Example 1, starting from Intermediate 4 and 5-benzoxazolecarboxaldehyde, 2,3-dihydro-2-oxo-. LCMS method B: $t_R$: 0.817 min; (M+H)$^+$=556.3.

Example 141. 5-Fluoro-N-isopropyl-N-methyl-2-(3-(1-((2-oxo-2,3-dihydro-1H-benzo[d]imidazol-5-yl)methyl)piperidin-3-yl)-1H-pyrrolo[2,3-c]pyridin-1-yl)benzamide mono-(2R,3S,4R,5S)-2,3,4,5-tetrahydroxyhexanedioic acid (mucate) salt

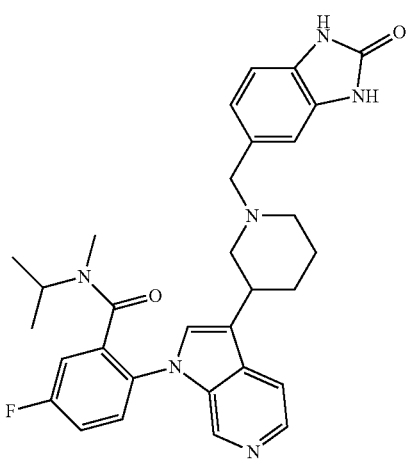

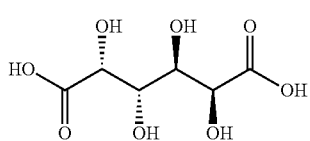

Step 1. tert-butyl 5-(1H-pyrrolo[2,3-c]pyridin-3-yl)-3,4-dihydropyridine-1(2H)-carboxylate and tert-butyl 5-(1H-pyrrolo[2,3-c]pyridin-3-yl)-3,6-dihydropyridine-1(2H)-carboxylate

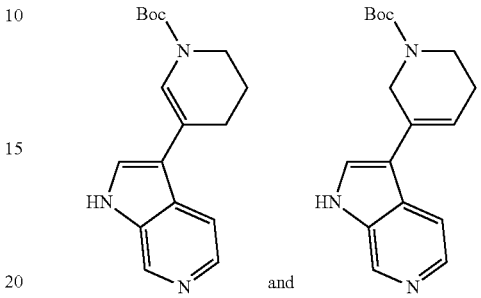

To a solution of 1H-pyrrolo[2,3-c]pyridine (70 g, 0.59 mol) in MeOH (1,050 mL) and H$_2$O (350 mL) was added KOH (83 g, 1.48 mol) and tert-butyl 3-oxopiperidine-1-carboxylate (259 g, 1.30 mol). The resulting mixture was stirred at 75-80° C. (oil bath temperature) for 18 h. The reaction mixture was concentrated under reduced pressure to remove MeOH, then H$_2$O (700 mL) was added and the mixture was extracted with EtOAc (3×1000 mL). The organic layers were filtered and the filtered cake was washed with EtOAc (2×150 mL) to afford tert-butyl 5-(1H-pyrrolo[2,3-c]pyridin-3-yl)-3,4-dihydropyridine-1(2H)-carboxylate (75 g, 42% yield) as white solid. The organic layer was concentrated under reduced pressure to about 250 mL. The residue was stirred at 5-9° C. for 18 h. The residue was filtered and the filtered cake was washed with EtOAc (2×60 mL) to give a mixture of tert-butyl 5-(1H-pyrrolo[2,3-c]pyridin-3-yl)-3,6-dihydropyridine-1(2H)-carboxylate and tert-butyl 5-(1H-pyrrolo[2,3-c]pyridin-3-yl)-3,4-dihydropyridine-1(2H)-carboxylate (1:3.5 via LCMS; (28 g, 16% yield) as white solid.

tert-butyl 5-(1H-pyrrolo[2,3-c]pyridin-3-yl)-3,4-dihydropyridine-1 (2H)-carboxylate: Yield: 75 g (42%); $R_f$ value: 0.570 (LCMS Method C); (M+H)$^+$=300.1; $^1$H NMR (MeOD, 400 MHz): δ ppm 8.65-8.70 (d, J=2.8 Hz, 1H), 8.05-8.15 (d, J=5.6 Hz, 1H), 7.70-7.90 (m, 1H), 7.54 (s, 1H), 7.35-7.50 (m, 1H), 3.60-3.75 (m, 2H), 2.50-2.60 (t, J=5.6 Hz, 2H), 2.00-2.10 (m, 2H), 1.55-1.60 (m, 9H).

Mixture of tert-butyl 5-(1H-pyrrolo[2,3-c]pyridin-3-yl)-3,6-dihydropyridine-1(2H)-carboxylate and tert-butyl 5-(1H-pyrrolo[2,3-c]pyridin-3-yl)-3,4-dihydropyridine-1 (2H)-carboxylate: $R_f$ value: 0.568 (LCMS Method C); (M+H)$^+$=300.1.

Step 2. 2-(3-(1-(tert-butoxycarbonyl)-1,4,5,6-tetra-hydropyridin-3-yl)-1H-pyrrolo[2,3-c]pyridin-1-yl)-5-fluorobenzoic acid and 2-(3-(1-(tert-butoxycarbonyl)-1,2,5,6-tetrahydropyridin-3-yl)-1H-pyrrolo[2,3-c]pyridin-1-yl)-5-fluorobenzoic acid

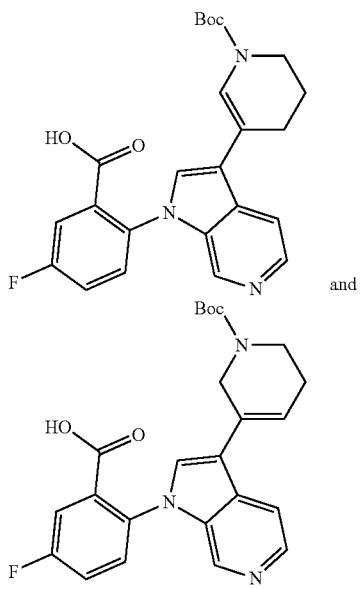

and

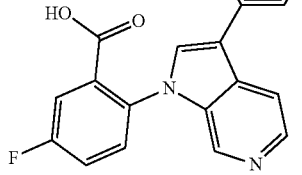

A suspension of tert-butyl 5-(1H-pyrrolo[2,3-c]pyridin-3-yl)-3,4-dihydropyridine-1(2H)-carboxylate and tert-butyl 5-(1H-pyrrolo[2,3-c]pyridin-3-yl)-3,6-dihydropyridine-1(2H)-carboxylate (1 g, 3.34 mmol, ~10:1 ratio of isomers), 5-fluoro-2-iodobenzoic acid (977 mg, 3.67 mmol), $K_2CO_3$ (1.15 g, 8.33 mmol), CuI (63 mg, 0.334 mmol) and 1,10-phenanthroline (60 mg, 0.334 mmol) in DMF (13 mL, 0.26 M reaction concentration) was degassed with $N_2$ for 15 min. The reaction mixture was then placed under $N_2$ and heated to 70° C. for 24 h. The reaction was then cooled to room temperature and filtered through a plug of Celite® using a small amount of DMF to rinse the filter cake. The DMF solution was cooled to 0° C. and a 1N aq. HCl solution (~10 mL) was added, maintaining a pH of ~5, followed by the addition of $H_2O$ (~10 mL) and EtOAc for the extraction. The EtOAc layer was separated and the aqueous layer (pH-5) was extracted three additional times with EtOAc. The EtOAc layers were combined and washed with $H_2O$ followed by brine. After drying over $Na_2SO_4$, the EtOAc layer was evaporated and the resulting residue was dried under high vacuum overnight to afford ~2 grams of crude 2-(3-(1-(tert-butoxycarbonyl)-1,4,5,6-tetrahydropyridin-3-yl)-1H-pyrrolo[2,3-c]pyridin-1-yl)-5-fluorobenzoic acid and 2-(3-(1-(tert-butoxycarbonyl)-1,2,5,6-tetrahydropyridin-3-yl)-1H-pyrrolo[2,3-c]pyridin-1-yl)-5-fluorobenzoic acid (>10:1 ratio of isomers). The crude material was used directly for the next step without further purification. LCMS: 5.748 min (LCMS Method G): 438.47 (M+1). $^1$H NMR (400 MHz, $CDCl_3$): δ 8.52-8.48 (m, 1H), 8.20-8.15 (m, 1H), 8.07 (bs, 1H), 8.01 (s, 1H), 7.85 (d, 1H, J=8.4 Hz), 7.76 (s, 1H), 7.55 (bs, 1H), 7.42 (d, 1H, J=5.2 Hz), 3.67 (bs, 2H), 2.50-2.47 (m, 2H), 2.06-2.01 (m, 2H), 1.54 (s, 9H).

Step 3. tert-butyl 5-(1-(4-fluoro-2-(isopropyl (methyl) carbamoyl)phenyl)-1H-pyrrolo[2,3-c]pyridin-3-yl)-3,4-dihydropyridine-1 (2H)-carboxylate

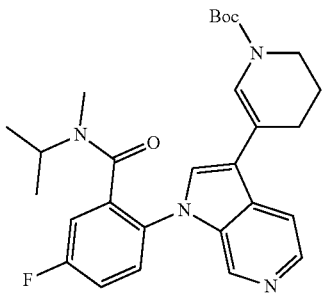 [SMILES: CC(C)N(C)C(=O)c1cc(F)ccc1-n1cc(C2=CN(C(=O)OC(C)(C)C)CCC2)c2ccncc21]

To a solution of the crude mixture from Step 2, (3.34 mmol), N-methylpropan-2-amine (731 mg, 10.02 mmol) and $iPr_2NEt$ (1.74 mL, 10.02 mmol) in EtOAc (9 mL) was added a 50 wt % solution of T3P in EtOAc (6 mL, 10.02 mmol) dropwise at ~10° C. The reaction was stirred for 2 h, cooled to 0° C., and a 1N aq. NaOH solution (~10 mL) was slowly added. The EtOAc layer was separated and the aqueous layer was extracted twice with EtOAc. The EtOAc layers were combined and washed with sat. $NH_4Cl$, $H_2O$, and then brine. After drying over $Na_2SO_4$, the EtOAc layer was evaporated to afford 1.65 grams of crude tert-butyl 5-(1-(4-fluoro-2-(isopropyl(methyl)carbamoyl)phenyl)-1H-pyrrolo[2,3-c]pyridin-3-yl)-3,4-dihydropyridine-1(2H)-carboxylate (purity: ~90% based on LCMS analysis). This material was used directly for the next step without further purification. LCMS: 6.247 min (LCMS Method G); 493.55 (M+1). $^1$H NMR (400 MHz, $CDCl_3$) The title compound was observed as a mixture of rotamers by NMR, the major rotamer isomer peaks were tabulated and are provided: δ 8.07-8.68 (m, 1H), 8.35-8.32 (m, 1H), 7.88 (d, 1H, J=5.2 Hz), 7.62 (bs, 1H), 7.55-7.52 (m, 1H), 7.43-7.41 (m, 1H), 7.29-7.18 (m, 2H), 4.65-4.75 (m, 1H), 3.60-3.65 (m, 2H), 2.69 (s, 3H), 2.40-2.45 (m, 2H), 1.90-2.00 (m, 2H), 1.57 (s, 9H), 0.95-0.94 (m, 3H), 0.56-0.59 (m, 3H).

Step 4. 5-fluoro-2-(3-(2-hydroxypiperidin-3-yl)-1H-pyrrolo[2,3-c]pyridin-1-yl)-N-isopropyl-N-methyl-benzamide and 5-fluoro-N-isopropyl-N-methyl-2-(3-(1,2,5,6-tetrahydropyridin-3-yl)-1H-pyrrolo[2,3-c]pyridin-1-yl)benzamide

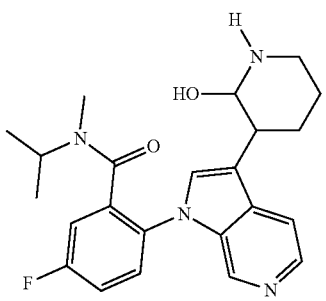

and

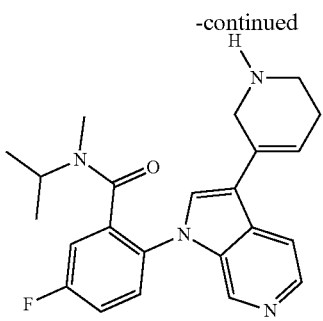

To a solution of crude tert-butyl 5-(1-(4-fluoro-2-(isopropyl(methyl)carbamoyl)phenyl)-1H-pyrrolo[2,3-c]pyridin-3-yl)-3,4-dihydropyridine-1(2H)-carboxylate (Step 3, 550 mg, 1.01 mmol, >10:1 ratio of piperidine olefin isomers) in MeOH (5 mL) was added conc. HCl (0.50 mL) slowly at room temperature. The reaction was heated at 40° C. for 4 h. LCMS showed deprotection of BOC group from the starting material and the formation of hemi-aminal 5-fluoro-2-(3-(2-hydroxypiperidin-3-yl)-1H-pyrrolo[2,3-c]pyridin-1-yl)-N-isopropyl-N-methylbenzamide and 5-fluoro-N-isopropyl-N-methyl-2-(3-(1,2,5,6-tetrahydropyridin-3-yl)-1H-pyrrolo[2,3-c]pyridin-1-yl)benzamide from the >10:1 ratio of olefin isomers in the starting material. The solvents were removed to afford a mixture of the hydrochloric acid salts of 5-fluoro-2-(3-(2-hydroxypiperidin-3-yl)-1H-pyrrolo[2,3-c]pyridin-1-yl)-N-isopropyl-N-methylbenzamide and 5-fluoro-N-isopropyl-N-methyl-2-(3-(1,2,5,6-tetrahydropyridin-3-yl)-1H-pyrrolo[2,3-c]pyridin-1-yl)benzamide as a glassy foam material. This crude material was used directly for the next step without further purification. LCMS: 1.68 min (LCMS Method G):

5-fluoro-2-(3-(2-hydroxypiperidin-3-yl)-1H-pyrrolo[2,3-c]pyridin-1-yl)-N-isopropyl-N-methylbenzamide (M+1): 411.18.

5-fluoro-N-isopropyl-N-methyl-2-(3-(1,2,5,6-tetrahydropyridin-3-yl)-1H-pyrrolo[2,3-c]pyridin-1-yl)benzamide (M+1): 393.15.

Step 5. 5-fluoro-N-isopropyl-N-methyl-2-(3-(piperidin-3-yl)-1H-pyrrolo[2,3-c]pyridin-1-yl)benzamide hydrochloric acid salt

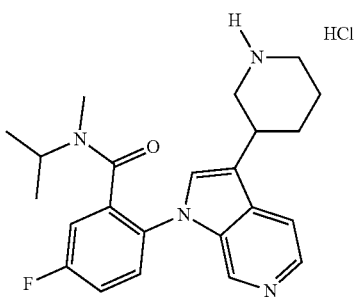 [SMILES: CC(C)N(C)C(=O)c1cc(F)ccc1-n1cc(C2CCCNC2)c2ccncc21 ; Cl]

A suspension of the crude product from Step 4 (1.10 mmol) and 5 mol % Pd/C (100 mg, 50% H$_2$O) in EtOH (4 mL, 0.25 M reaction concentration) was evacuated and backfilled with an H$_2$ balloon twice. The suspension was placed under 1 atm of H$_2$ and heated between 40° C. and 45° C. for 15 h. The reaction mixture was filtered through Celite® and evaporated to give a glassy foam. This HCl salt material was triturated with IPAC to afford an off-white solid (450 mg; ~86% purity by LCMS). LCMS: 1.68 min (LCMS Method G); (M+1): 395.25. $^1$H NMR (400 MHz, CD$_3$OD) the title compound was observed as a mixture of rotamers by NMR; the major rotamer isomer peaks were tabulated and are described provided: δ 8.62 (s, 1H), 8.53 (s, 1H), 8.20-8.16 (m, 1H), 7.74 (d, 1H, J=5.6 Hz), 7.66-7.65 (m, 1H), 7.44-7.36 (m, 1H), 7.37 (s, 1H), 7.34 (d, 1H, J=2.4 Hz), 4.49-4.42 (m, 1H), 3.10 (bs, 1H), 3.11-3.04 (m, 2H), 2.68-2.59 (m, 2H), 2.44 (s, 3H), 2.15 (bs, 1H), 1.84-1.68 (m, 3H), 1.00 (d, 3H, J=6.4 Hz), 0.20 (d, 3H, J=6.4 Hz).

Step 6. 5-fluoro-N-isopropyl-N-methyl-2-(3-(piperidin-3-yl)-1H-pyrrolo[2,3-c]pyridin-1-yl)benzamide (Free Base)

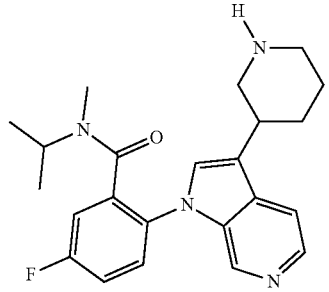 [SMILES: CC(C)N(C)C(=O)c1cc(F)ccc1-n1cc(C2CCCNC2)c2ccncc21]

To a suspension of 5-fluoro-N-isopropyl-N-methyl-2-(3-(piperidin-3-yl)-1H-pyrrolo[2,3-c]pyridin-1-yl)benzamide hydrochloric acid salt (4.36 g, 9.33 mmol) in MeCN (50 mL) was added K$_2$CO$_3$ (5.59 g, 40.4 mmol). The mixture was stirred for 30 min and filtered, and washed with MeCN. The filtrate was concentrated to afford 5.84 g of 5-fluoro-N-isopropyl-N-methyl-2-(3-(piperidin-3-yl)-1H-pyrrolo[2,3-c]pyridin-1-yl)benzamide bis-carbonate salt as light colored solid.

The bis-carbonate salt (4.28 g, 8.25 mmol) was suspended in EtOAc (50 mL) and 1 M NaOH aqueous solution (30 mL) was added. The mixture was stirred for 10 min and the organic phase was separated and washed with brine (3×30 mL), and dried over anhydrous Na$_2$SO$_4$, and filtered. The filtrate was concentrated to afford 3.01 g of 5-fluoro-N-isopropyl-N-methyl-2-(3-(piperidin-3-yl)-1H-pyrrolo[2,3-c]pyridin-1-yl)benzamide as an off-white foam.

Step 7. 5-fluoro-N-isopropyl-N-methyl-2-(3-(1-((2-oxo-2,3-dihydro-1H-benzo[d]imidazol-5-yl)methyl)piperidin-3-yl)-1H-pyrrolo[2,3-c]pyridin-1-yl)benzamide

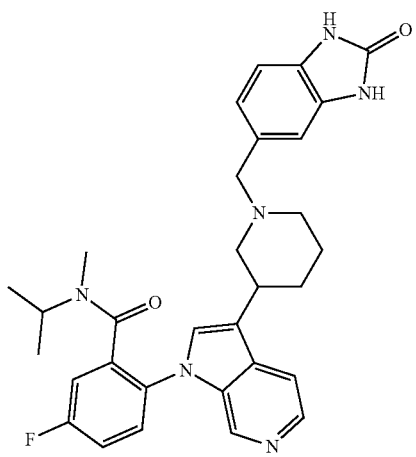 [SMILES: CC(C)N(C)C(=O)c1cc(F)ccc1-n1cc(C2CCCN(Cc3ccc4[nH]c(=O)[nH]c4c3)C2)c2ccncc21]

To a solution of 5-fluoro-N-isopropyl-N-methyl-2-(3-(piperidin-3-yl)-1H-pyrrolo[2,3-c]pyridin-1-yl)benzamide (555 mg, 1.407 mmol), 2-oxo-2,3-dihydro-1H-benzo[d]imidazole-5-carbaldehyde (273 mg, 1.688 mmol) in EtOAc/DMF (5/5 mL) was added TFA (209 mL, 2.814 mmol, 2 eq.) and the mixture was stirred for 10 min before NaBH(OAc)$_3$ (745 mg, 3.158 mmol, 2.5 eq.) was added. The mixture was heated at 50° C. under N$_2$ atmosphere for 2.5 days, and EtOAc was then removed from the reaction mixture under reduced pressure. 6 M HCl/H$_2$O (3 mL) was added to the residue and the mixture was stirred at 90° C. for 16 h. The reaction mixture was then cooled to RT, and extracted with EtOAc (30 mL each time) until no solid precipitated out between aqueous and organic phase. The aqueous phase was basified with aq. NaOH to a pH ~10. Brine (30 mL) was added, and the mixture was extracted with EtOAc (100 mL) containing MeOH (10 mL). The separated organic phase was washed with brine (3×30 mL), dried over anhydrous Na$_2$SO$_4$, and filtered. The filtrate was concentrated to afford 681 mg of 5-fluoro-N-isopropyl-N-methyl-2-(3-(1-((2-oxo-2,3-dihydro-1H-benzo[d]imidazol-5-yl)methyl)piperidin-3-yl)-1H-pyrrolo[2,3-c]pyridin-1-yl)benzamide as off-white foam (Yield 89%; Purity ≥99%) LCMS t$_R$=7.25 min (LCMS Method G). $^1$H NMR (400 MHz, CD$_3$OD): δ 8.62 and 8.54 (m, 1H), 8.17 (m, 1H), 7.67 (m, 2H), 7.47-7.33 (m, 3H), 7.10 (s, 1H), 7.05-6.98 (m, 2H), 4.36 (m, 0.5H), 3.72-3.52 (m, 2.5H), 3.21-2.88 (m, 3.5H), 2.68 (m, 1.5H), 2.57-2.47 (m, 1.5H), 2.17-2.10 (m, 3.5H), 1.85 (m, m, 2.5H), 1.57 (m, 1H), 1.00 (m, 2.5H), 0.37 (m, 1H), 0.13 (m, 1H).

Step 8. 5-fluoro-N-isopropyl-N-methyl-2-(3-(1-((2-oxo-2,3-dihydro-1H-benzo[d]imidazol-5-yl)methyl)piperidin-3-yl)-1H-pyrrolo[2,3-c]pyridin-1-yl)benzamide (2R,3S,4R,5S)-2,3,4,5-tetrahydroxyhexanedioic acid (mucate) salt To 5-fluoro-N-isopropyl-N-methyl-2-(3-(1-((2-oxo-2,3-dihydro-1H-benzo[d]imidazol-5-yl)methyl)piperidin-3-yl)-1H-pyrrolo[2,3-c]pyridin-1-yl)benzamide (Step 7, 681 mg, 1.26 mmol) was added (2R,3S,4R,5S)-2,3,4,5-tetrahydroxyhexanedioic acid (i.e., mucic acid; 265 mg, 1.26 mmol), deionized H$_2$O (4 mL), and EtOH (1 mL). The mixture was heated at 80-90° C. until a clear solution was achieved. The solution was cooled to RT and EtOH (7 mL) was added slowly with stirring (300 r/min). The mixture was stirred at RT for 24 h, then filtered through a filter paper. The cake was washed with H$_2$O/EtOH (1/2, v/v, 20 mL), EtOH (10 mL), and Et$_2$O (10 mL) successively. The resulting cake was collected and dried to afford 774 mg of desired product as 5-fluoro-N-isopropyl-N-methyl-2-(3-(1-((2-oxo-2,3-dihydro-1H-benzo[d]imidazol-5-yl)methyl)piperidin-3-yl)-1H-pyrrolo[2,3-c]pyridin-1-yl)benzamide (2R,3 S,4R,5S)-2,3,4,5-tetrahydroxyhexanedioic acid salt (1:1). Yield 81.8%; Purity 99.9%. $^1$H NMR (400 MHz, D$_2$O): δ 8.85 and 8.76 (br, 1H), 8.30 (m, 1H), 8.16 (m, 1H), 7.96 (m, 1H), 7.72 (m, 1H), 7.52 (m, 1H), 7.41 (m, 1H), 7.28-7.23 (m, 3H), 4.61-4.51 (m, 1H), 4.38 (m, 1H), 4.33 (s, 2H), 3.97 (s, 2H), 3.73-3.40 (m, 4H), 3.18 (m, 2H), 2.49 (m, 3H), 2.31-2.17 (m, 3H), 2.03 (m, 1H), 1.87 (m, 1H), 1.02-0.98 (m, 3H), 0.19 (m, 2H).

The X-ray powder diffraction (XRPD) pattern was determined for representative samples of the crystalline 5-fluoro-N-isopropyl-N-methyl-2-(3-(1-((2-oxo-2,3-dihydro-1H-benzo[d]imidazol-5-yl)methyl)piperidin-3-yl)-1H-pyrrolo[2,3-c]pyridin-1-yl)benzamide (2R,3S,4R,5S)-2,3,4,5-tetrahydroxyhexanedioic acid salt (XRPD Method A), and is shown in FIG. 1. It was found that the XRPD patterns for the representative samples were essentially identical and exhibited discreet crystalline peaks. A representative list of 2-theta peaks is provided in Table 14.

TABLE 14

| Peak No. | 2-theta (°) | Rel. Height (%) |
|---|---|---|
| 1 | 7.2 | 83.1 |
| 2 | 7.9 | 7.6 |
| 3 | 9.2 | 10.8 |
| 4 | 11.4 | 28.9 |
| 5 | 11.9 | 16.7 |
| 6 | 12.4 | 35.7 |
| 7 | 14.3 | 15.7 |
| 8 | 14.5 | 29.7 |
| 9 | 15.0 | 1.8 |
| 10 | 15.7 | 31.8 |
| 11 | 16.2 | 32.4 |
| 12 | 16.8 | 29.4 |
| 13 | 17.6 | 50.6 |
| 14 | 18.0 | 24.4 |
| 15 | 18.4 | 40.9 |
| 16 | 18.8 | 31.8 |
| 17 | 19.3 | 7.6 |
| 18 | 19.4 | 6.4 |
| 19 | 19.8 | 4.6 |
| 20 | 20.4 | 15.7 |
| 21 | 20.9 | 40.6 |
| 22 | 21.6 | 45.9 |
| 23 | 21.8 | 100.0 |
| 24 | 22.2 | 1.7 |
| 25 | 22.7 | 7.9 |
| 26 | 22.9 | 11.8 |
| 27 | 23.3 | 2.7 |
| 28 | 23.4 | 8.3% |
| 29 | 23.9 | 58.8% |
| 30 | 24.4 | 32.5% |
| 31 | 24.6 | 43.7 |
| 32 | 24.8 | 43.7 |
| 33 | 25.5 | 3.2 |
| 34 | 26.5 | 9.2 |
| 35 | 27.6 | 9.0 |
| 36 | 27.8 | 16.5 |
| 37 | 28.0 | 23.4 |
| 38 | 28.8 | 2.5 |
| 39 | 29.2 | 1.3 |
| 40 | 29.5 | 1.5 |

TABLE 14-continued

| Peak No. | 2-theta (°) | Rel. Height (%) |
|---|---|---|
| 41 | 29.9 | 33.0 |
| 42 | 30.2 | 11.4 |
| 43 | 30.6 | 7.3 |
| 44 | 31.7 | 4.6 |
| 45 | 32.5 | 2.4 |
| 46 | 32.9 | 2.0 |
| 47 | 33.4 | 1.3 |
| 48 | 34.4 | 4.4 |
| 49 | 35.0 | 9.7 |
| 50 | 35.4 | 1.5 |
| 51 | 36.2 | 2.3 |
| 52 | 36.4 | 2.9 |
| 53 | 37.3 | 12.3 |
| 54 | 38.2 | 2.5 |
| 55 | 38.8 | 1.8 |
| 56 | 39.1 | 0.8 |
| 57 | 39.8 | 1.9 |
| 58 | 40.0 | 3.8% |
| 59 | 40.7 | 2.1% |
| 60 | 41.6 | 2.8% |

Example 142. Crystalline Response Analysis

A percent crystalline response was determined for two representative samples (Sample A and Sample B) of 5-fluoro-N-isopropyl-N-methyl-2-(3-(1-((2-oxo-2,3-dihydro-1H-benzo[d]imidazol-5-yl)methyl)piperidin-3-yl)-1H-pyrrolo[2,3-c]pyridin-1-yl)benzamide (2R,3S,4R,5 S)-2,3,4,5-tetrahydroxyhexanedioic acid salt described in Example 141. In X-ray powder diffraction data, the presence of crystalline material is indicated by the presence of sharp well defined diffraction peaks. The percent crystalline response is essentially the total diffraction signal contained in all the crystalline peaks expressed as a percentage with respect to the total diffraction signal from the sample. To determine the diffraction response from the sample, the measured data were first pre-processed by removing the instrumental background and then normalized to a common area. The pre-processed data were then passed through two digital filters, one to remove the Compton and thermal diffuse scattering and the other to remove the non-crystalline sample response from the pattern. The percentage of the total normalized intensity remaining after passing the data through the digital filters indicates the percentage of perfect crystalline material in the sample. The percent crystalline response values determined using the digital filter are summarized in Table 15. These numbers do not include defected crystalline material and, as a result, are not the absolute percent crystallinity value for the sample. The percent crystallinity values as provided in Table 15, allow for relative comparison of percent crystallinity between samples containing the same crystalline polymorph.

TABLE 15

| Sample | Percent Crystallinity (%) |
|---|---|
| A | 87.0 |
| B | 79.9 |

Biological Assays
Assay 1 (Binding Assay)

Potencies of inhibitor compounds against menin/MLL binding were assessed by AlphaLISA assay using biotinylated (1) wild-type menin or (2) mutated menin (described in Nature (2012) Vol. 482, pp. 542-548) and MLL-AF9 fusion protein bearing a FLAG epitope at its C-terminus. Menin proteins were expressed in E. coli and covalently modified with biotin using EZ-Link™ Sulfo-NHS-Biotin (ThermoFisher Cat. No. 21217) according to manufacturer's protocol. MLL1-1,396 fused to AF91-92 and the C-terminal FLAG peptide was expressed in HEK293 cells and used as a lysate cleared at 21,000×g for 10 min.

Compounds (2 µL of solutions in DMSO) were dispensed in white 96-well half-area plates (Corning Cat. No. 3693) and incubated for 30 min at RT with 5 nM biotinylated menin and appropriate amount of MLL-AF9-FLAG lysate in 40 µL of 50 mM Tris-HCl buffer pH 7.4 containing 5% (v/v) DMSO, 50 mM NaCl, 0.01% (w/v) bovine serum albumin (BSA) and 1 mM DTT. To this incubation mixture, 40 µl of AlphaLISA anti-FLAG acceptor (PerkinElmer Cat. No. AL112C) and streptavidin donor (PerkinElmer Cat. No. 6760002) beads (10 µg/mL each) was added and incubation continued at RT for 60 min. Alpha (amplified luminescent proximity homogeneous assay) signal was measured on an Envision multi-label plate reader at the end of the incubation. All steps were conducted under dim fluorescent light.

Percent inhibition values were calculated based on uninhibited (DMSO) and fully inhibited (10 µM MI-2-2, EMD Millipore Cat. No. 444825) controls. These percent inhibition values were regressed against compound concentrations in the assay using four parameter logit non-linear curve fitting (XLFit, IDBS). The $IC_{50}$ values were derived from the curve fitting as inflection points on the dose-response curves and are set out in Table 14 below.

Assay 2: (Cell Proliferation Assay)

Potencies of inhibitor compounds against cell proliferation was assessed against the human acute monocytic leukemia cell line MV-4-11 (ATCC® CRL-9591™) based on ATP quantitation. MV-4-11 cells or toxicity control HL-60 cells (ATCC® CCL-240™) were incubated in 96-well tissue culture plates ($1.67 \times 10^4$ cells in 200 µL culture media containing 10% FBS per well) with or without test compound for 72 h at 37° C., 5% $CO_2$. After incubation, each well was mixed by pipetting and 95 µL from each well was transferred to a well in 96-well black OptiPlate® plates (PerkinElmer). An equal volume of CellTiter-Glo® Luminescent Cell Viability Assay reagent (Promega) was added to each well, followed by mixing for 5 min on an orbital plate shaker. Luminescence was measured on a Wallac EnVision 2104 Multilabel Reader (PerkinElmer) to quantitate ATP. Percent inhibition of cell proliferation by test compounds was calculated based on uninhibited cell growth (DMSO) versus cells treated with a potent menin inhibitor at a concentration yielding at least $100 \times LD_{50}$. $EC_{50}$ values were calculated based on dose response curves of percent inhibition versus compound concentration and are set out in Table 14 below.

Data for Assays 1 and 2 are provided below in Table 14 ("n/a" refers to data not available; "+++" means <100 nM; "++" means ≥100 nM and <1000 nM; and "+" means ≥1000 nM).

TABLE 14

| Example | Assay 1 | Assay 2 |
|---|---|---|
| Int. 1 | ++ | n/a |
| Int. 2 | + | n/a |
| Int. 10 | + | n/a |
| Int. 13 | ++ | n/a |
| Int. 17A | + | n/a |
| Int. 17B | + | n/a |
| Int. 17C | ++ | n/a |

TABLE 14-continued

| Example | Assay 1 | Assay 2 |
|---|---|---|
| 1 | +++ | +++ |
| 2 | +++ | +++ |
| 3 | +++ | ++ |
| 4 | +++ | + |
| 5 | +++ | ++ |
| 6 | +++ | ++ |
| 7 | +++ | +++ |
| 8 | +++ | +++ |
| 9 | +++ | ++ |
| 10 | +++ | ++ |
| 11 | +++ | n/a |
| 12 | +++ | ++ |
| 13 | ++ | n/a |
| 14 | +++ | ++ |
| 15 | +++ | ++ |
| 16 | +++ | ++ |
| 17 | ++ | n/a |
| 18 | +++ | ++ |
| 18A | +++ | ++ |
| 19 | +++ | +++ |
| 20 | +++ | ++ |
| 30A | +++ | + |
| 21 | +++ | ++ |
| 22 | +++ | n/a |
| 23 | +++ | + |
| 24 | +++ | ++ |
| 25 | +++ | n/a |
| 26 | +++ | ++ |
| 27 | +++ | + |
| 27A | +++ | + |
| 28 | +++ | ++ |
| 29 | +++ | ++ |
| 30 | +++ | ++ |
| 31 | +++ | +++ |
| 32 | +++ | +++ |
| 33 | +++ | +++ |
| 34 | +++ | ++ |
| 35 | +++ | n/a |
| 36 | +++ | +++ |
| 37 | +++ | ++ |
| 38 | ++ | n/a |
| 39 | ++ | n/a |
| 40 | ++ | n/a |
| 41A | ++ | n/a |
| 41 | +++ | +++ |
| 42 | +++ | ++ |
| 43 | +++ | +++ |
| 43A | +++ | +++ |
| 43B | +++ | +++ |
| 44 | +++ | +++ |
| 44A | +++ | +++ |
| 44B | +++ | +++ |
| 45 | +++ | ++ |
| 46 | +++ | ++ |
| 47 | +++ | +++ |
| 47A | +++ | +++ |
| 47B | +++ | +++ |
| 49 | +++ | +++ |
| 49A | +++ | +++ |
| 49B | +++ | +++ |
| 51 | ++ | n/a |
| 51A | ++ | n/a |
| 52 | ++ | n/a |
| 53 | + | n/a |
| 53A | + | n/a |
| 54 | +++ | + |
| 54A | ++ | + |
| 55 | +++ | ++ |
| 56 | +++ | ++ |
| 57 | +++ | + |
| 58 | ++ | + |
| 59 | ++ | n/a |
| 60 | +++ | ++ |
| 60A | +++ | + |
| 61 | +++ | ++ |
| 62 | +++ | + |
| 63 | +++ | +++ |
| 64 | +++ | n/a |
| 65 | + | n/a |
| 66 | ++ | n/a |
| 67 | + | n/a |
| 68 | + | n/a |
| 69 | ++ | n/a |
| 70 | ++ | n/a |
| 71 | + | n/a |
| 72 | + | n/a |
| 73 | + | n/a |
| 74 | +++ | + |
| 78 | +++ | ++ |
| 79 | + | n/a |
| 80 | +++ | + |
| 81 | +++ | n/a |
| 82 | +++ | +++ |
| 83 | ++ | n/a |
| 84 | +++ | +++ |
| 84A | +++ | +++ |
| 85 | +++ | +++ |
| 86 | +++ | +++ |
| 87 | +++ | +++ |
| 88 | +++ | +++ |
| 89 | +++ | n/a |
| 89A | ++ | n/a |
| 90 | +++ | n/a |
| 91 | +++ | n/a |
| 92 | +++ | n/a |
| 93 | +++ | ++ |
| 94 | +++ | n/a |
| 95 | +++ | ++ |
| 95A | +++ | n/a |
| 96 | +++ | ++ |
| 97 | +++ | n/a |
| 98 | +++ | n/a |
| 99 | ++ | n/a |
| 100 | +++ | ++ |
| 101 | +++ | n/a |
| 102 | +++ | n/a |
| 103 | +++ | n/a |
| 104 | +++ | ++ |
| 105 | ++ | n/a |
| 106 | +++ | ++ |
| 107 | +++ | n/a |
| 108 | ++ | n/a |
| 109 | +++ | ++ |
| 110 | +++ | ++ |
| 111 | ++ | n/a |
| 112 | +++ | + |
| 113 | +++ | ++ |
| 114 | +++ | n/a |
| 115 | ++ | n/a |
| 116 | ++ | n/a |
| 117 | +++ | + |
| 118 | +++ | n/a |
| 119 | ++ | n/a |
| 120 | ++ | n/a |
| 121 | +++ | +++ |
| 122 | +++ | +++ |
| 123 | +++ | +++ |
| 124 | +++ | ++ |
| 125 | +++ | +++ |
| 126 | +++ | +++ |
| 127 | +++ | +++ |
| 128 | +++ | +++ |
| 128A | +++ | n/a |
| 129 | + | n/a |
| 130 | + | n/a |
| 131 | + | n/a |
| 132 | +++ | n/a |
| 133 | ++ | n/a |
| 134 | +++ | ++ |
| 135 | ++ | n/a |
| 136 | +++ | +++ |
| 137 | +++ | +++ |
| 138 | +++ | ++ |

TABLE 14-continued

| Example | Assay 1 | Assay 2 |
|---------|---------|---------|
| 139 | +++ | n/a |
| 139A | +++ | n/a |
| 140 | +++ | +++ |

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

What is claimed is:

1. A compound of Formula I:

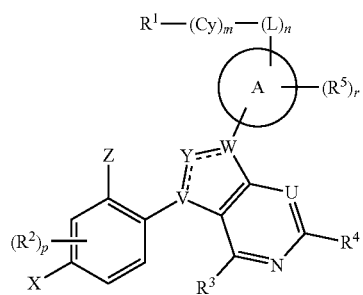

I or a pharmaceutically acceptable salt thereof, wherein:
Ring A is a $C_{6-10}$ aryl group, 5-14 membered heteroaryl group, $C_{3-14}$ cycloalkyl group, or 4-14 membered heterocycloalkyl group;
U is N or $CR^U$, wherein $R^U$ is H, halo, CN, OH, $C_{1-4}$ alkyl, $C_{1-4}$ alkoxy, amino, $C_{1-4}$ alkyl amino, or $C_{2-8}$ dialkylamino;
the moiety

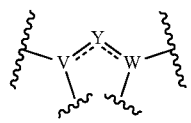

is selected from:

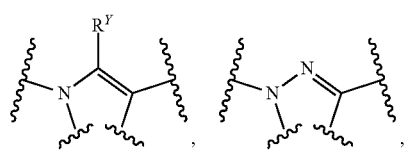

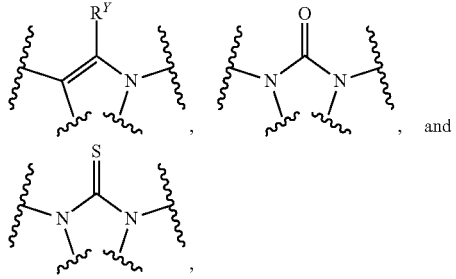
, and

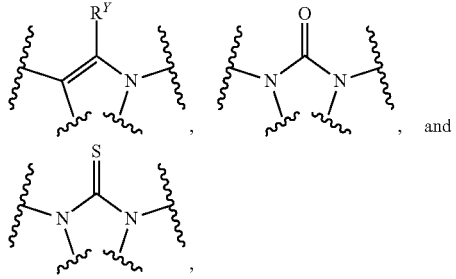
, wherein $R^Y$ is H, halo, CN, OH, $C_{1-4}$ alkyl, $C_{1-4}$ alkoxy, amino, $C_{1-4}$ alkyl amino, or $C_{2-8}$ dialkylamino;
X is F or Cl;
L is selected from —$C_{1-6}$ alkylene- and —($C_{1-4}$ alkylene)$_a$-Q-($C_{1-4}$ alkylene)$_b$-, wherein the $C_{1-6}$ alkylene group and any $C_{1-4}$ alkylene group of the —($C_{1-4}$ alkylene)$_a$-Q-($C_{1-4}$ alkylene)$_b$- group is optionally substituted with 1, 2, or 3 substituents independently selected from halo, CN, OH, $C_{1-3}$ alkyl, $C_{1-3}$ alkoxy, $C_{1-3}$ hydroxyalkyl, $C_{1-3}$ haloalkyl, $C_{1-3}$ haloalkoxy, amino, $C_{1-3}$ alkylamino, and di($C_{1-3}$ alkyl)amino;
Q is —O—, —S—, —S(=O)—, —S(=O)$_2$—, —C(=O)—, —C(=O)NR$^{q1}$—, —C(=O)O—, —OC(=O)NR$^{q1}$—, —NR$^{q1}$—, —NR$^{q1}$C(=O)O—, —NR$^{q1}$C(=O)NR$^{q1}$—, —S(=O)$_2$NR$^{q1}$—, —C(=NR$^{q2}$)—, or —C(=NR$^{q2}$)—NR$^{q1}$—, wherein each $R^{q1}$ is independently selected from H, $C_{1-6}$ alkyl, and $C_{1-3}$ hydroxyalkyl, and wherein each $R^{q2}$ is independently selected from H, $C_{1-6}$ alkyl, and CN;
Cy is a linking $C_{6-14}$ aryl, linking $C_{3-18}$ cycloalkyl, linking 5-16 membered heteroaryl, or linking 4-18 membered heterocycloalkyl group, each of which is optionally substituted with 1, 2, 3, or 4 substituents independently selected from $R^{Cy}$;
each $R^{Cy}$ is independently selected from halo, $C_{1-6}$ alkyl, $C_{1-4}$ haloalkyl, $C_{1-4}$ cyanoalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, C(=NR$^{e1}$)NR$^{c1}$R$^{d1}$, NR$^{c1}$C(=NR$^{e1}$)NR$^{c1}$R$^{d1}$, NR$^{c1}$R$^{d1}$, NR$^{c1}$C(O)R$^{b1}$, NR$^{c1}$C(O)OR$^{a1}$, NR$^{c1}$C(O)NR$^{c1}$R$^{d1}$, NR$^{c1}$S(O)R$^{b1}$, NR$^{c1}$S(O)$_2$R$^{b1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, and S(O)$_2$NR$^{c1}$R$^{d1}$, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl are each optionally substituted by 1, 2, 3, or 4 substituents independently selected from CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, C(=NR$^{e1}$)NR$^{c1}$R$^{d1}$, NR$^{c1}$C(=NR$^{e1}$)NR$^{c1}$R$^{d1}$, NR$^{c1}$R$^{d1}$, NR$^{c1}$C(O)R$^{b1}$, NR$^{c1}$C(O)OR$^{a1}$, NR$^{c1}$C(O)NR$^{c1}$R$^{d1}$, NR$^{c1}$S(O)R$^{b1}$, NR$^{c1}$S(O)$_2$R$^{b1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, and S(O)$_2$NR$^{c1}$R$^{d1}$, $R^1$ is H, Cy$^1$, halo, $C_{1-6}$ alkyl, $C_{1-4}$ haloalkyl, $C_{1-4}$ cyanoalkyl, $C_{2-6}$ alkenyl, $C_{2-6}$ alkynyl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, C(=NR$^{e2}$)NR$^{c2}$R$^{d2}$, NR$^{c2}$C(=NR$^{e2}$)NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, NR$^{c2}$S(O)R$^{b2}$, NR$^{c2}$S(O)$_2$R$^{b2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$ and S(O)$_2$NR$^{c2}$R$^{d2}$, wherein said $C_{1-6}$ alkyl, $C_{2-6}$ alkenyl, and $C_{2-6}$ alkynyl are each optionally substituted by 1, 2, 3, or 4 substituents independently selected from halo, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, C(=NR$^{e2}$)NR$^{c2}$R$^{d2}$, NR$^{c2}$C(=NR$^{e2}$)NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, NR$^{c2}$S(O)R$^{b2}$, NR$^{c2}$S(O)$_2$R$^{b2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, and S(O)$_2$NR$^{c2}$R$^{d2}$;

Z is Cy$^2$, halo, C$_{1-6}$ alkyl, C$_{1-4}$ haloalkyl, C$_{1-4}$ cyanoalkyl, C$_{2-6}$ alkenyl, C$_{2-6}$ alkynyl, CN, NO$_2$, OR$^{a3}$, SR$^{a3}$, C(O)R$^{b3}$, C(O)NR$^{c3}$R$^{d3}$, C(S)NR$^{c3}$R$^{d3}$, C(O)OR$^{a3}$, OC(O)R$^{b3}$, OC(O)NR$^{c3}$R$^{d3}$, C(=NR$^{e3}$)NR$^{c3}$R$^{d3}$, NR$^{c3}$C(=NR$^{e3}$)NR$^{c3}$R$^{d3}$, NR$^{c3}$R$^{d3}$, NR$^{c3}$C(O)R$^{b3}$, NR$^{c3}$C(O)OR$^{a3}$, NR$^{c3}$C(O)NR$^{c3}$R$^{d3}$, NR$^{c3}$S(O)R$^{b3}$, NR$^{c3}$S(O)$_2$R$^{b3}$, NR$^{c3}$S(O)$_2$NR$^{c3}$R$^{d3}$, S(O)R$^{b3}$, S(O)NR$^{c3}$R$^{d3}$, S(O)$_2$R$^{b3}$, S(O)$_2$NR$^{c3}$R$^{d3}$, and P(O)R$^{c3}$R$^{d3}$, wherein said C$_{1-6}$ alkyl, C$_{2-6}$ alkenyl, and C$_{2-6}$ alkynyl are each optionally substituted by 1, 2, 3, or 4 substituents independently selected from Cy$^2$, halo, CN, NO$_2$, CN, NO$_2$, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, C(=NR$^{e3}$)NR$^{c3}$R$^{d3}$, NR$^{c3}$C(=NR$^{e3}$)NR$^{c3}$R$^{d3}$, NR$^{c3}$R$^{d3}$, NR$^{c3}$C(O)R$^{b3}$, NR$^{c3}$S(O)R$^{b3}$, NR$^{c3}$S(O)$_2$R$^{b3}$, NR$^{c3}$S(O)$_2$NR$^{c3}$R$^{d3}$, S(O)R$^{b3}$, S(O)NR$^{c3}$R$^{d3}$, S(O)$_2$R$^{b3}$, and S(O)$_2$NR$^{b3}$R$^{d3}$;

each R$^2$, R$^3$, R$^4$, and R$^5$ is independently selected from H, halo, C$_{1-6}$ alkyl, C$_{1-4}$ haloalkyl, C$_{1-4}$ cyanoalkyl, C$_{2-6}$ alkenyl, C$_{2-6}$ alkynyl, CN, NO$_2$, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, C(=NR$^{e4}$)NR$^{c4}$R$^{d4}$, NR$^{c4}$C(=NR$^{e4}$)NR$^{c4}$R$^{d4}$, NR$^{c4}$R$^{d4}$, NR$^{c4}$C(O)R$^{b4}$, NR$^{c4}$C(O)OR$^{a4}$, NR$^{c4}$C(O)NR$^{c4}$R$^{d4}$, NR$^{c4}$S(O)R$^{b4}$, NR$^{c4}$S(O)$_2$R$^{b4}$, NR$^{c4}$S(O)$_2$NR$^{c4}$R$^{d4}$, S(O)R$^{b4}$, S(O)NR$^{c4}$R$^{d4}$, S(O)$_2$R$^{b4}$, and S(O)$_2$NR$^{c4}$R$^{d4}$, wherein said C$_{1-6}$ alkyl, C$_{2-6}$ alkenyl, and C$_{2-6}$ alkynyl are each optionally substituted by 1, 2, 3, or 4 substituents independently selected from halo, CN, NO$_2$, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, C(=NR$^{e4}$)NR$^{c4}$R$^{d4}$, NR$^{c4}$C(=NR$^{e4}$)NR$^{c4}$R$^{d4}$, NR$^{c4}$R$^{d4}$, NR$^{c4}$C(O)R$^{b4}$, NR$^{c4}$C(O)OR$^{a4}$, NR$^{c4}$C(O)NR$^{c4}$R$^{d4}$, NR$^{c4}$S(O)R$^{b4}$, NR$^{c4}$S(O)$_2$R$^{b4}$, NR$^{c4}$S(O)$_2$NR$^{c4}$R$^{d4}$, S(O)R$^{b4}$, S(O) NR$^{c4}$R$^{d4}$, S(O)$_2$R$^{b4}$, and S(O)$_2$NR$^{c4}$R$^{d4}$;

each Cy$^1$ is independently selected from C$_{6-14}$ aryl, C$_{3-18}$ cycloalkyl, 5-16 membered heteroaryl, and 4-18 membered heterocycloalkyl, each of which is optionally substituted with 1, 2, 3, or 4 substituents independently selected from R$^{Cy1}$;

each Cy$^2$ is independently selected from C$_{6-14}$ aryl, C$_{3-18}$ cycloalkyl, 5-16 membered heteroaryl, and 4-18 membered heterocycloalkyl, each of which is optionally substituted with 1, 2, 3, or 4 substituents independently selected from R$^{Cy2}$;

each R$^{Cy1}$ and R$^{Cy2}$ is independently selected from halo, C$_{1-6}$ alkyl, C$_{1-4}$ haloalkyl, C$_{1-4}$ cyanoalkyl, C$_{2-6}$ alkenyl, C$_{2-6}$ alkynyl, phenyl, C$_{3-7}$ cycloalkyl, 5-6 membered heteroaryl, and 4-7 membered heterocycloalkyl, CN, NO$_2$, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, C(=NR$^{e5}$) NR$^{c5}$R$^{d5}$, NR$^{c5}$C(=NR$^{e5}$)NR$^{c5}$R$^{d5}$, NR$^{c5}$R$^{d5}$, NR$^{c5}$C(O)R$^{b5}$, NR$^{c5}$C(O)OR$^{a5}$, NR$^{c5}$C(O)NR$^{c5}$R$^{d5}$, NR$^{c5}$S(O)R$^{b5}$, NR$^{c5}$S(O)$_2$R$^{b5}$, NR$^{c5}$S(O)$_2$NR$^{c5}$R$^{d5}$, S(O)R$^{b5}$, S(O)NR$^{c5}$R$^{d5}$, S(O)$_2$R$^{b5}$, and S(O)$_2$NR$^{c5}$R$^{d5}$, wherein said C$_{1-6}$ alkyl, C$_{2-6}$ alkenyl, C$_{2-6}$ alkynyl, phenyl, C$_{3-7}$ cycloalkyl, 5-6 membered heteroaryl, and 4-7 membered heterocycloalkyl are each optionally substituted by 1, 2, 3, or 4 substituents independently selected from CN, NO$_2$, OR$^{a5}$, SR$^{a5}$, C(O)R$^{b5}$, C(O)NR$^{c5}$R$^{d5}$, C(O) OR$^{a5}$, OC(O)R$^{b5}$, OC(O)NR$^{c5}$R$^{d5}$, C(=NR$^{e5}$) NR$^{c5}$R$^{d5}$, NR$^{c5}$C(=NR$^{e5}$)NR$^{c5}$R$^{d5}$, NR$^{c5}$R$^{d5}$, NR$^{c5}$C(O)R$^{b5}$, NR$^{c5}$C(O)OR$^{a5}$ NR$^{c5}$C(O)NR$^{c5}$R$^{d5}$, NR$^{c5}$S(O)R$^{b5}$, NR$^{c5}$S(O)$_2$R$^{b5}$, NR$^{c5}$S(O)$_2$NR$^{c5}$R$^{d5}$, S(O)R$^{b5}$, S(O)NR$^{c5}$R$^{d5}$, S(O)$_2$R$^{b5}$, and S(O)$_2$NR$^{c5}$R$^{d5}$;

each R$^{a1}$, R$^{b1}$, R$^{c1}$, R$^{d1}$, R$^{a2}$, R$^{b2}$, R$^{c2}$, R$^{d2}$, R$^{a3}$, R$^{b3}$, R$^{c3}$, R$^{d3}$, R$^{a4}$, R$^{b4}$, R$^{c4}$, R$^{d4}$, R$^{a5}$, R$^{b5}$, R$^{c5}$, and R$^{d5}$ is independently selected from H, C$_{1-6}$ alkyl, C$_{1-4}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl, C$_{3-10}$ cycloalkyl-C$_{1-6}$ alkyl, (5-10 membered heteroaryl)-C$_{1-6}$ alkyl, and (4-10 membered heterocycloalkyl)-C$_{1-6}$ alkyl, wherein said C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl, C$_{3-10}$ cycloalky-C$_{1-6}$ alkyl, (5-10 membered heteroaryl)-C$_{1-6}$ alkyl, and (4-10 membered heterocycloalkyl)-C$_{1-6}$ alkyl are each optionally substituted with 1, 2, 3, 4, or 5 substituents independently selected from R$^g$;

each R$^{e1}$, R$^{e2}$, R$^{e3}$, R$^{e4}$, and R$^{e5}$ is independently selected from H, C$_{1-4}$ alkyl, and CN;

each R$^g$ is independently selected from the group consisting of OH, NO$_2$, CN, halo, C$_{1-20}$ alkyl, C$_{2-6}$ alkenyl, C$_{2-6}$ alkynyl, C$_{1-4}$ haloalkyl, C$_{1-6}$ alkoxy, C$_{1-6}$ haloalkoxy, cyano-C$_{1-3}$ alkyl, HO—C$_{1-3}$ alkyl, amino, C$_{1-6}$ alkylamino, di(C$_{1-6}$ alkyl)amino, thiol, C$_{1-6}$ alkylthio, C$_{1-6}$ alkylsulfinyl, C$_{1-6}$ alkylsulfonyl, carboxy, C$_{1-6}$ alkylcarbonyl, and C$_{1-6}$ alkoxycarbonyl;

n is 0 or 1;
m is 1;
p is 0, 1, 2, or 3;
r is 0, 1, or 2;
a is 0 or 1; and
b is 0 or 1,
wherein any cycloalkyl or heterocycloalkyl group is optionally further substituted by 1 or 2 oxo groups.

2. The compound of claim 1, or a pharmaceutically acceptable salt thereof, wherein:

Ring A is a C$_{6-10}$ aryl group, 5-14 membered heteroaryl group, C$_{3-14}$ cycloalkyl group, or 4-14 membered heterocycloalkyl group;

U is N or CR$^U$, wherein R$^U$ is H, halo, CN, OH, C$_{1-4}$ alkyl, C$_{1-4}$ alkoxy, amino, C$_{1-4}$ alkyl amino, or C$_{2-8}$ dialkylamino;

the moiety

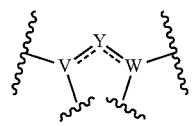

is selected from:

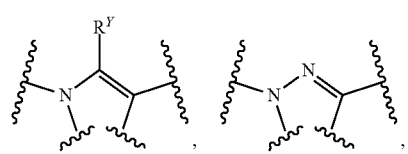

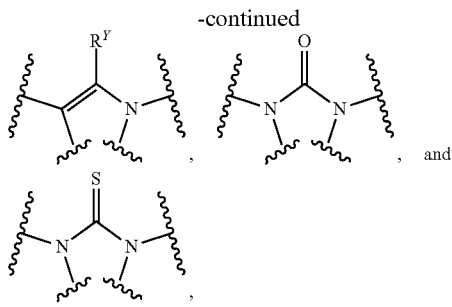

wherein R$^Y$ is H, halo, CN, OH, C$_{1-4}$ alkyl, C$_{1-4}$ alkoxy, amino, C$_{1-4}$ alkyl amino, or C$_{2-8}$ dialkylamino;

X is F or Cl;

L is selected from —C$_{1-6}$ alkylene- and —(C$_{1-4}$ alkylene)$_a$-Q-(C$_{1-4}$ alkylene)$_b$-, wherein the C$_{1-6}$ alkylene group and any C$_{1-4}$ alkylene group of the —(C$_{1-4}$ alkylene)$_a$-Q-(C$_{1-4}$ alkylene)$_b$- group is optionally substituted with 1, 2, or 3 substituents independently selected from halo, CN, OH, C$_{1-3}$ alkyl, C$_{1-3}$ alkoxy, C$_{1-3}$ haloalkyl, C$_{1-3}$ haloalkoxy, amino, C$_{1-3}$ alkylamino, and di(C$_{1-3}$ alkyl)amino;

Q is —O—, —S—, —S(=O)—, —S(=O)$_2$—, —C(=O)—, —C(=O)NR$^{q1}$—, —C(=O)O—, —OC(=O)NR$^{q1}$—, —NR$^{q1}$—, —NR$^{q1}$C(=O)O—, —NR$^{q1}$C(=O)NR$^{q1}$—, —S(=O)$_2$NR$^{q1}$—, —C(=NR$^{q2}$)—, or —C(=NR$^{q2}$)—NR$^{q1}$—, wherein each R$^{q1}$ is independently selected from H and C$_{1-6}$ alkyl, and wherein each R$^{q2}$ is independently selected from H, C$_{1-6}$ alkyl, and CN;

Cy is a linking C$_{6-14}$ aryl, linking C$_{3-18}$ cycloalkyl, linking 5-16 membered heteroaryl, or linking 4-18 membered heterocycloalkyl group, each of which is optionally substituted with 1, 2, 3, or 4 substituents independently selected from R$^{Cy}$;

each R$_{Cy}$ is independently selected from halo, C$_{1-6}$ alkyl, C$_{1-4}$ haloalkyl, C$_{1-4}$ cyanoalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, C(=NR$^{e1}$)NR$^{c1}$R$^{d1}$, NR$^{c1}$C(=NR$^{e1}$)NR$^{c1}$R$^{d1}$, NR$^{c1}$R$^{d1}$, NR$^{c1}$C(O)R$^{b1}$, NR$^{c1}$C(O)OR$^{a1}$, NR$^{c1}$C(O)NR$^{c1}$R$^{d1}$, NR$^{c1}$S(O)R$^{b1}$, NR$^{c1}$S(O)$_2$R$^{b1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, and S(O)$_2$NR$^{c1}$R$^{d1}$, wherein said C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, and 4-10 membered heterocycloalkyl are each optionally substituted by 1, 2, 3, or 4 substituents independently selected from CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, C(=NR$^{e1}$)NR$^{c1}$R$^{d1}$, NR$^{c1}$C(=NR$^{e1}$)NR$^{c1}$R$^{d1}$, NR$^{c1}$R$^{d1}$, NR$^{c1}$C(O)R$^{b1}$, NR$^{c1}$C(O)OR$^{a1}$, NR$^{c1}$C(O)NR$^{c1}$R$^{d1}$, NR$^{c1}$S(O)R$^{b1}$, NR$^{c1}$S(O)$_2$R$^{b1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, and S(O)$_2$NR$^{c1}$R$^{d1}$;

R$^1$ is H, Cy$^1$, halo, C$_{1-6}$ alkyl, C$_{1-4}$ haloalkyl, C$_{1-4}$ cyanoalkyl, C$_{2-6}$ alkenyl, C$_{2-6}$ alkynyl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, C(=NR$^{e2}$)NR$^{c2}$R$^{d2}$, NR$^{c2}$C(=NR$^{e2}$)NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, NR$^{c2}$S(O)R$^{b2}$, NR$^{c2}$S(O)$_2$R$^{b2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$ and S(O)$_2$NR$^{c2}$R$^{d2}$, wherein said C$_{1-6}$ alkyl, C$_{2-6}$ alkenyl, and C$_{2-6}$ alkynyl are each optionally substituted by 1, 2, 3, or 4 substituents independently selected from halo, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, C(=NR$^{e2}$)NR$^{c2}$R$^{d2}$, NR$^{c2}$C(=NR$^{e2}$)NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, NR$^{c2}$S(O)R$^{b2}$, NR$^{c2}$S(O)$_2$R$^{b2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, and S(O)$_2$ NR$^{c2}$R$^{d2}$;

Z is Cy$^2$, halo, C$_{1-6}$ alkyl, C$_{1-4}$ haloalkyl, C$_{1-4}$ cyanoalkyl, C$_{2-6}$ alkenyl, C$_{2-6}$ alkynyl, CN, NO$_2$, OR$^{a3}$, SR$^{a3}$, C(O)R$^{b3}$, C(O)NR$^{c3}$R$^{d3}$, C(S)NR$^{c3}$R$^{d3}$, C(O)OR$^{a3}$, OC(O)R$^{b3}$, OC(O)NR$^{c3}$R$^{d3}$, C(=NR$^{e3}$)NR$^{c3}$R$^{d3}$, NR$^{c3}$C(=NR$^{e3}$)NR$^{c3}$R$^{d3}$, NR$^{c3}$R$^{d3}$, NR$^{c3}$C(O)R$^{b3}$, NR$^{c3}$C(O)OR$^{a3}$, NR$^{c3}$C(O)NR$^{c3}$R$^{d3}$, NR$^{c3}$S(O)R$^{b3}$, NR$^{c3}$S(O)$_2$R$^{b3}$, NR$^{c3}$S(O)$_2$NR$^{c3}$R$^{d3}$, S(O)R$^{b3}$, S(O)NR$^{c3}$R$^{d3}$, S(O)$_2$R$^{b3}$, S(O)$_2$NR$^{c3}$R$^{d3}$, and P(O)R$^{c3}$R$^{d3}$, wherein said C$_{1-6}$ alkyl, C$_{2-6}$ alkenyl, and C$_{2-6}$ alkynyl are each optionally substituted by 1, 2, 3, or 4 substituents independently selected from Cy$^2$, halo, CN, NO$_2$, CN, NO$_2$, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, C(=NR$^{e3}$)NR$^{c3}$R$^{d3}$, NR$^{c3}$C(=NR$^{e3}$)NR$^{c3}$R$^{d3}$, NR$^{c3}$R$^{d3}$, NR$^{c3}$C(O)R$^{b3}$, NR$^{c3}$C(O)OR$^{a3}$, NR$^{c3}$C(O)NR$^{c3}$R$^{d3}$, NR$^{c3}$S(O)R$^{b3}$, NR$^{c3}$S(O)$_2$R$^{b3}$, NR$^{c3}$S(O)$_2$NR$^{c3}$R$^{d3}$, S(O)R$^{b3}$, S(O)NR$^{c3}$R$^{d3}$, S(O)$_2$R$^{b3}$, and S(O)$_2$NR$^{b3}$R$^{d3}$;

each R$^2$, R$^3$, R$^4$, and R$^5$ is independently selected from H, halo, C$_{1-6}$ alkyl, C$_{1-4}$ haloalkyl, C$_{1-4}$ cyanoalkyl, C$_{2-6}$ alkenyl, C$_{2-6}$ alkynyl, CN, NO$_2$, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, C(=NR$^{e4}$)NR$^{c4}$R$^{d4}$, NR$^{c4}$C(=NR$^{e4}$)NR$^{c4}$R$^{d4}$, NR$^{c4}$R$^{d4}$, NR$^{c4}$C(O)R$^{b4}$, NR$^{c4}$C(O)OR$^{a4}$, NR$^{c4}$C(O)NR$^{c4}$R$^{d4}$, NR$^{c4}$S(O)R$^{b4}$, NR$^{c4}$S(O)$_2$R$^{b4}$, NR$^{c4}$S(O)$_2$NR$^{c4}$R$^{d4}$, S(O)R$^{b4}$, S(O)NR$^{c4}$R$^{d4}$, S(O)$_2$R$^{b4}$, and S(O)$_2$NR$^{c4}$R$^{d4}$, wherein said C$_{1-6}$ alkyl, C$_{2-6}$ alkenyl, and C$_{2-6}$ alkynyl are each optionally substituted by 1, 2, 3, or 4 substituents independently selected from halo, CN, NO$_2$, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, C(=NR$^{e4}$)NR$^{c4}$R$^{d4}$, NR$^{c4}$C(=NR$^{e4}$)NR$^{c4}$R$^{d4}$, NR$^{c4}$R$^{d4}$, NR$^{c4}$C(O)R$^{b4}$, NR$^{c4}$C(O)OR$^{a4}$, NR$^{c4}$C(O)NR$^{c4}$R$^{d4}$, NR$^{c4}$S(O)R$^{b4}$, NR$^{c4}$S(O)$_2$R$^{b4}$, NR$^{c4}$S(O)$_2$NR$^{c4}$R$^{d4}$, S(O)R$^{b4}$, S(O)NR$^{c4}$R$^{d4}$, S(O)$_2$R$^{b4}$, and S(O)$_2$NR$^{c4}$R$^{d4}$;

each Cy$^1$ is independently selected from C$_{6-14}$ aryl, C$_{3-18}$ cycloalkyl, 5-16 membered heteroaryl, and 4-18 membered heterocycloalkyl, each of which is optionally substituted with 1, 2, 3, or 4 substituents independently selected from R$^{Cy1}$;

each Cy$^2$ is independently selected from C$_{6-14}$ aryl, C$_{3-18}$ cycloalkyl, 5-16 membered heteroaryl, and 4-18 membered heterocycloalkyl, each of which is optionally substituted with 1, 2, 3, or 4 substituents independently selected from R$^{Cy2}$;

each R$^{Cy1}$ and R$^{Cy2}$ is independently selected from halo, C$_{1-6}$ alkyl, C$_{1-4}$ haloalkyl, C$_{1-4}$ cyanoalkyl, C$_{2-6}$ alkenyl, C$_{2-6}$ alkynyl, phenyl, C$_{3-7}$ cycloalkyl, 5-6 membered heteroaryl, and 4-7 membered heterocycloalkyl, CN, NO$_2$, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, C(=NR$^{e5}$)NR$^{c5}$R$^{d5}$, NR$^{c5}$C(=NR$^{e5}$)NR$^{c5}$R$^{d5}$, NR$^{c5}$R$^{d5}$, NR$^{c5}$C(O)R$^{b5}$, NR$^{c5}$C(O)OR$^{a5}$, NR$^{c5}$C(O)NR$^{c5}$R$^{d5}$, NR$^{c5}$S(O)R$^{b5}$, NR$^{c5}$S(O)$_2$R$^{b5}$, NR$^{c5}$S(O)$_2$NR$^{c5}$R$^{d5}$, S(O)R$^{b5}$, S(O)NR$^{c5}$R$^{d5}$, S(O)$_2$R$^{b5}$, and S(O)$_2$NR$^{c5}$R$^{d5}$, wherein said C$_{1-6}$ alkyl, C$_{2-6}$ alkenyl, C$_{2-6}$ alkynyl, phenyl, C$_{3-7}$ cycloalkyl, 5-6 membered heteroaryl, and 4-7 membered heterocycloalkyl are each optionally substituted by 1, 2, 3, or 4 substituents independently selected from CN, NO$_2$, OR$^{a5}$, SR$^{a5}$, C(O)R$^{b5}$, C(O)NR$^{c5}$R$^{d5}$, C(O)

$OR^{a5}$, $OC(O)R^{b5}$, $OC(O)NR^{c5}R^{d5}$, $C(=NR^{e5})NR^{c5}R^{d5}$, $NR^{c5}C(=NR^{e5})NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$;

each $R^{a1}$, $R^{b1}$, $R^{c1}$, $R^{d1}$, $R^{a2}$, $R^{b2}$, $R^{c2}$, $R^{d2}$, $R^{a3}$, $R^{b3}$, $R^{c3}$, $R^{d3}$, $R^{a4}$, $R^{b4}$, $R^{c4}$, $R^{d4}$, $R^{a5}$, $R^{b5}$, $R^{c5}$, and $R^{d5}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl, $C_{3-10}$ cycloalkyl-$C_{1-6}$ alkyl, (5-10 membered heteroaryl)-$C_{1-6}$ alkyl, and (4-10 membered heterocycloalkyl)-$C_{1-6}$ alkyl, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl, $C_{3-10}$ cycloalkyl-$C_{1-6}$ alkyl, (5-10 membered heteroaryl)-$C_{1-6}$ alkyl, and (4-10 membered heterocycloalkyl)-$C_{1-6}$ alkyl are each optionally substituted with 1, 2, 3, 4, or 5 substituents independently selected from $R^g$;

each $R^{e1}$, $R^{e2}$, $R^{e3}$, $R^{e4}$, and $R^{e5}$ is independently selected from H, $C_{1-4}$ alkyl, and CN;

each $R^g$ is independently selected from the group consisting of OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thiol, $C_{1-6}$ alkylthio, $C_{1-6}$ alkylsulfinyl, $C_{1-6}$ alkylsulfonyl, carboxy, $C_{1-6}$ alkylcarbonyl, and $C_{1-6}$ alkoxycarbonyl, wherein the $C_{1-6}$ alkyl is further substituted by a $C_{1-6}$ alkyl group;

n is 0 or 1;
m is 1;
p is 0, 1, 2, or 3;
r is 0, 1, or 2;
a is 0 or 1; and
b is 0 or 1, wherein any cycloalkyl or heterocycloalkyl group is optionally further substituted by 1 or 2 oxo groups.

3. The compound of claim 1, wherein U is N.

4. The compound of claim 1, or a pharmaceutically acceptable salt thereof, wherein X is F.

5. The compound of claim 1, or a pharmaceutically acceptable salt thereof, wherein the moiety

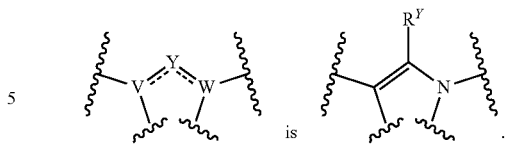

is

6. The compound of claim 1, or a pharmaceutically acceptable salt thereof, wherein the moiety is 7. The compound of claim 1, or a pharmaceutically acceptable salt thereof, wherein the moiety is 8. The compound of claim 1, or a pharmaceutically acceptable salt thereof, wherein Ring A is a 5-10 membered heteroaryl group, $C_{3-10}$ cycloalkyl group, or a 4-10 membered heterocycloalkyl group.

9. The compound of claim 1, or a pharmaceutically acceptable salt thereof, wherein Ring A is a group having the formula:

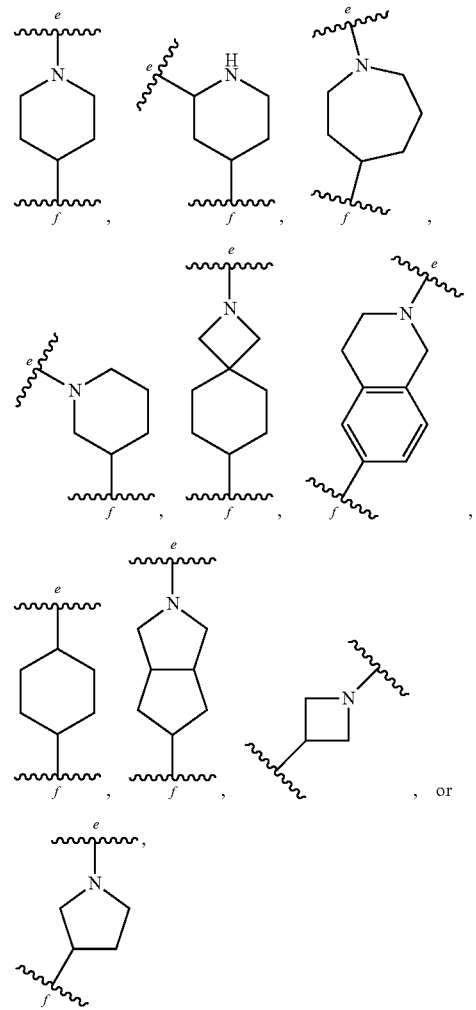

wherein e and f indicate points of attachment to the remainder of the molecule.

10. The compound of claim 1, or a pharmaceutically acceptable salt thereof, wherein L is —$C_{1-6}$ alkylene-optionally substituted with 1, 2, or 3 substituents independently selected from halo, CN, OH, $C_{1-3}$ alkyl, $C_{1-3}$ alkoxy, $C_{1-3}$ haloalkyl, $C_{1-3}$ haloalkoxy, amino, $C_{1-3}$ alkylamino, and di($C_{1-3}$ alkyl)amino.

11. The compound of claim 1, or a pharmaceutically acceptable salt thereof, wherein L is selected from methylene, ethylene, and butylene.

12. The compound of claim 1, or a pharmaceutically acceptable salt thereof, wherein L is —(C$_{1-4}$ alkylene)$_a$-Q-(C$_{1-4}$ alkylene)$_b$-, wherein any C$_{1-4}$ alkylene group of the —(C$_{1-4}$ alkylene)$_a$-Q-(C$_{1-4}$ alkylene)$_b$- group is optionally substituted with 1, 2, or 3 substituents independently selected from halo, CN, OH, C$_{1-3}$ alkyl, C$_{1-3}$ alkoxy, C$_{1-3}$ haloalkyl, C$_{1-3}$ haloalkoxy, amino, C$_{1-3}$ alkylamino, and di(C$_{1-3}$ alkyl)amino.

13. The compound of claim 1, or a pharmaceutically acceptable salt thereof, wherein L is selected from —NH$_2$CH$_2$—, —N(CH$_3$)CH$_2$—, —NHC(O)—, —O—, —C(O)—, and —C(O)CH$_2$—.

14. The compound of claim 1, or a pharmaceutically acceptable salt thereof, wherein Cy is a linking C$_{6-10}$ aryl, linking C$_{3-10}$ cycloalkyl, linking 5-10 membered heteroaryl, or linking 4-10 membered heterocycloalkyl group, each of which is optionally substituted with 1, 2, 3, or 4 substituents independently selected from R$^{Cy}$.

15. The compound of claim 1, or a pharmaceutically acceptable salt thereof, wherein Cy is a linking group having the formula:

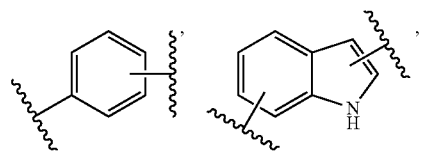

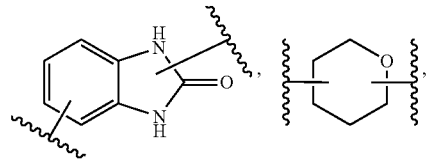

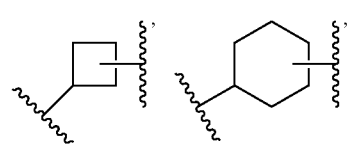

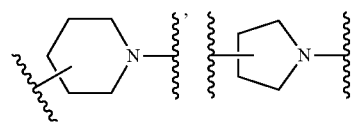

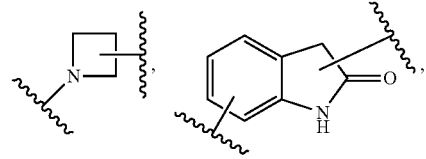

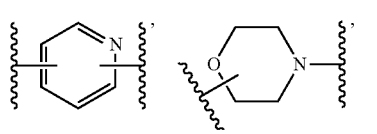

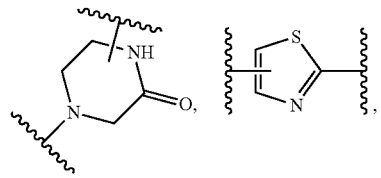

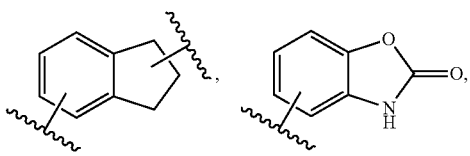

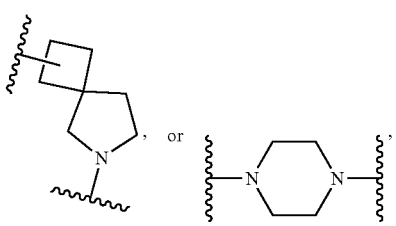

each of which is optionally substituted with 1, 2, 3, or 4 substituents independently selected from R$^{Cy}$.

16. The compound of claim 1, or a pharmaceutically acceptable salt thereof, wherein Z is C(O)NR$^{c3}$R$^{d3}$.

17. The compound of claim 1, or a pharmaceutically acceptable salt thereof, having Formula IIa, IIb, IIc, IId, IIe, IIIa, IIIb, IIIc, or IIId:

IIa

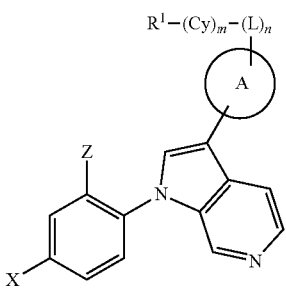

IIb

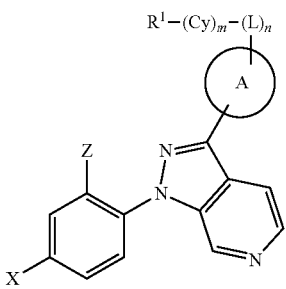

IIc

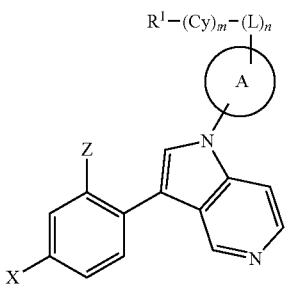

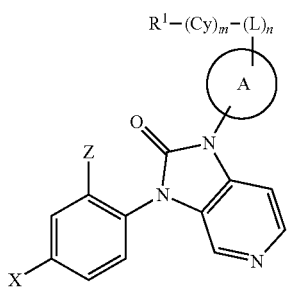
IId

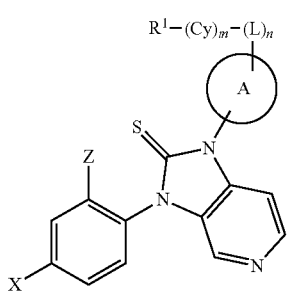
IIe

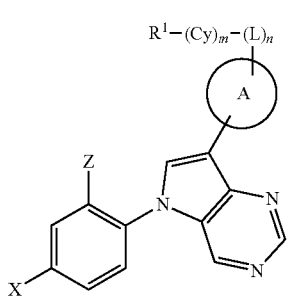
IIIa

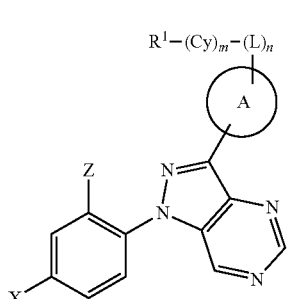
IIIb

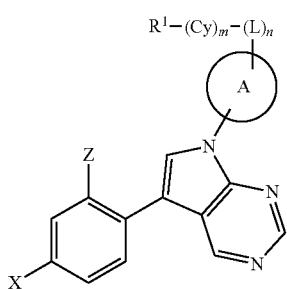
IIIc

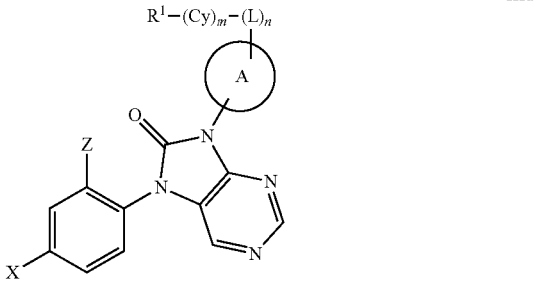
IIId

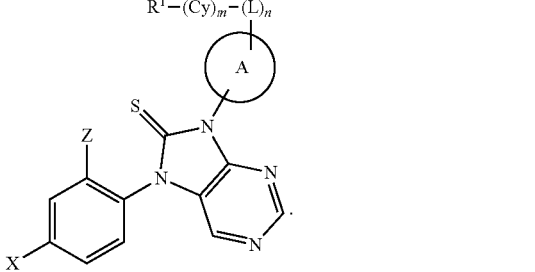
IIIe

18. A compound is selected from the group consisting of:
5-((7-(5-(4-fluoro-2-(trifluoromethyl)phenoxy)pyrimidin-4-yl)-2,7-diazaspiro[4.4]nonan-2-yl)methyl)-1H-benzo[d]imidazol-2(3H)-one;

2-(3-(1-(2-cyano-4-methyl-1H-indol-5-yl)methyl)piperidin-4-yl)-1H-pyrrolo[2,3-c]pyridin-1-yl)-5-fluoro-N-isopropyl-N-methylbenzamide;

5-((7-(5-(2,4-dichlorophenoxy)pyrimidin-4-yl)-2,7-diazaspiro[4.4]nonan-2-yl)methyl)-1H-benzo[d]imidazol-2(3H)-one;

5-fluoro-N-isopropyl-N-methyl-2-(3-(1-((tetrahydro-2H-pyran-4-yl)methyl)piperidin-4-yl)-1H-pyrrolo[2,3-c]pyridin-1-yl)benzamide;

5-fluoro-N-isopropyl-N-methyl-2-(3-(1-((2-oxo-2,3-dihydro-1H-benzo[d]imidazol-5-yl)methyl)piperidin-4-yl)-1H-pyrrolo[2,3-c]pyridin-1-yl)benzamide;

5-fluoro-N-isopropyl-N-methyl-2-(3-(1-(2-(tetrahydro-2H-pyran-4-yl)ethyl)piperidin-4-yl)-1H-pyrrolo[2,3-c]pyridin-1-yl)benzamide;

2-(3-(1-(2-cyano-1H-indol-5-yl)methyl)piperidin-4-yl)-1H-pyrrolo[2,3-c]pyridin-1-yl)-5-fluoro-N-isopropyl-N-methylbenzamide;

2-(3-(1-(2-cyano-1H-indol-6-yl)methyl)piperidin-4-yl)-1H-pyrrolo[2,3-c]pyridin-1-yl)-5-fluoro-N-isopropyl-N-methylbenzamide;

5-fluoro-2-(3-(1-(4-fluorobenzyl)piperidin-4-yl)-1H-pyrrolo[2,3-c]pyridin-1-yl)-N-isopropyl-N-methylbenzamide;

2-(3-(1-(4-chlorobenzyl)piperidin-4-yl)-1H-pyrrolo[2,3-c]pyridin-1-yl)-5-fluoro-N-isopropyl-N-methylbenzamide;

5-fluoro-N-isopropyl-N-methyl-2-(3-(1-(4-(trifluoromethyl)benzyl)piperidin-4-yl)-1H-pyrrolo[2,3-c]pyridin-1-yl)benzamide;

2-(3-(1-(4-cyanobenzyl)piperidin-4-yl)-1H-pyrrolo[2,3-c]pyridin-1-yl)-5-fluoro-N-isopropyl-N-methylbenzamide;

5-fluoro-N-isopropyl-N-methyl-2-(3-(1-(4-(methyl sulfonyl)benzyl)piperidin-4-yl)-1H-pyrrolo[2,3-c]pyridin-1-yl)benzamide;

5-fluoro-N-isopropyl-N-methyl-2-(3-(1-(2-methylbenzyl)piperidin-4-yl)-1H-pyrrolo[2,3-c]pyridin-1-yl)benzamide;
2-(3-(1-(2-chlorobenzyl)piperidin-4-yl)-1H-pyrrolo[2,3-c]pyridin-1-yl)-5-fluoro-N-isopropyl-N-methylbenzamide;
2-(3-(1-((3,3-difluorocyclobutyl)methyl)piperidin-4-yl)-1H-pyrrolo[2,3-c]pyridin-1-yl)-5-fluoro-N-isopropyl-N-methylbenzamide;
5-fluoro-N-isopropyl-N-methyl-2-(3-(1-methylpiperidin-4-yl)-1H-pyrrolo[2,3-c]pyridin-1-yl)benzamide;
tert-butyl (trans-4-(2-(4-(1-(4-fluoro-2-(isopropyl(methyl)carbamoyl)phenyl)-1H-pyrrolo[2,3-c]pyridin-3-yl)piperidin-1-yl)ethyl)cyclohexyl)carbamate;
2-(3-(1-(2-(trans-4-acetamidocyclohexyl)ethyl)piperidin-4-yl)-1H-pyrrolo[2,3-c]pyridin-1-yl)-5-fluoro-N-isopropyl-N-methylbenzamide;
5-fluoro-N-isopropyl-N-methyl-2-(3-(1-(2-(trans-4-(methylsulfonamido)cyclohexyl)ethyl)piperidin-4-yl)-1H-pyrrolo[2,3-c]pyridin-1-yl)benzamide;
tert-butyl (trans-4-((4-(1-(4-fluoro-2-(isopropyl(methyl)carbamoyl)phenyl)-1H-pyrrolo[2,3-c]pyridin-3-yl)piperidin-1-yl)methyl)cyclohexyl)carbamate;
2-(3-(1-(1-(trans-4-acetamidocyclohexyl)methyl)piperidin-4-yl)-1H-pyrrolo[2,3-c]pyridin-1-yl)-5-fluoro-N-isopropyl-N-methylbenzamide;
5-fluoro-N-isopropyl-N-methyl-2-(3-(1-((trans-4-(methylsulfonamido)cyclohexyl)methyl)piperidin-4-yl)-1H-pyrrolo[2,3-c]pyridin-1-yl)benzamide;
2-(3-(1-(4-acetamidobenzyl)piperidin-4-yl)-1H-pyrrolo[2,3-c]pyridin-1-yl)-5-fluoro-N-isopropyl-N-methylbenzamide;
5-fluoro-N-isopropyl-N-methyl-2-(3-(1-(4-(methylsulfonamido)benzyl)piperidin-4-yl)-1H-pyrrolo[2,3-c]pyridin-1-yl)benzamide;
5-fluoro-N-isopropyl-N-methyl-2-(3-(1-(4-(methyl sulfonyl)phenethyl)piperidin-4-yl)-1H-pyrrolo[2,3-c]pyridin-1-yl)benzamide;
2-(3-(1-(3-cyanophenethyl)piperidin-4-yl)-1H-pyrrolo[2,3-c]pyridin-1-yl)-5-fluoro-N-isopropyl-N-methylbenzamide;
5-fluoro-N-isopropyl-N-methyl-2-(3-(1-(3-(methylcarbamoyl)phenethyl)piperidin-4-yl)-1H-pyrrolo[2,3-c]pyridin-1-yl)benzamide;
trans-(5-fluoro-2-(3-(1-((4-hydroxycyclohexyl)methyl)piperidin-4-yl)-1H-pyrrolo[2,3-c]pyridin-1-yl)-N-isopropyl-N-methylbenzamide);
cis-(5-fluoro-2-(3-(1-((4-hydroxycyclohexyl)methyl)piperidin-4-yl)-1H-pyrrolo[2,3-c]pyridin-1-yl)-N-isopropyl-N-methylbenzamide);
5-fluoro-N-isopropyl-N-methyl-2-(3-(1-(2-(1-(methylsulfonyl)piperidin-4-yl)ethyl)piperidin-4-yl)-1H-pyrrolo[2,3-c]pyridin-1-yl)benzamide;
2-(3-(1-(4-(2-cyanopropan-2-yl)phenethyl)piperidin-4-yl)-1H-pyrrolo[2,3-c]pyridin-1-yl)-5-fluoro-N-isopropyl-N-methylbenzamide;
5-fluoro-N-isopropyl-N-methyl-2-(3-(1-(1-phenylethyl)piperidin-4-yl)-1H-pyrrolo[2,3-c]pyridin-1-yl)benzamide;
2-(3-(2-benzylpiperidin-4-yl)-1H-pyrrolo[2,3-c]pyridin-1-yl)-5-fluoro-N-isopropyl-N-methylbenzamide;
2-(3-(1-benzylpiperidin-4-yl)-1H-pyrrolo[2,3-c]pyridin-1-yl)-N-ethyl-5-fluoro-N-isopropylbenzamide;
2-(3-(1-benzylpiperidin-4-yl)-1H-pyrrolo[2,3-c]pyridin-1-yl)-5-fluoro-N,N-diisopropylbenzamide;
N-(trans-4-(2-(4-(1-(2-(cyclopropylmethoxy)-4-fluorophenyl)-1H-pyrrolo[2,3-c]pyridin-3-yl)piperidin-1-yl)ethyl)cyclohexyl)methanesulfonamide;
1-(2-(cyclopropylmethoxy)-4-fluorophenyl)-3-(1-(4-fluorobenzyl)piperidin-4-yl)-1H-pyrrolo[2,3-c]pyridine;
2-(3-(1-benzylpiperidin-4-yl)-1H-pyrrolo[2,3-c]pyridin-1-yl)-5-fluoro-N-(2-hydroxyethyl)-N-isopropylbenzamide;
5-fluoro-N-isopropyl-N-methyl-2-(3-(1-(((1r,4r)-4-(methylsulfonamido)cyclohexyl)methyl)azepan-4-yl)-1H-pyrrolo[2,3-c]pyridin-1-yl)benzamide;
2-(3-(azepan-4-yl)-1H-pyrrolo[2,3-c]pyridin-1-yl)-5-fluoro-N-isopropyl-N-methylbenzamide;
5-((4-(1-(4-fluoro-2-isobutylphenyl)-1H-pyrrolo[2,3-c]pyridin-3-yl)piperidin-1-yl)methyl)-4-methyl-1H-indole-2-carbonitrile;
5-fluoro-N-isopropyl-N-methyl-2-(3-(1-((2-oxo-2,3-dihydro-1H-benzo[d]imidazol-5-yl)methyl)piperidin-3-yl)-1H-pyrrolo[2,3-c]pyridin-1-yl)benzamide;
5-fluoro-2-(3-(1-((1-(2-hydroxyethyl)-2-oxo-2,3-dihydro-1H-benzo[d]imidazol-5-yl)methyl)piperidin-3-yl)-1H-pyrrolo[2,3-c]pyridin-1-yl)-N-isopropyl-N-methylbenzamide;
2-(3-(1-benzylpiperidin-3-yl)-1H-pyrrolo[2,3-c]pyridin-1-yl)-5-fluoro-N-isopropyl-N-methylbenzamide;
2-(3-(1-(cyclohexylmethyl)piperidin-3-yl)-1H-pyrrolo[2,3-c]pyridin-1-yl)-5-fluoro-N-isopropyl-N-methylbenzamide;
N-ethyl-5-fluoro-N-isopropyl-2-(3-(1-((2-oxo-2,3-dihydro-1H-benzo[d]imidazol-5-yl)methyl)piperidin-3-yl)-1H-pyrrolo[2,3-c]pyridin-1-yl)benzamide;
(S)—N-ethyl-5-fluoro-N-isopropyl-2-(3-(1-((2-oxo-2,3-dihydro-1H-benzo[d]imidazol-5-yl)methyl)piperidin-3-yl)-1H-pyrrolo[2,3-c]pyridin-1-yl)benzamide;
(R)—N-ethyl-5-fluoro-N-isopropyl-2-(3-(1-((2-oxo-2,3-dihydro-1H-benzo[d]imidazol-5-yl)methyl)piperidin-3-yl)-1H-pyrrolo[2,3-c]pyridin-1-yl)benzamide;
N-ethyl-5-fluoro-2-(3-(1-((1-(2-hydroxyethyl)-2-oxo-2,3-dihydro-1H-benzo[d]imidazol-5-yl)methyl)piperidin-3-yl)-1H-pyrrolo[2,3-c]pyridin-1-yl)-N-isopropylbenzamide;
(S)—N-ethyl-5-fluoro-2-(3-(1-((1-(2-hydroxyethyl)-2-oxo-2,3-dihydro-1H-benzo[d]imidazol-5-yl)methyl)piperidin-3-yl)-1H-pyrrolo[2,3-c]pyridin-1-yl)-N-isopropylbenzamide;
(R)—N-ethyl-5-fluoro-2-(3-(1-((1-(2-hydroxyethyl)-2-oxo-2,3-dihydro-1H-benzo[d]imidazol-5-yl)methyl)piperidin-3-yl)-1H-pyrrolo[2,3-c]pyridin-1-yl)-N-isopropylbenzamide;
2-(3-(2-azaspiro[3.5]nonan-7-yl)-1H-pyrrolo[2,3-c]pyridin-1-yl)-5-fluoro-N-isopropyl-N-methylbenzamide;
5-fluoro-N-isopropyl-N-methyl-2-(3-(2-methyl-2-azaspiro[3.5]nonan-7-yl)-1H-pyrrolo[2,3-c]pyridin-1-yl)benzamide;
5-fluoro-N-isopropyl-N-methyl-2-(3-(2-methyl-1,2,3,4-tetrahydroisoquinolin-6-yl)-1H-pyrrolo[2,3-c]pyridin-1-yl)benzamide;
5-fluoro-2-(3-(4-hydroxycyclohexyl)-1H-pyrrolo[2,3-c]pyridin-1-yl)-N-isopropyl-N-methylbenzamide;
2-(3-(4-(dimethylamino)cyclohexyl)-1H-pyrrolo[2,3-c]pyridin-1-yl)-5-fluoro-N-isopropyl-N-methylbenzamide;
5-fluoro-N-isopropyl-N-methyl-2-(3-(trans-4-(pyrrolidin-1-yl)cyclohexyl)-1H-pyrrolo[2,3-c]pyridin-1-yl)benzamide;

5-fluoro-N-isopropyl-N-methyl-2-(3-(cis-4-(pyrrolidin-1-yl)cyclohexyl)-1H-pyrrolo[2,3-c]pyridin-1-yl)benzamide;
2-(3-(trans-4-aminocyclohexyl)-1H-pyrrolo[2,3-c]pyridin-1-yl)-5-fluoro-N-isopropyl-N-methylbenzamide;
2-(3-(cis-4-aminocyclohexyl)-1H-pyrrolo[2,3-c]pyridin-1-yl)-5-fluoro-N-isopropyl-N-methylbenzamide;
5-fluoro-N-isopropyl-N-methyl-2-(3-(4-phenoxycyclohexyl)-1H-pyrrolo[2,3-c]pyridin-1-yl)benzamide;
5-fluoro-N-isopropyl-N-methyl-2-(3-(4-(((2-oxo-2,3-dihydro-1H-benzo[d]imidazol-5-yl)methyl)amino)cyclohexyl)-1H-pyrrolo[2,3-c]pyridin-1-yl)benzamide;
5-fluoro-N-isopropyl-N-methyl-2-(3-(4-(((4-(methylsulfonamido)cyclohexyl)methyl)amino)cyclohexyl)-1H-pyrrolo[2,3-c]pyridin-1-yl)benzamide;
2-(7-(1-((2-cyano-4-methyl-1H-indol-5-yl)methyl)piperidin-4-yl)-5H-pyrrolo[3,2-d]pyrimidin-5-yl)-5-fluoro-N-isopropyl-N-methylbenzamide;
2-(7-(1-((2-cyano-4-methyl-1H-indol-5-yl)methyl)piperidin-4-yl)-5H-pyrrolo[3,2-d]pyrimidin-5-yl)-5-fluoro-N,N-dimethylbenzamide;
5-(4-fluorophenyl)-7-(1-((tetrahydro-2H-pyran-4-yl)methyl)piperidin-4-yl)-5H-pyrrolo[3,2-d]pyrimidine;
5-((4-(5-(4-fluorophenyl)-5H-pyrrolo[3,2-d]pyrimidin-7-yl)piperidin-1-yl)methyl)-4-methyl-1H-indole-2-carbonitrile;
5-((4-(5-(4-fluorophenyl)-5H-pyrrolo[3,2-d]pyrimidin-7-yl)piperidin-1-yl)methyl)-1H-benzo[d]imidazol-2(3H)-one;
7-(1-((1H-indol-6-yl)methyl)piperidin-4-yl)-5-(4-fluorophenyl)-5H-pyrrolo[3,2-d]pyrimidine;
7-(1-((1H-indol-5-yl)methyl)piperidin-4-yl)-5-(4-fluorophenyl)-5H-pyrrolo[3,2-d]pyrimidine;
5-((4-(5-(4-fluoro-2-methylphenyl)-5H-pyrrolo[3,2-d]pyrimidin-7-yl)piperidin-1-yl)methyl)-4-methyl-1H-indole-2-carbonitrile;
5-((4-(5-(3-fluorophenyl)-5H-pyrrolo[3,2-d]pyrimidin-7-yl)piperidin-1-yl)methyl)-4-methyl-1H-indole-2-carbonitrile;
4-methyl-5-((4-(5-phenyl-5H-pyrrolo[3,2-d]pyrimidin-7-yl)piperidin-1-yl)methyl)-1H-indole-2-carbonitrile;
5-((4-(5-phenyl-5H-pyrrolo[3,2-d]pyrimidin-7-yl)piperidin-1-yl)methyl)-1H-benzo[d]imidazol-2(3H)-one;
5-fluoro-N-isopropyl-N-methyl-2-(1-(1-((2-oxo-2,3-dihydro-1H-benzo[d]imidazol-5-yl)methyl)piperidin-3-yl)-1H-pyrrolo[3,2-c]pyridin-3-yl)benzamide;
5-fluoro-N-isopropyl-N-methyl-2-(1-(1-(2-((1r,4r)-4-(methylsulfonamido)cyclohexyl)ethyl)piperidin-4-yl)-2-oxo-1,2-dihydro-3H-imidazo[4,5-c]pyridin-3-yl)benzamide;
5-fluoro-N-isopropyl-N-methyl-2-(2-oxo-1-(1-((2-oxo-2,3-dihydro-1H-benzo[d]imidazol-5-yl)methyl)piperidin-4-yl)-1,2-dihydro-3H-imidazo[4,5-c]pyridin-3-yl)benzamide;
5-((4-(3-(4-fluorophenyl)-2-oxo-2,3-dihydro-1H-imidazo[4,5-c]pyridin-1-yl)piperidin-1-yl)methyl)-4-methyl-1H-indole-2-carbonitrile;
2-(1-(1-(cyclohexylmethyl)piperidin-4-yl)-2-oxo-1,2-dihydro-3H-imidazo[4,5-c]pyridin-3-yl)-5-fluoro-N-isopropyl-N-methylbenzamide;
2-(1-(1-((2-cyano-4-methyl-1H-indol-5-yl)methyl)piperidin-4-yl)-2-oxo-1,2-dihydro-3H-imidazo[4,5-c]pyridin-3-yl)-5-fluoro-N-isopropyl-N-methylbenzamide;
5-fluoro-2-(1-(1-(4-fluorobenzyl)piperidin-4-yl)-2-oxo-1,2-dihydro-3H-imidazo[4,5-c]pyridin-3-yl)-N-isopropyl-N-methylbenzamide;
5-fluoro-2-(3-(1-((1-(2-hydroxyethyl)-2-oxo-2,3-dihydro-1H-benzo[d]imidazol-5-yl)methyl)piperidin-3-yl)-1H-pyrrolo[2,3-c]pyridin-1-yl)-N,N-diisopropylbenzamide;
5-fluoro-N,N-diisopropyl-2-(3-(1-((2-oxo-2,3-dihydro-1H-benzo[d]imidazol-5-yl)methyl)piperidin-3-yl)-1H-pyrrolo[2,3-c]pyridin-1-yl)benzamide;
5-fluoro-N,N-diisopropyl-2-(3-(piperidin-4-yl)-1H-pyrrolo[2,3-c]pyridin-1-yl)benzamide;
(R)-2-(5-((3-(1-(4-fluoro-2-(isopropyl(methyl)carbamoyl)phenyl)-1H-pyrrolo[2,3-c]pyridin-3-yl)piperidin-1-yl)methyl)-2-oxo-2,3-dihydro-1H-benzo[d]imidazol-1-yl)ethyl acetate;
(R)-2-(5-((3-(1-(4-fluoro-2-(isopropyl(methyl)carbamoyl)phenyl)-1H-pyrrolo[2,3-c]pyridin-3-yl)piperidin-1-yl)methyl)-2-oxo-2,3-dihydro-1H-benzo[d]imidazol-1-yl)ethyl stearate;
5-fluoro-N,N-diisopropyl-2-(3-(1-(((1r,4r)-4-(methylsulfonamido)cyclohexyl)methyl)piperidin-3-yl)-1H-pyrrolo[2,3-c]pyridin-1-yl)benzamide;
2-(3-(14(3-cyano-3-methyl-2-oxoindolin-6-yl)methyl)piperidin-3-yl)-1H-pyrrolo[2,3-c]pyridin-1-yl)-5-fluoro-N-isopropyl-N-methylbenzamide;
5-fluoro-N-isopropyl-N-methyl-2-(3-(2-((trans-3-(methylsulfonamido)cyclobutyl)methyl)octahydrocyclopenta[c]pyrrol-5-yl)-1H-pyrrolo[2,3-c]pyridin-1-yl)benzamide;
5-fluoro-N-isopropyl-N-methyl-2-(3-(2-((trans-4-(methylsulfonamido)cyclohexyl)methyl)octahydrocyclopenta[c]pyrrol-5-yl)-1H-pyrrolo[2,3-c]pyridin-1-yl)benzamide;
5-fluoro-N-isopropyl-N-methyl-2-(3-(2-((1-(methylsulfonyl)piperidin-4-yl)methyl)octahydrocyclopenta[c]pyrrol-5-yl)-1H-pyrrolo[2,3-c]pyridin-1-yl)benzamide;
5-fluoro-N-isopropyl-N-methyl-2-(3-(1-((cis-3-(methylsulfonamido)cyclobutyl)methyl)piperidin-4-yl)-1H-pyrrolo[2,3-c]pyridin-1-yl)benzamide;
5-fluoro-N-isopropyl-N-methyl-2-(3-(1-(2-(4-(methylsulfonamido)piperidin-1-yl)ethyl)piperidin-4-yl)-1H-pyrrolo[2,3-c]pyridin-1-yl)benzamide;
5-fluoro-N-isopropyl-N-methyl-2-(3-(1-(pyridin-2-yl)piperidin-4-yl)-1H-pyrrolo[2,3-c]pyridin-1-yl)benzamide;
5-fluoro-2-(3-(4-(3-hydroxypyrrolidin-1-yl)cyclohexyl)-1H-pyrrolo[2,3-c]pyridin-1-yl)-N-isopropyl-N-methylbenzamide;
5-fluoro-2-(3-(trans-4-((S)-2-(hydroxymethyl)pyrrolidin-1-yl)cyclohexyl)-1H-pyrrolo[2,3-c]pyridin-1-yl)-N-isopropyl-N-methylbenzamide;
5-fluoro-2-(3-(cis-4-((S)-2-(hydroxymethyl)pyrrolidin-1-yl)cyclohexyl)-1H-pyrrolo[2,3-c]pyridin-1-yl)-N-isopropyl-N-methylbenzamide;
5-fluoro-2-(3-(trans-4-(3-(hydroxymethyl)azetidin-1-yl)cyclohexyl)-1H-pyrrolo[2,3-c]pyridin-1-yl)-N-isopropyl-N-methylbenzamide;
5-fluoro-2-(3-(cis-4-(3-(hydroxymethyl)azetidin-1-yl)cyclohexyl)-1H-pyrrolo[2,3-c]pyridin-1-yl)-N-isopropyl-N-methylbenzamide;
5-fluoro-2-(3-(trans-4-((R)-2-(hydroxymethyl)pyrrolidin-1-yl)cyclohexyl)-1H-pyrrolo[2,3-c]pyridin-1-yl)-N-isopropyl-N-methylbenzamide;
5-fluoro-2-(3-(cis-4-((R)-2-(hydroxymethyl)pyrrolidin-1-yl)cyclohexyl)-1H-pyrrolo[2,3-c]pyridin-1-yl)-N-isopropyl-N-methylbenzamide;

5-fluoro-2-(3-(trans-4-((R)-3-(hydroxymethyl)pyrrolidin-1-yl)cyclohexyl)-1H-pyrrolo[2,3-c]pyridin-1-yl)-N-isopropyl-N-methylbenzamide;
5-fluoro-2-(3-(cis-4-((R)-3-(hydroxymethyl)pyrrolidin-1-yl)cyclohexyl)-1H-pyrrolo[2,3-c]pyridin-1-yl)-N-isopropyl-N-methylbenzamide;
5-fluoro-2-(3-(trans-4-((S)-3-(hydroxymethyl)pyrrolidin-1-yl)cyclohexyl)-1H-pyrrolo[2,3-c]pyridin-1-yl)-N-isopropyl-N-methylbenzamide;
5-fluoro-2-(3-(cis-4-((S)-3-(hydroxymethyl)pyrrolidin-1-yl)cyclohexyl)-1H-pyrrolo[2,3-c]pyridin-1-yl)-N-isopropyl-N-methylbenzamide;
5-fluoro-N-isopropyl-N-methyl-2-(3-(trans-4-(piperidin-1-yl)cyclohexyl)-1H-pyrrolo[2,3-c]pyridin-1-yl)benzamide;
5-fluoro-N-isopropyl-N-methyl-2-(3-(cis-4-(piperidin-1-yl)cyclohexyl)-1H-pyrrolo[2,3-c]pyridin-1-yl)benzamide;
5-fluoro-2-(3-(trans-4-(4-hydroxypiperidin-1-yl)cyclohexyl)-1H-pyrrolo[2,3-c]pyridin-1-yl)-N-isopropyl-N-methylbenzamide;
5-fluoro-2-(3-(cis-4-(4-hydroxypiperidin-1-yl)cyclohexyl)-1H-pyrrolo[2,3-c]pyridin-1-yl)-N-isopropyl-N-methylbenzamide;
2-(3-(trans-4-(4,4-difluoropiperidin-1-yl)cyclohexyl)-1H-pyrrolo[2,3-c]pyridin-1-yl)-5-fluoro-N-isopropyl-N-methylbenzamide;
2-(3-(cis-4-(4,4-difluoropiperidin-1-yl)cyclohexyl)-1H-pyrrolo[2,3-c]pyridin-1-yl)-5-fluoro-N-isopropyl-N-methylbenzamide;
5-fluoro-2-(3-(trans-4-(3-hydroxypiperidin-1-yl)cyclohexyl)-1H-pyrrolo[2,3-c]pyridin-1-yl)-N-isopropyl-N-methylbenzamide;
5-fluoro-2-(3-(cis-4-(3-hydroxypiperidin-1-yl)cyclohexyl)-1H-pyrrolo[2,3-c]pyridin-1-yl)-N-isopropyl-N-methylbenzamide;
5-fluoro-2-(3-(trans-4-(4-(2-hydroxyethyl)piperazin-1-yl)cyclohexyl)-1H-pyrrolo[2,3-c]pyridin-1-yl)-N-isopropyl-N-methylbenzamide;
5-fluoro-2-(3-(cis-4-(4-(2-hydroxyethyl)piperazin-1-yl)cyclohexyl)-1H-pyrrolo[2,3-c]pyridin-1-yl)-N-isopropyl-N-methylbenzamide;
5-fluoro-N-isopropyl-N-methyl-2-(3-(4-(3-oxopiperazin-1-yl)cyclohexyl)-1H-pyrrolo[2,3-c]pyridin-1-yl)benzamide;
5-fluoro-N-isopropyl-N-methyl-2-(3-(trans-4-morpholinocyclohexyl)-1H-pyrrolo[2,3-c]pyridin-1-yl)benzamide;
5-fluoro-N-isopropyl-N-methyl-2-(3-(cis-4-morpholinocyclohexyl)-1H-pyrrolo[2,3-c]pyridin-1-yl)benzamide;
1-(trans-4-(1-(4-fluoro-2-(isopropyl(methyl) carbamoyl)phenyl)-1H-pyrrolo[2,3-c]pyridin-3-yl)cyclohexyl)piperidine-4-carboxylic acid;
1-(cis-4-(1-(4-fluoro-2-(isopropyl(methyl) carbamoyl)phenyl)-1H-pyrrolo[2,3-c]pyridin-3-yl)cyclohexyl)piperidine-4-carboxylic acid;
5-((3-(1-(2-(3-cyclopropyl-5-methyl-4H-1,2,4-triazol-4-yl)-4-fluorophenyl)-1H-pyrrolo[2,3-c]pyridin-3-yl)piperidin-1-yl)methyl)-1H-benzo[d]imidazol-2(3H)-one;
5-fluoro-N-isopropyl-N-methyl-2-(3-(1-((2-oxo-2,3-dihydro-1H-benzo[d]imidazol-5-yl)methyl)pyrrolidin-3-yl)-1H-pyrrolo[2,3-c]pyridin-1-yl)benzamide;
5-fluoro-2-(3-(1-((1-(2-hydroxyethyl)-2-oxo-2,3-dihydro-1H-benzo[d]imidazol-5-yl)methyl)pyrrolidin-3-yl)-1H-pyrrolo[2,3-c]pyridin-1-yl)-N-isopropyl-N-methylbenzamide;
N-methyl-5-fluoro-N-isopropyl-2-(3-(1-((trans-4-(methyl sulfonamido)cyclohexyl)methyl)pyrrolidin-3-yl)-1H-pyrrolo[2,3-c]pyridin-1-yl)benzamide;
N-ethyl-5-fluoro-N-isopropyl-2-(3-(1-((trans-4-(methyl sulfonamido)cyclohexyl)methyl)pyrrolidin-3-yl)-1H-pyrrolo[2,3-c]pyridin-1-yl)benzamide;
5-fluoro-2-(3-(1-((1-(2-hydroxyethyl)-2-oxo-2,3-dihydro-1H-benzo[d]imidazol-5-yl)methyl)pyrrolidin-3-yl)-1H-pyrrolo[2,3-c]pyridin-1-yl)-N,N-diisopropylbenzamide;
5-fluoro-N,N-diisopropyl-2-(3-(1-((trans-4-(methyl sulfonamido)cyclohexyl)methyl)pyrrolidin-3-yl)-1H-pyrrolo[2,3-c]pyridin-1-yl)benzamide;
5-fluoro-N-isopropyl-N-methyl-2-(3-(4-(methyl((4-(methyl sulfonamido)cyclohexyl)methyl)amino)cyclohexyl)-1H-pyrrolo[2,3-c]pyridin-1-yl)benzamide;
2-(3-(trans-4-benzamidocyclohexyl)-1H-pyrrolo[2,3-c]pyridine-1-yl)-5-fluoro-N-isopropyl-N-methylbenzamide;
2-(3-(trans-4-(cyclohexanecarboxamido)cyclohexyl)-1H-pyrrolo[2,3-c]pyridin-1-yl)-5-fluoro-N-isopropyl-N-methylbenzamide;
2-(3-(trans-4-benzamidocyclohexyl)-1H-pyrrolo[2,3-c]pyridine-1-yl)-5-fluoro-N-isopropyl-N-methylbenzamide;
2-(3-(1-(2,3-dihydro-1H-indene-2-carbonyl)piperidin-4-yl)-1H-pyrrolo[2,3-c]pyridin-1-yl)-5-fluoro-N-isopropyl-N-methylbenzamide;
5-fluoro-N-isopropyl-N-methyl-2-(3-(1-(2-phenylacetyl)piperidin-4-yl)-1H-pyrrolo[2,3-c]pyridin-1-yl)benzamide;
5-fluoro-2-(3-(1-((1-(2-hydroxyethyl)-2-oxo-2,3-dihydro-1H-benzo[d]imidazol-5-yl)methyl)piperidin-3-yl)-1H-pyrrolo[2,3-c]pyridin-1-yl)-N,N-diisopropylbenzamide;
5-fluoro-N-isopropyl-N-methyl-2-(1-(1-((2-oxo-2,3-dihydro-1H-benzo[d]imidazol-5-yl)methyl)piperidin-3-yl)-2-thioxo-1,2-dihydro-3H-imidazo[4,5-c]pyridin-3-yl)benzamide;
tert-butyl ((1r,4r)-4-(2-(3-(1-(2-(diisopropylcarbamoyl)-4-fluorophenyl)-1H-pyrrolo[2,3-c]pyridin-3-yl)azetidin-1-yl)ethyl)cyclohexyl)carbamate;
5-fluoro-N,N-diisopropyl-2-(3-(1-(2-((1r,4r)-4-(methylsulfonamido)cyclohexyl)ethyl)azetidin-3-yl)-1H-pyrrolo[2,3-c]pyridin-1-yl)benzamide;
5-fluoro-N,N-diisopropyl-2-(3-(1-(((1r,4r)-4-(methylsulfonamido)cyclohexyl)methyl)azetidin-3-yl)-1H-pyrrolo[2,3-c]pyridin-1-yl)benzamide;
5-fluoro-N,N-diisopropyl-2-(3-(4-(2-(methylsulfonamido)-6-azaspiro[3.4]octan-6-yl)cyclohexyl)-1H-pyrrolo[2,3-c]pyridin-1-yl)benzamide;
5-fluoro-N,N-diisopropyl-2-(3-(1-((2-oxo-2,3-dihydrobenzo[d]oxazol-5-yl)methyl)pyrrolidin-3-yl)-1H-pyrrolo[2,3-c]pyridin-1-yl)benzamide;
or a pharmaceutically acceptable salt thereof.

19. A compound selected from the group consisting of:
5-fluoro-N-isopropyl-N-methyl-2-(3-(piperidin-4-yl)-1H-pyrrolo[2,3-c]pyridin-1-yl)benzamide;
2-(3-((2S,6R)-2,6-dimethylpiperidin-4-yl)-1H-pyrrolo[2,3-c]pyridin-1-yl)-5-fluoro-N-isopropyl-N-methylbenzamide;
5-fluoro-N,N-diisopropyl-2-(3-(piperidin-3-yl)-1H-pyrrolo[2,3-c]pyridin-1-yl)benzamide;
5-fluoro-N-isopropyl-N-methyl-2-(3-(octahydrocyclopenta[c]pyrrol-5-yl)-1H-pyrrolo[2,3-c]pyridin-1-yl)benzamide;

5-((4-(1-(4-fluorophenyl)-1H-pyrrolo[2,3-c]pyridin-3-yl)piperidin-1-yl)methyl)-4-methyl-1H-indole-2-carbonitrile;

5-((4-(1-(4-chlorophenyl)-1H-pyrrolo[2,3-c]pyridin-3-yl)piperidin-1-yl)methyl)-4-methyl-1H-indole-2-carbonitrile;

1-(4-fluorophenyl)-3-(1-isopentylpiperidin-4-yl)-1H-pyrrolo[2,3-c]pyridine;

1-(4-fluorophenyl)-3-(1-phenethylpiperidin-4-yl)-1H-pyrrolo[2,3-c]pyridine;

5-(4-fluorophenyl)-7-(1-((tetrahydro-2H-pyran-4-yl)methyl)piperidin-4-yl)-5H-pyrrolo[3,2-d]pyrimidine;

5-((4-(5-(4-fluorophenyl)-5H-pyrrolo[3,2-d]pyrimidin-7-yl)piperidin-1-yl)methyl)-4-methyl-1H-indole-2-carbonitrile;

5-((4-(5-(4-fluorophenyl)-5H-pyrrolo[3,2-d]pyrimidin-7-yl)piperidin-1-yl)methyl)-1H-benzo[d]imidazol-2(3H)-one;

7-(1-(1H-indol-6-yl)methyl)piperidin-4-yl)-5-(4-fluorophenyl)-5H-pyrrolo[3,2-d]pyrimidine;

7-(1-(1H-indol-5-yl)methyl)piperidin-4-yl)-5-(4-fluorophenyl)-5H-pyrrolo[3,2-d]pyrimidine;

5-((4-(5-(3-fluorophenyl)-5H-pyrrolo[3,2-d]pyrimidin-7-yl)piperidin-1-yl)methyl)-4-methyl-1H-indole-2-carbonitrile;

methyl-5-((4-(5-phenyl-5H-pyrrolo[3,2-d]pyrimidin-7-yl)piperidin-1-yl)methyl)-1H-indole-2-carbonitrile;

4-methyl-5-((4-(5-phenyl-5H-pyrrolo[3,2-d]pyrimidin-7-yl)piperidin-1-yl)methyl)-1H-indole-2-carbonitrile;

5-((4-(3-(4-fluorophenyl)-2-oxo-2,3-dihydro-1H-imidazo[4,5-c]pyridin-1-yl)piperidin-1-yl)methyl)-4-methyl-1H-indole-2-carbonitrile;

or a pharmaceutically acceptable salt thereof.

20. The compound of claim 1, which is 5-fluoro-N-isopropyl-N-methyl-2-(3-(1-((2-oxo-2,3-dihydro-1H-benzo[d]imidazol-5-yl)methyl)piperidin-3-yl)-1H-pyrrolo[2,3-c]pyridin-1-yl)benzamide, or a pharmaceutically acceptable salt thereof.

21. A pharmaceutically acceptable salt of the compound of claim 20, which is a mono-(2R,3S,4R,5S)-2,3,4,5-tetrahydroxyhexanedioic acid salt.

22. A pharmaceutical composition comprising a compound of claim 1, or a pharmaceutically acceptable salt thereof, and at least one pharmaceutically acceptable carrier.

23. A method of inhibiting the interaction between menin and MLL comprising contacting the menin and MLL with a compound of claim 1, or a pharmaceutically acceptable salt thereof.

24. A method of treating cancer in a patient comprising administering to the patient a therapeutically effective amount of a compound of claim 1, or a pharmaceutically acceptable salt thereof.

25. The method of claim 24, wherein the cancer is a hematological cancer, leukemia, lymphoma, mixed lineage leukemia (MLL), MLL-related leukemia, MLL-associated leukemia, MLL-positive leukemia, MLL-induced leukemia, rearranged mixed lineage leukemia (MLL-r), leukemia associated with a MLL rearrangement or a rearrangement of the MLL gene, acute leukemia, chronic leukemia, indolent leukemia, lymphoblastic leukemia, lymphocytic leukemia, myeloid leukemia, myelogenous leukemia, childhood leukemia, acute lymphocytic leukemia (ALL), acute myeloid leukemia (AML), acute granulocytic leukemia, acute non-lymphocytic leukemia, chronic lymphocytic leukemia (CLL), chronic myelogenous leukemia (CML), therapy related leukemia, myelodysplastic syndrome (MDS), myeloproliferative disease (MPD), myeloproliferative neoplasia (MPN), plasma cell neoplasm, multiple myeloma, myelodysplasia, cutaneous T-cell lymphoma, lymphoid neoplasm, AIDS-related lymphoma, thymoma, thymic carcinoma, mycosis fungoides, Alibert-Bazin syndrome, granuloma fungoides, Sézary Syndrome, hairy cell leukemia, T-cell prolymphocytic leukemia (T-PLL), large granular lymphocytic leukemia, meningeal leukemia, leukemic leptomeningitis, leukemic meningitis, multiple myeloma, Hodgkin's lymphoma, non Hodgkin's lymphoma (malignant lymphoma), or Waldenstrom's macroglobulinemia.

\* \* \* \* \*